US011096901B2

(12) United States Patent
Vitaliano et al.

(10) Patent No.: US 11,096,901 B2
(45) **Date of Patent: *Aug. 24, 2021**

(54) DYNAMIC BIO-NANOPARTICLE PLATFORMS

(71) Applicant: METAQOR LLC, Boston, MA (US)

(72) Inventors: Franco Vitaliano, Boston, MA (US); Gordana Dragan Vitaliano, Boston, MA (US)

(73) Assignee: METAQOR LLC, Lewes, DE (US)

( * ) Notice: Subject to any disclaimer, the term of this patent is extended or adjusted under 35 U.S.C. 154(b) by 358 days.

This patent is subject to a terminal disclaimer.

(21) Appl. No.: 13/847,058

(22) Filed: Mar. 19, 2013

(65) Prior Publication Data

US 2014/0288192 A1 Sep. 25, 2014

Related U.S. Application Data

(63) Continuation of application No. 12/399,906, filed on Mar. 6, 2009.

(51) Int. Cl.
*A61K 9/51* (2006.01)
*A61K 9/50* (2006.01)

(52) U.S. Cl.
CPC .......... *A61K 9/5169* (2013.01); *A61K 9/5068* (2013.01)

(58) Field of Classification Search
None
See application file for complete search history.

(56) References Cited

U.S. PATENT DOCUMENTS

| | | | |
|---|---|---|---|
| 5,427,767 | A | 6/1995 | Kresse et al. |
| 5,989,859 | A | 11/1999 | Bandman et al. |
| 6,277,142 | B1 | 8/2001 | Pinter |
| 6,437,413 | B1 | 8/2002 | Yamaguchi et al. |
| 6,456,994 | B1 | 9/2002 | Tucci |
| 6,459,097 | B1 | 10/2002 | Zagoskin |
| 6,472,681 | B1 | 10/2002 | Kane |
| 6,756,039 | B1 | 6/2004 | Yeates et al. |
| 7,033,834 | B2 | 4/2006 | Valerio et al. |
| 7,037,520 | B2 | 5/2006 | Smyth Templeton |
| 7,048,949 | B2 | 5/2006 | Sligar et al. |
| 7,060,291 | B1 | 6/2006 | Meers et al. |
| 7,063,860 | B2 | 6/2006 | Chancellor et al. |
| RE39,229 | E | 8/2006 | Choo et al. |
| 7,094,409 | B2 | 8/2006 | Bachmann et al. |
| 7,101,532 | B2 | 9/2006 | Aikawa et al. |
| 7,101,570 | B2 | 9/2006 | Hope et al. |
| 7,105,303 | B2 | 9/2006 | Ralston et al. |
| 7,108,863 | B2 | 9/2006 | Zalipsky et al. |
| 7,108,915 | B2 | 9/2006 | Adams et al. |
| 7,112,330 | B1 | 9/2006 | Buonamassa et al. |
| 7,112,337 | B2 | 9/2006 | Huang et al. |
| 7,113,967 | B2 | 9/2006 | Cleve et al. |
| 7,118,738 | B2 | 10/2006 | Schlom et al. |
| 7,118,740 | B1 | 10/2006 | Russell et al. |
| 7,151,789 | B2 | 12/2006 | Jette et al. |
| 7,170,142 | B2 | 1/2007 | Wojcik et al. |
| 7,216,038 | B2 | 5/2007 | Vitaliano et al. |
| 7,217,692 | B2 * | 5/2007 | Climent-Johansson ..................... C07K 14/47 514/21.2 |
| 7,219,017 | B2 | 5/2007 | Vitaliano et al. |
| 7,219,018 | B2 | 5/2007 | Vitaliano et al. |
| 7,268,116 | B2 | 9/2007 | Liang |
| 7,393,924 | B2 | 7/2008 | Vitaliano et al. |
| 7,404,969 | B2 | 7/2008 | Chen et al. |
| 7,413,727 | B2 | 8/2008 | Klaveness et al. |
| 7,417,119 | B2 | 8/2008 | Lincoln |
| 7,419,654 | B2 | 9/2008 | Dewanjee |
| 7,431,915 | B2 | 10/2008 | Jiang et al. |
| 7,449,200 | B2 | 11/2008 | Sung et al. |
| 7,452,551 | B1 | 11/2008 | Unger et al. |
| 7,473,531 | B1 | 1/2009 | Domon et al. |
| 7,498,177 | B2 | 3/2009 | De La Fuente et al. |
| 7,842,466 | B1 | 11/2010 | Kim et al. |
| 8,081,850 | B2 | 12/2011 | Beausoleil et al. |
| 8,263,358 | B2 | 9/2012 | Clark |
| 2004/0155184 | A1 | 8/2004 | Stockman et al. |
| 2006/0121016 | A1 | 6/2006 | Lee |
| 2006/0159692 | A1 | 7/2006 | Taya |

(Continued)

FOREIGN PATENT DOCUMENTS

| | | |
|---|---|---|
| WO | WO 9941373 | 8/1999 |
| WO | WO 03009814 | 2/2003 |

(Continued)

OTHER PUBLICATIONS

Smith et al.,"Clathrin coats at 21 Angstrom resolution: a cellular assembly designed to recycle multiple membrane receptors", The EMBO Journal vol. 17, No. 17, pp. 4943-4953. (Year: 1998).*
Article, Targeted High-Efficiency Delivery of Monoclonal Antibodies to Dopamine Brain Regions via Clathrin Nanoparticles, Authors: Gordana Vitaliano and Franco Vitaliano, [In Submission].
Vitaliano, et al. New Clathrin-Based Nanoplatforms for Magnetic Resonance Imaging, PLoS ONE, www.plosone.org, May 1, 2012, vol. 7, Issue 5, e35821.
Aime, Silvio, et al., Lanthanide(iii) chelates for NMR biomedical applications, Chemical Society Reviews, 1998, vol. 27, 19.
Augustine, G.J et al., Clathrin and synaptic vesicle endocytosis: studies at the squid giant synapse; Biochemical Society Transactions (2006) vol. 34, part 1.

(Continued)

*Primary Examiner* — Anand U Desai
(74) *Attorney, Agent, or Firm* — Fish & Richardson P.C.

(57) ABSTRACT

The invention in suitable embodiments is directed to dynamic bio-nanoparticle elements and bio-nanoparticle platforms employing such bio-nanoparticle elements. In one aspect, one or more elements of one or more types, formed from isolated, synthetic and or recombinant amino acid residues comprising in whole or in part one or more types of Clathrin and or Coatomer I/II proteins of one or more isoforms, execute one or more functions and or effect one or more ends, in vivo and or in vitro.

19 Claims, 6 Drawing Sheets

Specification includes a Sequence Listing.

(56) References Cited

U.S. PATENT DOCUMENTS

| | | | |
|---|---|---|---|
| 2007/0141163 A1 | 6/2007 | Vitaliano | |
| 2007/0253051 A1 | 11/2007 | Ishihara et al. | |
| 2007/0273959 A1 | 11/2007 | Lawandy et al. | |
| 2009/0011008 A1 | 1/2009 | Sung et al. | |
| 2009/0028956 A1 | 1/2009 | Slager et al. | |
| 2009/0047300 A1 | 2/2009 | Abulrob et al. | |
| 2009/0048331 A1 | 2/2009 | Soon-Shiong et al. | |
| 2010/0226856 A1* | 9/2010 | Vitaliano ............ | A61K 9/5169 424/9.1 |
| 2016/0060309 A1 | 3/2016 | Vitaliano et al. | |
| 2016/0143992 A1 | 5/2016 | Vitaliano et al. | |
| 2016/0158313 A1 | 6/2016 | Vitaliano et al. | |
| 2016/0158367 A1 | 6/2016 | Vitaliano et al. | |
| 2016/0178652 A1 | 6/2016 | Vitaliano et al. | |
| 2016/0158366 A1 | 9/2016 | Vitaliano et al. | |
| 2016/0310616 A1 | 10/2016 | Vitaliano et al. | |
| 2017/0014475 A1 | 1/2017 | Vitaliano et al. | |
| 2017/0165324 A1 | 6/2017 | Vitaliano et al. | |
| 2017/0202784 A1 | 7/2017 | Vitaliano et al. | |
| 2018/0207106 A1 | 7/2018 | Vitaliano et al. | |
| 2018/0256510 A1 | 9/2018 | Vitaliano et al. | |
| 2018/0256511 A1 | 9/2018 | Vitaliano et al. | |

FOREIGN PATENT DOCUMENTS

| | | |
|---|---|---|
| WO | WO 03016475 | 2/2003 |
| WO | WO 03040301 | 5/2003 |
| WO | WO 03064467 | 8/2003 |
| WO | WO 2004/001019 | 12/2003 |
| WO | WO 2004/076483 | 9/2004 |
| WO | WO 2004/078112 | 9/2004 |

OTHER PUBLICATIONS

Beduneau, Arnaud, et al., Active targeting of brain tumors using nanocarriers; Biomaterials 28 (2007) 4947-4967.

Begley, David J., Delivery of therapeutic agents to the central nervous system: the problems and the possibilities, Pharmacology & Therapeutics 104 (2004) 29-45.

Boado, Ruben J., RNA Interference and Nonviral Targeted Gene Therapy of Experimental Brain Cancer, vol. 2, 139-150, Jan. 2005, The American Society for Experimental NeuroTherapeutics, Inc.

Brodsky, Frances M., Clathrin's Achilles' ankle, Nature, vol. 432, Dec. 2, 2004.

Crowther, R. A., et al., Assembly and Packing of Clathrin Into Coats, The Journal of Cell Biology vol. 91 Dec. 1981 790-797.

Datta, Ankona, et al., High Relaxivity Gadolinium Hydroxypyridonate-Viral Capsid Conjugates: Nanosized MRI Contrast Agents, J. Am. Chem. Soc. 2008, 130, 2546-2552.

De Boer, A.G., et al., Drug Targeting to the Brain, Annu. Rev. Pharmacol. Toxicol. 2007. 47:323-55.

Denardo, S.J., et al., Effect of Molecular Size of Pegylated Peptide on the Pharmacokinetics and Tumor Targeting in Lymphoma-Bearing Mice; Clinical Cancer Research vol. 9, 3854S-3864S, Sep. 1, 2003.

Dhuria, Shyeilla V., et al., Novel vasoconstrictor formulation to enhance intranasal targeting of neuropeptide therapeutics to the central nervous system, JPET Fast Forward. Published on Oct. 22, 2008 as DOI:10.1124/jpet.108.145565.

Edeling, Melissa A., et al., Life of a clathrin coat: insights from clathrin and AP structures, Nature Reviews, Molecular Cell Biology vol. 7, Jan. 2006.

Ehrlich, Marcelo, et al. Endocytosis by Random Initiation and Stabilization of Clathrin-Coated Pits, Cell, vol. 118, 591-605, Sep. 3, 2004.

Enari, Masato, et al., Requirement of clathrin heavy chain for p53-mediated transcription, Genes & Development 20:1087-1099, 2006.

Fotin, Alexander, et al., Structure of an auxilin-bound clathrin coat and its implications for the mechanism of uncoating, Nature, vol. 432, Dec. 2, 2004.

Fotin, Alexander, et al., Molecular model for a complete Clathrin lattice from electron cryomicroscopy, Nature, vol. 432, Dec. 2, 2004.

Graff, Candace L., et al., Nasal Drug Administration: Potential for Targeted Central Nervous System Delivery, Journal of Pharmaceutical Sciences, vol. 94, No. 6, Jun. 2005.

Gragera, R.R., et al. Molecular and ultrastructural basis of the blood-brain barrier function. Immunohistochemical demonstration of Na+/K+ ATPase, alpha-actin, phosphocreatine and clathrin in the capillary wall and its microenvironment, Cell Mol Biol (Noisy-le-grand). Dec. 1993;39(8):819-28.

Granseth, Bjorn, et al., Clathrin-mediated endocytosis: the physiological mechanism of vesicle retrieval at hippocampal synapses, J Physiol. 585.3 (2007) pp. 681-686.

Granseth, Bjorn, et al., The role of endocytosis in regulating the strength of hippocampal synapses, J Physiol 586.24 (2008) pp. 5969-5982.

Haar, Ernst Ter, et al., Atomic Structure of Clathrin: A b Propeller Terminal Domain Joins a Zigzag Linker, Cell, vol. 95, 563-573, Nov. 13, 1998.

Heerssen, Heather, Clathrin Dependence of Synaptic-Vesicle Formation at the *Drosophila* Neuromuscular Junction, Current Biology 18, 401-409, Mar. 25, 2008.

Higgins, Matthew K., et al., Snap-shots of clathrin-mediated endocytosis, Trends in Biochemical Sciences vol. 27 No. 5 May 2002.

Hooker, Jacob M., et al., Magnetic Resonance Contrast Agents from Viral Capsid Shells: A Comparison of Exterior and Interior Cargo Strategies, Nano Lett., vol. 7, No. 8, 2007.

Huang, Fangtian, et al., Analysis of clathrin-mediated endocytosis of EGF receptor by RNA interference, JBC Papers in Press. Published on Feb. 25, 2004 as Manuscript C400046200.

Illum, Lisbeth, Nanoparticulate Systems for Nasal Delivery of Drugs: A Real Improvement over Simple Systems?, Journal of Pharmaceutical Sciences, vol. 96, No. 3, Mar. 2007.

Kabanov, A.V., et al., New Technologies for Drug Delivery Across the Blood Brain Barrier, Current Pharmaceutical Design, 2004, vol. 10, No. 12.

Kirchhausen, et al, Configuration of clathrin trimers: evidence from electron microscopy. J Ultrastruct Mol Struct Res, 1986. 94(3): p. 199-208.

Kirchhausen, et al., Clathrin heavy chain: molecular cloning and complete primary structure, PNAS Dec. 1, 1987 vol. 84 No. 24 8805-8809.

Keen, James, H., Clathrin Assembly Proteins: Affinity Purification and a Model for Coat Assembly, The Journal of Cell Biology, vol. 105, Nov. 1987; p. 1989-1998.

Kocsis, E., et al., Image averaging of flexible fibrous macromolecules: the clathrin triskelion has an elastic proximal segment. J Struct Biol, 1991. 107(1): p. 6-14.

Kotova, S., et al., AFM visualization of clathrin triskelia under fluid and in air. FEBS Lett. 584(1): p. 44-48; 2010.

Ferguson, M.L., et al., Conformation of a clathrin triskelion in solution. Biochemistry, 2006. 45(18): p. 5916-22.

Liu, Shu-Hui, et al., Regulation of Clathrin Assembly and Trimerization, Defined Using Recombinant Triskelion Hubs, Cell, vol. 83, 257-267, Oct. 20, 1995.

Mainardes, Rubiana Mara, et al., Liposomes and Micro/Nanoparticles as Colloidal Carriers for Nasal Drug Delivery, Current Drug Delivery, 2006, 3, 275-285.

Morille, Marie, et al., Progress in developing cationic vectors for non-viral systemic gene therapy against cancer, Biomaterials 29 (2008) 3477-3496.

Nathke, Inke, et al., The Calcium-Binding Site of Clathrin Light Chains, The Journal of Biological Chemistry vol. 265, No. 30, Issue of Oct. 25, pp. 18621-18627, 1990.

Nathke, Inke, et al., Folding and Trimerization of Clathrin Subunits at the Triskelion Hub, Cell, vol. 66, 899-910, Mar. 6, 1992.

Ohno, Hiroshi, Clathrin-associated adaptor protein complexes, Journal of Cell Science 119 (18), 3719-3721; 2006.

Royle, S.J., The cellular functions of Clathrin, Cell. Mol. Life Sci., vol. 63, 2006.

Vieira, Amandio V., et al., Control of EGF Receptor Signaling by Clathrin-Mediated Endocytosis, Science, vol. 274, Dec. 20, 1996.

(56) References Cited

OTHER PUBLICATIONS

Ungewickell, Ernst, Clathrin: A good view of a shapely leg, Current Biology, 1999, 9:R32-R35.
Vitaliano, et al., New Clathrin-Based Nanoplatforms for Magnetic Resonance Imaging, PloS One, May 2012, vol. 7, Issue 5, e35821.
Vitaliano, et al., High-relaxivity magnetic resonance clathrin-based nanoprobes for molecular imaging of dopamine receptors, Neuroscience Annual Meeting, 2011, Program#/Poster#: 619.21/YY13.
Vitaliano, et al., Clathrin Triskelia as Potential High-Relaxivity Magnetic Resonance Nanoprobes for Molecular Imaging of Dopamine Receptors, 2010 ACNP Annual Meeting, Panel, Session No. 274, Dec. 9, 2010.
Vitaliano, et al., Clathrin Triskelia As Potential High-Relaxivity Magnetic Resonance Nanoprobes for Molecular Imaging of Dopamine Receptors, WMIC 2011, Presentation No. P040 Poster Session 2, Sep. 8, 2011.
Wakeham, Diane E., et al., Clathrin self-assembly involves coordinated weak interactions favorable for cellular regulation, The EMBO Journal vol. 22 No. 19 pp. 4980±4990, 2003.
Ybe, Joel A., et al., Clathrin self-assembly is regulated by three light-chain residues controlling the formation of critical salt bridges, The EMBO Journal vol. 17 No. 5 pp. 1297-1303, 1998.
Yoshimura, T., et al., Skeletal structure of clathrin triskelion in solution: experimental and theoretical approaches. Biochemistry, 1991. 30(18): p. 4528-34.
Zhang, Fang, et al., Clathrin Adaptor GGA1 Polymerizes Clathrin into Tubules, The Journal of Biological Chemistry vol. 282, No. 18, pp. 13282-13289, May 4, 2007.
Presentation, "Emerging Nanotechnology-Based Drug Delivery Methods and Their Applications to Addiction Research". Presented at the annual 2010 meeting of the American College of Neuropsychopharmacology. Authors: Gordana Vitaliano and Franco Vitaliano.
Presentation. "New Nanoprobes for Magnetic Resonance Imaging of Dopamine Transporters". Presented at the annual 2013 World Molecular Imaging Congress. Authors: Gordana Vitaliano and Franco Vitaliano.
Presentation. "Targeting Microglia in the Brain by Delivering Antibodies via Nanoparticles" Presented at the 2013 Society for Neuroscience annual meeting. Authors: Gordana Vitaliano and Franco Vitaliano.
Vitaliano G., Rios D., Vitaliano F., and Teicher M. (2009) Clathrin Nanoparticles as Potential High-Relaxivity Magnetic Resonance Nanoprobes for Molecular Brain Imaging, 2009 Molecular Imaging Congress, Montreal, Canada.
Vitaliano G., Rios D., Vitaliano F., Renshaw P., Teicher M. (2011) High-Relaxivity Magnetic Resonance Clathrin-based Nanoprobes for Molecular Imaging of Dopamine Receptors, Neuroscience 2011, Washington, DC.
Vitaliano G., Rios D., Vitaliano F, Renshaw, P. F., Teicher M. (2011) Clathrin Triskelia As Potential High-Relaxivity Magnetic Resonance Nanoprobes, 2011 World Molecular Imaging Congress, San Diego, CA.
Vitaliano G., Rios D., Vitaliano F., Teicher M. (2012) New Clathrin-based Nanotechnology for Delivering Antibodies to the Brain, Neuroscience 2012, New Orleans.
Vitaliano G., Kramer T., Shanmugavadivu A., Vitaliano F., Neumeyer J., Teicher M. (2014) Detecting Activated Microglia in the Brain by Delivering Antibodies via Nanoparticles, Society of Biological Psychiatry 69th Annual Convention, New York, NY.
Vitaliano G., Kramer T., Shanmugavadivu A., Vitaliano F., Neumeyer J., Teicher M. (2014) Targeting Activated Microglia in the Brain by Delivering Antibodies via Clathrin Nanoparticles,53rd Meeting of American College of Neuropsychopharmacology, Phoenix, AZ.
Vitaliano G., Rios D., Vitaliano F., Young L., Lee D., Renshaw, P. F., Teicher M. H. (2015) Dopamine Transporter Nanoprobes for CNS Molecular Magnetic Resonance Imaging and Targeted Drug Delivery, Society of Biological Psychiatry 70th Annual Convention, Toronto, Canada.
Vitaliano G., Vitaliano F., Rios D., Kramer T., Renshaw P., Teicher M. (2015) Clathrin Nanoparticles Efficiently Deliver Antibodies to Targeted Dopamine Brain Regions, 54th Meeting of American College of Neuropsychopharmacology, Hollywood, FL.
Vitaliano G., Adam C., Guzman J.F., McLaughlin J., Kaufman M., Vitaliano F. (2016) Clathrin Nanoparticles Efficiently Deliver BDNF to the Hippocampus, Reverse BDNF Deficits and Improve Cell Survival and Proliferation in a Gt-Tg Mouse Model of HIV. 55th Meeting of American College of Neuropsychopharmacology, Dec. 4-8, Hollywood, FL.
Vitaliano G., Kim J., Adam C., McLaughlin J., Kaufman M., Vitaliano F. Clathrin Nanoparticles Efficiently Deliver BDNF to the Hippocampus, Reverse BDNF Deficits and Improve Cell Survival and Proliferation in a HIV-Tat Mouse Model. 72nd Annual Meeting of the Society of Biological Psychiatry (SOBP), May 18-20, 2017, San Diego, CA, USA.
Kim J., Adam C., Anchaliya D., McLaughlin J., Kaufman M., Vitaliano F., Vitaliano G. Clathrin nanoparticles efficiently deliver brain-derived neurotrophic factor to the hippocampus, reverse BDNF deficits and enhance neurogenesis and memory in a HIV-tat mouse model. Society of Neuroscience, Nov. 11-15, 2017, Washington, DC.
Vitaliano G., Kim J., Adam C., McLaughlin J., Kaufman M., Vitaliano F. Clathrin Nanoparticles Efficiently Deliver BDNF to the Hippocampus, Enhance Neurogenesis and Synaptogenesis and Reverse Memory Deficits in a Mouse Model of HIV-Tat Neurotoxicity. 56th Meeting of American College of Neuropsychopharmacology, Dec. 3-7, Palm Sprins, CA.
Vitaliano G., Kim J., Mintzopoulos D. Adam C., Vitaliano F., Lukas S. Kaufman M. Novel Targeted Clathrin-Based Superparamagnetic Iron Oxide Nanoparticles for CNS Magnetic Resonance Imaging of Dopamine Transporters. 73rd Annual Meeting of the Society of Biological Psychiatry (SOBP), May 10-12, 2018, New York, NY, USA.
Kim, J.K., Mintzopoulos, D., Adam, C.W., Lukas, S.E, Kaufman, M.J., Vitaliano, F., Vitaliano, G.D. Targeted Noninvasive Delivery of Novel Clathrin-based Superparamagnetic Iron Oxide Nanoparticles for Magnetic Resonance Imaging of Dopamine Transporters in Mouse Brain. Society of Neuroscience, Nov. 3-7, 2018, San Diego, CA.
Bifrare et al., "Brain-Derived Neurotrophic Factor Protects against Multiple Forms of Brain Injury in Bacterial Meningitis," The Journal of Infectious Diseases, 2005, 191(1):40-5.
Brodsky et al., "Biological basket weaving: formation and function of clathrin-coated vesicles," Annu. Rev. Cell Dev. Biol., 2001, 17:517-568.
Parham et al., "The Occurrence of Disulphide Bonds in Purified Clathrin Light Chains," Biochem. J., 1989, 257:775-781.
Wilbur et al., "Conformation Switching of Clathrin Light Chain Regulates Clathrin Lattice Assembly," Developmental Cell, 2010, 18(5):854-861.
Battistelli, et al. Ultra-bright and stimuli-responsive fluorescent nanoparticles for bioimaging, WIREs Nanomed Nanobiotechnol, 2016, 8:139-150.
Bethune et al., "Coatomer, the Coat Protein of COPI Transport Vesicles, Discriminates Endoplasmic Reticulum Residents from p24 Proteins," Mol. Cell. Biol., Nov. 2006, 26(21):8011-8021.
Campbell et al., "Identification of a Protein Kinase as an Intrinsic Component of Rat Liver Coated Vesicles," Biochemistry, 1984, 23:4420-4426.
Carbonaro et al., High efficient fluorescent stable colloidal sealed dye-doped mesostructured silica nanoparticles, Microporous and Mesoporous Materials, 2016, 225:432-439.
Cotten et al., "Receptor-Mediated Transport of DNA into Eukaryotic Cells," Methods Enzym, 1993, 217:618-644.
Crosetto et al., "Oncogenic breakdowns in endocytic adaptor proteins," FEBS Letters, 2005, 579:3231-3238.
Davidson et al., "Molecular medicine for the brain: silencing of disease genes with RNA interference," Lancet Neurology, Mar. 2004, 3:145-149.
ExQor Quad Chard, RFI Response to President's Council on Science & Technology meeting, PCAST/The White House, Jun. 22, 2010, Poster, 1 page.

(56) References Cited

OTHER PUBLICATIONS

ExQor Technologies, Inc. "A 21st Century Pharma Platform for CNS Drugs & Cognitive Sensors," presentation, 2016, Vitaliano, et al, 10 pages.
ExQor Technologies, Inc. TruStudy, "A Unified Drug Development & Cognitive Analysis Platform," presentation, 2015, Vitaliano, et al., 6 pages.
Exqor Technologies, Inc., ExQor DuoThera, Feb. 2015, Presentation to Royal College of Surgeons in Ireland, Dublin, Ireland, 14 pages.
Fda.gov[online] "Route of Administration," Nov. 2017, [retrieved on Aug. 12, 2019], retrieved from:URLwww.fda.gov/drugs/data-standards-manual-monographs/route-administration>, 5 pages.
Futatsumori, "Identificittion and characterization of novel isoforms of COP I subunits." J. Biochem., 2000, 128:793-801.
Greene et al., "Complete Reconstitution of Clathrin Basket Formation with Recombinant Protein Fragments: Adaptor Control of Clathrin Self-Assembly," Traffic, 2000, 1:69-75.
Gurkan et al., "The COPII cage: unifying principles of vesicle coat assembly," Nature Reviews, Molecular Cell Biology, 2006, 7:727-738.
Hanczyc et al., Multiphoton absorption in amyloid protein fibres, Nature Photonics, Nov. 3, 2013, 7:969-972.
Heuser et al., "Evidence for recycling of synaptic vesicle membrane during transmitter release at the frog neuromuscular junction," The Journal of Cell Biology,1973, 57(2):315-44.
Illum et al., "Nasal drug delivery: new developments and strategies," Dec. 2002, DDT, 7(23):1184-1189.
Ivanov et al., "Exocytosis and Endocytosis," Human Press, 2008, Book, ISBN: 1588298655, 9781588298652, 16 pages.
Jacob et al., "Quantum Plasmonics," MRS Bulletin, Aug. 2012, 37(8):761-767.
Karu et al., "Multiple Roles of Cytochrome c Oxidase in Mammalian Cells Under Action of Red and IR—A Radiation," IUBMB Life, Jul. 28, 2010, 62(8): 607-610.
Kasprowicz et al., "Inactivation of Clathrin hemy chain inhibits synaptic recycling but allows bulk membrane uptake," J. Cell Biol. vol. 182 Nov. 5 1007-1016.
Kedersha et al., "Isolation and Characterization of a Novel Ribonucleoprotein Particle Large Structures contain a Single Species of Small RNA,"J. Cell Biology, 1986, 103:699-709.
Kirchhausen et al., "Clathrin," Annu. Rev. Biochem., 2000, 69:699-727.
Liske et al., "Optical control of neuronal excitation and inhibition using a single opsin protein, ChR2," Scientific Reports, 3:3110.
Lowe et al., "In Vivo Assembly of Coatomer, the COP-I Coat Precursor," The Journal of Biological Chemistry, 996, 271(48):30725-30730.
Ma et al., "Intranasally delivered TGF-B1 enters brain and regulates gene expressions of its receptors in rats," Brain Research Bulletin, 2007, 74:271-277.
McMahon et al., "COP and clathrin-coated vesicle budding: different pathways, common approaches," Current Opinion in Cell Biology, 2004, 16:379-391.
Mulder et al., "Quantum Dots with a Paramagnetic Coating as a Bimodal Molecular Imaging Probe," Nano Lett. 2006, 6(1):1-6.
Mural et al., A comparison of whole-genome shotgun-derived mouse chromosome 16 and the human genome. Science 296:1661-1671(2002).
Pearse et al., "Purification and properties of 100-kd proteins from coated vesicles and their reconstitution with clathrin," EMBO J. 1984, 3(9):1951-1957.
Podgorski et al., "Ultra-Bright and -Stable Red and Near-Infrared Squaraine Fluorophores for In Vivo Two-Photon Imaging," Dec. 14, 2012, 7(12):PloS One, 7 pages.
Qualmann et al., "Molecular links between endocytosis and the actin cytoskeleton," The Journal of cell biology, 2000, 150(5):F111-6, 6 pages.
Rautio et al., "Drug Delivery Systems for Brain Tumor Therapy," Current Pharmaceutical Design, 2004, 10:1341-1353.
Reddy et al., "Vascular Targeted nanoparticles for Imaging and Treatment of Brain Tumors," Clin Cancer Res. 2006, 12(22):6677-6686.
Ringstad et al., "Endophilin/SH3p4 is required for the transition from early to late stages in clathrin-mediated synaptic vesicle endocytosis," Neuron, 1999, 24(1):143-54.
Rodal et al., "Synaptic Endocytosis: Illuminating the Role of Clathrin Assembly," Current Biology, 2008, 8(6): R259-R261.
Sadasivan et al., "Novel protein-inorganic nanoparticles prepared by inorganic replication of self-assembled clathrin cages and triskelia," Soft Matter, 2008, 4, 2054, 5 pages.
Sheff et al., "Biochemical Heterogeneity and Phosphorylation of Coatomer Subunits," The Journal of Biological Chemistry, 1996, 271(12):7230-7236.
Spang et al.,"Coatomer, Arflp, and nucleotide are required to bud coat protein complex I-coated vesicles from large synthetic liposomes," Proc. Natl. Acad. Sci. USA., 1998, 95(19):11199-11204.
Teng et al., "Clathrin-mediated endocytosis near active zones in snake motor boutons," Journal of Neuroscience, 2000, 20(21):7986-93.
Thorne et al., "Quantitative analysis of the olfactory pathway for drug delivery to the brain," Brain Research, 1995, 692:278-282.
Troutman et al., "Biodegradable Plasmon Resonant Nanoshells,"Adv. Mater. 2008, 20:2604-2608.
Turker et al., "Nasal route and drug delivery systems," Pharm Wold Sci, 2004, 26:137-142.
Vigh, et al. "Nonvisual photoreceptors of the deep brain, pineal organs and retina," Histology and Histopathology, 2002, 17:555-590.
Vinck et al., "Increased fibroblast proliferation induced by light emitting diode and low power laser irradiation," Lasers Med Sci (2003) 18(2):95-99.
Virshup et al., "Clathrin-coated Vesicle Assembly Polypeptides: Physical Properties and Reconstitution Studies with Brain Membranes," The Journal of Cell Biology, vol. 106, Jan. 1988 39-50.
Vitaliano et al., "Bioengineered Clathrin MRI Nanoprobes for Molecular Imaging of Dopamine Receptors," Presentation, American College of Neuropsychopharmacology (ACNP) 2010, 36 pages.
Vitaliano et al., New Clathrin Nanotechnology for Delivering Antibodies to the Brain. Presentation given at Society of Biological Psychiatry's 68th annual meeting, May 16-18, 2013, San Francisco, 12 pages.
Vitaliano et al., Presentation, "New Clathrin Nanoparticles Efficiently Deliver Antibodies to Targeted Dopamine Brain Region," May 13, 2016, Annual Meeting of the Society of Biological Psychiatry (SOBP), 18 pages.
Waters et al., "Coatomer: a cytosolic Protein complex containing subunits of non-clathrin-coated Golgi Transport vesicles," Nature, 1991, 349:248-251.
Wu et al., "Receptor-Mediated Gene Delivery and Expression in Vivo," J. Biol. Chem., 1988, 263:14621-14624.
Ybe et al., "Contribution of Cysteines to Clathrin Trimerization Domain Stability and Mapping of Light Chain Binding," Traffic, 2003, 4:850-856.
Ybe et al., "Light Chain C-Terminal Region Reinforces the Stability of Clathrin Heavy Chain Trimers," Traffic, 2007, 8:1101-1110.
Zhang et al., "Fabrication of novel biomaterials through molecular self-assembly," Nature Biotechnology, Oct. 2003, 21(10):1171-1178.
Zhu et al., "Adaptor Protein l-Dependent Clathrin Coat Assembly on Synthetic Liposomes and Golgi Membranes," Methods in Enzymology, 2001, 329(40):379-387.
Redlingshöfer et al., "Clathrin light chain diversity regulates membrane deformation in vitro and synaptic vesicle formation in vivo," PNAS, 2020, 117(38):23527-23538.
Seppen et al., "Interation of Clathrin with Large Unilamellar Phospholipid Vesicles at Neutral pH. Lipid Dependence and Protein Penetration," Biochimica et Biophysica Acta, 1992, 1106:209-215.
Vitaliano et al., "A Novel Neurotheranostic for Magnetic Resonance Imaging of Dopamine Transporters and Treatment of Dopaminergic Neurodegeneration," 74th Annual Meeting of the Society of Biological Psychiatry (SOBP), Chicago, IL, May 16-18, 2019, 1 page.

(56) References Cited

OTHER PUBLICATIONS

Vitaliano et al., "Clathrin MRI Nanoprobes for Molecular Imaging of Dopamine Receptors," 49th Meeting of American College of Neuropsycho-Pharmacology, Oral Presentation, Miami, FL, 2010, 36 pages.

Vitaliano et al., "Clathrin Nanoparticles Efficiently Deliver BDNF to the Hippocampus, Reverse Oxidative Stress, Enhance Synaptogenesis and Memory in Alzheimer's Mouse Model," Neuroscience, Poster, Chicago, IL, Oct. 19-23, 2019, 1 page.

Vitaliano et al., "Clathrin Nanoparticles Efficiently Deliver Brain-Derived Neurotrophic Factor (BDNF) to the Hippocampus, Reverse Oxidative Stress and Enhance Synaptogenesis and Memory in Alzheimer's Mouse Model," 75th Annual Meeting of the Society of Biological Psychiatry (SOBP), Virtual, Apr. 30-May 1, 2020, 1 page.

Vitaliano et al., "Neurotheranostic for Magnetic Resonance Imaging of Dopamine Transporters and Treatment of Dopaminergic Neurodegeneration," Society of Neuroscience, Virtual Event Session: (P383), Jan. 11, 2021, 1 page.

Vitaliano et al., "Neurotheranostic for MRI of Dopamine Transporters (DAT) and Treatment of Dopaminergic Neurodegeneration," Contrast Media Research (CMR) Symposium, Erice, Italy, Oral Presentation, Nov. 10-15, 2019, 18 pages.

Vitaliano et al., "New Clathrin Nanoparticles Efficiently Deliver Antibodies to Targeted Dopamine Brain Region," 71st Annual Meeting of the Society of Biological Psychiatry (SOBP), Oral Presentation, Atlanta, GA, USA, 2016, 18 pages.

Vitaliano et al., "New Clathrin Nanoparticles Efficiently Deliver D3 Antibodies to Targeted Dopamine Brain Regions," College on Problems of Drug Dependence (CPDD) Conference, Oral Presentation, San Diego, Jun. 2018, 19 pages.

Vitaliano et al., "New Dopamine Transporter Nanoprobes for CNS Molecular Magnetic Resonance Imaging and Targeted Drug Delivery," Society of Biological Psychiatry, 70th Annual Convention, Toronto, Canada, 2015, 1 page.

Vitaliano et al., "New Quantum Bio-Nanotechnologies for MRI Therapeutics in the CNS," Proc. QIM, Knowledge Federation Dialog, in press, presented in Belgrade Serbia, 2018, 21 pages.

Vitaliano et al., "Novel Antibody-Targeted Clathrin-Based Superparamagnetic Iron Oxide Nanoprobes for MR Imaging of Dopamine Transporters," WMIC, Virtual, Oct. 7-9, 2020, 15 pages.

Vitaliano, "Harvard Medical School/Harvard School of Dental Medicine Curriculum Vitae," MIC, McLean Hospital, 2020, 30 pages.

Wu et al., "Clathrin exchange during clathrin-mediated endocytosis," The Journal of Cell Biology, 2001, 155(2):291-300.

* cited by examiner

SEQUENCE LISTING

```
<160> NUMBER OF SEQ ID NOS: 30

<210> SEQ ID NO 1
<211> LENGTH: 1675
<212> TYPE: PRT
<213> ORGANISM: Homo sapiens
<300> PUBLICATION INFORMATION:
<308> DATABASE ACCESSION NUMBER: UniProtKB/Q00610
<309> DATABASE ENTRY DATE: 2009-05-26
<313> RELEVANT RESIDUES IN SEQ ID NO: (1)..(1675)

<400> SEQUENCE: 1

Met Ala Gln Ile Leu Pro Ile Arg Phe Gln Glu His Leu Gln Leu Gln
1               5                   10                  15
```

-continued

```
Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430
```

```
Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
```

```
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895

Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                1015                1020

Leu Gln  Asn Leu Leu Ile Leu  Thr Ala Ile Lys Ala  Asp Arg Thr
    1025                1030                1035

Arg Val  Met Glu Tyr Ile Asn  Arg Leu Asp Asn Tyr  Asp Ala Pro
    1040                1045                1050

Asp Ile  Ala Asn Ile Ala Ile  Ser Asn Glu Leu Phe  Glu Glu Ala
    1055                1060                1065

Phe Ala  Ile Phe Arg Lys Phe  Asp Val Asn Thr Ser  Ala Val Gln
    1070                1075                1080

Val Leu  Ile Glu His Ile Gly  Asn Leu Asp Arg Ala  Tyr Glu Phe
    1085                1090                1095

Ala Glu  Arg Cys Asn Glu Pro  Ala Val Trp Ser Gln  Leu Ala Lys
    1100                1105                1110

Ala Gln  Leu Gln Lys Gly Met  Val Lys Glu Ala Ile  Asp Ser Tyr
    1115                1120                1125

Ile Lys  Ala Asp Asp Pro Ser  Ser Tyr Met Glu Val  Val Gln Ala
    1130                1135                1140

Ala Asn  Thr Ser Gly Asn Trp  Glu Glu Leu Val Lys  Tyr Leu Gln
    1145                1150                1155

Met Ala  Arg Lys Lys Ala Arg  Glu Ser Tyr Val Glu  Thr Glu Leu
    1160                1165                1170

Ile Phe  Ala Leu Ala Lys Thr  Asn Arg Leu Ala Glu  Leu Glu Glu
    1175                1180                1185

Phe Ile  Asn Gly Pro Asn Asn  Ala His Ile Gln Gln  Val Gly Asp
    1190                1195                1200

Arg Cys  Tyr Asp Glu Lys Met  Tyr Asp Ala Ala Lys  Leu Leu Tyr
    1205                1210                1215

Asn Asn  Val Ser Asn Phe Gly  Arg Leu Ala Ser Thr  Leu Val His
    1220                1225                1230

Leu Gly  Glu Tyr Gln Ala Ala  Val Asp Gly Ala Arg  Lys Ala Asn
    1235                1240                1245

Ser Thr  Arg Thr Trp Lys Glu  Val Cys Phe Ala Cys  Val Asp Gly
    1250                1255                1260
```

-continued

```
Lys Glu  Phe Arg Leu Ala Gln  Met Cys Gly Leu His  Ile Val Val
    1265                 1270                 1275

His Ala  Asp Glu Leu Glu Glu  Leu Ile Asn Tyr Tyr  Gln Asp Arg
    1280                 1285                 1290

Gly Tyr  Phe Glu Glu Leu Ile  Thr Met Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Arg Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Ile  Ile Thr Met Met Asn  His Pro Thr
    1370                 1375                 1380

Asp Ala  Trp Lys Glu Gly Gln  Phe Lys Asp Ile Ile  Thr Lys Val
    1385                 1390                 1395

Ala Asn  Val Glu Leu Tyr Tyr  Arg Ala Ile Gln Phe  Tyr Leu Glu
    1400                 1405                 1410

Phe Lys  Pro Leu Leu Leu Asn  Asp Leu Leu Met Val  Leu Ser Pro
    1415                 1420                 1425

Arg Leu  Asp His Thr Arg Ala  Val Asn Tyr Phe Ser  Lys Val Lys
    1430                 1435                 1440

Gln Leu  Pro Leu Val Lys Pro  Tyr Leu Arg Ser Val  Gln Asn His
    1445                 1450                 1455

Asn Asn  Lys Ser Val Asn Glu  Ser Leu Asn Asn Leu  Phe Ile Thr
    1460                 1465                 1470

Glu Glu  Asp Tyr Gln Ala Leu  Arg Thr Ser Ile Asp  Ala Tyr Asp
    1475                 1480                 1485

Asn Phe  Asp Asn Ile Ser Leu  Ala Gln Arg Leu Glu  Lys His Glu
    1490                 1495                 1500

Leu Ile  Glu Phe Arg Arg Ile  Ala Ala Tyr Leu Phe  Lys Gly Asn
    1505                 1510                 1515

Asn Arg  Trp Lys Gln Ser Val  Glu Leu Cys Lys Lys  Asp Ser Leu
    1520                 1525                 1530

Tyr Lys  Asp Ala Met Gln Tyr  Ala Ser Glu Ser Lys  Asp Thr Glu
    1535                 1540                 1545

Leu Ala  Glu Glu Leu Leu Gln  Trp Phe Leu Gln Glu  Glu Lys Arg
    1550                 1555                 1560

Glu Cys  Phe Gly Ala Cys Leu  Phe Thr Cys Tyr Asp  Leu Leu Arg
    1565                 1570                 1575

Pro Asp  Val Val Leu Glu Thr  Ala Trp Arg His Asn  Ile Met Asp
    1580                 1585                 1590

Phe Ala  Met Pro Tyr Phe Ile  Gln Val Met Lys Glu  Tyr Leu Thr
    1595                 1600                 1605

Lys Val  Asp Lys Leu Asp Ala  Ser Glu Ser Leu Arg  Lys Glu Glu
    1610                 1615                 1620

Glu Gln  Ala Thr Glu Thr Gln  Pro Ile Val Tyr Gly  Gln Pro Gln
    1625                 1630                 1635

Leu Met  Leu Thr Ala Gly Pro  Ser Val Ala Val Pro  Pro Gln Ala
    1640                 1645                 1650
```

Pro Phe Gly Tyr Gly Tyr Thr Ala Pro Pro Tyr Gly Gln Pro Gln
1655 1660 1665

Pro Gly Phe Gly Tyr Ser Met
1670 1675

<210> SEQ ID NO 2
<211> LENGTH: 1640
<212> TYPE: PRT
<213> ORGANISM: Homo sapiens
<300> PUBLICATION INFORMATION:
<308> DATABASE ACCESSION NUMBER: UniProtKB/P53675
<309> DATABASE ENTRY DATE: 2009-05-26
<313> RELEVANT RESIDUES IN SEQ ID NO: (1)..(1640)

<400> SEQUENCE: 2

Met Ala Gln Ile Leu Pro Val Arg Phe Gln Glu His Phe Gln Leu Gln
1 5 10 15

Asn Leu Gly Ile Asn Pro Ala Asn Ile Gly Phe Ser Thr Leu Thr Met
20 25 30

Glu Ser Asp Lys Phe Ile Cys Ile Arg Glu Lys Val Gly Glu Gln Ala
35 40 45

Gln Val Thr Ile Ile Asp Met Ser Asp Pro Met Ala Pro Ile Arg Arg
50 55 60

Pro Ile Ser Ala Glu Ser Ala Ile Met Asn Pro Ala Ser Lys Val Ile
65 70 75 80

Ala Leu Lys Ala Gly Lys Thr Leu Gln Ile Phe Asn Ile Glu Met Lys
85 90 95

Ser Lys Met Lys Ala His Thr Met Ala Glu Glu Val Ile Phe Trp Lys
100 105 110

Trp Val Ser Val Asn Thr Val Ala Leu Val Thr Glu Thr Ala Val Tyr
115 120 125

His Trp Ser Met Glu Gly Asp Ser Gln Pro Met Lys Met Phe Asp Arg
130 135 140

His Thr Ser Leu Val Gly Cys Gln Val Ile His Tyr Arg Thr Asp Glu
145 150 155 160

Tyr Gln Lys Trp Leu Leu Leu Val Gly Ile Ser Ala Gln Gln Asn Arg
165 170 175

Val Val Gly Ala Met Gln Leu Tyr Ser Val Asp Arg Lys Val Ser Gln
180 185 190

Pro Ile Glu Gly His Ala Ala Ala Phe Ala Glu Phe Lys Met Glu Gly
195 200 205

Asn Ala Lys Pro Ala Thr Leu Phe Cys Phe Ala Val Arg Asn Pro Thr
210 215 220

Gly Gly Lys Leu His Ile Ile Glu Val Gly Gln Pro Ala Ala Gly Asn
225 230 235 240

Gln Pro Phe Val Lys Lys Ala Val Asp Val Phe Phe Pro Pro Glu Ala
245 250 255

Gln Asn Asp Phe Pro Val Ala Met Gln Ile Gly Ala Lys His Gly Val
260 265 270

Ile Tyr Leu Ile Thr Lys Tyr Gly Tyr Leu His Leu Tyr Asp Leu Glu
275 280 285

Ser Gly Val Cys Ile Cys Met Asn Arg Ile Ser Ala Asp Thr Ile Phe
290 295 300

Val Thr Ala Pro His Lys Pro Thr Ser Gly Ile Ile Gly Val Asn Thr
305 310 315 320

Lys Gly Gln Val Leu Ser Val Cys Val Glu Glu Asp Asn Ile Val Asn

-continued

```
                325                 330                 335

Tyr Ala Thr Asn Val Leu Gln Asn Pro Asp Leu Gly Leu Arg Leu Ala
            340                 345                 350

Val Arg Ser Asn Leu Ala Gly Ala Glu Lys Leu Phe Val Arg Lys Phe
        355                 360                 365

Asn Thr Leu Phe Ala Gln Gly Ser Tyr Ala Glu Ala Ala Lys Val Ala
    370                 375                 380

Ala Ser Ala Pro Lys Gly Ile Leu Arg Thr Arg Glu Thr Val Gln Lys
385                 390                 395                 400

Phe Gln Ser Ile Pro Ala Gln Ser Gly Gln Ala Ser Pro Leu Leu Gln
                405                 410                 415

Tyr Phe Gly Ile Leu Leu Asp Gln Gly Gln Leu Asn Lys Leu Glu Ser
            420                 425                 430

Leu Glu Leu Cys His Leu Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Thr Thr Asp Pro Met Leu Ala Leu Ser Val Tyr Leu
465                 470                 475                 480

Arg Ala Asn Val Pro Ser Lys Val Ile Gln Cys Phe Ala Glu Thr Gly
                485                 490                 495

Gln Phe Gln Lys Ile Val Leu Tyr Ala Lys Lys Val Gly Tyr Thr Pro
            500                 505                 510

Asp Trp Ile Phe Leu Leu Arg Gly Val Met Lys Ile Ser Pro Glu Gln
        515                 520                 525

Gly Leu Gln Phe Ser Arg Met Leu Val Gln Asp Glu Glu Pro Leu Ala
    530                 535                 540

Asn Ile Ser Gln Ile Val Asp Ile Phe Met Glu Asn Ser Leu Ile Gln
545                 550                 555                 560

Gln Cys Thr Ser Phe Leu Leu Asp Ala Leu Lys Asn Asn Arg Pro Ala
                565                 570                 575

Glu Gly Leu Leu Gln Thr Trp Leu Leu Glu Met Asn Leu Val His Ala
            580                 585                 590

Pro Gln Val Ala Asp Ala Ile Leu Gly Asn Lys Met Phe Thr His Tyr
        595                 600                 605

Asp Arg Ala His Ile Ala Gln Leu Cys Glu Lys Ala Gly Leu Leu Gln
    610                 615                 620

Gln Ala Leu Glu His Tyr Thr Asp Leu Tyr Asp Ile Lys Arg Ala Val
625                 630                 635                 640

Val His Thr His Leu Leu Asn Pro Glu Trp Leu Val Asn Phe Phe Gly
                645                 650                 655

Ser Leu Ser Val Glu Asp Ser Val Glu Cys Leu His Ala Met Leu Ser
            660                 665                 670

Ala Asn Ile Arg Gln Asn Leu Gln Leu Cys Val Gln Val Ala Ser Lys
        675                 680                 685

Tyr His Glu Gln Leu Gly Thr Gln Ala Leu Val Glu Leu Phe Glu Ser
    690                 695                 700

Phe Lys Ser Tyr Lys Gly Leu Phe Tyr Phe Leu Gly Ser Ile Val Asn
705                 710                 715                 720

Phe Ser Gln Asp Pro Asp Val His Leu Lys Tyr Ile Gln Ala Ala Cys
                725                 730                 735

Lys Thr Gly Gln Ile Lys Glu Val Glu Arg Ile Cys Arg Glu Ser Ser
            740                 745                 750
```

-continued

```
Cys Tyr Asn Pro Glu Arg Val Lys Asn Phe Leu Lys Glu Ala Lys Leu
        755                 760                 765

Thr Asp Gln Leu Pro Leu Ile Ile Val Cys Asp Arg Phe Gly Phe Val
    770                 775                 780

His Asp Leu Val Leu Tyr Leu Tyr Arg Asn Asn Leu Gln Arg Tyr Ile
785                 790                 795                 800

Glu Ile Tyr Val Gln Lys Val Asn Pro Ser Arg Thr Pro Ala Val Ile
                805                 810                 815

Gly Gly Leu Leu Asp Val Asp Cys Ser Glu Glu Val Ile Lys His Leu
            820                 825                 830

Ile Met Ala Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ser
    850                 855                 860

Gln Ile Gln Glu Gly Cys Glu Glu Pro Ala Thr His Asn Ala Leu Ala
865                 870                 875                 880

Lys Ile Tyr Ile Asp Ser Asn Asn Ser Pro Glu Cys Phe Leu Arg Glu
                885                 890                 895

Asn Ala Tyr Tyr Asp Ser Ser Val Val Gly Arg Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Lys Val Cys Asn Glu Asn Ser Leu Phe Lys Ser Glu Ala
    930                 935                 940

Arg Tyr Leu Val Cys Arg Lys Asp Pro Glu Leu Trp Ala His Val Leu
945                 950                 955                 960

Glu Glu Thr Asn Pro Ser Arg Arg Gln Leu Ile Asp Gln Val Val Gln
                965                 970                 975

Thr Ala Leu Ser Glu Thr Arg Asp Pro Glu Glu Ile Ser Val Thr Val
            980                 985                 990

Lys Ala Phe Met Thr Ala Asp Leu  Pro Asn Glu Leu Ile  Glu Leu Leu
        995                 1000                 1005

Glu Lys  Ile Val Leu Asp Asn  Ser Val Phe Ser Glu  His Arg Asn
    1010                 1015                 1020

Leu Gln  Asn Leu Leu Ile Leu  Thr Ala Ile Lys Ala  Asp Arg Thr
    1025                 1030                 1035

Arg Val  Met Glu Tyr Ile Ser  Arg Leu Asp Asn Tyr  Asp Ala Leu
    1040                 1045                 1050

Asp Ile  Ala Ser Ile Ala Val  Ser Ser Ala Leu Tyr  Glu Glu Ala
    1055                 1060                 1065

Phe Thr  Val Phe His Lys Phe  Asp Met Asn Ala Ser  Ala Ile Gln
    1070                 1075                 1080

Val Leu  Ile Glu His Ile Gly  Asn Leu Asp Arg Ala  Tyr Glu Phe
    1085                 1090                 1095

Ala Glu  Arg Cys Asn Glu Pro  Ala Val Trp Ser Gln  Leu Ala Gln
    1100                 1105                 1110

Ala Gln  Leu Gln Lys Asp Leu  Val Lys Glu Ala Ile  Asn Ser Tyr
    1115                 1120                 1125

Ile Arg  Gly Asp Asp Pro Ser  Ser Tyr Leu Glu Val  Val Gln Ser
    1130                 1135                 1140

Ala Ser  Arg Ser Asn Asn Trp  Glu Asp Leu Val Lys  Phe Leu Gln
    1145                 1150                 1155
```

-continued

```
Met Ala  Arg Lys Lys Gly Arg  Glu Ser Tyr Ile Glu  Thr Glu Leu
    1160                 1165                 1170

Ile Phe  Ala Leu Ala Lys Thr  Ser Arg Val Ser Glu  Leu Glu Asp
    1175                 1180                 1185

Phe Ile  Asn Gly Pro Asn Asn  Ala His Ile Gln Gln  Val Gly Asp
    1190                 1195                 1200

Arg Cys  Tyr Glu Glu Gly Met  Tyr Glu Ala Ala Lys  Leu Leu Tyr
    1205                 1210                 1215

Ser Asn  Val Ser Asn Phe Ala  Arg Leu Ala Ser Thr  Leu Val His
    1220                 1225                 1230

Leu Gly  Glu Tyr Gln Ala Ala  Val Asp Asn Ser Arg  Lys Ala Ser
    1235                 1240                 1245

Ser Thr  Arg Thr Trp Lys Glu  Val Cys Phe Ala Cys  Met Asp Gly
    1250                 1255                 1260

Gln Glu  Phe Arg Phe Ala Gln  Leu Cys Gly Leu His  Ile Val Ile
    1265                 1270                 1275

His Ala  Asp Glu Leu Glu Glu  Leu Met Cys Tyr Tyr  Gln Asp Arg
    1280                 1285                 1290

Gly Tyr  Phe Glu Glu Leu Ile  Leu Leu Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Leu Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Val  Leu Thr Met Met Ser  His Pro Thr
    1370                 1375                 1380

Glu Ala  Trp Lys Glu Gly Gln  Phe Lys Asp Ile Ile  Thr Lys Val
    1385                 1390                 1395

Ala Asn  Val Glu Leu Cys Tyr  Arg Ala Leu Gln Phe  Tyr Leu Asp
    1400                 1405                 1410

Tyr Lys  Pro Leu Leu Ile Asn  Asp Leu Leu Leu Val  Leu Ser Pro
    1415                 1420                 1425

Arg Leu  Asp His Thr Trp Thr  Val Ser Phe Phe Ser  Lys Ala Gly
    1430                 1435                 1440

Gln Leu  Pro Leu Val Lys Pro  Tyr Leu Arg Ser Val  Gln Ser His
    1445                 1450                 1455

Asn Asn  Lys Ser Val Asn Glu  Ala Leu Asn His Leu  Leu Thr Glu
    1460                 1465                 1470

Glu Glu  Asp Tyr Gln Gly Leu  Arg Ala Ser Ile Asp  Ala Tyr Asp
    1475                 1480                 1485

Asn Phe  Asp Asn Ile Ser Leu  Ala Gln Gln Leu Glu  Lys His Gln
    1490                 1495                 1500

Leu Met  Glu Phe Arg Cys Ile  Ala Ala Tyr Leu Tyr  Lys Gly Asn
    1505                 1510                 1515

Asn Trp  Trp Ala Gln Ser Val  Glu Leu Cys Lys Lys  Asp His Leu
    1520                 1525                 1530

Tyr Lys  Asp Ala Met Gln His  Ala Ala Glu Ser Arg  Asp Ala Glu
    1535                 1540                 1545

Leu Ala  Gln Lys Leu Leu Gln  Trp Phe Leu Glu Glu  Gly Lys Arg
```

```
    1550                1555                1560

Glu Cys  Phe Ala Ala Cys Leu  Phe Thr Cys Tyr Asp  Leu Leu Arg
    1565                1570                1575

Pro Asp  Met Val Leu Glu Leu  Ala Trp Arg His Asn  Leu Val Asp
    1580                1585                1590

Leu Ala  Met Pro Tyr Phe Ile  Gln Val Met Arg Glu  Tyr Leu Ser
    1595                1600                1605

Lys Val  Asp Lys Leu Asp Ala  Leu Glu Ser Leu Arg  Lys Gln Glu
    1610                1615                1620

Glu His  Val Thr Glu Pro Ala  Pro Leu Val Phe Asp  Phe Asp Gly
    1625                1630                1635

His Glu
    1640


<210> SEQ ID NO 3
<211> LENGTH: 1583
<212> TYPE: PRT
<213> ORGANISM: Homo sapiens
<300> PUBLICATION INFORMATION:
<308> DATABASE ACCESSION NUMBER: NCBI/EAX03047
<309> DATABASE ENTRY DATE: 2006-12-18
<313> RELEVANT RESIDUES IN SEQ ID NO: (1)..(1583)

<400> SEQUENCE: 3

Met Ala Gln Ile Leu Pro Val Arg Phe Gln Glu His Phe Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Thr Ile Ile Asp Met Ser Asp Pro Met Ala Pro Ile Arg Arg
    50                  55                  60

Pro Ile Ser Ala Glu Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Ala Glu Glu Val Ile Phe Trp Lys
            100                 105                 110

Trp Val Ser Val Asn Thr Val Ala Leu Val Thr Glu Thr Ala Val Tyr
        115                 120                 125

His Trp Ser Met Glu Gly Asp Ser Gln Pro Met Lys Met Phe Asp Arg
    130                 135                 140

His Thr Ser Leu Val Gly Cys Gln Val Ile His Tyr Arg Thr Asp Glu
145                 150                 155                 160

Tyr Gln Lys Trp Leu Leu Leu Val Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ala Phe Ala Glu Phe Lys Met Glu Gly
        195                 200                 205

Asn Ala Lys Pro Ala Thr Leu Phe Cys Phe Ala Val Arg Asn Pro Thr
    210                 215                 220

Gly Gly Lys Leu His Ile Ile Glu Val Gly Gln Pro Ala Ala Gly Asn
225                 230                 235                 240

Gln Pro Phe Val Lys Lys Ala Val Asp Val Phe Phe Pro Pro Glu Ala
                245                 250                 255
```

-continued

```
Gln Asn Asp Phe Pro Val Ala Met Gln Ile Gly Ala Lys His Gly Val
            260                 265                 270

Ile Tyr Leu Ile Thr Lys Tyr Gly Tyr Leu His Leu Tyr Asp Leu Glu
        275                 280                 285

Ser Gly Val Cys Ile Cys Met Asn Arg Ile Ser Ala Asp Thr Ile Phe
    290                 295                 300

Val Thr Ala Pro His Lys Pro Thr Ser Gly Ile Ile Gly Val Asn Lys
305                 310                 315                 320

Lys Gly Gln Val Leu Ser Val Cys Val Glu Glu Asp Asn Ile Val Asn
                325                 330                 335

Tyr Ala Thr Asn Val Leu Gln Asn Pro Asp Leu Gly Leu Arg Leu Ala
            340                 345                 350

Val Arg Ser Asn Leu Ala Gly Ala Glu Lys Leu Phe Val Arg Lys Phe
        355                 360                 365

Asn Thr Leu Phe Ala Gln Gly Ser Tyr Ala Glu Ala Ala Lys Val Ala
    370                 375                 380

Ala Ser Ala Pro Lys Gly Ile Leu Arg Thr Arg Glu Thr Val Gln Lys
385                 390                 395                 400

Phe Gln Ser Ile Pro Ala Gln Ser Gly Gln Ala Ser Pro Leu Leu Gln
                405                 410                 415

Tyr Phe Gly Ile Leu Leu Asp Gln Gly Gln Leu Asn Lys Leu Glu Ser
            420                 425                 430

Leu Glu Leu Cys His Leu Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Thr Thr Asp Pro Met Leu Ala Leu Ser Val Tyr Leu
465                 470                 475                 480

Arg Ala Asn Val Pro Ser Lys Val Ile Gln Cys Phe Ala Glu Thr Gly
                485                 490                 495

Gln Phe Gln Lys Ile Val Leu Tyr Ala Lys Lys Val Gly Tyr Thr Pro
            500                 505                 510

Asp Trp Ile Phe Leu Leu Arg Gly Val Met Lys Ile Ser Pro Glu Gln
        515                 520                 525

Gly Leu Gln Phe Ser Arg Met Leu Val Gln Asp Glu Glu Pro Leu Ala
    530                 535                 540

Asn Ile Ser Gln Ile Val Asp Ile Phe Met Glu Asn Ser Leu Ile Gln
545                 550                 555                 560

Gln Cys Thr Ser Phe Leu Leu Asp Ala Leu Lys Asn Asn Arg Pro Ala
                565                 570                 575

Glu Gly Leu Leu Gln Thr Trp Leu Leu Glu Met Asn Leu Val His Ala
            580                 585                 590

Pro Gln Val Ala Asp Ala Ile Leu Gly Asn Lys Met Phe Thr His Tyr
        595                 600                 605

Asp Arg Ala His Ile Ala Gln Leu Cys Glu Lys Ala Gly Leu Leu Gln
    610                 615                 620

Gln Ala Leu Glu His Tyr Thr Asp Leu Tyr Asp Ile Lys Arg Ala Val
625                 630                 635                 640

Val His Thr His Leu Leu Asn Pro Glu Trp Leu Val Asn Phe Phe Gly
                645                 650                 655

Ser Leu Ser Val Glu Asp Ser Val Glu Cys Leu His Ala Met Leu Ser
            660                 665                 670
```

-continued

```
Ala Asn Ile Arg Gln Asn Leu Gln Leu Cys Val Gln Val Ala Ser Lys
        675                 680                 685

Tyr His Glu Gln Leu Gly Thr Gln Ala Leu Val Glu Leu Phe Glu Ser
    690                 695                 700

Phe Lys Ser Tyr Lys Gly Leu Phe Tyr Phe Leu Gly Ser Ile Val Asn
705                 710                 715                 720

Phe Ser Gln Asp Pro Asp Val His Leu Lys Tyr Ile Gln Ala Ala Cys
                725                 730                 735

Lys Thr Gly Gln Ile Lys Glu Val Glu Arg Ile Cys Arg Glu Ser Ser
            740                 745                 750

Cys Tyr Asn Pro Glu Arg Val Lys Asn Phe Leu Lys Glu Ala Lys Leu
        755                 760                 765

Thr Asp Gln Leu Pro Leu Ile Ile Val Cys Asp Arg Phe Gly Phe Val
    770                 775                 780

His Asp Leu Val Leu Tyr Leu Tyr Arg Asn Asn Leu Gln Arg Tyr Ile
785                 790                 795                 800

Glu Ile Tyr Val Gln Lys Val Asn Pro Ser Arg Thr Pro Ala Val Ile
                805                 810                 815

Gly Gly Leu Leu Asp Val Asp Cys Ser Glu Glu Val Ile Lys His Leu
            820                 825                 830

Ile Met Ala Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ser
    850                 855                 860

Gln Ile Gln Glu Gly Cys Glu Glu Pro Ala Thr His Asn Ala Leu Ala
865                 870                 875                 880

Lys Ile Tyr Ile Asp Ser Asn Asn Ser Pro Glu Cys Phe Leu Arg Glu
                885                 890                 895

Asn Ala Tyr Tyr Asp Ser Ser Val Val Gly Arg Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Lys Val Cys Asn Glu Asn Ser Leu Phe Lys Ser Glu Ala
    930                 935                 940

Arg Tyr Leu Val Cys Arg Lys Asp Pro Glu Leu Trp Ala His Val Leu
945                 950                 955                 960

Glu Glu Thr Asn Pro Ser Arg Arg Gln Leu Ile Asp Gln Val Val Gln
                965                 970                 975

Thr Ala Leu Ser Glu Thr Arg Asp Pro Glu Glu Ile Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                1015                1020

Leu Gln  Asn Leu Leu Ile Leu  Thr Ala Ile Lys Ala  Asp Arg Thr
    1025                1030                1035

Arg Val  Met Glu Tyr Ile Ser  Arg Leu Asp Asn Tyr  Asp Ala Leu
    1040                1045                1050

Asp Ile  Ala Ser Ile Ala Val  Ser Ser Ala Leu Tyr  Glu Glu Ala
    1055                1060                1065

Phe Thr  Val Phe His Lys Phe  Asp Met Asn Ala Ser  Ala Ile Gln
    1070                1075                1080

Val Leu  Ile Glu His Ile Gly  Asn Leu Asp Arg Ala  Tyr Glu Phe
```

-continued

```
    1085                1090                1095

Ala Glu  Arg Cys Asn Glu Pro  Ala Val Trp Ser Gln  Leu Ala Gln
    1100                1105                1110

Ala Gln  Leu Gln Lys Asp Leu  Val Lys Glu Ala Ile  Asn Ser Tyr
    1115                1120                1125

Ile Arg  Gly Asp Asp Pro Ser  Ser Tyr Leu Glu Val  Val Gln Ser
    1130                1135                1140

Ala Ser  Arg Ser Asn Asn Trp  Glu Asp Leu Val Lys  Phe Leu Gln
    1145                1150                1155

Met Ala  Arg Lys Lys Gly Arg  Glu Ser Tyr Ile Glu  Thr Glu Leu
    1160                1165                1170

Ile Phe  Ala Leu Ala Lys Thr  Ser Arg Val Ser Glu  Leu Glu Asp
    1175                1180                1185

Phe Ile  Asn Gly Pro Asn Asn  Ala His Ile Gln Gln  Val Gly Asp
    1190                1195                1200

Arg Cys  Tyr Glu Glu Gly Met  Tyr Glu Ala Ala Lys  Leu Leu Tyr
    1205                1210                1215

Ser Asn  Val Ser Asn Phe Ala  Arg Leu Ala Ser Thr  Leu Val His
    1220                1225                1230

Leu Gly  Glu Tyr Gln Ala Ala  Val Asp Asn Ser Arg  Lys Ala Ser
    1235                1240                1245

Ser Thr  Arg Thr Trp Lys Glu  Val Cys Phe Ala Cys  Met Asp Gly
    1250                1255                1260

Gln Glu  Phe Arg Phe Ala Gln  Leu Cys Gly Leu His  Ile Val Ile
    1265                1270                1275

His Ala  Asp Glu Leu Glu Glu  Leu Met Cys Tyr Tyr  Gln Asp Arg
    1280                1285                1290

Gly Tyr  Phe Glu Glu Leu Ile  Leu Leu Leu Glu Ala  Ala Leu Gly
    1295                1300                1305

Leu Glu  Arg Ala His Met Gly  Met Phe Thr Glu Leu  Ala Ile Leu
    1310                1315                1320

Tyr Ser  Lys Phe Lys Pro Gln  Lys Met Leu Glu His  Leu Glu Leu
    1325                1330                1335

Phe Trp  Ser Arg Val Asn Ile  Pro Lys Val Leu Arg  Ala Ala Glu
    1340                1345                1350

Gln Ala  His Leu Trp Ala Glu  Leu Val Phe Leu Tyr  Asp Lys Tyr
    1355                1360                1365

Glu Glu  Tyr Asp Asn Ala Val  Leu Thr Met Met Ser  His Pro Thr
    1370                1375                1380

Glu Ala  Trp Lys Glu Gly Gln  Phe Lys Asp Ile Ile  Thr Lys Val
    1385                1390                1395

Ala Asn  Val Glu Leu Cys Tyr  Arg Ala Leu Gln Phe  Tyr Leu Asp
    1400                1405                1410

Tyr Lys  Pro Leu Leu Ile Asn  Asp Leu Leu Leu Val  Leu Ser Pro
    1415                1420                1425

Arg Leu  Asp His Thr Trp Thr  Val Ser Phe Phe Ser  Lys Ala Gly
    1430                1435                1440

Gln Leu  Pro Leu Val Lys Pro  Tyr Leu Arg Ser Val  Gln Ser His
    1445                1450                1455

Asn Asn  Lys Ser Val Asn Glu  Ala Leu Asn His Leu  Leu Thr Glu
    1460                1465                1470

Glu Glu  Asp Tyr Gln Asp Ala  Met Gln His Ala Ala  Glu Ser Arg
    1475                1480                1485
```

```
Asp Ala  Glu Leu Ala Gln Lys  Leu Leu Gln Trp Phe  Leu Glu Glu
    1490                 1495                 1500

Gly Lys  Arg Glu Cys Phe Ala  Ala Cys Leu Phe Thr  Cys Tyr Asp
    1505                 1510                 1515

Leu Leu  Arg Pro Asp Met Val  Leu Glu Leu Ala Trp  Arg His Asn
    1520                 1525                 1530

Leu Val  Asp Leu Ala Met Pro  Tyr Phe Ile Gln Val  Met Arg Glu
    1535                 1540                 1545

Tyr Leu  Ser Lys Val Asp Lys  Leu Asp Ala Leu Glu  Ser Leu Arg
    1550                 1555                 1560

Lys Gln  Glu Glu His Val Thr  Glu Pro Ala Pro Leu  Val Phe Asp
    1565                 1570                 1575

Phe Asp  Gly His Glu
    1580


<210> SEQ ID NO 4
<211> LENGTH: 1685
<212> TYPE: PRT
<213> ORGANISM: Homo sapiens
<300> PUBLICATION INFORMATION:
<308> DATABASE ACCESSION NUMBER: NCBI/BAA04801
<309> DATABASE ENTRY DATE: 2004-01-10
<313> RELEVANT RESIDUES IN SEQ ID NO: (1)..(1685)

<400> SEQUENCE: 4

Gln Glu Glu Thr Ile Thr Pro Asp Ser Ala Met Ala Gln Ile Leu Pro
1               5                   10                  15

Ile Arg Phe Gln Glu His Leu Gln Leu Gln Asn Leu Gly Ile Asn Pro
            20                  25                  30

Ala Asn Ile Gly Phe Ser Thr Leu Thr Met Glu Ser Asp Lys Phe Ile
        35                  40                  45

Cys Ile Arg Glu Lys Val Gly Glu Gln Ala Gln Val Val Ile Ile Asp
    50                  55                  60

Met Asn Asp Pro Ser Asn Pro Ile Arg Arg Pro Ile Ser Ala Asp Ser
65                  70                  75                  80

Ala Ile Met Asn Pro Ala Ser Lys Val Ile Ala Leu Lys Ala Gly Lys
                85                  90                  95

Thr Leu Gln Ile Phe Asn Ile Glu Met Lys Ser Lys Met Lys Ala His
            100                 105                 110

Thr Met Thr Asp Asp Val Thr Phe Trp Lys Trp Ile Ser Leu Asn Thr
        115                 120                 125

Val Ala Leu Val Thr Asp Asn Ala Val Tyr His Trp Ser Met Glu Gly
    130                 135                 140

Glu Ser Gln Pro Val Lys Met Phe Asp Arg His Ser Ser Leu Ala Gly
145                 150                 155                 160

Cys Gln Ile Ile Asn Tyr Arg Thr Asp Ala Lys Gln Lys Trp Leu Leu
                165                 170                 175

Leu Thr Gly Ile Ser Ala Gln Gln Asn Arg Val Val Gly Ala Met Gln
            180                 185                 190

Leu Tyr Ser Val Asp Arg Lys Val Ser Gln Pro Ile Glu Gly His Ala
        195                 200                 205

Ala Ser Phe Ala Gln Phe Lys Met Glu Gly Asn Ala Glu Glu Ser Thr
    210                 215                 220

Leu Phe Cys Phe Ala Val Arg Gly Gln Ala Gly Gly Lys Leu His Ile
225                 230                 235                 240
```

-continued

```
Ile Glu Val Gly Thr Pro Pro Thr Gly Asn Gln Pro Phe Pro Lys Lys
                245                 250                 255

Ala Val Asp Val Phe Phe Pro Pro Glu Ala Gln Asn Asp Phe Pro Val
            260                 265                 270

Ala Met Gln Ile Ser Glu Lys His Asp Val Val Phe Leu Ile Thr Lys
        275                 280                 285

Tyr Gly Tyr Ile His Leu Tyr Asp Leu Glu Thr Gly Thr Cys Ile Tyr
    290                 295                 300

Met Asn Arg Ile Ser Gly Glu Thr Ile Phe Val Thr Ala Pro His Glu
305                 310                 315                 320

Ala Thr Ala Gly Ile Ile Gly Val Asn Arg Lys Gly Gln Val Leu Ser
                325                 330                 335

Val Cys Val Glu Glu Glu Asn Ile Ile Pro Tyr Ile Thr Asn Val Leu
            340                 345                 350

Gln Asn Pro Asp Leu Ala Leu Arg Met Ala Val Arg Asn Asn Leu Ala
        355                 360                 365

Gly Ala Glu Glu Leu Phe Ala Arg Lys Phe Asn Ala Leu Phe Ala Gln
    370                 375                 380

Gly Asn Tyr Ser Glu Ala Ala Lys Val Ala Ala Asn Ala Pro Lys Gly
385                 390                 395                 400

Ile Leu Arg Thr Pro Asp Thr Ile Arg Arg Phe Gln Ser Val Pro Ala
                405                 410                 415

Gln Pro Gly Gln Thr Ser Pro Leu Leu Gln Tyr Phe Gly Ile Leu Leu
            420                 425                 430

Asp Gln Gly Gln Leu Asn Lys Tyr Glu Ser Leu Glu Leu Cys Arg Pro
        435                 440                 445

Val Leu Gln Gln Gly Arg Lys Gln Leu Leu Glu Lys Trp Leu Lys Glu
    450                 455                 460

Asp Lys Leu Glu Cys Ser Glu Glu Leu Gly Asp Leu Val Lys Ser Val
465                 470                 475                 480

Asp Pro Thr Leu Ala Leu Ser Val Tyr Leu Arg Ala Asn Val Pro Asn
                485                 490                 495

Lys Val Ile Gln Cys Phe Ala Glu Thr Gly Gln Val Gln Lys Ile Val
            500                 505                 510

Leu Tyr Ala Lys Lys Val Gly Tyr Thr Pro Asp Trp Ile Phe Leu Leu
        515                 520                 525

Arg Asn Val Met Arg Ile Ser Pro Asp Gln Gly Gln Gln Phe Ala Gln
    530                 535                 540

Met Leu Val Gln Asp Glu Glu Pro Leu Ala Asp Ile Thr Gln Ile Val
545                 550                 555                 560

Asp Val Phe Met Glu Tyr Asn Leu Ile Gln Gln Cys Thr Ala Phe Leu
                565                 570                 575

Leu Asp Ala Leu Lys Asn Asn Arg Pro Ser Glu Gly Pro Leu Gln Thr
            580                 585                 590

Arg Leu Leu Glu Met Asn Leu Met His Ala Pro Gln Val Ala Asp Ala
        595                 600                 605

Ile Leu Gly Asn Gln Met Phe Thr His Tyr Asp Arg Ala His Ile Ala
    610                 615                 620

Gln Leu Cys Glu Lys Ala Gly Leu Leu Gln Arg Ala Leu Glu His Phe
625                 630                 635                 640

Thr Asp Leu Tyr Asp Ile Lys Arg Ala Val Val His Thr His Leu Leu
                645                 650                 655

Asn Pro Glu Trp Leu Val Asn Tyr Phe Gly Ser Leu Ser Val Glu Asp
```

```
            660                 665                 670

Ser Leu Glu Cys Leu Arg Ala Met Leu Ser Ala Asn Ile Arg Gln Asn
        675                 680                 685

Leu Gln Ile Cys Val Gln Val Ala Ser Lys Tyr His Glu Gln Leu Ser
    690                 695                 700

Thr Gln Ser Leu Ile Glu Leu Phe Glu Ser Phe Lys Ser Phe Glu Gly
705                 710                 715                 720

Leu Phe Tyr Phe Leu Gly Ser Ile Val Asn Phe Ser Gln Asp Pro Asp
                725                 730                 735

Val His Phe Lys Tyr Ile Gln Ala Ala Cys Lys Thr Gly Gln Ile Lys
            740                 745                 750

Glu Val Glu Arg Ile Cys Arg Glu Ser Asn Cys Tyr Asp Pro Glu Arg
        755                 760                 765

Val Lys Asn Phe Leu Lys Glu Ala Lys Leu Thr Asp Gln Leu Pro Leu
    770                 775                 780

Ile Ile Val Cys Asp Arg Phe Asp Phe Val His Asp Leu Val Leu Tyr
785                 790                 795                 800

Leu Tyr Arg Asn Asn Leu Gln Lys Tyr Ile Glu Ile Tyr Val Gln Lys
                805                 810                 815

Val Asn Pro Ser Arg Leu Pro Val Val Ile Gly Gly Leu Leu Asp Val
            820                 825                 830

Asp Cys Ser Glu Asp Val Ile Lys Asn Leu Ile Leu Val Val Arg Gly
        835                 840                 845

Gln Phe Ser Thr Asp Glu Leu Val Ala Glu Val Glu Lys Arg Asn Arg
    850                 855                 860

Leu Lys Leu Leu Leu Pro Trp Leu Glu Ala Arg Ile His Glu Gly Cys
865                 870                 875                 880

Glu Glu Pro Ala Thr His Asn Ala Leu Ala Lys Ile Tyr Ile Asp Ser
                885                 890                 895

Asn Asn Asn Pro Glu Arg Phe Leu Arg Glu Asn Pro Tyr Tyr Asp Ser
            900                 905                 910

Arg Val Val Gly Lys Tyr Cys Glu Lys Arg Asp Pro His Leu Ala Cys
        915                 920                 925

Val Ala Tyr Glu Arg Gly Gln Cys Asp Leu Glu Leu Ile Asn Val Cys
    930                 935                 940

Asn Glu Asn Ser Leu Phe Lys Ser Leu Ser Arg Tyr Leu Val Arg Arg
945                 950                 955                 960

Lys Asp Pro Glu Leu Trp Gly Ser Val Leu Leu Glu Ser Asn Pro Tyr
                965                 970                 975

Arg Arg Pro Leu Ile Asp Gln Val Val Gln Thr Ala Leu Ser Glu Thr
            980                 985                 990

Gln Asp Pro Glu Glu Val Ser Val  Thr Val Lys Ala Phe  Met Thr Ala
        995                 1000                1005

Asp Leu  Pro Asn Glu Leu Ile  Glu Leu Leu Glu Lys  Ile Val Leu
    1010                1015                1020

Asp Asn  Ser Val Phe Ser Glu  His Arg Asn Leu Gln  Asn Leu Leu
    1025                1030                1035

Ile Leu  Thr Ala Ile Lys Ala  Asp Arg Thr Arg Val  Met Glu Tyr
    1040                1045                1050

Ile Asn  Arg Leu Asp Asn Tyr  Asp Ala Pro Asp Ile  Ala Asn Ile
    1055                1060                1065

Ala Ile  Ser Asn Glu Leu Phe  Glu Glu Ala Phe Ala  Ile Phe Arg
    1070                1075                1080
```

-continued

```
Lys Phe  Asp Val Asn Thr Ser  Ala Val Gln Val Leu  Ile Glu His
    1085                 1090                 1095

Ile Gly  Asn Leu Asp Arg Ala  Tyr Glu Phe Ala Glu  Arg Cys Asn
    1100                 1105                 1110

Glu Pro  Ala Val Trp Ser Gln  Leu Ala Lys Ala Gln  Leu Gln Lys
    1115                 1120                 1125

Gly Met  Val Lys Glu Ala Ile  Asp Ser Tyr Ile Lys  Ala Asp Asp
    1130                 1135                 1140

Pro Ser  Ser Tyr Met Glu Val  Val Gln Ala Ala Asn  Thr Ser Gly
    1145                 1150                 1155

Asn Trp  Glu Glu Leu Val Lys  Tyr Leu Gln Met Ala  Arg Lys Lys
    1160                 1165                 1170

Ala Arg  Glu Ser Tyr Val Glu  Thr Glu Leu Ile Phe  Ala Leu Ala
    1175                 1180                 1185

Lys Thr  Asn Arg Leu Ala Glu  Leu Glu Glu Phe Ile  Asn Gly Pro
    1190                 1195                 1200

Asn Asn  Ala His Ile Gln Gln  Val Gly Asp Arg Cys  Tyr Asp Glu
    1205                 1210                 1215

Lys Met  Tyr Asp Ala Ala Lys  Leu Leu Tyr Asn Asn  Val Ser Asn
    1220                 1225                 1230

Phe Gly  Arg Leu Ala Ser Thr  Leu Val His Leu Gly  Glu Tyr Gln
    1235                 1240                 1245

Ala Ala  Val Asp Gly Ala Arg  Lys Ala Asn Ser Thr  Arg Thr Trp
    1250                 1255                 1260

Lys Glu  Val Cys Phe Ala Cys  Val Asp Gly Lys Glu  Phe Arg Leu
    1265                 1270                 1275

Ala Gln  Met Cys Gly Leu His  Ile Val Val His Ala  Asp Glu Leu
    1280                 1285                 1290

Glu Glu  Leu Ile Asn Tyr Tyr  Gln Asp Arg Gly Tyr  Phe Glu Glu
    1295                 1300                 1305

Leu Ile  Thr Met Leu Glu Ala  Ala Leu Gly Leu Glu  Arg Ala His
    1310                 1315                 1320

Met Gly  Met Phe Thr Glu Leu  Ala Ile Leu Tyr Ser  Lys Phe Lys
    1325                 1330                 1335

Pro Gln  Lys Met Arg Glu His  Leu Glu Leu Phe Trp  Ser Arg Val
    1340                 1345                 1350

Asn Ile  Pro Lys Val Leu Arg  Ala Ala Glu Gln Ala  His Leu Trp
    1355                 1360                 1365

Ala Glu  Leu Val Phe Leu Tyr  Asp Lys Tyr Glu Glu  Tyr Asp Asn
    1370                 1375                 1380

Ala Ile  Ile Thr Met Met Asn  His Pro Thr Asp Ala  Trp Lys Glu
    1385                 1390                 1395

Gly Gln  Phe Lys Asp Ile Ile  Thr Lys Val Ala Asn  Val Glu Leu
    1400                 1405                 1410

Tyr Tyr  Arg Ala Ile Gln Phe  Tyr Leu Glu Phe Lys  Pro Leu Leu
    1415                 1420                 1425

Leu Asn  Asp Leu Leu Met Val  Leu Ser Pro Arg Leu  Asp His Thr
    1430                 1435                 1440

Arg Ala  Val Asn Tyr Phe Ser  Lys Val Lys Gln Leu  Pro Leu Val
    1445                 1450                 1455

Lys Pro  Tyr Leu Arg Ser Val  Gln Asn His Asn Asn  Lys Ser Val
    1460                 1465                 1470
```

-continued

```
Asn Glu  Ser Leu Asn Asn Leu  Phe Ile Thr Glu Glu  Asp Tyr Gln
    1475                 1480                 1485

Ala Leu  Arg Thr Ser Ile Asp  Ala Tyr Asp Asn Phe  Asp Asn Ile
    1490                 1495                 1500

Ser Leu  Ala Gln Arg Leu Glu  Lys His Glu Leu Ile  Glu Phe Arg
    1505                 1510                 1515

Arg Ile  Ala Ala Tyr Leu Phe  Lys Gly Asn Asn Arg  Trp Lys Gln
    1520                 1525                 1530

Ser Val  Glu Leu Cys Lys Lys  Asp Ser Leu Tyr Lys  Asp Ala Met
    1535                 1540                 1545

Gln Tyr  Ala Ser Glu Ser Lys  Asp Thr Glu Leu Ala  Glu Glu Leu
    1550                 1555                 1560

Leu Gln  Trp Phe Leu Gln Glu  Glu Lys Arg Glu Cys  Phe Gly Ala
    1565                 1570                 1575

Cys Leu  Phe Thr Cys Tyr Asp  Leu Leu Arg Pro Asp  Val Val Leu
    1580                 1585                 1590

Glu Thr  Ala Trp Arg His Asn  Ile Met Asp Phe Ala  Met Pro Tyr
    1595                 1600                 1605

Phe Ile  Gln Val Met Lys Glu  Tyr Leu Thr Lys Val  Asp Lys Leu
    1610                 1615                 1620

Asp Ala  Ser Glu Ser Leu Arg  Lys Glu Glu Glu Gln  Ala Thr Glu
    1625                 1630                 1635

Thr Gln  Pro Ile Val Tyr Gly  Gln Pro Gln Leu Met  Leu Thr Ala
    1640                 1645                 1650

Gly Pro  Ser Val Ala Val Pro  Pro Gln Ala Pro Phe  Gly Tyr Gly
    1655                 1660                 1665

Tyr Thr  Ala Pro Pro Tyr Gly  Gln Pro Gln Pro Gly  Phe Gly Tyr
    1670                 1675                 1680

Ser Met
    1685
```

<210> SEQ ID NO 5
<211> LENGTH: 1682
<212> TYPE: PRT
<213> ORGANISM: Homo sapiens
<300> PUBLICATION INFORMATION:
<308> DATABASE ACCESSION NUMBER: NCBI/EAW94395
<309> DATABASE ENTRY DATE: 2006-12-18
<313> RELEVANT RESIDUES IN SEQ ID NO: (1)..(1682)

<400> SEQUENCE: 5

```
Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
```

-continued

```
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Glu Pro Leu Ala
    530                 535                 540
```

-continued

```
Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895

Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960
```

-continued

```
Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu  Pro Asn Glu Leu Ile  Glu Leu Leu
        995                 1000                 1005

Glu Lys  Ile Val Leu Asp Asn  Ser Val Phe Ser Glu  His Arg Asn
    1010                 1015                 1020

Leu Gln  Asn Leu Leu Ile Leu  Thr Ala Ile Lys Ala  Asp Arg Thr
    1025                 1030                 1035

Arg Val  Met Glu Tyr Ile Asn  Arg Leu Asp Asn Tyr  Asp Ala Pro
    1040                 1045                 1050

Asp Ile  Ala Asn Ile Ala Ile  Ser Asn Glu Leu Phe  Glu Glu Ala
    1055                 1060                 1065

Phe Ala  Ile Phe Arg Lys Phe  Asp Val Asn Thr Ser  Ala Val Gln
    1070                 1075                 1080

Val Leu  Ile Glu His Ile Gly  Asn Leu Asp Arg Ala  Tyr Glu Phe
    1085                 1090                 1095

Ala Glu  Arg Cys Asn Glu Pro  Ala Val Trp Ser Gln  Leu Ala Lys
    1100                 1105                 1110

Ala Gln  Leu Gln Lys Gly Met  Val Lys Glu Ala Ile  Asp Ser Tyr
    1115                 1120                 1125

Ile Lys  Ala Asp Asp Pro Ser  Ser Tyr Met Glu Val  Val Gln Ala
    1130                 1135                 1140

Ala Asn  Thr Ser Gly Asn Trp  Glu Glu Leu Val Lys  Tyr Leu Gln
    1145                 1150                 1155

Met Ala  Arg Lys Lys Ala Arg  Glu Ser Tyr Val Glu  Thr Glu Leu
    1160                 1165                 1170

Ile Phe  Ala Leu Ala Lys Thr  Asn Arg Leu Ala Glu  Leu Glu Glu
    1175                 1180                 1185

Phe Ile  Asn Gly Pro Asn Asn  Ala His Ile Gln Gln  Val Gly Asp
    1190                 1195                 1200

Arg Cys  Tyr Asp Glu Lys Met  Tyr Asp Ala Ala Lys  Leu Leu Tyr
    1205                 1210                 1215

Asn Asn  Val Ser Asn Phe Gly  Arg Leu Ala Ser Thr  Leu Val His
    1220                 1225                 1230

Leu Gly  Glu Tyr Gln Ala Ala  Val Asp Gly Ala Arg  Lys Ala Asn
    1235                 1240                 1245

Ser Thr  Arg Thr Trp Lys Glu  Val Cys Phe Ala Cys  Val Asp Gly
    1250                 1255                 1260

Lys Glu  Phe Arg Leu Ala Gln  Met Cys Gly Leu His  Ile Val Val
    1265                 1270                 1275

His Ala  Asp Glu Leu Glu Glu  Leu Ile Asn Tyr Tyr  Gln Asp Arg
    1280                 1285                 1290

Gly Tyr  Phe Glu Glu Leu Ile  Thr Met Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Arg Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
```

1355 1360 1365

Glu Glu Tyr Asp Asn Ala Ile Ile Thr Met Met Asn His Pro Thr
1370 1375 1380

Asp Ala Trp Lys Glu Gly Gln Phe Lys Asp Ile Ile Thr Lys Val
1385 1390 1395

Ala Asn Val Glu Leu Tyr Tyr Arg Ala Ile Gln Phe Tyr Leu Glu
1400 1405 1410

Phe Lys Pro Leu Leu Leu Asn Asp Leu Leu Met Val Leu Ser Pro
1415 1420 1425

Arg Leu Asp His Thr Arg Ala Val Asn Tyr Phe Ser Lys Val Lys
1430 1435 1440

Gln Leu Pro Leu Val Lys Pro Tyr Leu Arg Ser Val Gln Asn His
1445 1450 1455

Asn Asn Lys Ser Val Asn Glu Ser Leu Asn Asn Leu Phe Ile Thr
1460 1465 1470

Glu Glu Asp Tyr Gln Ala Leu Arg Thr Ser Ile Asp Ala Tyr Asp
1475 1480 1485

Asn Phe Asp Asn Ile Ser Leu Ala Gln Arg Leu Glu Lys His Glu
1490 1495 1500

Leu Ile Glu Phe Arg Arg Ile Ala Ala Tyr Leu Phe Lys Gly Asn
1505 1510 1515

Asn Arg Trp Lys Gln Ser Val Glu Leu Cys Lys Lys Asp Ser Leu
1520 1525 1530

Tyr Lys Asp Ala Met Gln Tyr Ala Ser Glu Ser Lys Asp Thr Glu
1535 1540 1545

Leu Ala Glu Glu Leu Leu Gln Trp Phe Leu Gln Glu Glu Lys Arg
1550 1555 1560

Glu Cys Phe Gly Ala Cys Leu Phe Thr Cys Tyr Asp Leu Leu Arg
1565 1570 1575

Pro Asp Val Val Leu Glu Thr Ala Trp Arg His Asn Ile Met Asp
1580 1585 1590

Phe Ala Met Pro Tyr Phe Ile Gln Val Met Lys Glu Tyr Leu Thr
1595 1600 1605

Lys Val Asp Ala Ile Lys Glu Lys Val Asp Lys Leu Asp Ala Ser
1610 1615 1620

Glu Ser Leu Arg Lys Glu Glu Glu Gln Ala Thr Glu Thr Gln Pro
1625 1630 1635

Ile Val Tyr Gly Gln Pro Gln Leu Met Leu Thr Ala Gly Pro Ser
1640 1645 1650

Val Ala Val Pro Pro Gln Ala Pro Phe Gly Tyr Gly Tyr Thr Ala
1655 1660 1665

Pro Pro Tyr Gly Gln Pro Gln Pro Gly Phe Gly Tyr Ser Met
1670 1675 1680

<210> SEQ ID NO 6
<211> LENGTH: 1675
<212> TYPE: PRT
<213> ORGANISM: Homo sapiens
<300> PUBLICATION INFORMATION:
<308> DATABASE ACCESSION NUMBER: NCBI/EAW94399
<309> DATABASE ENTRY DATE: 2006-12-18
<313> RELEVANT RESIDUES IN SEQ ID NO: (1)..(1675)

<400> SEQUENCE: 6

Met Ala Gln Ile Leu Pro Ile Arg Phe Gln Glu His Leu Gln Leu Gln
1 5 10 15

-continued

```
Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430
```

```
Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
```

```
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895

Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                1015                1020

Leu Gln  Asn Leu Leu Ile Leu  Thr Ala Ile Lys Ala  Asp Arg Thr
    1025                1030                1035

Arg Val  Met Glu Tyr Ile Asn  Arg Leu Asp Asn Tyr  Asp Ala Pro
    1040                1045                1050

Asp Ile  Ala Asn Ile Ala Ile  Ser Asn Glu Leu Phe  Glu Glu Ala
    1055                1060                1065

Phe Ala  Ile Phe Arg Lys Phe  Asp Val Asn Thr Ser  Ala Val Gln
    1070                1075                1080

Val Leu  Ile Glu His Ile Gly  Asn Leu Asp Arg Ala  Tyr Glu Phe
    1085                1090                1095

Ala Glu  Arg Cys Asn Glu Pro  Ala Val Trp Ser Gln  Leu Ala Lys
    1100                1105                1110

Ala Gln  Leu Gln Lys Gly Met  Val Lys Glu Ala Ile  Asp Ser Tyr
    1115                1120                1125

Ile Lys  Ala Asp Asp Pro Ser  Ser Tyr Met Glu Val  Val Gln Ala
    1130                1135                1140

Ala Asn  Thr Ser Gly Asn Trp  Glu Glu Leu Val Lys  Tyr Leu Gln
    1145                1150                1155

Met Ala  Arg Lys Lys Ala Arg  Glu Ser Tyr Val Glu  Thr Glu Leu
    1160                1165                1170

Ile Phe  Ala Leu Ala Lys Thr  Asn Arg Leu Ala Glu  Leu Glu Glu
    1175                1180                1185

Phe Ile  Asn Gly Pro Asn Asn  Ala His Ile Gln Gln  Val Gly Asp
    1190                1195                1200

Arg Cys  Tyr Asp Glu Lys Met  Tyr Asp Ala Ala Lys  Leu Leu Tyr
    1205                1210                1215

Asn Asn  Val Ser Asn Phe Gly  Arg Leu Ala Ser Thr  Leu Val His
    1220                1225                1230

Leu Gly  Glu Tyr Gln Ala Ala  Val Asp Gly Ala Arg  Lys Ala Asn
    1235                1240                1245

Ser Thr  Arg Thr Trp Lys Glu  Val Cys Phe Ala Cys  Val Asp Gly
    1250                1255                1260
```

-continued

```
Lys Glu  Phe Arg Leu Ala Gln  Met Cys Gly Leu His  Ile Val Val
    1265                 1270                 1275

His Ala  Asp Glu Leu Glu Glu  Leu Ile Asn Tyr Tyr  Gln Asp Arg
    1280                 1285                 1290

Gly Tyr  Phe Glu Glu Leu Ile  Thr Met Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Arg Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Ile  Ile Thr Met Met Asn  His Pro Thr
    1370                 1375                 1380

Asp Ala  Trp Lys Glu Gly Gln  Phe Lys Asp Ile Ile  Thr Lys Val
    1385                 1390                 1395

Ala Asn  Val Glu Leu Tyr Tyr  Arg Ala Ile Gln Phe  Tyr Leu Glu
    1400                 1405                 1410

Phe Lys  Pro Leu Leu Leu Asn  Asp Leu Leu Met Val  Leu Ser Pro
    1415                 1420                 1425

Arg Leu  Asp His Thr Arg Ala  Val Asn Tyr Phe Ser  Lys Val Lys
    1430                 1435                 1440

Gln Leu  Pro Leu Val Lys Pro  Tyr Leu Arg Ser Val  Gln Asn His
    1445                 1450                 1455

Asn Asn  Lys Ser Val Asn Glu  Ser Leu Asn Asn Leu  Phe Ile Thr
    1460                 1465                 1470

Glu Glu  Asp Tyr Gln Ala Leu  Arg Thr Ser Ile Asp  Ala Tyr Asp
    1475                 1480                 1485

Asn Phe  Asp Asn Ile Ser Leu  Ala Gln Arg Leu Glu  Lys His Glu
    1490                 1495                 1500

Leu Ile  Glu Phe Arg Arg Ile  Ala Ala Tyr Leu Phe  Lys Gly Asn
    1505                 1510                 1515

Asn Arg  Trp Lys Gln Ser Val  Glu Leu Cys Lys Lys  Asp Ser Leu
    1520                 1525                 1530

Tyr Lys  Asp Ala Met Gln Tyr  Ala Ser Glu Ser Lys  Asp Thr Glu
    1535                 1540                 1545

Leu Ala  Glu Glu Leu Leu Gln  Trp Phe Leu Gln Glu  Glu Lys Arg
    1550                 1555                 1560

Glu Cys  Phe Gly Ala Cys Leu  Phe Thr Cys Tyr Asp  Leu Leu Arg
    1565                 1570                 1575

Pro Asp  Val Val Leu Glu Thr  Ala Trp Arg His Asn  Ile Met Asp
    1580                 1585                 1590

Phe Ala  Met Pro Tyr Phe Ile  Gln Val Met Lys Glu  Tyr Leu Thr
    1595                 1600                 1605

Lys Val  Asp Lys Leu Asp Ala  Ser Glu Ser Leu Arg  Lys Glu Glu
    1610                 1615                 1620

Glu Gln  Ala Thr Glu Thr Gln  Pro Ile Val Tyr Gly  Gln Pro Gln
    1625                 1630                 1635

Leu Met  Leu Thr Ala Gly Pro  Ser Val Ala Val Pro  Pro Gln Ala
    1640                 1645                 1650
```

```
Pro Phe  Gly Tyr Gly Tyr Thr  Ala Pro Pro Tyr Gly  Gln Pro Gln
    1655                1660                1665

Pro Gly  Phe Gly Tyr Ser Met
    1670                1675


<210> SEQ ID NO 7
<211> LENGTH: 1679
<212> TYPE: PRT
<213> ORGANISM: Homo sapiens
<300> PUBLICATION INFORMATION:
<308> DATABASE ACCESSION NUMBER: NCBI/EAW94397
<309> DATABASE ENTRY DATE: 2006-12-18
<313> RELEVANT RESIDUES IN SEQ ID NO: (1)..(1679)

<400> SEQUENCE: 7

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Gly Ile Lys Glu Ser Gly Lys Thr Leu Gln Ile Phe Asn
                85                  90                  95

Ile Glu Met Lys Ser Lys Met Lys Ala His Thr Met Thr Asp Asp Val
            100                 105                 110

Thr Phe Trp Lys Trp Ile Ser Leu Asn Thr Val Ala Leu Val Thr Asp
        115                 120                 125

Asn Ala Val Tyr His Trp Ser Met Glu Gly Glu Ser Gln Pro Val Lys
    130                 135                 140

Met Phe Asp Arg His Ser Ser Leu Ala Gly Cys Gln Ile Ile Asn Tyr
145                 150                 155                 160

Arg Thr Asp Ala Lys Gln Lys Trp Leu Leu Leu Thr Gly Ile Ser Ala
                165                 170                 175

Gln Gln Asn Arg Val Val Gly Ala Met Gln Leu Tyr Ser Val Asp Arg
            180                 185                 190

Lys Val Ser Gln Pro Ile Glu Gly His Ala Ala Ser Phe Ala Gln Phe
        195                 200                 205

Lys Met Glu Gly Asn Ala Glu Glu Ser Thr Leu Phe Cys Phe Ala Val
    210                 215                 220

Arg Gly Gln Ala Gly Gly Lys Leu His Ile Ile Glu Val Gly Thr Pro
225                 230                 235                 240

Pro Thr Gly Asn Gln Pro Phe Pro Lys Lys Ala Val Asp Val Phe Phe
                245                 250                 255

Pro Pro Glu Ala Gln Asn Asp Phe Pro Val Ala Met Gln Ile Ser Glu
            260                 265                 270

Lys His Asp Val Val Phe Leu Ile Thr Lys Tyr Gly Tyr Ile His Leu
        275                 280                 285

Tyr Asp Leu Glu Thr Gly Thr Cys Ile Tyr Met Asn Arg Ile Ser Gly
    290                 295                 300

Glu Thr Ile Phe Val Thr Ala Pro His Glu Ala Thr Ala Gly Ile Ile
305                 310                 315                 320

Gly Val Asn Arg Lys Gly Gln Val Leu Ser Val Cys Val Glu Glu Glu
```

```
                325                 330                 335

Asn Ile Ile Pro Tyr Ile Thr Asn Val Leu Gln Asn Pro Asp Leu Ala
            340                 345                 350

Leu Arg Met Ala Val Arg Asn Asn Leu Ala Gly Ala Glu Glu Leu Phe
        355                 360                 365

Ala Arg Lys Phe Asn Ala Leu Phe Ala Gln Gly Asn Tyr Ser Glu Ala
    370                 375                 380

Ala Lys Val Ala Ala Asn Ala Pro Lys Gly Ile Leu Arg Thr Pro Asp
385                 390                 395                 400

Thr Ile Arg Arg Phe Gln Ser Val Pro Ala Gln Pro Gly Gln Thr Ser
                405                 410                 415

Pro Leu Leu Gln Tyr Phe Gly Ile Leu Leu Asp Gln Gly Gln Leu Asn
            420                 425                 430

Lys Tyr Glu Ser Leu Glu Leu Cys Arg Pro Val Leu Gln Gln Gly Arg
        435                 440                 445

Lys Gln Leu Leu Glu Lys Trp Leu Lys Glu Asp Lys Leu Glu Cys Ser
    450                 455                 460

Glu Glu Leu Gly Asp Leu Val Lys Ser Val Asp Pro Thr Leu Ala Leu
465                 470                 475                 480

Ser Val Tyr Leu Arg Ala Asn Val Pro Asn Lys Val Ile Gln Cys Phe
                485                 490                 495

Ala Glu Thr Gly Gln Val Gln Lys Ile Val Leu Tyr Ala Lys Lys Val
            500                 505                 510

Gly Tyr Thr Pro Asp Trp Ile Phe Leu Leu Arg Asn Val Met Arg Ile
        515                 520                 525

Ser Pro Asp Gln Gly Gln Gln Phe Ala Gln Met Leu Val Gln Asp Glu
    530                 535                 540

Glu Pro Leu Ala Asp Ile Thr Gln Ile Val Asp Val Phe Met Glu Tyr
545                 550                 555                 560

Asn Leu Ile Gln Gln Cys Thr Ala Phe Leu Leu Asp Ala Leu Lys Asn
                565                 570                 575

Asn Arg Pro Ser Glu Gly Pro Leu Gln Thr Arg Leu Leu Glu Met Asn
            580                 585                 590

Leu Met His Ala Pro Gln Val Ala Asp Ala Ile Leu Gly Asn Gln Met
        595                 600                 605

Phe Thr His Tyr Asp Arg Ala His Ile Ala Gln Leu Cys Glu Lys Ala
    610                 615                 620

Gly Leu Leu Gln Arg Ala Leu Glu His Phe Thr Asp Leu Tyr Asp Ile
625                 630                 635                 640

Lys Arg Ala Val Val His Thr His Leu Leu Asn Pro Glu Trp Leu Val
                645                 650                 655

Asn Tyr Phe Gly Ser Leu Ser Val Glu Asp Ser Leu Glu Cys Leu Arg
            660                 665                 670

Ala Met Leu Ser Ala Asn Ile Arg Gln Asn Leu Gln Ile Cys Val Gln
        675                 680                 685

Val Ala Ser Lys Tyr His Glu Gln Leu Ser Thr Gln Ser Leu Ile Glu
    690                 695                 700

Leu Phe Glu Ser Phe Lys Ser Phe Glu Gly Leu Phe Tyr Phe Leu Gly
705                 710                 715                 720

Ser Ile Val Asn Phe Ser Gln Asp Pro Asp Val His Phe Lys Tyr Ile
                725                 730                 735

Gln Ala Ala Cys Lys Thr Gly Gln Ile Lys Glu Val Glu Arg Ile Cys
            740                 745                 750
```

```
Arg Glu Ser Asn Cys Tyr Asp Pro Glu Arg Val Lys Asn Phe Leu Lys
        755                 760                 765

Glu Ala Lys Leu Thr Asp Gln Leu Pro Leu Ile Ile Val Cys Asp Arg
    770                 775                 780

Phe Asp Phe Val His Asp Leu Val Leu Tyr Leu Tyr Arg Asn Asn Leu
785                 790                 795                 800

Gln Lys Tyr Ile Glu Ile Tyr Val Gln Lys Val Asn Pro Ser Arg Leu
                805                 810                 815

Pro Val Val Ile Gly Gly Leu Leu Asp Val Asp Cys Ser Glu Asp Val
            820                 825                 830

Ile Lys Asn Leu Ile Leu Val Val Arg Gly Gln Phe Ser Thr Asp Glu
        835                 840                 845

Leu Val Ala Glu Val Glu Lys Arg Asn Arg Leu Lys Leu Leu Leu Pro
    850                 855                 860

Trp Leu Glu Ala Arg Ile His Glu Gly Cys Glu Glu Pro Ala Thr His
865                 870                 875                 880

Asn Ala Leu Ala Lys Ile Tyr Ile Asp Ser Asn Asn Asn Pro Glu Arg
                885                 890                 895

Phe Leu Arg Glu Asn Pro Tyr Tyr Asp Ser Arg Val Val Gly Lys Tyr
            900                 905                 910

Cys Glu Lys Arg Asp Pro His Leu Ala Cys Val Ala Tyr Glu Arg Gly
        915                 920                 925

Gln Cys Asp Leu Glu Leu Ile Asn Val Cys Asn Glu Asn Ser Leu Phe
    930                 935                 940

Lys Ser Leu Ser Arg Tyr Leu Val Arg Arg Lys Asp Pro Glu Leu Trp
945                 950                 955                 960

Gly Ser Val Leu Leu Glu Ser Asn Pro Tyr Arg Arg Pro Leu Ile Asp
                965                 970                 975

Gln Val Val Gln Thr Ala Leu Ser Glu Thr Gln Asp Pro Glu Glu Val
            980                 985                 990

Ser Val Thr Val Lys Ala Phe Met  Thr Ala Asp Leu Pro  Asn Glu Leu
        995                 1000                1005

Ile Glu  Leu Leu Glu Lys Ile  Val Leu Asp Asn Ser  Val Phe Ser
    1010                 1015                 1020

Glu His  Arg Asn Leu Gln Asn  Leu Leu Ile Leu Thr  Ala Ile Lys
    1025                 1030                 1035

Ala Asp  Arg Thr Arg Val Met  Glu Tyr Ile Asn Arg  Leu Asp Asn
    1040                 1045                 1050

Tyr Asp  Ala Pro Asp Ile Ala  Asn Ile Ala Ile Ser  Asn Glu Leu
    1055                 1060                 1065

Phe Glu  Glu Ala Phe Ala Ile  Phe Arg Lys Phe Asp  Val Asn Thr
    1070                 1075                 1080

Ser Ala  Val Gln Val Leu Ile  Glu His Ile Gly Asn  Leu Asp Arg
    1085                 1090                 1095

Ala Tyr  Glu Phe Ala Glu Arg  Cys Asn Glu Pro Ala  Val Trp Ser
    1100                 1105                 1110

Gln Leu  Ala Lys Ala Gln Leu  Gln Lys Gly Met Val  Lys Glu Ala
    1115                 1120                 1125

Ile Asp  Ser Tyr Ile Lys Ala  Asp Asp Pro Ser Ser  Tyr Met Glu
    1130                 1135                 1140

Val Val  Gln Ala Ala Asn Thr  Ser Gly Asn Trp Glu  Glu Leu Val
    1145                 1150                 1155
```

```
Lys Tyr  Leu Gln Met Ala Arg  Lys Lys Ala Arg Glu  Ser Tyr Val
    1160                 1165                 1170

Glu Thr  Glu Leu Ile Phe Ala  Leu Ala Lys Thr Asn  Arg Leu Ala
    1175                 1180                 1185

Glu Leu  Glu Glu Phe Ile Asn  Gly Pro Asn Asn Ala  His Ile Gln
    1190                 1195                 1200

Gln Val  Gly Asp Arg Cys Tyr  Asp Glu Lys Met Tyr  Asp Ala Ala
    1205                 1210                 1215

Lys Leu  Leu Tyr Asn Asn Val  Ser Asn Phe Gly Arg  Leu Ala Ser
    1220                 1225                 1230

Thr Leu  Val His Leu Gly Glu  Tyr Gln Ala Ala Val  Asp Gly Ala
    1235                 1240                 1245

Arg Lys  Ala Asn Ser Thr Arg  Thr Trp Lys Glu Val  Cys Phe Ala
    1250                 1255                 1260

Cys Val  Asp Gly Lys Glu Phe  Arg Leu Ala Gln Met  Cys Gly Leu
    1265                 1270                 1275

His Ile  Val Val His Ala Asp  Glu Leu Glu Glu Leu  Ile Asn Tyr
    1280                 1285                 1290

Tyr Gln  Asp Arg Gly Tyr Phe  Glu Glu Leu Ile Thr  Met Leu Glu
    1295                 1300                 1305

Ala Ala  Leu Gly Leu Glu Arg  Ala His Met Gly Met  Phe Thr Glu
    1310                 1315                 1320

Leu Ala  Ile Leu Tyr Ser Lys  Phe Lys Pro Gln Lys  Met Arg Glu
    1325                 1330                 1335

His Leu  Glu Leu Phe Trp Ser  Arg Val Asn Ile Pro  Lys Val Leu
    1340                 1345                 1350

Arg Ala  Ala Glu Gln Ala His  Leu Trp Ala Glu Leu  Val Phe Leu
    1355                 1360                 1365

Tyr Asp  Lys Tyr Glu Glu Tyr  Asp Asn Ala Ile Ile  Thr Met Met
    1370                 1375                 1380

Asn His  Pro Thr Asp Ala Trp  Lys Glu Gly Gln Phe  Lys Asp Ile
    1385                 1390                 1395

Ile Thr  Lys Val Ala Asn Val  Glu Leu Tyr Tyr Arg  Ala Ile Gln
    1400                 1405                 1410

Phe Tyr  Leu Glu Phe Lys Pro  Leu Leu Leu Asn Asp  Leu Leu Met
    1415                 1420                 1425

Val Leu  Ser Pro Arg Leu Asp  His Thr Arg Ala Val  Asn Tyr Phe
    1430                 1435                 1440

Ser Lys  Val Lys Gln Leu Pro  Leu Val Lys Pro Tyr  Leu Arg Ser
    1445                 1450                 1455

Val Gln  Asn His Asn Asn Lys  Ser Val Asn Glu Ser  Leu Asn Asn
    1460                 1465                 1470

Leu Phe  Ile Thr Glu Glu Asp  Tyr Gln Ala Leu Arg  Thr Ser Ile
    1475                 1480                 1485

Asp Ala  Tyr Asp Asn Phe Asp  Asn Ile Ser Leu Ala  Gln Arg Leu
    1490                 1495                 1500

Glu Lys  His Glu Leu Ile Glu  Phe Arg Arg Ile Ala  Ala Tyr Leu
    1505                 1510                 1515

Phe Lys  Gly Asn Asn Arg Trp  Lys Gln Ser Val Glu  Leu Cys Lys
    1520                 1525                 1530

Lys Asp  Ser Leu Tyr Lys Asp  Ala Met Gln Tyr Ala  Ser Glu Ser
    1535                 1540                 1545

Lys Asp  Thr Glu Leu Ala Glu  Glu Leu Leu Gln Trp  Phe Leu Gln
```

```
    1550                1555                1560

Glu Glu  Lys Arg Glu Cys Phe  Gly Ala Cys Leu Phe  Thr Cys Tyr
    1565                1570                1575

Asp Leu  Leu Arg Pro Asp Val  Val Leu Glu Thr Ala  Trp Arg His
    1580                1585                1590

Asn Ile  Met Asp Phe Ala Met  Pro Tyr Phe Ile Gln  Val Met Lys
    1595                1600                1605

Glu Tyr  Leu Thr Lys Val Asp  Lys Leu Asp Ala Ser  Glu Ser Leu
    1610                1615                1620

Arg Lys  Glu Glu Glu Gln Ala  Thr Glu Thr Gln Pro  Ile Val Tyr
    1625                1630                1635

Gly Gln  Pro Gln Leu Met Leu  Thr Ala Gly Pro Ser  Val Ala Val
    1640                1645                1650

Pro Pro  Gln Ala Pro Phe Gly  Tyr Gly Tyr Thr Ala  Pro Pro Tyr
    1655                1660                1665

Gly Gln  Pro Gln Pro Gly Phe  Gly Tyr Ser Met
    1670                1675


<210> SEQ ID NO 8
<211> LENGTH: 1569
<212> TYPE: PRT
<213> ORGANISM: Homo sapiens
<300> PUBLICATION INFORMATION:
<308> DATABASE ACCESSION NUMBER: NCBI/AAB40909
<309> DATABASE ENTRY DATE: 1997-01-15
<313> RELEVANT RESIDUES IN SEQ ID NO: (1)..(1569)

<400> SEQUENCE: 8

Met Ala Gln Ile Leu Pro Val Arg Phe Gln Glu His Phe Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Thr Ile Ile Asp Met Ser Asp Pro Met Ala Pro Ile Arg Arg
    50                  55                  60

Pro Ile Ser Ala Glu Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Ala Glu Glu Val Ile Phe Trp Lys
            100                 105                 110

Trp Val Ser Val Asn Thr Val Ala Leu Val Thr Glu Thr Ala Val Tyr
        115                 120                 125

His Trp Ser Met Glu Gly Asp Ser Gln Pro Met Lys Met Phe Asp Arg
    130                 135                 140

His Thr Ser Leu Val Gly Cys Gln Val Ile His Tyr Arg Thr Asp Glu
145                 150                 155                 160

Tyr Gln Lys Trp Leu Leu Leu Val Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ala Phe Ala Glu Phe Lys Met Glu Gly
        195                 200                 205

Asn Ala Lys Pro Ala Thr Leu Phe Cys Phe Ala Val Arg Asn Pro Thr
    210                 215                 220
```

```
Gly Gly Lys Leu His Ile Ile Glu Val Gly Gln Pro Ala Ala Gly Asn
225                 230                 235                 240

Gln Pro Phe Val Lys Lys Ala Val Asp Val Phe Phe Pro Pro Glu Ala
                245                 250                 255

Gln Asn Asp Phe Pro Val Ala Met Gln Ile Gly Ala Lys His Gly Val
            260                 265                 270

Ile Tyr Leu Ile Thr Lys Tyr Gly Tyr Leu His Leu Tyr Asp Leu Glu
        275                 280                 285

Ser Gly Val Cys Ile Cys Met Asn Arg Ile Ser Ala Asp Thr Ile Phe
    290                 295                 300

Val Thr Ala Pro His Lys Pro Thr Ser Gly Ile Ile Gly Val Asn Lys
305                 310                 315                 320

Lys Gly Gln Val Leu Ser Val Cys Val Glu Glu Asp Asn Ile Val Asn
                325                 330                 335

Tyr Ala Thr Asn Val Leu Gln Asn Pro Asp Leu Gly Leu Arg Leu Ala
            340                 345                 350

Val Arg Ser Asn Leu Ala Gly Ala Glu Lys Leu Phe Val Arg Lys Phe
        355                 360                 365

Asn Thr Leu Phe Ala Gln Gly Ser Tyr Ala Glu Ala Ala Lys Val Ala
    370                 375                 380

Ala Ser Ala Pro Lys Gly Ile Leu Arg Thr Arg Glu Thr Val Gln Lys
385                 390                 395                 400

Phe Gln Ser Ile Pro Ala Gln Ser Gly Gln Ala Ser Pro Leu Leu Gln
                405                 410                 415

Tyr Phe Gly Ile Leu Leu Asp Gln Gly Gln Leu Asn Lys Leu Glu Ser
            420                 425                 430

Leu Glu Leu Cys His Leu Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Thr Thr Asp Pro Met Leu Ala Leu Ser Val Tyr Leu
465                 470                 475                 480

Arg Ala Asn Val Pro Ser Lys Val Ile Gln Cys Phe Ala Glu Thr Gly
                485                 490                 495

Gln Phe Gln Lys Ile Val Leu Tyr Ala Lys Lys Val Gly Tyr Thr Pro
            500                 505                 510

Asp Trp Ile Phe Leu Leu Arg Gly Val Met Lys Ile Ser Pro Glu Gln
        515                 520                 525

Gly Leu Gln Phe Ser Arg Met Leu Val Gln Asp Glu Glu Pro Leu Ala
    530                 535                 540

Asn Ile Ser Gln Ile Val Asp Ile Phe Met Glu Asn Ser Leu Ile Gln
545                 550                 555                 560

Gln Cys Thr Ser Phe Leu Leu Asp Ala Leu Lys Asn Asn Arg Pro Ala
                565                 570                 575

Glu Gly Leu Leu Gln Thr Trp Leu Leu Glu Met Asn Leu Val His Ala
            580                 585                 590

Pro Gln Val Ala Asp Ala Ile Leu Gly Asn Lys Met Phe Thr His Tyr
        595                 600                 605

Asp Arg Ala His Ile Ala Gln Leu Cys Glu Lys Ala Gly Leu Leu Gln
    610                 615                 620

Gln Ala Leu Glu His Tyr Thr Asp Leu Tyr Asp Ile Lys Arg Ala Val
625                 630                 635                 640
```

-continued

```
Val His Thr His Leu Leu Asn Pro Glu Trp Leu Val Asn Phe Phe Gly
                645                 650                 655

Ser Leu Ser Val Glu Asp Ser Val Glu Cys Leu His Ala Met Leu Ser
            660                 665                 670

Ala Asn Ile Arg Gln Asn Leu Gln Leu Cys Val Gln Val Ala Ser Lys
        675                 680                 685

Tyr His Lys Gln Leu Gly Thr Gln Ala Leu Val Glu Leu Phe Glu Ser
    690                 695                 700

Phe Lys Ser Tyr Lys Gly Leu Phe Tyr Phe Leu Gly Ser Ile Val Asn
705                 710                 715                 720

Phe Ser Gln Asp Pro Asp Val His Leu Lys Tyr Ile Gln Ala Ala Cys
                725                 730                 735

Lys Thr Gly Gln Ile Lys Glu Val Glu Arg Ile Cys Arg Glu Ser Ser
            740                 745                 750

Cys Tyr Asn Pro Glu Arg Val Lys Asn Phe Leu Lys Glu Ala Lys Leu
        755                 760                 765

Thr Asp Gln Leu Pro Leu Ile Ile Val Cys Asp Arg Phe Gly Phe Val
    770                 775                 780

His Asp Leu Val Leu Tyr Leu Tyr Arg Asn Asn Leu Gln Arg Tyr Ile
785                 790                 795                 800

Glu Ile Tyr Val Gln Lys Val Asn Pro Ser Arg Thr Pro Ala Val Ile
                805                 810                 815

Gly Gly Leu Leu Asp Val Asp Cys Ser Glu Glu Val Ile Lys His Leu
            820                 825                 830

Ile Met Ala Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ser
    850                 855                 860

Gln Ile Gln Glu Gly Cys Glu Glu Pro Ala Thr His Asn Ala Leu Ala
865                 870                 875                 880

Lys Ile Tyr Ile Asp Ser Asn Asn Ser Pro Glu Cys Phe Leu Arg Glu
                885                 890                 895

Asn Ala Tyr Tyr Asp Ser Ser Val Val Gly Arg Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Lys Val Cys Asn Glu Asn Ser Leu Phe Lys Ser Glu Ala
    930                 935                 940

Arg Tyr Leu Val Cys Arg Lys Asp Pro Glu Leu Trp Ala His Val Leu
945                 950                 955                 960

Glu Glu Thr Asn Pro Ser Arg Arg Gln Leu Ile Asp Gln Val Val Gln
                965                 970                 975

Thr Ala Leu Ser Glu Thr Arg Asp Pro Glu Glu Ile Ser Val Thr Val
            980                 985                 990

Lys Ala Phe Met Thr Ala Asp Leu  Pro Asn Glu Leu Ile  Glu Leu Leu
        995                 1000                 1005

Glu Lys  Ile Val Leu Asp Asn  Ser Val Phe Ser Glu  His Arg Asn
    1010                 1015                 1020

Leu Gln  Asn Leu Leu Ile Leu  Thr Ala Ile Lys Ala  Asp Arg Thr
    1025                 1030                 1035

Arg Val  Met Glu Tyr Ile Ser  Arg Leu Asp Asn Tyr  Asp Ala Leu
    1040                 1045                 1050

Asp Ile  Ala Ser Ile Ala Val  Ser Ser Ala Leu Tyr  Glu Glu Ala
```

```
    1055                1060                1065

Phe Thr  Val Phe His Lys Phe  Asp Met Asn Ala Ser  Ala Ile Gln
    1070                1075                1080

Val Leu  Ile Glu His Ile Gly  Asn Leu Asp Arg Ala  Tyr Glu Phe
    1085                1090                1095

Ala Glu  Arg Cys Asn Glu Pro  Ala Val Trp Ser Gln  Leu Ala Gln
    1100                1105                1110

Ala Gln  Leu Gln Lys Asp Leu  Val Lys Glu Ala Ile  Asn Ser Tyr
    1115                1120                1125

Ile Arg  Gly Asp Asp Pro Ser  Ser Tyr Leu Glu Val  Val Gln Ser
    1130                1135                1140

Ala Ser  Arg Ser Asn Asn Trp  Glu Asp Leu Val Lys  Phe Leu Gln
    1145                1150                1155

Met Ala  Arg Lys Lys Gly Arg  Glu Ser Tyr Ile Glu  Thr Glu Leu
    1160                1165                1170

Ile Phe  Ala Leu Ala Lys Thr  Ser Arg Val Ser Glu  Leu Glu Asp
    1175                1180                1185

Phe Ile  Asn Gly Pro Asn Asn  Ala His Ile Gln Gln  Val Gly Asp
    1190                1195                1200

Arg Cys  Tyr Glu Glu Gly Met  Tyr Glu Ala Ala Lys  Leu Leu Tyr
    1205                1210                1215

Ser Asn  Val Ser Asn Phe Ala  Arg Leu Ala Ser Thr  Leu Val His
    1220                1225                1230

Leu Gly  Glu Tyr Gln Ala Ala  Val Asp Asn Ser Arg  Lys Ala Ser
    1235                1240                1245

Ser Thr  Arg Thr Trp Lys Glu  Val Cys Phe Ala Cys  Met Asp Gly
    1250                1255                1260

Gln Glu  Phe Arg Phe Ala Gln  Leu Cys Gly Leu His  Ile Val Ile
    1265                1270                1275

His Ala  Asp Glu Leu Glu Glu  Leu Met Cys Tyr Tyr  Gln Asp Arg
    1280                1285                1290

Gly Tyr  Phe Glu Glu Leu Ile  Leu Leu Leu Glu Ala  Ala Leu Gly
    1295                1300                1305

Leu Glu  Arg Ala His Met Gly  Met Phe Thr Glu Leu  Ala Ile Leu
    1310                1315                1320

Tyr Ser  Lys Phe Lys Pro Gln  Lys Met Leu Glu His  Leu Glu Leu
    1325                1330                1335

Phe Trp  Ser Arg Val Asn Ile  Pro Lys Val Leu Arg  Ala Ala Glu
    1340                1345                1350

Gln Ala  His Leu Trp Ala Glu  Leu Val Phe Leu Tyr  Asp Lys Tyr
    1355                1360                1365

Glu Glu  Tyr Asp Asn Ala Val  Leu Thr Met Met Ser  His Pro Thr
    1370                1375                1380

Glu Ala  Trp Lys Glu Gly Gln  Phe Lys Asp Ile Ile  Thr Lys Val
    1385                1390                1395

Ala Asn  Val Glu Leu Cys Tyr  Arg Ala Leu Gln Phe  Tyr Leu Asp
    1400                1405                1410

Tyr Lys  Pro Leu Leu Ile Asn  Asp Leu Leu Leu Val  Leu Ser Pro
    1415                1420                1425

Arg Leu  Asp His Thr Trp Thr  Val Ser Phe Phe Ser  Lys Ala Gly
    1430                1435                1440

Gln Leu  Pro Leu Val Lys Pro  Tyr Leu Arg Ser Val  Gln Ser His
    1445                1450                1455
```

```
Asn Asn  Lys Ser Val Asn Glu  Ala Leu Asn His Leu  Leu Thr Glu
    1460                 1465                 1470

Lys Glu  Asp Tyr Gln Asp Ala  Met Gln His Ala Ala  Glu Ser Arg
    1475                 1480                 1485

Asp Ala  Glu Leu Ala Gln Lys  Leu Leu Gln Trp Phe  Leu Glu Glu
    1490                 1495                 1500

Gly Lys  Arg Glu Cys Phe Ala  Ala Cys Leu Phe Thr  Cys Tyr Asp
    1505                 1510                 1515

Leu Leu  Arg Pro Asp Met Val  Leu Glu Leu Ala Trp  Arg His Asn
    1520                 1525                 1530

Leu Val  Asp Leu Ala Met Pro  Tyr Phe Ile Gln Val  Met Arg Glu
    1535                 1540                 1545

Tyr Leu  Ser Lys Val Asp Lys  Leu Asp Ala Leu Glu  Ser Leu Pro
    1550                 1555                 1560

Pro Ser  Lys Arg Ser Met
    1565


<210> SEQ ID NO 9
<211> LENGTH: 1639
<212> TYPE: PRT
<213> ORGANISM: Homo sapiens
<300> PUBLICATION INFORMATION:
<308> DATABASE ACCESSION NUMBER: NCBI/AAH51800
<309> DATABASE ENTRY DATE: 2006-10-06
<313> RELEVANT RESIDUES IN SEQ ID NO: (1)..(1639)

<400> SEQUENCE: 9

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220
```

-continued

```
Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
```

-continued

```
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895

Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                1015                1020

Leu Gln  Asn Leu Leu Ile Leu  Thr Ala Ile Lys Ala  Asp Arg Thr
    1025                1030                1035

Arg Val  Met Glu Tyr Ile Asn  Arg Leu Asp Asn Tyr  Asp Ala Pro
    1040                1045                1050

Asp Ile  Ala Asn Ile Ala Ile  Ser Asn Glu Leu Phe  Glu Glu Ala
    1055                1060                1065
```

-continued

```
Phe Ala  Ile Phe Arg Lys Phe  Asp Val Asn Thr Ser  Ala Val Gln
    1070                 1075                 1080

Val Leu  Ile Glu His Ile Gly  Asn Leu Asp Arg Ala  Tyr Glu Phe
    1085                 1090                 1095

Ala Glu  Arg Cys Asn Glu Pro  Ala Val Trp Ser Gln  Leu Ala Lys
    1100                 1105                 1110

Ala Gln  Leu Gln Lys Gly Met  Val Lys Glu Ala Ile  Asp Ser Tyr
    1115                 1120                 1125

Ile Lys  Ala Asp Asp Pro Ser  Ser Tyr Met Glu Val  Val Gln Ala
    1130                 1135                 1140

Ala Asn  Thr Ser Gly Asn Trp  Glu Glu Leu Val Lys  Tyr Leu Gln
    1145                 1150                 1155

Met Ala  Arg Lys Lys Ala Arg  Glu Ser Tyr Val Glu  Thr Glu Leu
    1160                 1165                 1170

Ile Phe  Ala Leu Ala Lys Thr  Asn Arg Leu Ala Glu  Leu Glu Glu
    1175                 1180                 1185

Phe Ile  Asn Gly Pro Asn Asn  Ala His Ile Gln Gln  Val Gly Asp
    1190                 1195                 1200

Arg Cys  Tyr Asp Glu Lys Met  Tyr Asp Ala Ala Lys  Leu Leu Tyr
    1205                 1210                 1215

Asn Asn  Val Ser Asn Phe Gly  Arg Leu Ala Ser Thr  Leu Val His
    1220                 1225                 1230

Leu Gly  Glu Tyr Gln Ala Ala  Val Asp Gly Ala Arg  Lys Ala Asn
    1235                 1240                 1245

Ser Thr  Arg Thr Trp Lys Glu  Val Cys Phe Ala Cys  Val Asp Gly
    1250                 1255                 1260

Lys Glu  Phe Arg Leu Ala Gln  Met Cys Gly Leu His  Ile Val Val
    1265                 1270                 1275

His Ala  Asp Glu Leu Glu Glu  Leu Ile Asn Tyr Tyr  Gln Asp Arg
    1280                 1285                 1290

Gly Tyr  Phe Glu Glu Leu Ile  Thr Met Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Arg Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Ile  Ile Thr Met Met Asn  His Pro Thr
    1370                 1375                 1380

Asp Ala  Trp Lys Glu Gly Gln  Phe Lys Asp Ile Ile  Thr Lys Val
    1385                 1390                 1395

Ala Asn  Val Glu Leu Tyr Tyr  Arg Ala Ile Gln Phe  Tyr Leu Glu
    1400                 1405                 1410

Phe Lys  Pro Leu Leu Leu Asn  Asp Leu Leu Met Val  Leu Ser Pro
    1415                 1420                 1425

Arg Leu  Asp His Thr Arg Ala  Val Asn Tyr Phe Ser  Lys Val Lys
    1430                 1435                 1440

Gln Leu  Pro Leu Val Lys Pro  Tyr Leu Arg Ser Val  Gln Asn His
    1445                 1450                 1455
```

```
Asn Asn  Lys Ser Val Asn Glu  Ser Leu Asn Asn Leu  Phe Ile Thr
    1460                1465                1470

Glu Glu  Asp Tyr Gln Ala Leu  Arg Thr Ser Ile Asp  Ala Tyr Asp
    1475                1480                1485

Asn Phe  Asp Asn Ile Ser Leu  Ala Gln Arg Leu Glu  Lys His Glu
    1490                1495                1500

Leu Ile  Glu Phe Arg Arg Ile  Ala Ala Tyr Leu Phe  Lys Gly Asn
    1505                1510                1515

Asn Arg  Trp Lys Gln Ser Val  Glu Leu Cys Lys Lys  Asp Ser Leu
    1520                1525                1530

Tyr Lys  Asp Ala Met Gln Tyr  Ala Ser Glu Ser Lys  Asp Thr Glu
    1535                1540                1545

Leu Ala  Glu Glu Leu Leu Gln  Trp Phe Leu Gln Glu  Glu Lys Arg
    1550                1555                1560

Glu Cys  Phe Gly Ala Cys Leu  Phe Thr Cys Tyr Asp  Leu Leu Arg
    1565                1570                1575

Pro Asp  Val Val Leu Glu Thr  Ala Trp Arg His Asn  Ile Met Asp
    1580                1585                1590

Phe Ala  Met Pro Tyr Phe Ile  Gln Val Met Lys Glu  Tyr Leu Thr
    1595                1600                1605

Lys Val  Asp Lys Leu Asp Ala  Ser Glu Ser Leu Arg  Lys Glu Glu
    1610                1615                1620

Glu Gln  Ala Thr Glu Thr Gln  Pro Ile Val Tyr Gly  Asn Leu Ser
    1625                1630                1635

Leu


<210> SEQ ID NO 10
<211> LENGTH: 1626
<212> TYPE: PRT
<213> ORGANISM: Homo sapiens
<300> PUBLICATION INFORMATION:
<308> DATABASE ACCESSION NUMBER: NCBI/AAB40908
<309> DATABASE ENTRY DATE: 1997-01-15
<313> RELEVANT RESIDUES IN SEQ ID NO: (1)..(1626)

<400> SEQUENCE: 10

Met Ala Gln Ile Leu Pro Val Arg Phe Gln Glu His Phe Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Thr Ile Ile Asp Met Ser Asp Pro Met Ala Pro Ile Arg Arg
    50                  55                  60

Pro Ile Ser Ala Glu Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Ala Glu Glu Val Ile Phe Trp Lys
            100                 105                 110

Trp Val Ser Val Asn Thr Val Ala Leu Val Thr Glu Thr Ala Val Tyr
        115                 120                 125

His Trp Ser Met Glu Gly Asp Ser Gln Pro Met Lys Met Phe Asp Arg
    130                 135                 140

His Thr Ser Leu Val Gly Cys Gln Val Ile His Tyr Arg Thr Asp Glu
145                 150                 155                 160
```

-continued

```
Tyr Gln Lys Trp Leu Leu Leu Val Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ala Phe Ala Glu Phe Lys Met Glu Gly
        195                 200                 205

Asn Ala Lys Pro Ala Thr Leu Phe Cys Phe Ala Val Arg Asn Pro Thr
    210                 215                 220

Gly Gly Lys Leu His Ile Ile Glu Val Gly Gln Pro Ala Ala Gly Asn
225                 230                 235                 240

Gln Pro Phe Val Lys Lys Ala Val Asp Val Phe Phe Pro Pro Glu Ala
                245                 250                 255

Gln Asn Asp Phe Pro Val Ala Met Gln Ile Gly Ala Lys His Gly Val
            260                 265                 270

Ile Tyr Leu Ile Thr Lys Tyr Gly Tyr Leu His Leu Tyr Asp Leu Glu
        275                 280                 285

Ser Gly Val Cys Ile Cys Met Asn Arg Ile Ser Ala Asp Thr Ile Phe
    290                 295                 300

Val Thr Ala Pro His Lys Pro Thr Ser Gly Ile Ile Gly Val Asn Lys
305                 310                 315                 320

Lys Gly Gln Val Leu Ser Val Cys Val Glu Glu Asp Asn Ile Val Asn
                325                 330                 335

Tyr Ala Thr Asn Val Leu Gln Asn Pro Asp Leu Gly Leu Arg Leu Ala
            340                 345                 350

Val Arg Ser Asn Leu Ala Gly Ala Glu Lys Leu Phe Val Arg Lys Phe
        355                 360                 365

Asn Thr Leu Phe Ala Gln Gly Ser Tyr Ala Glu Ala Ala Lys Val Ala
    370                 375                 380

Ala Ser Ala Pro Lys Gly Ile Leu Arg Thr Arg Glu Thr Val Gln Lys
385                 390                 395                 400

Phe Gln Ser Ile Pro Ala Gln Ser Gly Gln Ala Ser Pro Leu Leu Gln
                405                 410                 415

Tyr Phe Gly Ile Leu Leu Asp Gln Gly Gln Leu Asn Lys Leu Glu Ser
            420                 425                 430

Leu Glu Leu Cys His Leu Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Thr Thr Asp Pro Met Leu Ala Leu Ser Val Tyr Leu
465                 470                 475                 480

Arg Ala Asn Val Pro Ser Lys Val Ile Gln Cys Phe Ala Glu Thr Gly
                485                 490                 495

Gln Phe Gln Lys Ile Val Leu Tyr Ala Lys Lys Val Gly Tyr Thr Pro
            500                 505                 510

Asp Trp Ile Phe Leu Leu Arg Gly Val Met Lys Ile Ser Pro Glu Gln
        515                 520                 525

Gly Leu Gln Phe Ser Arg Met Leu Val Gln Asp Glu Glu Pro Leu Ala
    530                 535                 540

Asn Ile Ser Gln Ile Val Asp Ile Phe Met Glu Asn Ser Leu Ile Gln
545                 550                 555                 560

Gln Cys Thr Ser Phe Leu Leu Asp Ala Leu Lys Asn Asn Arg Pro Ala
                565                 570                 575
```

-continued

```
Glu Gly Leu Leu Gln Thr Trp Leu Leu Glu Met Asn Leu Val His Ala
            580                 585                 590

Pro Gln Val Ala Asp Ala Ile Leu Gly Asn Lys Met Phe Thr His Tyr
        595                 600                 605

Asp Arg Ala His Ile Ala Gln Leu Cys Glu Lys Ala Gly Leu Leu Gln
    610                 615                 620

Gln Ala Leu Glu His Tyr Thr Asp Leu Tyr Asp Ile Lys Arg Ala Val
625                 630                 635                 640

Val His Thr His Leu Leu Asn Pro Glu Trp Leu Val Asn Phe Phe Gly
                645                 650                 655

Ser Leu Ser Val Glu Asp Ser Val Glu Cys Leu His Ala Met Leu Ser
            660                 665                 670

Ala Asn Ile Arg Gln Asn Leu Gln Leu Cys Val Gln Val Ala Ser Lys
        675                 680                 685

Tyr His Lys Gln Leu Gly Thr Gln Ala Leu Val Glu Leu Phe Glu Ser
    690                 695                 700

Phe Lys Ser Tyr Lys Gly Leu Phe Tyr Phe Leu Gly Ser Ile Val Asn
705                 710                 715                 720

Phe Ser Gln Asp Pro Asp Val His Leu Lys Tyr Ile Gln Ala Ala Cys
                725                 730                 735

Lys Thr Gly Gln Ile Lys Glu Val Glu Arg Ile Cys Arg Glu Ser Ser
            740                 745                 750

Cys Tyr Asn Pro Glu Arg Val Lys Asn Phe Leu Lys Glu Ala Lys Leu
        755                 760                 765

Thr Asp Gln Leu Pro Leu Ile Ile Val Cys Asp Arg Phe Gly Phe Val
    770                 775                 780

His Asp Leu Val Leu Tyr Leu Tyr Arg Asn Asn Leu Gln Arg Tyr Ile
785                 790                 795                 800

Glu Ile Tyr Val Gln Lys Val Asn Pro Ser Arg Thr Pro Ala Val Ile
                805                 810                 815

Gly Gly Leu Leu Asp Val Asp Cys Ser Glu Glu Val Ile Lys His Leu
            820                 825                 830

Ile Met Ala Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ser
    850                 855                 860

Gln Ile Gln Glu Gly Cys Glu Glu Pro Ala Thr His Asn Ala Leu Ala
865                 870                 875                 880

Lys Ile Tyr Ile Asp Ser Asn Asn Ser Pro Glu Cys Phe Leu Arg Glu
                885                 890                 895

Asn Ala Tyr Tyr Asp Ser Ser Val Val Gly Arg Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Lys Val Cys Asn Glu Asn Ser Leu Phe Lys Ser Glu Ala
    930                 935                 940

Arg Tyr Leu Val Cys Arg Lys Asp Pro Glu Leu Trp Ala His Val Leu
945                 950                 955                 960

Glu Glu Thr Asn Pro Ser Arg Arg Gln Leu Ile Asp Gln Val Val Gln
                965                 970                 975

Thr Ala Leu Ser Glu Thr Arg Asp Pro Glu Glu Ile Ser Val Thr Val
            980                 985                 990

Lys Ala Phe Met Thr Ala Asp Leu  Pro Asn Glu Leu Ile  Glu Leu Leu
```

-continued

```
        995                 1000                1005

Glu Lys  Ile Val Leu Asp Asn  Ser Val Phe Ser Glu  His Arg Asn
    1010                 1015                 1020

Leu Gln  Asn Leu Leu Ile Leu  Thr Ala Ile Lys Ala  Asp Arg Thr
    1025                 1030                 1035

Arg Val  Met Glu Tyr Ile Ser  Arg Leu Asp Asn Tyr  Asp Ala Leu
    1040                 1045                 1050

Asp Ile  Ala Ser Ile Ala Val  Ser Ser Ala Leu Tyr  Glu Glu Ala
    1055                 1060                 1065

Phe Thr  Val Phe His Lys Phe  Asp Met Asn Ala Ser  Ala Ile Gln
    1070                 1075                 1080

Val Leu  Ile Glu His Ile Gly  Asn Leu Asp Arg Ala  Tyr Glu Phe
    1085                 1090                 1095

Ala Glu  Arg Cys Asn Glu Pro  Ala Val Trp Ser Gln  Leu Ala Gln
    1100                 1105                 1110

Ala Gln  Leu Gln Lys Asp Leu  Val Lys Glu Ala Ile  Asn Ser Tyr
    1115                 1120                 1125

Ile Arg  Gly Asp Asp Pro Ser  Ser Tyr Leu Glu Val  Val Gln Ser
    1130                 1135                 1140

Ala Ser  Arg Ser Asn Asn Trp  Glu Asp Leu Val Lys  Phe Leu Gln
    1145                 1150                 1155

Met Ala  Arg Lys Lys Gly Arg  Glu Ser Tyr Ile Glu  Thr Glu Leu
    1160                 1165                 1170

Ile Phe  Ala Leu Ala Lys Thr  Ser Arg Val Ser Glu  Leu Glu Asp
    1175                 1180                 1185

Phe Ile  Asn Gly Pro Asn Asn  Ala His Ile Gln Gln  Val Gly Asp
    1190                 1195                 1200

Arg Cys  Tyr Glu Glu Gly Met  Tyr Glu Ala Ala Lys  Leu Leu Tyr
    1205                 1210                 1215

Ser Asn  Val Ser Asn Phe Ala  Arg Leu Ala Ser Thr  Leu Val His
    1220                 1225                 1230

Leu Gly  Glu Tyr Gln Ala Ala  Val Asp Asn Ser Arg  Lys Ala Ser
    1235                 1240                 1245

Ser Thr  Arg Thr Trp Lys Glu  Val Cys Phe Ala Cys  Met Asp Gly
    1250                 1255                 1260

Gln Glu  Phe Arg Phe Ala Gln  Leu Cys Gly Leu His  Ile Val Ile
    1265                 1270                 1275

His Ala  Asp Glu Leu Glu Glu  Leu Met Cys Tyr Tyr  Gln Asp Arg
    1280                 1285                 1290

Gly Tyr  Phe Glu Glu Leu Ile  Leu Leu Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Leu Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Val  Leu Thr Met Met Ser  His Pro Thr
    1370                 1375                 1380

Glu Ala  Trp Lys Glu Gly Gln  Phe Lys Asp Ile Ile  Thr Lys Val
    1385                 1390                 1395
```

Ala Asn Val Glu Leu Cys Tyr Arg Ala Leu Gln Phe Tyr Leu Asp
1400 1405 1410

Tyr Lys Pro Leu Leu Ile Asn Asp Leu Leu Leu Val Leu Ser Pro
1415 1420 1425

Arg Leu Asp His Thr Trp Thr Val Ser Phe Phe Ser Lys Ala Gly
1430 1435 1440

Gln Leu Pro Leu Val Lys Pro Tyr Leu Arg Ser Val Gln Ser His
1445 1450 1455

Asn Asn Lys Ser Val Asn Glu Ala Leu Asn His Leu Leu Thr Glu
1460 1465 1470

Lys Glu Asp Tyr Gln Gly Leu Arg Ala Ser Ile Asp Ala Tyr Asp
1475 1480 1485

Asn Phe Asp Asn Ile Ser Leu Ala Gln Gln Leu Glu Lys His Gln
1490 1495 1500

Leu Met Glu Phe Arg Cys Ile Ala Ala Tyr Leu Tyr Lys Gly Asn
1505 1510 1515

Asn Trp Trp Ala Gln Ser Val Glu Leu Cys Lys Lys Asp His Leu
1520 1525 1530

Tyr Lys Asp Ala Met Gln His Ala Ala Glu Ser Arg Asp Ala Glu
1535 1540 1545

Leu Ala Gln Lys Leu Leu Gln Trp Phe Leu Glu Glu Gly Lys Arg
1550 1555 1560

Glu Cys Phe Ala Ala Cys Leu Phe Thr Cys Tyr Asp Leu Leu Arg
1565 1570 1575

Pro Asp Met Val Leu Glu Leu Ala Trp Arg His Asn Leu Val Asp
1580 1585 1590

Leu Ala Met Pro Tyr Phe Ile Gln Val Met Arg Glu Tyr Leu Ser
1595 1600 1605

Lys Val Asp Lys Leu Asp Ala Leu Glu Ser Leu Pro Pro Ser Lys
1610 1615 1620

Arg Ser Met
1625

<210> SEQ ID NO 11
<211> LENGTH: 1639
<212> TYPE: PRT
<213> ORGANISM: Homo sapiens
<300> PUBLICATION INFORMATION:
<308> DATABASE ACCESSION NUMBER: NCBI/EAW94398
<309> DATABASE ENTRY DATE: 2006-12-18
<313> RELEVANT RESIDUES IN SEQ ID NO: (1)..(1639)

<400> SEQUENCE: 11

Met Ala Gln Ile Leu Pro Ile Arg Phe Gln Glu His Leu Gln Leu Gln
1 5 10 15

Asn Leu Gly Ile Asn Pro Ala Asn Ile Gly Phe Ser Thr Leu Thr Met
20 25 30

Glu Ser Asp Lys Phe Ile Cys Ile Arg Glu Lys Val Gly Glu Gln Ala
35 40 45

Gln Val Val Ile Ile Asp Met Asn Asp Pro Ser Asn Pro Ile Arg Arg
50 55 60

Pro Ile Ser Ala Asp Ser Ala Ile Met Asn Pro Ala Ser Lys Val Ile
65 70 75 80

Ala Leu Lys Ala Gly Lys Thr Leu Gln Ile Phe Asn Ile Glu Met Lys
85 90 95

-continued

```
Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
```

-continued

```
        515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895

Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940
```

Arg Tyr Leu Val Arg Arg Lys Asp Pro Glu Leu Trp Gly Ser Val Leu
945 950 955 960

Leu Glu Ser Asn Pro Tyr Arg Arg Pro Leu Ile Asp Gln Val Val Gln
965 970 975

Thr Ala Leu Ser Glu Thr Gln Asp Pro Glu Glu Val Ser Val Thr Val
980 985 990

Lys Ala Phe Met Thr Ala Asp Leu Pro Asn Glu Leu Ile Glu Leu Leu
995 1000 1005

Glu Lys Ile Val Leu Asp Asn Ser Val Phe Ser Glu His Arg Asn
1010 1015 1020

Leu Gln Asn Leu Leu Ile Leu Thr Ala Ile Lys Ala Asp Arg Thr
1025 1030 1035

Arg Val Met Glu Tyr Ile Asn Arg Leu Asp Asn Tyr Asp Ala Pro
1040 1045 1050

Asp Ile Ala Asn Ile Ala Ile Ser Asn Glu Leu Phe Glu Glu Ala
1055 1060 1065

Phe Ala Ile Phe Arg Lys Phe Asp Val Asn Thr Ser Ala Val Gln
1070 1075 1080

Val Leu Ile Glu His Ile Gly Asn Leu Asp Arg Ala Tyr Glu Phe
1085 1090 1095

Ala Glu Arg Cys Asn Glu Pro Ala Val Trp Ser Gln Leu Ala Lys
1100 1105 1110

Ala Gln Leu Gln Lys Gly Met Val Lys Glu Ala Ile Asp Ser Tyr
1115 1120 1125

Ile Lys Ala Asp Asp Pro Ser Ser Tyr Met Glu Val Val Gln Ala
1130 1135 1140

Ala Asn Thr Ser Gly Asn Trp Glu Glu Leu Val Lys Tyr Leu Gln
1145 1150 1155

Met Ala Arg Lys Lys Ala Arg Glu Ser Tyr Val Glu Thr Glu Leu
1160 1165 1170

Ile Phe Ala Leu Ala Lys Thr Asn Arg Leu Ala Glu Leu Glu Glu
1175 1180 1185

Phe Ile Asn Gly Pro Asn Asn Ala His Ile Gln Gln Val Gly Asp
1190 1195 1200

Arg Cys Tyr Asp Glu Lys Met Tyr Asp Ala Ala Lys Leu Leu Tyr
1205 1210 1215

Asn Asn Val Ser Asn Phe Gly Arg Leu Ala Ser Thr Leu Val His
1220 1225 1230

Leu Gly Glu Tyr Gln Ala Ala Val Asp Gly Ala Arg Lys Ala Asn
1235 1240 1245

Ser Thr Arg Thr Trp Lys Glu Val Cys Phe Ala Cys Val Asp Gly
1250 1255 1260

Lys Glu Phe Arg Leu Ala Gln Met Cys Gly Leu His Ile Val Val
1265 1270 1275

His Ala Asp Glu Leu Glu Glu Leu Ile Asn Tyr Tyr Gln Asp Arg
1280 1285 1290

Gly Tyr Phe Glu Glu Leu Ile Thr Met Leu Glu Ala Ala Leu Gly
1295 1300 1305

Leu Glu Arg Ala His Met Gly Met Phe Thr Glu Leu Ala Ile Leu
1310 1315 1320

Tyr Ser Lys Phe Lys Pro Gln Lys Met Arg Glu His Leu Glu Leu
1325 1330 1335

-continued

```
Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Ile  Ile Thr Met Met Asn  His Pro Thr
    1370                 1375                 1380

Asp Ala  Trp Lys Glu Gly Gln  Phe Lys Asp Ile Ile  Thr Lys Val
    1385                 1390                 1395

Ala Asn  Val Glu Leu Tyr Tyr  Arg Ala Ile Gln Phe  Tyr Leu Glu
    1400                 1405                 1410

Phe Lys  Pro Leu Leu Leu Asn  Asp Leu Leu Met Val  Leu Ser Pro
    1415                 1420                 1425

Arg Leu  Asp His Thr Arg Ala  Val Asn Tyr Phe Ser  Lys Val Lys
    1430                 1435                 1440

Gln Leu  Pro Leu Val Lys Pro  Tyr Leu Arg Ser Val  Gln Asn His
    1445                 1450                 1455

Asn Asn  Lys Ser Val Asn Glu  Ser Leu Asn Asn Leu  Phe Ile Thr
    1460                 1465                 1470

Glu Glu  Asp Tyr Gln Ala Leu  Arg Thr Ser Ile Asp  Ala Tyr Asp
    1475                 1480                 1485

Asn Phe  Asp Asn Ile Ser Leu  Ala Gln Arg Leu Glu  Lys His Glu
    1490                 1495                 1500

Leu Ile  Glu Phe Arg Arg Ile  Ala Ala Tyr Leu Phe  Lys Gly Asn
    1505                 1510                 1515

Asn Arg  Trp Lys Gln Ser Val  Glu Leu Cys Lys Lys  Asp Ser Leu
    1520                 1525                 1530

Tyr Lys  Asp Ala Met Gln Tyr  Ala Ser Glu Ser Lys  Asp Thr Glu
    1535                 1540                 1545

Leu Ala  Glu Glu Leu Leu Gln  Trp Phe Leu Gln Glu  Glu Lys Arg
    1550                 1555                 1560

Glu Cys  Phe Gly Ala Cys Leu  Phe Thr Cys Tyr Asp  Leu Leu Arg
    1565                 1570                 1575

Pro Asp  Val Val Leu Glu Thr  Ala Trp Arg His Asn  Ile Met Asp
    1580                 1585                 1590

Phe Ala  Met Pro Tyr Phe Ile  Gln Val Met Lys Glu  Tyr Leu Thr
    1595                 1600                 1605

Lys Val  Asp Lys Leu Asp Ala  Ser Glu Ser Leu Arg  Lys Glu Glu
    1610                 1615                 1620

Glu Gln  Ala Thr Glu Thr Gln  Pro Ile Val Tyr Gly  Asn Leu Ser
    1625                 1630                 1635

Leu


<210> SEQ ID NO 12
<211> LENGTH: 248
<212> TYPE: PRT
<213> ORGANISM: Homo sapiens
<300> PUBLICATION INFORMATION:
<308> DATABASE ACCESSION NUMBER: UniProtKB/P09496
<309> DATABASE ENTRY DATE: 2009-05-26
<313> RELEVANT RESIDUES IN SEQ ID NO: (1)..(248)

<400> SEQUENCE: 12

Met Ala Glu Leu Asp Pro Phe Gly Ala Pro Ala Gly Ala Pro Gly Gly
1               5                   10                  15

Pro Ala Leu Gly Asn Gly Val Ala Gly Ala Gly Glu Glu Asp Pro Ala
            20                  25                  30
```

```
Ala Ala Phe Leu Ala Gln Gln Glu Ser Glu Ile Ala Gly Ile Glu Asn
        35                  40                  45

Asp Glu Ala Phe Ala Ile Leu Asp Gly Gly Ala Pro Gly Pro Gln Pro
    50                  55                  60

His Gly Glu Pro Pro Gly Gly Pro Asp Ala Val Asp Gly Val Met Asn
65                  70                  75                  80

Gly Glu Tyr Tyr Gln Glu Ser Asn Gly Pro Thr Asp Ser Tyr Ala Ala
                85                  90                  95

Ile Ser Gln Val Asp Arg Leu Gln Ser Glu Pro Glu Ser Ile Arg Lys
            100                 105                 110

Trp Arg Glu Glu Gln Met Glu Arg Leu Glu Ala Leu Asp Ala Asn Ser
        115                 120                 125

Arg Lys Gln Glu Ala Glu Trp Lys Glu Lys Ala Ile Lys Glu Leu Glu
    130                 135                 140

Glu Trp Tyr Ala Arg Gln Asp Glu Gln Leu Gln Lys Thr Lys Ala Asn
145                 150                 155                 160

Asn Arg Val Ala Asp Glu Ala Phe Tyr Lys Gln Pro Phe Ala Asp Val
                165                 170                 175

Ile Gly Tyr Val Thr Asn Ile Asn His Pro Cys Tyr Ser Leu Glu Gln
            180                 185                 190

Ala Ala Glu Glu Ala Phe Val Asn Asp Ile Asp Glu Ser Ser Pro Gly
        195                 200                 205

Thr Glu Trp Glu Arg Val Ala Arg Leu Cys Asp Phe Asn Pro Lys Ser
    210                 215                 220

Ser Lys Gln Ala Lys Asp Val Ser Arg Met Arg Ser Val Leu Ile Ser
225                 230                 235                 240

Leu Lys Gln Ala Pro Leu Val His
                245
```

<210> SEQ ID NO 13
<211> LENGTH: 229
<212> TYPE: PRT
<213> ORGANISM: Homo sapiens
<300> PUBLICATION INFORMATION:
<308> DATABASE ACCESSION NUMBER: UniProtKB/P09497
<309> DATABASE ENTRY DATE: 2009-05-26
<313> RELEVANT RESIDUES IN SEQ ID NO: (1)..(229)

<400> SEQUENCE: 13

```
Met Ala Asp Asp Phe Gly Phe Phe Ser Ser Ser Glu Ser Gly Ala Pro
1               5                   10                  15

Glu Ala Ala Glu Glu Asp Pro Ala Ala Ala Phe Leu Ala Gln Gln Glu
            20                  25                  30

Ser Glu Ile Ala Gly Ile Glu Asn Asp Glu Gly Phe Gly Ala Pro Ala
        35                  40                  45

Gly Ser His Ala Ala Pro Ala Gln Pro Gly Pro Thr Ser Gly Ala Gly
    50                  55                  60

Ser Glu Asp Met Gly Thr Thr Val Asn Gly Asp Val Phe Gln Glu Ala
65                  70                  75                  80

Asn Gly Pro Ala Asp Gly Tyr Ala Ala Ile Ala Gln Ala Asp Arg Leu
                85                  90                  95

Thr Gln Glu Pro Glu Ser Ile Arg Lys Trp Arg Glu Glu Gln Arg Lys
            100                 105                 110

Arg Leu Gln Glu Leu Asp Ala Ala Ser Lys Val Thr Glu Gln Glu Trp
        115                 120                 125
```

```
Arg Glu Lys Ala Lys Lys Asp Leu Glu Glu Trp Asn Gln Arg Gln Ser
    130                 135                 140

Glu Gln Val Glu Lys Asn Lys Ile Asn Asn Arg Ile Ala Asp Lys Ala
145                 150                 155                 160

Phe Tyr Gln Gln Pro Asp Ala Asp Ile Ile Gly Tyr Val Ala Ser Glu
                165                 170                 175

Glu Ala Phe Val Lys Glu Ser Lys Glu Glu Thr Pro Gly Thr Glu Trp
            180                 185                 190

Glu Lys Val Ala Gln Leu Cys Asp Phe Asn Pro Lys Ser Ser Lys Gln
        195                 200                 205

Cys Lys Asp Val Ser Arg Leu Arg Ser Val Leu Met Ser Leu Lys Gln
    210                 215                 220

Thr Pro Leu Ser Arg
225


<210> SEQ ID NO 14
<211> LENGTH: 236
<212> TYPE: PRT
<213> ORGANISM: Homo sapiens
<300> PUBLICATION INFORMATION:
<308> DATABASE ACCESSION NUMBER: NCBI/NP_001070145
<309> DATABASE ENTRY DATE: 2008-05-01
<313> RELEVANT RESIDUES IN SEQ ID NO: (1)..(236)

<400> SEQUENCE: 14

Met Ala Glu Leu Asp Pro Phe Gly Ala Pro Ala Gly Ala Pro Gly Gly
1               5                   10                  15

Pro Ala Leu Gly Asn Gly Val Ala Gly Ala Gly Glu Glu Asp Pro Ala
            20                  25                  30

Ala Ala Phe Leu Ala Gln Gln Glu Ser Glu Ile Ala Gly Ile Glu Asn
        35                  40                  45

Asp Glu Ala Phe Ala Ile Leu Asp Gly Gly Ala Pro Gly Pro Gln Pro
    50                  55                  60

His Gly Glu Pro Pro Gly Gly Pro Asp Ala Val Asp Gly Val Met Asn
65                  70                  75                  80

Gly Glu Tyr Tyr Gln Glu Ser Asn Gly Pro Thr Asp Ser Tyr Ala Ala
                85                  90                  95

Ile Ser Gln Val Asp Arg Leu Gln Ser Glu Pro Glu Ser Ile Arg Lys
            100                 105                 110

Trp Arg Glu Glu Gln Met Glu Arg Leu Glu Ala Leu Asp Ala Asn Ser
        115                 120                 125

Arg Lys Gln Glu Ala Glu Trp Lys Glu Lys Ala Ile Lys Glu Leu Glu
    130                 135                 140

Glu Trp Tyr Ala Arg Gln Asp Glu Gln Leu Gln Lys Thr Lys Ala Asn
145                 150                 155                 160

Asn Arg Val Ala Asp Glu Ala Phe Tyr Lys Gln Pro Phe Ala Asp Val
                165                 170                 175

Ile Gly Tyr Val Ala Ala Glu Glu Ala Phe Val Asn Asp Ile Asp Glu
            180                 185                 190

Ser Ser Pro Gly Thr Glu Trp Glu Arg Val Ala Arg Leu Cys Asp Phe
        195                 200                 205

Asn Pro Lys Ser Ser Lys Gln Ala Lys Asp Val Ser Arg Met Arg Ser
    210                 215                 220

Val Leu Ile Ser Leu Lys Gln Ala Pro Leu Val His
225                 230                 235
```

<210> SEQ ID NO 15
<211> LENGTH: 1224
<212> TYPE: PRT
<213> ORGANISM: Homo sapiens
<300> PUBLICATION INFORMATION:
<308> DATABASE ACCESSION NUMBER: UniProtKB/P53621
<309> DATABASE ENTRY DATE: 2009-05-26
<313> RELEVANT RESIDUES IN SEQ ID NO: (1)..(1224)

<400> SEQUENCE: 15

```
Met Leu Thr Lys Phe Glu Thr Lys Ser Ala Arg Val Lys Gly Leu Ser
1               5                   10                  15

Phe His Pro Lys Arg Pro Trp Ile Leu Thr Ser Leu His Asn Gly Val
            20                  25                  30

Ile Gln Leu Trp Asp Tyr Arg Met Cys Thr Leu Ile Asp Lys Phe Asp
        35                  40                  45

Glu His Asp Gly Pro Val Arg Gly Ile Asp Phe His Lys Gln Gln Pro
    50                  55                  60

Leu Phe Val Ser Gly Gly Asp Asp Tyr Lys Ile Lys Val Trp Asn Tyr
65                  70                  75                  80

Lys Leu Arg Arg Cys Leu Phe Thr Leu Leu Gly His Leu Asp Tyr Ile
                85                  90                  95

Arg Thr Thr Phe Phe His His Glu Tyr Pro Trp Ile Leu Ser Ala Ser
            100                 105                 110

Asp Asp Gln Thr Ile Arg Val Trp Asn Trp Gln Ser Arg Thr Cys Val
        115                 120                 125

Cys Val Leu Thr Gly His Asn His Tyr Val Met Cys Ala Gln Phe His
    130                 135                 140

Pro Thr Glu Asp Leu Val Val Ser Ala Ser Leu Asp Gln Thr Val Arg
145                 150                 155                 160

Val Trp Asp Ile Ser Gly Leu Arg Lys Lys Asn Leu Ser Pro Gly Ala
                165                 170                 175

Val Glu Ser Asp Val Arg Gly Ile Thr Gly Val Asp Leu Phe Gly Thr
            180                 185                 190

Thr Asp Ala Val Val Lys His Val Leu Glu Gly His Asp Arg Gly Val
        195                 200                 205

Asn Trp Ala Ala Phe His Pro Thr Met Pro Leu Ile Val Ser Gly Ala
    210                 215                 220

Asp Asp Arg Gln Val Lys Ile Trp Arg Met Asn Glu Ser Lys Ala Trp
225                 230                 235                 240

Glu Val Asp Thr Cys Arg Gly His Tyr Asn Asn Val Ser Cys Ala Val
                245                 250                 255

Phe His Pro Arg Gln Glu Leu Ile Leu Ser Asn Ser Glu Asp Lys Ser
            260                 265                 270

Ile Arg Val Trp Asp Met Ser Lys Arg Thr Gly Val Gln Thr Phe Arg
        275                 280                 285

Arg Asp His Asp Arg Phe Trp Val Leu Ala Ala His Pro Asn Leu Asn
    290                 295                 300

Leu Phe Ala Ala Gly His Asp Gly Gly Met Ile Val Phe Lys Leu Glu
305                 310                 315                 320

Arg Glu Arg Pro Ala Tyr Ala Val His Gly Asn Met Leu His Tyr Val
                325                 330                 335

Lys Asp Arg Phe Leu Arg Gln Leu Asp Phe Asn Ser Ser Lys Asp Val
            340                 345                 350

Ala Val Met Gln Leu Arg Ser Gly Ser Lys Phe Pro Val Phe Asn Met
        355                 360                 365
```

Ser Tyr Asn Pro Ala Glu Asn Ala Val Leu Leu Cys Thr Arg Ala Ser
370 375 380

Asn Leu Glu Asn Ser Thr Tyr Asp Leu Tyr Thr Ile Pro Lys Asp Ala
385 390 395 400

Asp Ser Gln Asn Pro Asp Ala Pro Glu Gly Lys Arg Ser Ser Gly Leu
405 410 415

Thr Ala Val Trp Val Ala Arg Asn Arg Phe Ala Val Leu Asp Arg Met
420 425 430

His Ser Leu Leu Ile Lys Asn Leu Lys Asn Glu Ile Thr Lys Lys Val
435 440 445

Gln Val Pro Asn Cys Asp Glu Ile Phe Tyr Ala Gly Thr Gly Asn Leu
450 455 460

Leu Leu Arg Asp Ala Asp Ser Ile Thr Leu Phe Asp Val Gln Gln Lys
465 470 475 480

Arg Thr Leu Ala Ser Val Lys Ile Ser Lys Val Lys Tyr Val Ile Trp
485 490 495

Ser Ala Asp Met Ser His Val Ala Leu Leu Ala Lys His Ala Ile Val
500 505 510

Ile Cys Asn Arg Lys Leu Asp Ala Leu Cys Asn Ile His Glu Asn Ile
515 520 525

Arg Val Lys Ser Gly Ala Trp Asp Glu Ser Gly Val Phe Ile Tyr Thr
530 535 540

Thr Ser Asn His Ile Lys Tyr Ala Val Thr Thr Gly Asp His Gly Ile
545 550 555 560

Ile Arg Thr Leu Asp Leu Pro Ile Tyr Val Thr Arg Val Lys Gly Asn
565 570 575

Asn Val Tyr Cys Leu Asp Arg Glu Cys Arg Pro Arg Val Leu Thr Ile
580 585 590

Asp Pro Thr Glu Phe Lys Phe Lys Leu Ala Leu Ile Asn Arg Lys Tyr
595 600 605

Asp Glu Val Leu His Met Val Arg Asn Ala Lys Leu Val Gly Gln Ser
610 615 620

Ile Ile Ala Tyr Leu Gln Lys Lys Gly Tyr Pro Glu Val Ala Leu His
625 630 635 640

Phe Val Lys Asp Glu Lys Thr Arg Phe Ser Leu Ala Leu Glu Cys Gly
645 650 655

Asn Ile Glu Ile Ala Leu Glu Ala Ala Lys Ala Leu Asp Asp Lys Asn
660 665 670

Cys Trp Glu Lys Leu Gly Glu Val Ala Leu Leu Gln Gly Asn His Gln
675 680 685

Ile Val Glu Met Cys Tyr Gln Arg Thr Lys Asn Phe Asp Lys Leu Ser
690 695 700

Phe Leu Tyr Leu Ile Thr Gly Asn Leu Glu Lys Leu Arg Lys Met Met
705 710 715 720

Lys Ile Ala Glu Ile Arg Lys Asp Met Ser Gly His Tyr Gln Asn Ala
725 730 735

Leu Tyr Leu Gly Asp Val Ser Glu Arg Val Arg Ile Leu Lys Asn Cys
740 745 750

Gly Gln Lys Ser Leu Ala Tyr Leu Thr Ala Ala Thr His Gly Leu Asp
755 760 765

Glu Glu Ala Glu Ser Leu Lys Glu Thr Phe Asp Pro Glu Lys Glu Thr
770 775 780

-continued

```
Ile Pro Asp Ile Asp Pro Asn Ala Lys Leu Leu Gln Pro Pro Ala Pro
785                 790                 795                 800

Ile Met Pro Leu Asp Thr Asn Trp Pro Leu Leu Thr Val Ser Lys Gly
                805                 810                 815

Phe Phe Glu Gly Thr Ile Ala Ser Lys Gly Lys Gly Gly Ala Leu Ala
            820                 825                 830

Ala Asp Ile Asp Ile Asp Thr Val Gly Thr Glu Gly Trp Gly Glu Asp
        835                 840                 845

Ala Glu Leu Gln Leu Asp Glu Asp Gly Phe Val Glu Ala Thr Glu Gly
    850                 855                 860

Leu Gly Asp Asp Ala Leu Gly Lys Gly Gln Glu Glu Gly Gly Gly Trp
865                 870                 875                 880

Asp Val Glu Glu Asp Leu Glu Leu Pro Pro Glu Leu Asp Ile Ser Pro
                885                 890                 895

Gly Ala Ala Gly Gly Ala Glu Asp Gly Phe Phe Val Pro Pro Thr Lys
            900                 905                 910

Gly Thr Ser Pro Thr Gln Ile Trp Cys Asn Asn Ser Gln Leu Pro Val
        915                 920                 925

Asp His Ile Leu Ala Gly Ser Phe Glu Thr Ala Met Arg Leu Leu His
    930                 935                 940

Asp Gln Val Gly Val Ile Gln Phe Gly Pro Tyr Lys Gln Leu Phe Leu
945                 950                 955                 960

Gln Thr Tyr Ala Arg Gly Arg Thr Thr Tyr Gln Ala Leu Pro Cys Leu
                965                 970                 975

Pro Ser Met Tyr Gly Tyr Pro Asn Arg Asn Trp Lys Asp Ala Gly Leu
            980                 985                 990

Lys Asn Gly Val Pro Ala Val Gly  Leu Lys Leu Asn Asp  Leu Ile Gln
        995                 1000                 1005

Arg Leu  Gln Leu Cys Tyr Gln  Leu Thr Thr Val Gly  Lys Phe Glu
    1010                 1015                 1020

Glu Ala  Val Glu Lys Phe Arg  Ser Ile Leu Leu Ser  Val Pro Leu
    1025                 1030                 1035

Leu Val  Val Asp Asn Lys Gln  Glu Ile Ala Glu Ala  Gln Gln Leu
    1040                 1045                 1050

Ile Thr  Ile Cys Arg Glu Tyr  Ile Val Gly Leu Ser  Val Glu Thr
    1055                 1060                 1065

Glu Arg  Lys Lys Leu Pro Lys  Glu Thr Leu Glu Gln  Gln Lys Arg
    1070                 1075                 1080

Ile Cys  Glu Met Ala Ala Tyr  Phe Thr His Ser Asn  Leu Gln Pro
    1085                 1090                 1095

Val His  Met Ile Leu Val Leu  Arg Thr Ala Leu Asn  Leu Phe Phe
    1100                 1105                 1110

Lys Leu  Lys Asn Phe Lys Thr  Ala Ala Thr Phe Ala  Arg Arg Leu
    1115                 1120                 1125

Leu Glu  Leu Gly Pro Lys Pro  Glu Val Ala Gln Gln  Thr Arg Lys
    1130                 1135                 1140

Ile Leu  Ser Ala Cys Glu Lys  Asn Pro Thr Asp Ala  Tyr Gln Leu
    1145                 1150                 1155

Asn Tyr  Asp Met His Asn Pro  Phe Asp Ile Cys Ala  Ala Ser Tyr
    1160                 1165                 1170

Arg Pro  Ile Tyr Arg Gly Lys  Pro Val Glu Lys Cys  Pro Leu Ser
    1175                 1180                 1185

Gly Ala  Cys Tyr Ser Pro Glu  Phe Lys Gly Gln Ile  Cys Arg Val
```

```
    1190                1195                1200

Thr Thr  Val Thr Glu Ile Gly  Lys Asp Val Ile Gly  Leu Arg Ile
    1205                1210                1215

Ser Pro  Leu Gln Phe Arg
    1220


<210> SEQ ID NO 16
<211> LENGTH: 1224
<212> TYPE: PRT
<213> ORGANISM: Homo sapiens
<300> PUBLICATION INFORMATION:
<308> DATABASE ACCESSION NUMBER: NCBI/NP_004362
<309> DATABASE ENTRY DATE: 2008-05-11
<313> RELEVANT RESIDUES IN SEQ ID NO: (1)..(1224)

<400> SEQUENCE: 16

Met Leu Thr Lys Phe Glu Thr Lys Ser Ala Arg Val Lys Gly Leu Ser
1               5                   10                  15

Phe His Pro Lys Arg Pro Trp Ile Leu Thr Ser Leu His Asn Gly Val
            20                  25                  30

Ile Gln Leu Trp Asp Tyr Arg Met Cys Thr Leu Ile Asp Lys Phe Asp
        35                  40                  45

Glu His Asp Gly Pro Val Arg Gly Ile Asp Phe His Lys Gln Gln Pro
    50                  55                  60

Leu Phe Val Ser Gly Gly Asp Asp Tyr Lys Ile Lys Val Trp Asn Tyr
65                  70                  75                  80

Lys Leu Arg Arg Cys Leu Phe Thr Leu Leu Gly His Leu Asp Tyr Ile
                85                  90                  95

Arg Thr Thr Phe Phe His His Glu Tyr Pro Trp Ile Leu Ser Ala Ser
            100                 105                 110

Asp Asp Gln Thr Ile Arg Val Trp Asn Trp Gln Ser Arg Thr Cys Val
        115                 120                 125

Cys Val Leu Thr Gly His Asn His Tyr Val Met Cys Ala Gln Phe His
    130                 135                 140

Pro Thr Glu Asp Leu Val Val Ser Ala Ser Leu Asp Gln Thr Val Arg
145                 150                 155                 160

Val Trp Asp Ile Ser Gly Leu Arg Lys Lys Asn Leu Ser Pro Gly Ala
                165                 170                 175

Val Glu Ser Asp Val Arg Gly Ile Thr Gly Val Asp Leu Phe Gly Thr
            180                 185                 190

Thr Asp Ala Val Val Lys His Val Leu Glu Gly His Asp Arg Gly Val
        195                 200                 205

Asn Trp Ala Ala Phe His Pro Thr Met Pro Leu Ile Val Ser Gly Ala
    210                 215                 220

Asp Asp Arg Gln Val Lys Ile Trp Arg Met Asn Glu Ser Lys Ala Trp
225                 230                 235                 240

Glu Val Asp Thr Cys Arg Gly His Tyr Asn Asn Val Ser Cys Ala Val
                245                 250                 255

Phe His Pro Arg Gln Glu Leu Ile Leu Ser Asn Ser Glu Asp Lys Ser
            260                 265                 270

Ile Arg Val Trp Asp Met Ser Lys Arg Thr Gly Val Gln Thr Phe Arg
        275                 280                 285

Arg Asp His Asp Arg Phe Trp Val Leu Ala Ala His Pro Asn Leu Asn
    290                 295                 300

Leu Phe Ala Ala Gly His Asp Gly Gly Met Ile Val Phe Lys Leu Glu
305                 310                 315                 320
```

Arg Glu Arg Pro Ala Tyr Ala Val His Gly Asn Met Leu His Tyr Val
325 330 335

Lys Asp Arg Phe Leu Arg Gln Leu Asp Phe Asn Ser Ser Lys Asp Val
340 345 350

Ala Val Met Gln Leu Arg Ser Gly Ser Lys Phe Pro Val Phe Asn Met
355 360 365

Ser Tyr Asn Pro Ala Glu Asn Ala Val Leu Leu Cys Thr Arg Ala Ser
370 375 380

Asn Leu Glu Asn Ser Thr Tyr Asp Leu Tyr Thr Ile Pro Lys Asp Ala
385 390 395 400

Asp Ser Gln Asn Pro Asp Ala Pro Glu Gly Lys Arg Ser Ser Gly Leu
405 410 415

Thr Ala Val Trp Val Ala Arg Asn Arg Phe Ala Val Leu Asp Arg Met
420 425 430

His Ser Leu Leu Ile Lys Asn Leu Lys Asn Glu Ile Thr Lys Lys Val
435 440 445

Gln Val Pro Asn Cys Asp Glu Ile Phe Tyr Ala Gly Thr Gly Asn Leu
450 455 460

Leu Leu Arg Asp Ala Asp Ser Ile Thr Leu Phe Asp Val Gln Gln Lys
465 470 475 480

Arg Thr Leu Ala Ser Val Lys Ile Ser Lys Val Lys Tyr Val Ile Trp
485 490 495

Ser Ala Asp Met Ser His Val Ala Leu Leu Ala Lys His Ala Ile Val
500 505 510

Ile Cys Asn Arg Lys Leu Asp Ala Leu Cys Asn Ile His Glu Asn Ile
515 520 525

Arg Val Lys Ser Gly Ala Trp Asp Glu Ser Gly Val Phe Ile Tyr Thr
530 535 540

Thr Ser Asn His Ile Lys Tyr Ala Val Thr Thr Gly Asp His Gly Ile
545 550 555 560

Ile Arg Thr Leu Asp Leu Pro Ile Tyr Val Thr Arg Val Lys Gly Asn
565 570 575

Asn Val Tyr Cys Leu Asp Arg Glu Cys Arg Pro Arg Val Leu Thr Ile
580 585 590

Asp Pro Thr Glu Phe Lys Phe Lys Leu Ala Leu Ile Asn Arg Lys Tyr
595 600 605

Asp Glu Val Leu His Met Val Arg Asn Ala Lys Leu Val Gly Gln Ser
610 615 620

Ile Ile Ala Tyr Leu Gln Lys Lys Gly Tyr Pro Glu Val Ala Leu His
625 630 635 640

Phe Val Lys Asp Glu Lys Thr Arg Phe Ser Leu Ala Leu Glu Cys Gly
645 650 655

Asn Ile Glu Ile Ala Leu Glu Ala Ala Lys Ala Leu Asp Asp Lys Asn
660 665 670

Cys Trp Glu Lys Leu Gly Glu Val Ala Leu Leu Gln Gly Asn His Gln
675 680 685

Ile Val Glu Met Cys Tyr Gln Arg Thr Lys Asn Phe Asp Lys Leu Ser
690 695 700

Phe Leu Tyr Leu Ile Thr Gly Asn Leu Glu Lys Leu Arg Lys Met Met
705 710 715 720

Lys Ile Ala Glu Ile Arg Lys Asp Met Ser Gly His Tyr Gln Asn Ala
725 730 735

-continued

```
Leu Tyr Leu Gly Asp Val Ser Glu Arg Val Arg Ile Leu Lys Asn Cys
            740                 745                 750

Gly Gln Lys Ser Leu Ala Tyr Leu Thr Ala Ala Thr His Gly Leu Asp
        755                 760                 765

Glu Glu Ala Glu Ser Leu Lys Glu Thr Phe Asp Pro Glu Lys Glu Thr
    770                 775                 780

Ile Pro Asp Ile Asp Pro Asn Ala Lys Leu Leu Gln Pro Pro Ala Pro
785                 790                 795                 800

Ile Met Pro Leu Asp Thr Asn Trp Pro Leu Leu Thr Val Ser Lys Gly
                805                 810                 815

Phe Phe Glu Gly Thr Ile Ala Ser Lys Gly Lys Gly Gly Ala Leu Ala
            820                 825                 830

Ala Asp Ile Asp Ile Asp Thr Val Gly Thr Glu Gly Trp Gly Glu Asp
        835                 840                 845

Ala Glu Leu Gln Leu Asp Glu Asp Gly Phe Val Glu Ala Thr Glu Gly
    850                 855                 860

Leu Gly Asp Asp Ala Leu Gly Lys Gly Gln Glu Glu Gly Gly Gly Trp
865                 870                 875                 880

Asp Val Glu Glu Asp Leu Glu Leu Pro Pro Glu Leu Asp Ile Ser Pro
                885                 890                 895

Gly Ala Ala Gly Gly Ala Glu Asp Gly Phe Phe Val Pro Pro Thr Lys
            900                 905                 910

Gly Thr Ser Pro Thr Gln Ile Trp Cys Asn Asn Ser Gln Leu Pro Val
        915                 920                 925

Asp His Ile Leu Ala Gly Ser Phe Glu Thr Ala Met Arg Leu Leu His
    930                 935                 940

Asp Gln Val Gly Val Ile Gln Phe Gly Pro Tyr Lys Gln Leu Phe Leu
945                 950                 955                 960

Gln Thr Tyr Ala Arg Gly Arg Thr Thr Tyr Gln Ala Leu Pro Cys Leu
                965                 970                 975

Pro Ser Met Tyr Gly Tyr Pro Asn Arg Asn Trp Lys Asp Ala Gly Leu
            980                 985                 990

Lys Asn Gly Val Pro Ala Val Gly  Leu Lys Leu Asn Asp  Leu Ile Gln
        995                 1000                1005

Arg Leu  Gln Leu Cys Tyr Gln  Leu Thr Thr Val Gly  Lys Phe Glu
    1010                1015                1020

Glu Ala  Val Glu Lys Phe Arg  Ser Ile Leu Leu Ser  Val Pro Leu
    1025                1030                1035

Leu Val  Val Asp Asn Lys Gln  Glu Ile Ala Glu Ala  Gln Gln Leu
    1040                1045                1050

Ile Thr  Ile Cys Arg Glu Tyr  Ile Val Gly Leu Ser  Val Glu Thr
    1055                1060                1065

Glu Arg  Lys Lys Leu Pro Lys  Glu Thr Leu Glu Gln  Gln Lys Arg
    1070                1075                1080

Ile Cys  Glu Met Ala Ala Tyr  Phe Thr His Ser Asn  Leu Gln Pro
    1085                1090                1095

Val His  Met Ile Leu Val Leu  Arg Thr Ala Leu Asn  Leu Phe Phe
    1100                1105                1110

Lys Leu  Lys Asn Phe Lys Thr  Ala Ala Thr Phe Ala  Arg Arg Leu
    1115                1120                1125

Leu Glu  Leu Gly Pro Lys Pro  Glu Val Ala Gln Gln  Thr Arg Lys
    1130                1135                1140

Ile Leu  Ser Ala Cys Glu Lys  Asn Pro Thr Asp Ala  Tyr Gln Leu
```

```
    1145                1150                1155

Asn Tyr  Asp Met His Asn Pro  Phe Asp Ile Cys Ala  Ala Ser Tyr
    1160                1165                1170

Arg Pro  Ile Tyr Arg Gly Lys  Pro Val Glu Lys Cys  Pro Leu Ser
    1175                1180                1185

Gly Ala  Cys Tyr Ser Pro Glu  Phe Lys Gly Gln Ile  Cys Arg Val
    1190                1195                1200

Thr Thr  Val Thr Glu Ile Gly  Lys Asp Val Ile Gly  Leu Arg Ile
    1205                1210                1215

Ser Pro  Leu Gln Phe Arg
    1220


<210> SEQ ID NO 17
<211> LENGTH: 1233
<212> TYPE: PRT
<213> ORGANISM: Homo sapiens
<300> PUBLICATION INFORMATION:
<308> DATABASE ACCESSION NUMBER: NCBI/NP_001091868
<309> DATABASE ENTRY DATE: 2008-05-11
<313> RELEVANT RESIDUES IN SEQ ID NO: (1)..(1233)

<400> SEQUENCE: 17

Met Leu Thr Lys Phe Glu Thr Lys Ser Ala Arg Val Lys Gly Leu Ser
1               5                   10                  15

Phe His Pro Lys Arg Pro Trp Ile Leu Thr Ser Leu His Asn Gly Val
            20                  25                  30

Ile Gln Leu Trp Asp Tyr Arg Met Cys Thr Leu Ile Asp Lys Phe Asp
        35                  40                  45

Glu His Asp Gly Pro Val Arg Gly Ile Asp Phe His Lys Gln Gln Pro
    50                  55                  60

Leu Phe Val Ser Gly Gly Asp Asp Tyr Lys Ile Lys Val Trp Asn Tyr
65                  70                  75                  80

Lys Leu Arg Arg Cys Leu Phe Thr Leu Leu Gly His Leu Asp Tyr Ile
                85                  90                  95

Arg Thr Thr Phe Phe His His Glu Tyr Pro Trp Ile Leu Ser Ala Ser
            100                 105                 110

Asp Asp Gln Thr Ile Arg Val Trp Asn Trp Gln Ser Arg Thr Cys Val
        115                 120                 125

Cys Val Leu Thr Gly His Asn His Tyr Val Met Cys Ala Gln Phe His
    130                 135                 140

Pro Thr Glu Asp Leu Val Val Ser Ala Ser Leu Asp Gln Thr Val Arg
145                 150                 155                 160

Val Trp Asp Ile Ser Gly Leu Arg Lys Lys Asn Leu Ser Pro Gly Ala
                165                 170                 175

Val Glu Ser Asp Val Arg Gly Ile Thr Gly Val Asp Leu Phe Gly Thr
            180                 185                 190

Thr Asp Ala Val Val Lys His Val Leu Glu Gly His Asp Arg Gly Val
        195                 200                 205

Asn Trp Ala Ala Phe His Pro Thr Met Pro Leu Ile Val Ser Gly Ala
    210                 215                 220

Asp Asp Arg Gln Val Lys Ile Trp Arg Met Asn Glu Ser Lys Ala Trp
225                 230                 235                 240

Glu Val Asp Thr Cys Arg Gly His Tyr Asn Asn Val Ser Cys Ala Val
                245                 250                 255

Phe His Pro Arg Gln Glu Leu Ile Leu Ser Asn Ser Glu Asp Lys Ser
            260                 265                 270
```

-continued

```
Ile Arg Val Trp Asp Met Ser Lys Arg Thr Gly Val Gln Thr Phe Arg
        275                 280                 285

Arg Asp His Asp Arg Phe Trp Val Leu Ala Ala His Pro Asn Leu Asn
    290                 295                 300

Leu Phe Ala Ala Gly His Asp Gly Gly Met Ile Val Phe Lys Leu Glu
305                 310                 315                 320

Arg Glu Arg Pro Ala Tyr Ala Val His Gly Asn Met Leu His Tyr Val
                325                 330                 335

Lys Asp Arg Phe Leu Arg Gln Leu Asp Phe Asn Ser Ser Lys Asp Val
            340                 345                 350

Ala Val Met Gln Leu Arg Ser Gly Ser Lys Phe Pro Val Phe Asn Met
        355                 360                 365

Ser Tyr Asn Pro Ala Glu Asn Ala Val Leu Leu Cys Thr Arg Ala Ser
    370                 375                 380

Asn Leu Glu Asn Ser Thr Tyr Asp Leu Tyr Thr Ile Pro Lys Asp Ala
385                 390                 395                 400

Asp Ser Gln Asn Pro Asp Ala Pro Glu Gly Lys Arg Ser Ser Gly Leu
                405                 410                 415

Thr Ala Val Trp Val Ala Arg Asn Arg Phe Ala Val Leu Asp Arg Met
            420                 425                 430

His Ser Leu Leu Ile Lys Asn Leu Lys Asn Glu Ile Thr Lys Lys Val
        435                 440                 445

Gln Val Pro Asn Cys Asp Glu Ile Phe Tyr Ala Gly Thr Gly Asn Leu
    450                 455                 460

Leu Leu Arg Asp Ala Asp Ser Ile Thr Leu Phe Asp Val Gln Gln Lys
465                 470                 475                 480

Arg Thr Leu Ala Ser Val Lys Ile Ser Lys Val Lys Tyr Val Ile Trp
                485                 490                 495

Ser Ala Asp Met Ser His Val Ala Leu Leu Ala Lys His Glu His Ser
            500                 505                 510

Cys Pro Leu Pro Leu Thr Ala Ile Val Ile Cys Asn Arg Lys Leu Asp
        515                 520                 525

Ala Leu Cys Asn Ile His Glu Asn Ile Arg Val Lys Ser Gly Ala Trp
    530                 535                 540

Asp Glu Ser Gly Val Phe Ile Tyr Thr Thr Ser Asn His Ile Lys Tyr
545                 550                 555                 560

Ala Val Thr Thr Gly Asp His Gly Ile Ile Arg Thr Leu Asp Leu Pro
                565                 570                 575

Ile Tyr Val Thr Arg Val Lys Gly Asn Asn Val Tyr Cys Leu Asp Arg
            580                 585                 590

Glu Cys Arg Pro Arg Val Leu Thr Ile Asp Pro Thr Glu Phe Lys Phe
        595                 600                 605

Lys Leu Ala Leu Ile Asn Arg Lys Tyr Asp Glu Val Leu His Met Val
    610                 615                 620

Arg Asn Ala Lys Leu Val Gly Gln Ser Ile Ile Ala Tyr Leu Gln Lys
625                 630                 635                 640

Lys Gly Tyr Pro Glu Val Ala Leu His Phe Val Lys Asp Glu Lys Thr
                645                 650                 655

Arg Phe Ser Leu Ala Leu Glu Cys Gly Asn Ile Glu Ile Ala Leu Glu
            660                 665                 670

Ala Ala Lys Ala Leu Asp Asp Lys Asn Cys Trp Glu Lys Leu Gly Glu
        675                 680                 685
```

```
Val Ala Leu Leu Gln Gly Asn His Gln Ile Val Glu Met Cys Tyr Gln
    690                 695                 700

Arg Thr Lys Asn Phe Asp Lys Leu Ser Phe Leu Tyr Leu Ile Thr Gly
705                 710                 715                 720

Asn Leu Glu Lys Leu Arg Lys Met Met Lys Ile Ala Glu Ile Arg Lys
                725                 730                 735

Asp Met Ser Gly His Tyr Gln Asn Ala Leu Tyr Leu Gly Asp Val Ser
            740                 745                 750

Glu Arg Val Arg Ile Leu Lys Asn Cys Gly Gln Lys Ser Leu Ala Tyr
        755                 760                 765

Leu Thr Ala Ala Thr His Gly Leu Asp Glu Glu Ala Glu Ser Leu Lys
    770                 775                 780

Glu Thr Phe Asp Pro Glu Lys Glu Thr Ile Pro Asp Ile Asp Pro Asn
785                 790                 795                 800

Ala Lys Leu Leu Gln Pro Pro Ala Pro Ile Met Pro Leu Asp Thr Asn
                805                 810                 815

Trp Pro Leu Leu Thr Val Ser Lys Gly Phe Phe Glu Gly Thr Ile Ala
            820                 825                 830

Ser Lys Gly Lys Gly Gly Ala Leu Ala Ala Asp Ile Asp Ile Asp Thr
        835                 840                 845

Val Gly Thr Glu Gly Trp Gly Glu Asp Ala Glu Leu Gln Leu Asp Glu
    850                 855                 860

Asp Gly Phe Val Glu Ala Thr Glu Gly Leu Gly Asp Asp Ala Leu Gly
865                 870                 875                 880

Lys Gly Gln Glu Glu Gly Gly Gly Trp Asp Val Glu Glu Asp Leu Glu
                885                 890                 895

Leu Pro Pro Glu Leu Asp Ile Ser Pro Gly Ala Ala Gly Gly Ala Glu
            900                 905                 910

Asp Gly Phe Phe Val Pro Pro Thr Lys Gly Thr Ser Pro Thr Gln Ile
        915                 920                 925

Trp Cys Asn Asn Ser Gln Leu Pro Val Asp His Ile Leu Ala Gly Ser
    930                 935                 940

Phe Glu Thr Ala Met Arg Leu Leu His Asp Gln Val Gly Val Ile Gln
945                 950                 955                 960

Phe Gly Pro Tyr Lys Gln Leu Phe Leu Gln Thr Tyr Ala Arg Gly Arg
                965                 970                 975

Thr Thr Tyr Gln Ala Leu Pro Cys Leu Pro Ser Met Tyr Gly Tyr Pro
            980                 985                 990

Asn Arg Asn Trp Lys Asp Ala Gly  Leu Lys Asn Gly Val  Pro Ala Val
        995                 1000                1005

Gly Leu  Lys Leu Asn Asp Leu  Ile Gln Arg Leu Gln  Leu Cys Tyr
    1010                1015                1020

Gln Leu  Thr Thr Val Gly Lys  Phe Glu Glu Ala Val  Glu Lys Phe
    1025                1030                1035

Arg Ser  Ile Leu Leu Ser Val  Pro Leu Leu Val Val  Asp Asn Lys
    1040                1045                1050

Gln Glu  Ile Ala Glu Ala Gln  Gln Leu Ile Thr Ile  Cys Arg Glu
    1055                1060                1065

Tyr Ile  Val Gly Leu Ser Val  Glu Thr Glu Arg Lys  Lys Leu Pro
    1070                1075                1080

Lys Glu  Thr Leu Glu Gln Gln  Lys Arg Ile Cys Glu  Met Ala Ala
    1085                1090                1095

Tyr Phe  Thr His Ser Asn Leu  Gln Pro Val His Met  Ile Leu Val
```

```
    1100                1105                1110

Leu Arg  Thr Ala Leu Asn Leu  Phe Phe Lys Leu Lys  Asn Phe Lys
    1115                1120                1125

Thr Ala  Ala Thr Phe Ala Arg  Arg Leu Leu Glu Leu  Gly Pro Lys
    1130                1135                1140

Pro Glu  Val Ala Gln Gln Thr  Arg Lys Ile Leu Ser  Ala Cys Glu
    1145                1150                1155

Lys Asn  Pro Thr Asp Ala Tyr  Gln Leu Asn Tyr Asp  Met His Asn
    1160                1165                1170

Pro Phe  Asp Ile Cys Ala Ala  Ser Tyr Arg Pro Ile  Tyr Arg Gly
    1175                1180                1185

Lys Pro  Val Glu Lys Cys Pro  Leu Ser Gly Ala Cys  Tyr Ser Pro
    1190                1195                1200

Glu Phe  Lys Gly Gln Ile Cys  Arg Val Thr Thr Val  Thr Glu Ile
    1205                1210                1215

Gly Lys  Asp Val Ile Gly Leu  Arg Ile Ser Pro Leu  Gln Phe Arg
    1220                1225                1230


<210> SEQ ID NO 18
<211> LENGTH: 953
<212> TYPE: PRT
<213> ORGANISM: Homo sapiens
<300> PUBLICATION INFORMATION:
<308> DATABASE ACCESSION NUMBER: UniProtKB/P53618
<309> DATABASE ENTRY DATE: 2009-05-05
<313> RELEVANT RESIDUES IN SEQ ID NO: (1)..(953)

<400> SEQUENCE: 18

Met Thr Ala Ala Glu Asn Val Cys Tyr Thr Leu Ile Asn Val Pro Met
1               5                   10                  15

Asp Ser Glu Pro Pro Ser Glu Ile Ser Leu Lys Asn Asp Leu Glu Lys
            20                  25                  30

Gly Asp Val Lys Ser Lys Thr Glu Ala Leu Lys Lys Val Ile Ile Met
        35                  40                  45

Ile Leu Asn Gly Glu Lys Leu Pro Gly Leu Leu Met Thr Ile Ile Arg
    50                  55                  60

Phe Val Leu Pro Leu Gln Asp His Thr Ile Lys Lys Leu Leu Leu Val
65                  70                  75                  80

Phe Trp Glu Ile Val Pro Lys Thr Thr Pro Asp Gly Arg Leu Leu His
                85                  90                  95

Glu Met Ile Leu Val Cys Asp Ala Tyr Arg Lys Asp Leu Gln His Pro
            100                 105                 110

Asn Glu Phe Ile Arg Gly Ser Thr Leu Arg Phe Leu Cys Lys Leu Lys
        115                 120                 125

Glu Ala Glu Leu Leu Glu Pro Leu Met Pro Ala Ile Arg Ala Cys Leu
    130                 135                 140

Glu His Arg His Ser Tyr Val Arg Arg Asn Ala Val Leu Ala Ile Tyr
145                 150                 155                 160

Thr Ile Tyr Arg Asn Phe Glu His Leu Ile Pro Asp Ala Pro Glu Leu
                165                 170                 175

Ile His Asp Phe Leu Val Asn Glu Lys Asp Ala Ser Cys Lys Arg Asn
            180                 185                 190

Ala Phe Met Met Leu Ile His Ala Asp Gln Asp Arg Ala Leu Asp Tyr
        195                 200                 205

Leu Ser Thr Cys Ile Asp Gln Val Gln Thr Phe Gly Asp Ile Leu Gln
    210                 215                 220
```

-continued

```
Leu Val Ile Val Glu Leu Ile Tyr Lys Val Cys His Ala Asn Pro Ser
225                 230                 235                 240

Glu Arg Ala Arg Phe Ile Arg Cys Ile Tyr Asn Leu Leu Gln Ser Ser
                245                 250                 255

Ser Pro Ala Val Lys Tyr Glu Ala Ala Gly Thr Leu Val Thr Leu Ser
            260                 265                 270

Ser Ala Pro Thr Ala Ile Lys Ala Ala Ala Gln Cys Tyr Ile Asp Leu
        275                 280                 285

Ile Ile Lys Glu Ser Asp Asn Asn Val Lys Leu Ile Val Leu Asp Arg
    290                 295                 300

Leu Ile Glu Leu Lys Glu His Pro Ala His Glu Arg Val Leu Gln Asp
305                 310                 315                 320

Leu Val Met Asp Ile Leu Arg Val Leu Ser Thr Pro Asp Leu Glu Val
                325                 330                 335

Arg Lys Lys Thr Leu Gln Leu Ala Leu Asp Leu Val Ser Ser Arg Asn
            340                 345                 350

Val Glu Glu Leu Val Ile Val Leu Lys Lys Glu Val Ile Lys Thr Asn
        355                 360                 365

Asn Val Ser Glu His Glu Asp Thr Asp Lys Tyr Arg Gln Leu Leu Val
    370                 375                 380

Arg Thr Leu His Ser Cys Ser Val Arg Phe Pro Asp Met Ala Ala Asn
385                 390                 395                 400

Val Ile Pro Val Leu Met Glu Phe Leu Ser Asp Asn Asn Glu Ala Ala
                405                 410                 415

Ala Ala Asp Val Leu Glu Phe Val Arg Glu Ala Ile Gln Arg Phe Asp
            420                 425                 430

Asn Leu Arg Met Leu Ile Val Glu Lys Met Leu Glu Val Phe His Ala
        435                 440                 445

Ile Lys Ser Val Lys Ile Tyr Arg Gly Ala Leu Trp Ile Leu Gly Glu
    450                 455                 460

Tyr Cys Ser Thr Lys Glu Asp Ile Gln Ser Val Met Thr Glu Ile Arg
465                 470                 475                 480

Arg Ser Leu Gly Glu Ile Pro Ile Val Glu Ser Glu Ile Lys Lys Glu
                485                 490                 495

Ala Gly Glu Leu Lys Pro Glu Glu Glu Ile Thr Val Gly Pro Val Gln
            500                 505                 510

Lys Leu Val Thr Glu Met Gly Thr Tyr Ala Thr Gln Ser Ala Leu Ser
        515                 520                 525

Ser Ser Arg Pro Thr Lys Lys Glu Glu Asp Arg Pro Pro Leu Arg Gly
    530                 535                 540

Phe Leu Leu Asp Gly Asp Phe Phe Val Ala Ala Ser Leu Ala Thr Thr
545                 550                 555                 560

Leu Thr Lys Ile Ala Leu Arg Tyr Val Ala Leu Val Gln Glu Lys Lys
                565                 570                 575

Lys Gln Asn Ser Phe Val Ala Glu Ala Met Leu Leu Met Ala Thr Ile
            580                 585                 590

Leu His Leu Gly Lys Ser Ser Leu Pro Lys Lys Pro Ile Thr Asp Asp
        595                 600                 605

Asp Val Asp Arg Ile Ser Leu Cys Leu Lys Val Leu Ser Glu Cys Ser
    610                 615                 620

Pro Leu Met Asn Asp Ile Phe Asn Lys Glu Cys Arg Gln Ser Leu Ser
625                 630                 635                 640
```

```
His Met Leu Ser Ala Lys Leu Glu Glu Glu Lys Leu Ser Gln Lys Lys
                645                 650                 655

Glu Ser Glu Lys Arg Asn Val Thr Val Gln Pro Asp Asp Pro Ile Ser
            660                 665                 670

Phe Met Gln Leu Thr Ala Lys Asn Glu Met Asn Cys Lys Glu Asp Gln
        675                 680                 685

Phe Gln Leu Ser Leu Leu Ala Ala Met Gly Asn Thr Gln Arg Lys Glu
    690                 695                 700

Ala Ala Asp Pro Leu Ala Ser Lys Leu Asn Lys Val Thr Gln Leu Thr
705                 710                 715                 720

Gly Phe Ser Asp Pro Val Tyr Ala Glu Ala Tyr Val His Val Asn Gln
                725                 730                 735

Tyr Asp Ile Val Leu Asp Val Leu Val Val Asn Gln Thr Ser Asp Thr
            740                 745                 750

Leu Gln Asn Cys Thr Leu Glu Leu Ala Thr Leu Gly Asp Leu Lys Leu
        755                 760                 765

Val Glu Lys Pro Ser Pro Leu Thr Leu Ala Pro His Asp Phe Ala Asn
    770                 775                 780

Ile Lys Ala Asn Val Lys Val Ala Ser Thr Glu Asn Gly Ile Ile Phe
785                 790                 795                 800

Gly Asn Ile Val Tyr Asp Val Ser Gly Ala Ala Ser Asp Arg Asn Cys
                805                 810                 815

Val Val Leu Ser Asp Ile His Ile Asp Ile Met Asp Tyr Ile Gln Pro
            820                 825                 830

Ala Thr Cys Thr Asp Ala Glu Phe Arg Gln Met Trp Ala Glu Phe Glu
        835                 840                 845

Trp Glu Asn Lys Val Thr Val Asn Thr Asn Met Val Asp Leu Asn Asp
    850                 855                 860

Tyr Leu Gln His Ile Leu Lys Ser Thr Asn Met Lys Cys Leu Thr Pro
865                 870                 875                 880

Glu Lys Ala Leu Ser Gly Tyr Cys Gly Phe Met Ala Ala Asn Leu Tyr
                885                 890                 895

Ala Arg Ser Ile Phe Gly Glu Asp Ala Leu Ala Asn Val Ser Ile Glu
            900                 905                 910

Lys Pro Ile His Gln Gly Pro Asp Ala Ala Val Thr Gly His Ile Arg
        915                 920                 925

Ile Arg Ala Lys Ser Gln Gly Met Ala Leu Ser Leu Gly Asp Lys Ile
    930                 935                 940

Asn Leu Ser Gln Lys Lys Thr Ser Ile
945                 950


<210> SEQ ID NO 19
<211> LENGTH: 906
<212> TYPE: PRT
<213> ORGANISM: Homo sapiens
<300> PUBLICATION INFORMATION:
<308> DATABASE ACCESSION NUMBER: UniProtKB/P35606
<309> DATABASE ENTRY DATE: 2009-05-05
<313> RELEVANT RESIDUES IN SEQ ID NO: (1)..(906)

<400> SEQUENCE: 19

Met Pro Leu Arg Leu Asp Ile Lys Arg Lys Leu Thr Ala Arg Ser Asp
1               5                   10                  15

Arg Val Lys Ser Val Asp Leu His Pro Thr Glu Pro Trp Met Leu Ala
            20                  25                  30

Ser Leu Tyr Asn Gly Ser Val Cys Val Trp Asn His Glu Thr Gln Thr
```

```
        35                  40                  45

Leu Val Lys Thr Phe Glu Val Cys Asp Leu Pro Val Arg Ala Ala Lys
    50                  55                  60

Phe Val Ala Arg Lys Asn Trp Val Val Thr Gly Ala Asp Asp Met Gln
65                  70                  75                  80

Ile Arg Val Phe Asn Tyr Asn Thr Leu Glu Arg Val His Met Phe Glu
                85                  90                  95

Ala His Ser Asp Tyr Ile Arg Cys Ile Ala Val His Pro Thr Gln Pro
            100                 105                 110

Phe Ile Leu Thr Ser Ser Asp Asp Met Leu Ile Lys Leu Trp Asp Trp
        115                 120                 125

Asp Lys Lys Trp Ser Cys Ser Gln Val Phe Glu Gly His Thr His Tyr
    130                 135                 140

Val Met Gln Ile Val Ile Asn Pro Lys Asp Asn Asn Gln Phe Ala Ser
145                 150                 155                 160

Ala Ser Leu Asp Arg Thr Ile Lys Val Trp Gln Leu Gly Ser Ser Ser
                165                 170                 175

Pro Asn Phe Thr Leu Glu Gly His Glu Lys Gly Val Asn Cys Ile Asp
            180                 185                 190

Tyr Tyr Ser Gly Gly Asp Lys Pro Tyr Leu Ile Ser Gly Ala Asp Asp
        195                 200                 205

Arg Leu Val Lys Ile Trp Asp Tyr Gln Asn Lys Thr Cys Val Gln Thr
    210                 215                 220

Leu Glu Gly His Ala Gln Asn Val Ser Cys Ala Ser Phe His Pro Glu
225                 230                 235                 240

Leu Pro Ile Ile Ile Thr Gly Ser Glu Asp Gly Thr Val Arg Ile Trp
                245                 250                 255

His Ser Ser Thr Tyr Arg Leu Glu Ser Thr Leu Asn Tyr Gly Met Glu
            260                 265                 270

Arg Val Trp Cys Val Ala Ser Leu Arg Gly Ser Asn Asn Val Ala Leu
        275                 280                 285

Gly Tyr Asp Glu Gly Ser Ile Ile Val Lys Leu Gly Arg Glu Glu Pro
    290                 295                 300

Ala Met Ser Met Asp Ala Asn Gly Lys Ile Ile Trp Ala Lys His Ser
305                 310                 315                 320

Glu Val Gln Gln Ala Asn Leu Lys Ala Met Gly Asp Ala Glu Ile Lys
                325                 330                 335

Asp Gly Glu Arg Leu Pro Leu Ala Val Lys Asp Met Gly Ser Cys Glu
            340                 345                 350

Ile Tyr Pro Gln Thr Ile Gln His Asn Pro Asn Gly Arg Phe Val Val
        355                 360                 365

Val Cys Gly Asp Gly Glu Tyr Ile Ile Tyr Thr Ala Met Ala Leu Arg
    370                 375                 380

Asn Lys Ser Phe Gly Ser Ala Gln Glu Phe Ala Trp Ala His Asp Ser
385                 390                 395                 400

Ser Glu Tyr Ala Ile Arg Glu Ser Asn Ser Ile Val Lys Ile Phe Lys
                405                 410                 415

Asn Phe Lys Glu Lys Lys Ser Phe Lys Pro Asp Phe Gly Ala Glu Ser
            420                 425                 430

Ile Tyr Gly Gly Phe Leu Leu Gly Val Arg Ser Val Asn Gly Leu Ala
        435                 440                 445

Phe Tyr Asp Trp Asp Asn Thr Glu Leu Ile Arg Arg Ile Glu Ile Gln
    450                 455                 460
```

```
Pro Lys His Ile Phe Trp Ser Asp Ser Gly Glu Leu Val Cys Ile Ala
465                 470                 475                 480

Thr Glu Glu Ser Phe Phe Ile Leu Lys Tyr Leu Ser Glu Lys Val Leu
                485                 490                 495

Ala Ala Gln Glu Thr His Glu Gly Val Thr Glu Asp Gly Ile Glu Asp
            500                 505                 510

Ala Phe Glu Val Leu Gly Glu Ile Gln Glu Ile Val Lys Thr Gly Leu
        515                 520                 525

Trp Val Gly Asp Cys Phe Ile Tyr Thr Ser Ser Val Asn Arg Leu Asn
    530                 535                 540

Tyr Tyr Val Gly Gly Glu Ile Val Thr Ile Ala His Leu Asp Arg Thr
545                 550                 555                 560

Met Tyr Leu Leu Gly Tyr Ile Pro Lys Asp Asn Arg Leu Tyr Leu Gly
                565                 570                 575

Asp Lys Glu Leu Asn Ile Ile Ser Tyr Ser Leu Leu Val Ser Val Leu
            580                 585                 590

Glu Tyr Gln Thr Ala Val Met Arg Arg Asp Phe Ser Met Ala Asp Lys
        595                 600                 605

Val Leu Pro Thr Ile Pro Lys Glu Gln Arg Thr Arg Val Ala His Phe
    610                 615                 620

Leu Glu Lys Gln Gly Phe Lys Gln Gln Ala Leu Thr Val Ser Thr Asp
625                 630                 635                 640

Pro Glu His Arg Phe Glu Leu Ala Leu Gln Leu Gly Glu Leu Lys Ile
                645                 650                 655

Ala Tyr Gln Leu Ala Val Glu Ala Glu Ser Glu Gln Lys Trp Lys Gln
            660                 665                 670

Leu Ala Glu Leu Ala Ile Ser Lys Cys Gln Phe Gly Leu Ala Gln Glu
        675                 680                 685

Cys Leu His His Ala Gln Asp Tyr Gly Gly Leu Leu Leu Leu Ala Thr
    690                 695                 700

Ala Ser Gly Asn Ala Asn Met Val Asn Lys Leu Ala Glu Gly Ala Glu
705                 710                 715                 720

Arg Asp Gly Lys Asn Asn Val Ala Phe Met Ser Tyr Phe Leu Gln Gly
                725                 730                 735

Lys Val Asp Ala Cys Leu Glu Leu Leu Ile Arg Thr Gly Arg Leu Pro
            740                 745                 750

Glu Ala Ala Phe Leu Ala Arg Thr Tyr Leu Pro Ser Gln Val Ser Arg
        755                 760                 765

Val Val Lys Leu Trp Arg Glu Asn Leu Ser Lys Val Asn Gln Lys Ala
    770                 775                 780

Ala Glu Ser Leu Ala Asp Pro Thr Glu Tyr Glu Asn Leu Phe Pro Gly
785                 790                 795                 800

Leu Lys Glu Ala Phe Val Val Glu Glu Trp Val Lys Glu Thr His Ala
                805                 810                 815

Asp Leu Trp Pro Ala Lys Gln Tyr Pro Leu Val Thr Pro Asn Glu Glu
            820                 825                 830

Arg Asn Val Met Glu Glu Gly Lys Asp Phe Gln Pro Ser Arg Ser Thr
        835                 840                 845

Ala Gln Gln Glu Leu Asp Gly Lys Pro Ala Ser Pro Thr Pro Val Ile
    850                 855                 860

Val Ala Ser His Thr Ala Asn Lys Glu Glu Lys Ser Leu Leu Glu Leu
865                 870                 875                 880
```

```
Glu Val Asp Leu Asp Asn Leu Glu Leu Glu Asp Ile Asp Thr Thr Asp
                885                 890                 895

Ile Asn Leu Asp Glu Asp Ile Leu Asp Asp
            900                 905


<210> SEQ ID NO 20
<211> LENGTH: 877
<212> TYPE: PRT
<213> ORGANISM: Homo sapiens
<300> PUBLICATION INFORMATION:
<308> DATABASE ACCESSION NUMBER: NCBI/EAW79040
<309> DATABASE ENTRY DATE: 2006-12-18
<313> RELEVANT RESIDUES IN SEQ ID NO: (1)..(877)

<400> SEQUENCE: 20

Met Leu Ala Ser Leu Tyr Asn Gly Ser Val Cys Val Trp Asn His Glu
1               5                   10                  15

Thr Gln Thr Leu Val Lys Thr Phe Glu Val Cys Asp Leu Pro Val Arg
            20                  25                  30

Ala Ala Lys Phe Val Ala Arg Lys Asn Trp Val Val Thr Gly Ala Asp
        35                  40                  45

Asp Met Gln Ile Arg Val Phe Asn Tyr Asn Thr Leu Glu Arg Val His
    50                  55                  60

Met Phe Glu Ala His Ser Asp Tyr Ile Arg Cys Ile Ala Val His Pro
65                  70                  75                  80

Thr Gln Pro Phe Ile Leu Thr Ser Ser Asp Asp Met Leu Ile Lys Leu
                85                  90                  95

Trp Asp Trp Asp Lys Lys Trp Ser Cys Ser Gln Val Phe Glu Gly His
            100                 105                 110

Thr His Tyr Val Met Gln Ile Val Ile Asn Pro Lys Asp Asn Asn Gln
        115                 120                 125

Phe Ala Ser Ala Ser Leu Asp Arg Thr Ile Lys Val Trp Gln Leu Gly
    130                 135                 140

Ser Ser Ser Pro Asn Phe Thr Leu Glu Gly His Glu Lys Gly Val Asn
145                 150                 155                 160

Cys Ile Asp Tyr Tyr Ser Gly Gly Asp Lys Pro Tyr Leu Ile Ser Gly
                165                 170                 175

Ala Asp Asp Arg Leu Val Lys Ile Trp Asp Tyr Gln Asn Lys Thr Cys
            180                 185                 190

Val Gln Thr Leu Glu Gly His Ala Gln Asn Val Ser Cys Ala Ser Phe
        195                 200                 205

His Pro Glu Leu Pro Ile Ile Ile Thr Gly Ser Glu Asp Gly Thr Val
    210                 215                 220

Arg Ile Trp His Ser Ser Thr Tyr Arg Leu Glu Ser Thr Leu Asn Tyr
225                 230                 235                 240

Gly Met Glu Arg Val Trp Cys Val Ala Ser Leu Arg Gly Ser Asn Asn
                245                 250                 255

Val Ala Leu Gly Tyr Asp Glu Gly Ser Ile Ile Val Lys Leu Gly Arg
            260                 265                 270

Glu Glu Pro Ala Met Ser Met Asp Ala Asn Gly Lys Ile Ile Trp Ala
        275                 280                 285

Lys His Ser Glu Val Gln Gln Ala Asn Leu Lys Ala Met Gly Asp Ala
    290                 295                 300

Glu Ile Lys Asp Gly Glu Arg Leu Pro Leu Ala Val Lys Asp Met Gly
305                 310                 315                 320

Ser Cys Glu Ile Tyr Pro Gln Thr Ile Gln His Asn Pro Asn Gly Arg
```

```
                325                 330                 335

Phe Val Val Val Cys Gly Asp Gly Glu Tyr Ile Ile Tyr Thr Ala Met
            340                 345                 350

Ala Leu Arg Asn Lys Ser Phe Gly Ser Ala Gln Glu Phe Ala Trp Ala
        355                 360                 365

His Asp Ser Ser Glu Tyr Ala Ile Arg Glu Ser Asn Ser Ile Val Lys
    370                 375                 380

Ile Phe Lys Asn Phe Lys Glu Lys Lys Ser Phe Lys Pro Asp Phe Gly
385                 390                 395                 400

Ala Glu Ser Ile Tyr Gly Gly Phe Leu Leu Gly Val Arg Ser Val Asn
                405                 410                 415

Gly Leu Ala Phe Tyr Asp Trp Asp Asn Thr Glu Leu Ile Arg Arg Ile
            420                 425                 430

Glu Ile Gln Pro Lys His Ile Phe Trp Ser Asp Ser Gly Glu Leu Val
        435                 440                 445

Cys Ile Ala Thr Glu Glu Ser Phe Phe Ile Leu Lys Tyr Leu Ser Glu
    450                 455                 460

Lys Val Leu Ala Ala Gln Glu Thr His Glu Gly Val Thr Glu Asp Gly
465                 470                 475                 480

Ile Glu Asp Ala Phe Glu Val Leu Gly Glu Ile Gln Glu Ile Val Lys
                485                 490                 495

Thr Gly Leu Trp Val Gly Asp Cys Phe Ile Tyr Thr Ser Ser Val Asn
            500                 505                 510

Arg Leu Asn Tyr Tyr Val Gly Gly Glu Ile Val Thr Ile Ala His Leu
        515                 520                 525

Asp Arg Thr Met Tyr Leu Leu Gly Tyr Ile Pro Lys Asp Asn Arg Leu
    530                 535                 540

Tyr Leu Gly Asp Lys Glu Leu Asn Ile Ile Ser Tyr Ser Leu Leu Val
545                 550                 555                 560

Ser Val Leu Glu Tyr Gln Thr Ala Val Met Arg Arg Asp Phe Ser Met
                565                 570                 575

Ala Asp Lys Val Leu Pro Thr Ile Pro Lys Glu Gln Arg Thr Arg Val
            580                 585                 590

Ala His Phe Leu Glu Lys Gln Gly Phe Lys Gln Gln Ala Leu Thr Val
        595                 600                 605

Ser Thr Asp Pro Glu His Arg Phe Glu Leu Ala Leu Gln Leu Gly Glu
    610                 615                 620

Leu Lys Ile Ala Tyr Gln Leu Ala Val Glu Ala Glu Ser Glu Gln Lys
625                 630                 635                 640

Trp Lys Gln Leu Ala Glu Leu Ala Ile Ser Lys Cys Gln Phe Gly Leu
                645                 650                 655

Ala Gln Glu Cys Leu His His Ala Gln Asp Tyr Gly Gly Leu Leu Leu
            660                 665                 670

Leu Ala Thr Ala Ser Gly Asn Ala Asn Met Val Asn Lys Leu Ala Glu
        675                 680                 685

Gly Ala Glu Arg Asp Gly Lys Asn Asn Val Ala Phe Met Ser Tyr Phe
    690                 695                 700

Leu Gln Gly Lys Val Asp Ala Cys Leu Glu Leu Leu Ile Arg Thr Gly
705                 710                 715                 720

Arg Leu Pro Glu Ala Ala Phe Leu Ala Arg Thr Tyr Leu Pro Ser Gln
                725                 730                 735

Val Ser Arg Val Val Lys Leu Trp Arg Glu Asn Leu Ser Lys Val Asn
            740                 745                 750
```

```
Gln Lys Ala Ala Glu Ser Leu Ala Asp Pro Thr Glu Tyr Glu Asn Leu
        755                 760                 765

Phe Pro Gly Leu Lys Glu Ala Phe Val Val Glu Glu Trp Val Lys Glu
    770                 775                 780

Thr His Ala Asp Leu Trp Pro Ala Lys Gln Tyr Pro Leu Val Thr Pro
785                 790                 795                 800

Asn Glu Glu Arg Asn Val Met Glu Glu Gly Lys Asp Phe Gln Pro Ser
                805                 810                 815

Arg Ser Thr Ala Gln Gln Glu Leu Asp Gly Lys Pro Ala Ser Pro Thr
            820                 825                 830

Pro Val Ile Val Ala Ser His Thr Ala Asn Lys Glu Glu Lys Ser Leu
        835                 840                 845

Leu Glu Leu Glu Val Asp Leu Asp Asn Leu Glu Leu Glu Asp Ile Asp
    850                 855                 860

Thr Thr Asp Ile Asn Leu Asp Glu Asp Ile Leu Asp Asp
865                 870                 875


<210> SEQ ID NO 21
<211> LENGTH: 511
<212> TYPE: PRT
<213> ORGANISM: Homo sapiens
<300> PUBLICATION INFORMATION:
<308> DATABASE ACCESSION NUMBER: UniProtKB/ P48444
<309> DATABASE ENTRY DATE: 2009-05-26
<313> RELEVANT RESIDUES IN SEQ ID NO: (1)..(511)

<400> SEQUENCE: 21

Met Val Leu Leu Ala Ala Ala Val Cys Thr Lys Ala Gly Lys Ala Ile
1               5                   10                  15

Val Ser Arg Gln Phe Val Glu Met Thr Arg Thr Arg Ile Glu Gly Leu
            20                  25                  30

Leu Ala Ala Phe Pro Lys Leu Met Asn Thr Gly Lys Gln His Thr Phe
        35                  40                  45

Val Glu Thr Glu Ser Val Arg Tyr Val Tyr Gln Pro Met Glu Lys Leu
    50                  55                  60

Tyr Met Val Leu Ile Thr Thr Lys Asn Ser Asn Ile Leu Glu Asp Leu
65                  70                  75                  80

Glu Thr Leu Arg Leu Phe Ser Arg Val Ile Pro Glu Tyr Cys Arg Ala
                85                  90                  95

Leu Glu Glu Asn Glu Ile Ser Glu His Cys Phe Asp Leu Ile Phe Ala
            100                 105                 110

Phe Asp Glu Ile Val Ala Leu Gly Tyr Arg Glu Asn Val Asn Leu Ala
        115                 120                 125

Gln Ile Arg Thr Phe Thr Glu Met Asp Ser His Glu Glu Lys Val Phe
    130                 135                 140

Arg Ala Val Arg Glu Thr Gln Glu Arg Glu Ala Lys Ala Glu Met Arg
145                 150                 155                 160

Arg Lys Ala Lys Glu Leu Gln Gln Ala Arg Arg Asp Ala Glu Arg Gln
                165                 170                 175

Gly Lys Lys Ala Pro Gly Phe Gly Gly Phe Gly Ser Ser Ala Val Ser
            180                 185                 190

Gly Gly Ser Thr Ala Ala Met Ile Thr Glu Thr Ile Ile Glu Thr Asp
        195                 200                 205

Lys Pro Lys Val Ala Pro Ala Pro Ala Arg Pro Ser Gly Pro Ser Lys
    210                 215                 220
```

```
Ala Leu Lys Leu Gly Ala Lys Gly Lys Glu Val Asp Asn Phe Val Asp
225                 230                 235                 240

Lys Leu Lys Ser Glu Gly Glu Thr Ile Met Ser Ser Ser Met Gly Lys
                245                 250                 255

Arg Thr Ser Glu Ala Thr Lys Met His Ala Pro Pro Ile Asn Met Glu
            260                 265                 270

Ser Val His Met Lys Ile Glu Glu Lys Ile Thr Leu Thr Cys Gly Arg
        275                 280                 285

Asp Gly Gly Leu Gln Asn Met Glu Leu His Gly Met Ile Met Leu Arg
    290                 295                 300

Ile Ser Asp Asp Lys Tyr Gly Arg Ile Arg Leu His Val Glu Asn Glu
305                 310                 315                 320

Asp Lys Lys Gly Val Gln Leu Gln Thr His Pro Asn Val Asp Lys Lys
                325                 330                 335

Leu Phe Thr Ala Glu Ser Leu Ile Gly Leu Lys Asn Pro Glu Lys Ser
            340                 345                 350

Phe Pro Val Asn Ser Asp Val Gly Val Leu Lys Trp Arg Leu Gln Thr
        355                 360                 365

Thr Glu Glu Ser Phe Ile Pro Leu Thr Ile Asn Cys Trp Pro Ser Glu
    370                 375                 380

Ser Gly Asn Gly Cys Asp Val Asn Ile Glu Tyr Glu Leu Gln Glu Asp
385                 390                 395                 400

Asn Leu Glu Leu Asn Asp Val Val Ile Thr Ile Pro Leu Pro Ser Gly
                405                 410                 415

Val Gly Ala Pro Val Ile Gly Glu Ile Asp Gly Glu Tyr Arg His Asp
            420                 425                 430

Ser Arg Arg Asn Thr Leu Glu Trp Cys Leu Pro Val Ile Asp Ala Lys
        435                 440                 445

Asn Lys Ser Gly Ser Leu Glu Phe Ser Ile Ala Gly Gln Pro Asn Asp
    450                 455                 460

Phe Phe Pro Val Gln Val Ser Phe Val Ser Lys Lys Asn Tyr Cys Asn
465                 470                 475                 480

Ile Gln Val Thr Lys Val Thr Gln Val Asp Gly Asn Ser Pro Val Arg
                485                 490                 495

Phe Ser Thr Glu Thr Thr Phe Leu Val Asp Lys Tyr Glu Ile Leu
            500                 505                 510
```

<210> SEQ ID NO 22
<211> LENGTH: 552
<212> TYPE: PRT
<213> ORGANISM: Homo sapiens
<300> PUBLICATION INFORMATION:
<308> DATABASE ACCESSION NUMBER: NCBI/ACA05944
<309> DATABASE ENTRY DATE: 2008-02-20
<313> RELEVANT RESIDUES IN SEQ ID NO: (1)..(552)

<400> SEQUENCE: 22

```
Met Ala Glu Cys Asn Leu Val Ala Ile Leu Ile Ser Ser Ile Asp Asn
1               5                   10                  15

Pro Leu Asp Lys Asn Leu Asp Asn Gly Gly Asn Ser Cys Leu Asp Phe
            20                  25                  30

Arg Pro Leu Asn Ser Phe Ser Gln Pro Gln Val Leu Leu Ala Ala Ala
        35                  40                  45

Val Cys Thr Lys Ala Gly Lys Ala Ile Val Ser Arg Gln Phe Val Glu
    50                  55                  60

Met Thr Arg Thr Arg Ile Glu Gly Leu Leu Ala Ala Phe Pro Lys Leu
```

-continued

```
65                  70                  75                  80

Met Asn Thr Gly Lys Gln His Thr Phe Val Glu Thr Glu Ser Val Arg
                85                  90                  95

Tyr Val Tyr Gln Pro Met Glu Lys Leu Tyr Met Val Leu Ile Thr Thr
            100                 105                 110

Lys Asn Ser Asn Ile Leu Glu Asp Leu Glu Thr Leu Arg Leu Phe Ser
        115                 120                 125

Arg Val Ile Pro Glu Tyr Cys Arg Ala Leu Glu Glu Asn Glu Ile Ser
    130                 135                 140

Glu His Cys Phe Asp Leu Ile Phe Ala Phe Asp Glu Ile Val Ala Leu
145                 150                 155                 160

Gly Tyr Arg Glu Asn Val Asn Leu Ala Gln Ile Arg Thr Phe Thr Glu
                165                 170                 175

Met Asp Ser His Glu Glu Lys Val Phe Arg Ala Val Arg Glu Thr Gln
            180                 185                 190

Glu Arg Glu Ala Lys Ala Glu Met Arg Arg Lys Ala Lys Glu Leu Gln
        195                 200                 205

Gln Ala Arg Arg Asp Ala Glu Arg Gln Gly Lys Lys Ala Pro Gly Phe
    210                 215                 220

Gly Gly Phe Gly Ser Ser Ala Val Ser Gly Gly Ser Thr Ala Ala Met
225                 230                 235                 240

Ile Thr Glu Thr Ile Ile Glu Thr Asp Lys Pro Lys Val Ala Pro Ala
                245                 250                 255

Pro Ala Arg Pro Ser Gly Pro Ser Lys Ala Leu Lys Leu Gly Ala Lys
            260                 265                 270

Gly Lys Glu Val Asp Asn Phe Val Asp Lys Leu Lys Ser Glu Gly Glu
        275                 280                 285

Thr Ile Met Ser Ser Ser Met Gly Lys Arg Thr Ser Glu Ala Thr Lys
    290                 295                 300

Met His Ala Pro Pro Ile Asn Met Glu Ser Val His Met Lys Ile Glu
305                 310                 315                 320

Glu Lys Ile Thr Leu Thr Cys Gly Arg Asp Gly Gly Leu Gln Asn Met
                325                 330                 335

Glu Leu His Gly Met Ile Met Leu Arg Ile Ser Asp Asp Lys Tyr Gly
            340                 345                 350

Arg Ile Arg Leu His Val Glu Asn Glu Asp Lys Lys Gly Val Gln Leu
        355                 360                 365

Gln Thr His Pro Asn Val Asp Lys Lys Leu Phe Thr Ala Glu Ser Leu
    370                 375                 380

Ile Gly Leu Lys Asn Pro Glu Lys Ser Phe Pro Val Asn Ser Asp Val
385                 390                 395                 400

Gly Val Leu Lys Trp Arg Leu Gln Thr Thr Glu Glu Ser Phe Ile Pro
                405                 410                 415

Leu Thr Ile Asn Cys Trp Pro Ser Glu Ser Gly Asn Gly Cys Asp Val
            420                 425                 430

Asn Ile Glu Tyr Glu Leu Gln Glu Asp Asn Leu Glu Leu Asn Asp Val
        435                 440                 445

Val Ile Thr Ile Pro Leu Pro Ser Gly Val Gly Ala Pro Val Ile Gly
    450                 455                 460

Glu Ile Asp Gly Glu Tyr Arg His Asp Ser Arg Arg Asn Thr Leu Glu
465                 470                 475                 480

Trp Cys Leu Pro Val Ile Asp Ala Lys Asn Lys Ser Gly Ser Leu Glu
                485                 490                 495
```

-continued

Phe Ser Ile Ala Gly Gln Pro Asn Asp Phe Phe Pro Val Gln Val Ser
500 505 510

Phe Val Ser Lys Lys Asn Tyr Cys Asn Ile Gln Val Thr Lys Val Thr
515 520 525

Gln Val Asp Gly Asn Ser Pro Val Arg Phe Ser Thr Glu Thr Thr Phe
530 535 540

Leu Val Asp Lys Tyr Glu Ile Leu
545 550

<210> SEQ ID NO 23
<211> LENGTH: 308
<212> TYPE: PRT
<213> ORGANISM: Homo sapiens
<300> PUBLICATION INFORMATION:
<308> DATABASE ACCESSION NUMBER: UniProtKB/O14579
<309> DATABASE ENTRY DATE: 2009-05-05
<313> RELEVANT RESIDUES IN SEQ ID NO: (1)..(308)

<400> SEQUENCE: 23

Met Ala Pro Pro Ala Pro Gly Pro Ala Ser Gly Gly Ser Gly Glu Val
1 5 10 15

Asp Glu Leu Phe Asp Val Lys Asn Ala Phe Tyr Ile Gly Ser Tyr Gln
20 25 30

Gln Cys Ile Asn Glu Ala Gln Arg Val Lys Leu Ser Ser Pro Glu Arg
35 40 45

Asp Val Glu Arg Asp Val Phe Leu Tyr Arg Ala Tyr Leu Ala Gln Arg
50 55 60

Lys Phe Gly Val Val Leu Asp Glu Ile Lys Pro Ser Ser Ala Pro Glu
65 70 75 80

Leu Gln Ala Val Arg Met Phe Ala Asp Tyr Leu Ala His Glu Ser Arg
85 90 95

Arg Asp Ser Ile Val Ala Glu Leu Asp Arg Glu Met Ser Arg Ser Val
100 105 110

Asp Val Thr Asn Thr Thr Phe Leu Leu Met Ala Ala Ser Ile Tyr Leu
115 120 125

His Asp Gln Asn Pro Asp Ala Ala Leu Arg Ala Leu His Gln Gly Asp
130 135 140

Ser Leu Glu Cys Thr Ala Met Thr Val Gln Ile Leu Leu Lys Leu Asp
145 150 155 160

Arg Leu Asp Leu Ala Arg Lys Glu Leu Lys Arg Met Gln Asp Leu Asp
165 170 175

Glu Asp Ala Thr Leu Thr Gln Leu Ala Thr Ala Trp Val Ser Leu Ala
180 185 190

Thr Gly Gly Glu Lys Leu Gln Asp Ala Tyr Tyr Ile Phe Gln Glu Met
195 200 205

Ala Asp Lys Cys Ser Pro Thr Leu Leu Leu Leu Asn Gly Gln Ala Ala
210 215 220

Cys His Met Ala Gln Gly Arg Trp Glu Ala Ala Glu Gly Leu Leu Gln
225 230 235 240

Glu Ala Leu Asp Lys Asp Ser Gly Tyr Pro Glu Thr Leu Val Asn Leu
245 250 255

Ile Val Leu Ser Gln His Leu Gly Lys Pro Pro Glu Val Thr Asn Arg
260 265 270

Tyr Leu Ser Gln Leu Lys Asp Ala His Arg Ser His Pro Phe Ile Lys
275 280 285

```
Glu Tyr Gln Ala Lys Glu Asn Asp Phe Asp Arg Leu Val Leu Gln Tyr
    290                 295                 300

Ala Pro Ser Ala
305


<210> SEQ ID NO 24
<211> LENGTH: 256
<212> TYPE: PRT
<213> ORGANISM: Homo sapiens
<300> PUBLICATION INFORMATION:
<308> DATABASE ACCESSION NUMBER: NCBI/NP_955476
<309> DATABASE ENTRY DATE: 2008-09-28
<313> RELEVANT RESIDUES IN SEQ ID NO: (1)..(256)

<400> SEQUENCE: 24

Met Ala Pro Pro Ala Pro Gly Pro Ala Ser Gly Gly Ser Gly Glu Val
1               5                   10                  15

Asp Glu Leu Phe Asp Val Lys Asn Ala Phe Tyr Ile Gly Ser Tyr Gln
            20                  25                  30

Gln Cys Ile Asn Glu Ala Gln Arg Val Lys Leu Ser Ser Pro Glu Arg
        35                  40                  45

Asp Val Glu Arg Asp Val Phe Leu Tyr Arg Ala Tyr Leu Ala Gln Arg
    50                  55                  60

Lys Phe Gly Val Val Leu Asp Glu Ile Lys Pro Ser Ser Ala Pro Glu
65                  70                  75                  80

Leu Gln Ala Val Arg Met Phe Ala Asp Tyr Leu Ala His Glu Ser Arg
                85                  90                  95

Arg Asp Ser Ile Val Ala Glu Leu Asp Arg Glu Met Ser Arg Ser Val
            100                 105                 110

Asp Val Thr Asn Thr Thr Phe Leu Leu Met Ala Ala Ser Ile Tyr Leu
        115                 120                 125

His Asp Gln Asn Pro Asp Ala Ala Leu Arg Ala Leu His Gln Gly Asp
    130                 135                 140

Ser Leu Glu Cys Thr Ala Met Thr Val Gln Ile Leu Leu Lys Leu Asp
145                 150                 155                 160

Arg Leu Asp Leu Ala Arg Lys Glu Leu Lys Arg Met Gln Asp Leu Asp
                165                 170                 175

Glu Asp Ala Thr Leu Thr Gln Leu Ala Thr Ala Trp Val Ser Leu Ala
            180                 185                 190

Thr Asp Ser Gly Tyr Pro Glu Thr Leu Val Asn Leu Ile Val Leu Ser
        195                 200                 205

Gln His Leu Gly Lys Pro Pro Glu Val Thr Asn Arg Tyr Leu Ser Gln
    210                 215                 220

Leu Lys Asp Ala His Arg Ser His Pro Phe Ile Lys Glu Tyr Gln Ala
225                 230                 235                 240

Lys Glu Asn Asp Phe Asp Arg Leu Val Leu Gln Tyr Ala Pro Ser Ala
                245                 250                 255


<210> SEQ ID NO 25
<211> LENGTH: 257
<212> TYPE: PRT
<213> ORGANISM: Homo sapiens
<300> PUBLICATION INFORMATION:
<308> DATABASE ACCESSION NUMBER: NCBI/NP_955474
<309> DATABASE ENTRY DATE: 2008-09-28
<313> RELEVANT RESIDUES IN SEQ ID NO: (1)..(257)

<400> SEQUENCE: 25

Met Ala Pro Pro Ala Pro Gly Pro Ala Ser Gly Gly Ser Gly Glu Val
```

```
1               5                   10                  15

Asp Glu Leu Phe Asp Val Lys Asn Ala Phe Tyr Ile Gly Ser Tyr Gln
            20                  25                  30

Gln Cys Ile Asn Glu Ala Gln Arg Val Lys Leu Ser Ser Pro Glu Arg
        35                  40                  45

Asp Val Glu Arg Asp Val Phe Leu Tyr Arg Ala Tyr Leu Ala Gln Arg
    50                  55                  60

Lys Phe Gly Val Val Leu Asp Glu Ile Lys Pro Ser Ser Ala Pro Glu
65                  70                  75                  80

Leu Gln Ala Val Arg Met Phe Ala Asp Tyr Leu Ala His Glu Ser Arg
                85                  90                  95

Ser Thr Ala Met Thr Val Gln Ile Leu Leu Lys Leu Asp Arg Leu Asp
            100                 105                 110

Leu Ala Arg Lys Glu Leu Lys Arg Met Gln Asp Leu Asp Glu Asp Ala
        115                 120                 125

Thr Leu Thr Gln Leu Ala Thr Ala Trp Val Ser Leu Ala Thr Gly Gly
    130                 135                 140

Glu Lys Leu Gln Asp Ala Tyr Tyr Ile Phe Gln Glu Met Ala Asp Lys
145                 150                 155                 160

Cys Ser Pro Thr Leu Leu Leu Leu Asn Gly Gln Ala Ala Cys His Met
                165                 170                 175

Ala Gln Gly Arg Trp Glu Ala Ala Glu Gly Leu Leu Gln Glu Ala Leu
            180                 185                 190

Asp Lys Asp Ser Gly Tyr Pro Glu Thr Leu Val Asn Leu Ile Val Leu
        195                 200                 205

Ser Gln His Leu Gly Lys Pro Pro Glu Val Thr Asn Arg Tyr Leu Ser
    210                 215                 220

Gln Leu Lys Asp Ala His Arg Ser His Pro Phe Ile Lys Glu Tyr Gln
225                 230                 235                 240

Ala Lys Glu Asn Asp Phe Asp Arg Leu Val Leu Gln Tyr Ala Pro Ser
                245                 250                 255

Ala


<210> SEQ ID NO 26
<211> LENGTH: 874
<212> TYPE: PRT
<213> ORGANISM: Homo sapiens
<300> PUBLICATION INFORMATION:
<308> DATABASE ACCESSION NUMBER: UniProtKB/ Q9Y678
<309> DATABASE ENTRY DATE: 2009-04-14
<313> RELEVANT RESIDUES IN SEQ ID NO: (1)..(874)

<400> SEQUENCE: 26

Met Leu Lys Lys Phe Asp Lys Lys Asp Glu Glu Ser Gly Gly Gly Ser
1               5                   10                  15

Asn Pro Phe Gln His Leu Glu Lys Ser Ala Val Leu Gln Glu Ala Arg
            20                  25                  30

Val Phe Asn Glu Thr Pro Ile Asn Pro Arg Lys Cys Ala His Ile Leu
        35                  40                  45

Thr Lys Ile Leu Tyr Leu Ile Asn Gln Gly Glu His Leu Gly Thr Thr
    50                  55                  60

Glu Ala Thr Glu Ala Phe Phe Ala Met Thr Lys Leu Phe Gln Ser Asn
65                  70                  75                  80

Asp Pro Thr Leu Arg Arg Met Cys Tyr Leu Thr Ile Lys Glu Met Ser
                85                  90                  95
```

-continued

```
Cys Ile Ala Glu Asp Val Ile Ile Val Thr Ser Ser Leu Thr Lys Asp
            100                 105                 110

Met Thr Gly Lys Glu Asp Asn Tyr Arg Gly Pro Ala Val Arg Ala Leu
        115                 120                 125

Cys Gln Ile Thr Asp Ser Thr Met Leu Gln Ala Ile Glu Arg Tyr Met
    130                 135                 140

Lys Gln Ala Ile Val Asp Lys Val Pro Ser Val Ser Ser Ser Ala Leu
145                 150                 155                 160

Val Ser Ser Leu His Leu Leu Lys Cys Ser Phe Asp Val Val Lys Arg
                165                 170                 175

Trp Val Asn Glu Ala Gln Glu Ala Ala Ser Ser Asp Asn Ile Met Val
            180                 185                 190

Gln Tyr His Ala Leu Gly Leu Leu Tyr His Val Arg Lys Asn Asp Arg
        195                 200                 205

Leu Ala Val Asn Lys Met Ile Ser Lys Val Thr Arg His Gly Leu Lys
    210                 215                 220

Ser Pro Phe Ala Tyr Cys Met Met Ile Arg Val Ala Ser Lys Gln Leu
225                 230                 235                 240

Glu Glu Glu Asp Gly Ser Arg Asp Ser Pro Leu Phe Asp Phe Ile Glu
                245                 250                 255

Ser Cys Leu Arg Asn Lys His Glu Met Val Val Tyr Glu Ala Ala Ser
            260                 265                 270

Ala Ile Val Asn Leu Pro Gly Cys Ser Ala Lys Glu Leu Ala Pro Ala
        275                 280                 285

Val Ser Val Leu Gln Leu Phe Cys Ser Ser Pro Lys Ala Ala Leu Arg
    290                 295                 300

Tyr Ala Ala Val Arg Thr Leu Asn Lys Val Ala Met Lys His Pro Ser
305                 310                 315                 320

Ala Val Thr Ala Cys Asn Leu Asp Leu Glu Asn Leu Val Thr Asp Ser
                325                 330                 335

Asn Arg Ser Ile Ala Thr Leu Ala Ile Thr Thr Leu Leu Lys Thr Gly
            340                 345                 350

Ser Glu Ser Ser Ile Asp Arg Leu Met Lys Gln Ile Ser Ser Phe Met
        355                 360                 365

Ser Glu Ile Ser Asp Glu Phe Lys Val Val Val Val Gln Ala Ile Ser
    370                 375                 380

Ala Leu Cys Gln Lys Tyr Pro Arg Lys His Ala Val Leu Met Asn Phe
385                 390                 395                 400

Leu Phe Thr Met Leu Arg Glu Glu Gly Gly Phe Glu Tyr Lys Arg Ala
                405                 410                 415

Ile Val Asp Cys Ile Ile Ser Ile Ile Glu Glu Asn Ser Glu Ser Lys
            420                 425                 430

Glu Thr Gly Leu Ser His Leu Cys Glu Phe Ile Glu Asp Cys Glu Phe
        435                 440                 445

Thr Val Leu Ala Thr Arg Ile Leu His Leu Leu Gly Gln Glu Gly Pro
    450                 455                 460

Lys Thr Thr Asn Pro Ser Lys Tyr Ile Arg Phe Ile Tyr Asn Arg Val
465                 470                 475                 480

Val Leu Glu His Glu Glu Val Arg Ala Gly Ala Val Ser Ala Leu Ala
                485                 490                 495

Lys Phe Gly Ala Gln Asn Glu Glu Met Leu Pro Ser Ile Leu Val Leu
            500                 505                 510

Leu Lys Arg Cys Val Met Asp Asp Asp Asn Glu Val Arg Asp Arg Ala
```

```
        515                 520                 525

Thr Phe Tyr Leu Asn Val Leu Glu Gln Lys Gln Lys Ala Leu Asn Ala
    530                 535                 540

Gly Tyr Ile Leu Asn Gly Leu Thr Val Ser Ile Pro Gly Leu Glu Arg
545                 550                 555                 560

Ala Leu Gln Gln Tyr Thr Leu Glu Pro Ser Glu Lys Pro Phe Asp Leu
                565                 570                 575

Lys Ser Val Pro Leu Ala Thr Ala Pro Met Ala Glu Gln Arg Thr Glu
            580                 585                 590

Ser Thr Pro Ile Thr Ala Val Lys Gln Pro Glu Lys Val Ala Ala Thr
        595                 600                 605

Arg Gln Glu Ile Phe Gln Glu Gln Leu Ala Ala Val Pro Glu Phe Arg
    610                 615                 620

Gly Leu Gly Pro Leu Phe Lys Ser Ser Pro Glu Pro Val Ala Leu Thr
625                 630                 635                 640

Glu Ser Glu Thr Glu Tyr Val Ile Arg Cys Thr Lys His Thr Phe Thr
                645                 650                 655

Asn His Met Val Phe Gln Phe Asp Cys Thr Asn Thr Leu Asn Asp Gln
            660                 665                 670

Thr Leu Glu Asn Val Thr Val Gln Met Glu Pro Thr Glu Ala Tyr Glu
        675                 680                 685

Val Leu Cys Tyr Val Pro Ala Arg Ser Leu Pro Tyr Asn Gln Pro Gly
    690                 695                 700

Thr Cys Tyr Thr Leu Val Ala Leu Pro Lys Glu Asp Pro Thr Ala Val
705                 710                 715                 720

Ala Cys Thr Phe Ser Cys Met Met Lys Phe Thr Val Lys Asp Cys Asp
                725                 730                 735

Pro Thr Thr Gly Glu Thr Asp Asp Glu Gly Tyr Glu Asp Glu Tyr Val
            740                 745                 750

Leu Glu Asp Leu Glu Val Thr Val Ala Asp His Ile Gln Lys Val Met
        755                 760                 765

Lys Leu Asn Phe Glu Ala Ala Trp Asp Glu Val Gly Asp Glu Phe Glu
    770                 775                 780

Lys Glu Glu Thr Phe Thr Leu Ser Thr Ile Lys Thr Leu Glu Glu Ala
785                 790                 795                 800

Val Gly Asn Ile Val Lys Phe Leu Gly Met His Pro Cys Glu Arg Ser
                805                 810                 815

Asp Lys Val Pro Asp Asn Lys Asn Thr His Thr Leu Leu Leu Ala Gly
            820                 825                 830

Val Phe Arg Gly Gly His Asp Ile Leu Val Arg Ser Arg Leu Leu Leu
        835                 840                 845

Leu Asp Thr Val Thr Met Gln Val Thr Ala Arg Ser Leu Glu Glu Leu
    850                 855                 860

Pro Val Asp Ile Ile Leu Ala Ser Val Gly
865                 870


<210> SEQ ID NO 27
<211> LENGTH: 871
<212> TYPE: PRT
<213> ORGANISM: Homo sapiens
<300> PUBLICATION INFORMATION:
<308> DATABASE ACCESSION NUMBER: NCBI/NP_036265
<309> DATABASE ENTRY DATE: 2008-08-20
<313> RELEVANT RESIDUES IN SEQ ID NO: (1)..(871)

<400> SEQUENCE: 27
```

-continued

```
Met Ile Lys Lys Phe Asp Lys Lys Asp Glu Glu Ser Gly Ser Gly Ser
1               5                   10                  15

Asn Pro Phe Gln His Leu Glu Lys Ser Ala Val Leu Gln Glu Ala Arg
            20                  25                  30

Ile Phe Asn Glu Thr Pro Ile Asn Pro Arg Arg Cys Leu His Ile Leu
        35                  40                  45

Thr Lys Ile Leu Tyr Leu Leu Asn Gln Gly Glu His Phe Gly Thr Thr
    50                  55                  60

Glu Ala Thr Glu Ala Phe Phe Ala Met Thr Arg Leu Phe Gln Ser Asn
65                  70                  75                  80

Asp Gln Thr Leu Arg Arg Met Cys Tyr Leu Thr Ile Lys Glu Met Ala
                85                  90                  95

Thr Ile Ser Glu Asp Val Ile Ile Val Thr Ser Ser Leu Thr Lys Asp
            100                 105                 110

Met Thr Gly Lys Glu Asp Val Tyr Arg Gly Pro Ala Ile Arg Ala Leu
        115                 120                 125

Cys Arg Ile Thr Asp Gly Thr Met Leu Gln Ala Ile Glu Arg Tyr Met
    130                 135                 140

Lys Gln Ala Ile Val Asp Lys Val Ser Ser Val Ser Ser Ser Ala Leu
145                 150                 155                 160

Val Ser Ser Leu His Met Met Lys Ile Ser Tyr Asp Val Val Lys Arg
                165                 170                 175

Trp Ile Asn Glu Ala Gln Glu Ala Ala Ser Ser Asp Asn Ile Met Val
            180                 185                 190

Gln Tyr His Ala Leu Gly Val Leu Tyr His Leu Arg Lys Asn Asp Arg
        195                 200                 205

Leu Ala Val Ser Lys Met Leu Asn Lys Phe Thr Lys Ser Gly Leu Lys
    210                 215                 220

Ser Gln Phe Ala Tyr Cys Met Leu Ile Arg Ile Ala Ser Arg Leu Leu
225                 230                 235                 240

Lys Glu Thr Glu Asp Gly His Glu Ser Pro Leu Phe Asp Phe Ile Glu
                245                 250                 255

Ser Cys Leu Arg Asn Lys His Glu Met Val Ile Tyr Glu Ala Ala Ser
            260                 265                 270

Ala Ile Ile His Leu Pro Asn Cys Thr Ala Arg Glu Leu Ala Pro Ala
        275                 280                 285

Val Ser Val Leu Gln Leu Phe Cys Ser Ser Pro Lys Pro Ala Leu Arg
    290                 295                 300

Tyr Ala Ala Val Arg Thr Leu Asn Lys Val Ala Met Lys His Pro Ser
305                 310                 315                 320

Ala Val Thr Ala Cys Asn Leu Asp Leu Glu Asn Leu Ile Thr Asp Ser
                325                 330                 335

Asn Arg Ser Ile Ala Thr Leu Ala Ile Thr Thr Leu Leu Lys Thr Gly
            340                 345                 350

Ser Glu Ser Ser Val Asp Arg Leu Met Lys Gln Ile Ser Ser Phe Val
        355                 360                 365

Ser Glu Ile Ser Asp Glu Phe Lys Val Val Val Val Gln Ala Ile Ser
    370                 375                 380

Ala Leu Cys Gln Lys Tyr Pro Arg Lys His Ser Val Met Met Thr Phe
385                 390                 395                 400

Leu Ser Asn Met Leu Arg Asp Asp Gly Gly Phe Glu Tyr Lys Arg Ala
                405                 410                 415
```

-continued

```
Ile Val Asp Cys Ile Ile Ser Ile Val Glu Glu Asn Pro Glu Ser Lys
            420                 425                 430

Glu Ala Gly Leu Ala His Leu Cys Glu Phe Ile Glu Asp Cys Glu His
        435                 440                 445

Thr Val Leu Ala Thr Lys Ile Leu His Leu Leu Gly Lys Glu Gly Pro
    450                 455                 460

Arg Thr Pro Val Pro Ser Lys Tyr Ile Arg Phe Ile Phe Asn Arg Val
465                 470                 475                 480

Val Leu Glu Asn Glu Ala Val Arg Ala Ala Ala Val Ser Ala Leu Ala
                485                 490                 495

Lys Phe Gly Ala Gln Asn Glu Ser Leu Leu Pro Ser Ile Leu Val Leu
            500                 505                 510

Leu Gln Arg Cys Met Met Asp Thr Asp Asp Glu Val Arg Asp Arg Ala
        515                 520                 525

Thr Phe Tyr Leu Asn Val Leu Gln Gln Arg Gln Met Ala Leu Asn Ala
    530                 535                 540

Thr Tyr Ile Phe Asn Gly Leu Thr Val Ser Val Pro Gly Met Glu Lys
545                 550                 555                 560

Ala Leu His Gln Tyr Thr Leu Glu Pro Ser Glu Lys Pro Phe Asp Met
                565                 570                 575

Lys Ser Ile Pro Leu Ala Met Ala Pro Val Phe Glu Gln Lys Ala Glu
            580                 585                 590

Ile Thr Leu Val Ala Thr Lys Pro Glu Lys Leu Ala Pro Ser Arg Gln
        595                 600                 605

Asp Ile Phe Gln Glu Gln Leu Ala Ala Ile Pro Glu Phe Leu Asn Ile
    610                 615                 620

Gly Pro Leu Phe Lys Ser Ser Glu Pro Val Gln Leu Thr Glu Ala Glu
625                 630                 635                 640

Thr Glu Tyr Phe Val Arg Cys Ile Lys His Met Phe Thr Asn His Ile
                645                 650                 655

Val Phe Gln Phe Asp Cys Thr Asn Thr Leu Asn Asp Gln Leu Leu Glu
            660                 665                 670

Lys Val Thr Val Gln Met Glu Pro Ser Asp Ser Tyr Glu Val Leu Ser
        675                 680                 685

Cys Ile Pro Ala Pro Ser Leu Pro Tyr Asn Gln Pro Gly Ile Cys Tyr
    690                 695                 700

Thr Leu Val Arg Leu Pro Asp Asp Asp Pro Thr Ala Val Ala Gly Ser
705                 710                 715                 720

Phe Ser Cys Thr Met Lys Phe Thr Val Arg Asp Cys Asp Pro Asn Thr
                725                 730                 735

Gly Val Pro Asp Glu Asp Gly Tyr Asp Asp Glu Tyr Val Leu Glu Asp
            740                 745                 750

Leu Glu Val Thr Val Ser Asp His Ile Gln Lys Val Leu Lys Pro Asn
        755                 760                 765

Phe Ala Ala Ala Trp Glu Glu Val Gly Asp Thr Phe Glu Lys Glu Glu
    770                 775                 780

Thr Phe Ala Leu Ser Ser Thr Lys Thr Leu Glu Glu Ala Val Asn Asn
785                 790                 795                 800

Ile Ile Thr Phe Leu Gly Met Gln Pro Cys Glu Arg Ser Asp Lys Val
                805                 810                 815

Pro Glu Asn Lys Asn Ser His Ser Leu Tyr Leu Ala Gly Ile Phe Arg
            820                 825                 830

Gly Gly Tyr Asp Leu Leu Val Arg Ser Arg Leu Ala Leu Ala Asp Gly
```

```
        835                 840                 845

Val Thr Met Gln Val Thr Val Arg Ser Lys Glu Arg Thr Pro Val Asp
    850                 855                 860

Val Ile Leu Ala Ser Val Gly
865                 870


<210> SEQ ID NO 28
<211> LENGTH: 768
<212> TYPE: PRT
<213> ORGANISM: Homo sapiens
<300> PUBLICATION INFORMATION:
<308> DATABASE ACCESSION NUMBER: NCBI/EAW79270
<309> DATABASE ENTRY DATE: 2006-12-18
<313> RELEVANT RESIDUES IN SEQ ID NO: (1)..(768)

<400> SEQUENCE: 28

Met Ile Leu Thr Lys Asp Met Thr Gly Lys Glu Asp Asn Tyr Arg Gly
1               5                   10                  15

Pro Ala Val Arg Ala Leu Cys Gln Ile Thr Asp Ser Thr Met Leu Gln
            20                  25                  30

Ala Ile Glu Arg Tyr Met Lys Gln Ala Ile Val Asp Lys Val Pro Ser
        35                  40                  45

Val Ser Ser Ser Ala Leu Val Ser Ser Leu His Leu Leu Lys Cys Ser
    50                  55                  60

Phe Asp Val Val Lys Arg Trp Val Asn Glu Ala Gln Glu Ala Ala Ser
65                  70                  75                  80

Ser Asp Asn Ile Met Val Gln Tyr His Ala Leu Gly Leu Leu Tyr His
                85                  90                  95

Val Arg Lys Asn Asp Arg Leu Ala Val Asn Lys Met Ile Ser Lys Val
            100                 105                 110

Thr Arg His Gly Leu Lys Ser Pro Phe Ala Tyr Cys Met Met Ile Arg
        115                 120                 125

Val Ala Ser Lys Gln Leu Glu Glu Glu Asp Gly Ser Arg Asp Ser Pro
    130                 135                 140

Leu Phe Asp Phe Ile Glu Ser Cys Leu Arg Asn Lys His Glu Met Val
145                 150                 155                 160

Val Tyr Glu Ala Ala Ser Ala Ile Val Asn Leu Pro Gly Cys Ser Ala
                165                 170                 175

Lys Glu Leu Ala Pro Ala Val Ser Val Leu Gln Leu Phe Cys Ser Ser
            180                 185                 190

Pro Lys Ala Ala Leu Arg Tyr Ala Ala Val Arg Thr Leu Asn Lys Val
        195                 200                 205

Ala Met Lys His Pro Ser Ala Val Thr Ala Cys Asn Leu Asp Leu Glu
    210                 215                 220

Asn Leu Val Thr Asp Ser Asn Arg Ser Ile Ala Thr Leu Ala Ile Thr
225                 230                 235                 240

Thr Leu Leu Lys Thr Gly Ser Glu Ser Ser Ile Asp Arg Leu Met Lys
                245                 250                 255

Gln Ile Ser Ser Phe Met Ser Glu Ile Ser Asp Glu Phe Lys Val Val
            260                 265                 270

Val Val Gln Ala Ile Ser Ala Leu Cys Gln Lys Tyr Pro Arg Lys His
        275                 280                 285

Ala Val Leu Met Asn Phe Leu Phe Thr Met Leu Arg Glu Glu Gly Gly
    290                 295                 300

Phe Glu Tyr Lys Arg Ala Ile Val Asp Cys Ile Ile Ser Ile Ile Glu
305                 310                 315                 320
```

-continued

```
Glu Asn Ser Glu Ser Lys Glu Thr Gly Leu Ser His Leu Cys Glu Phe
                325                 330                 335

Ile Glu Asp Cys Glu Phe Thr Val Leu Ala Thr Arg Ile Leu His Leu
            340                 345                 350

Leu Gly Gln Glu Gly Pro Lys Thr Thr Asn Pro Ser Lys Tyr Ile Arg
        355                 360                 365

Phe Ile Tyr Asn Arg Val Val Leu Glu His Glu Glu Val Arg Ala Gly
    370                 375                 380

Ala Val Ser Ala Leu Ala Lys Phe Gly Ala Gln Asn Glu Glu Met Leu
385                 390                 395                 400

Pro Ser Ile Leu Val Leu Leu Lys Arg Cys Val Met Asp Asp Asp Asn
                405                 410                 415

Glu Val Arg Asp Arg Ala Thr Phe Tyr Leu Asn Val Leu Glu Gln Lys
            420                 425                 430

Gln Lys Ala Leu Asn Ala Gly Tyr Ile Leu Asn Gly Leu Thr Val Ser
        435                 440                 445

Ile Pro Gly Leu Glu Arg Ala Leu Gln Gln Tyr Thr Leu Glu Pro Ser
    450                 455                 460

Glu Lys Pro Phe Asp Leu Lys Ser Val Pro Leu Ala Thr Ala Pro Met
465                 470                 475                 480

Ala Glu Gln Arg Thr Glu Ser Thr Pro Ile Thr Ala Val Lys Gln Pro
                485                 490                 495

Glu Lys Val Ala Ala Thr Arg Gln Glu Ile Phe Gln Glu Gln Leu Ala
            500                 505                 510

Ala Val Pro Glu Phe Arg Gly Leu Gly Pro Leu Phe Lys Ser Ser Pro
        515                 520                 525

Glu Pro Val Ala Leu Thr Glu Ser Glu Thr Glu Tyr Val Ile Arg Cys
    530                 535                 540

Thr Lys His Thr Phe Thr Asn His Met Val Phe Gln Phe Asp Cys Thr
545                 550                 555                 560

Asn Thr Leu Asn Asp Gln Thr Leu Glu Asn Val Thr Val Gln Met Glu
                565                 570                 575

Pro Thr Glu Ala Tyr Glu Val Leu Cys Tyr Val Pro Ala Arg Ser Leu
            580                 585                 590

Pro Tyr Asn Gln Pro Gly Thr Cys Tyr Thr Leu Val Ala Leu Pro Lys
        595                 600                 605

Glu Asp Pro Thr Ala Val Ala Cys Thr Phe Ser Cys Met Met Lys Phe
    610                 615                 620

Thr Val Lys Asp Cys Asp Pro Thr Thr Gly Glu Thr Asp Asp Glu Gly
625                 630                 635                 640

Tyr Glu Asp Glu Tyr Val Leu Glu Asp Leu Glu Val Thr Val Ala Asp
                645                 650                 655

His Ile Gln Lys Val Met Lys Leu Asn Phe Glu Ala Ala Trp Asp Glu
            660                 665                 670

Val Gly Asp Glu Phe Glu Lys Glu Glu Thr Phe Thr Leu Ser Thr Ile
        675                 680                 685

Lys Thr Leu Glu Glu Ala Val Gly Asn Ile Val Lys Phe Leu Gly Met
    690                 695                 700

His Pro Cys Glu Arg Ser Asp Lys Val Pro Asp Asn Lys Asn Thr His
705                 710                 715                 720

Thr Leu Leu Leu Ala Gly Val Phe Arg Gly Gly His Asp Ile Leu Val
                725                 730                 735
```

```
Arg Ser Arg Leu Leu Leu Leu Asp Thr Val Thr Met Gln Val Thr Ala
            740                 745                 750

Arg Ser Leu Glu Glu Leu Pro Val Asp Ile Ile Leu Ala Ser Val Gly
        755                 760                 765
```

<210> SEQ ID NO 29
<211> LENGTH: 177
<212> TYPE: PRT
<213> ORGANISM: Homo sapiens
<300> PUBLICATION INFORMATION:
<308> DATABASE ACCESSION NUMBER: UniProtKB/P61923
<309> DATABASE ENTRY DATE: 2009-05-05
<313> RELEVANT RESIDUES IN SEQ ID NO: (1)..(177)

<400> SEQUENCE: 29

```
Met Glu Ala Leu Ile Leu Glu Pro Ser Leu Tyr Thr Val Lys Ala Ile
1               5                   10                  15

Leu Ile Leu Asp Asn Asp Gly Asp Arg Leu Phe Ala Lys Tyr Tyr Asp
            20                  25                  30

Asp Thr Tyr Pro Ser Val Lys Glu Gln Lys Ala Phe Glu Lys Asn Ile
        35                  40                  45

Phe Asn Lys Thr His Arg Thr Asp Ser Glu Ile Ala Leu Leu Glu Gly
    50                  55                  60

Leu Thr Val Val Tyr Lys Ser Ser Ile Asp Leu Tyr Phe Tyr Val Ile
65                  70                  75                  80

Gly Ser Ser Tyr Glu Asn Glu Leu Met Leu Met Ala Val Leu Asn Cys
                85                  90                  95

Leu Phe Asp Ser Leu Ser Gln Met Leu Arg Lys Asn Val Glu Lys Arg
            100                 105                 110

Ala Leu Leu Glu Asn Met Glu Gly Leu Phe Leu Ala Val Asp Glu Ile
        115                 120                 125

Val Asp Gly Gly Val Ile Leu Glu Ser Asp Pro Gln Gln Val Val His
    130                 135                 140

Arg Val Ala Leu Arg Gly Glu Asp Val Pro Leu Thr Glu Gln Thr Val
145                 150                 155                 160

Ser Gln Val Leu Gln Ser Ala Lys Glu Gln Ile Lys Trp Ser Leu Leu
                165                 170                 175

Arg
```

<210> SEQ ID NO 30
<211> LENGTH: 210
<212> TYPE: PRT
<213> ORGANISM: Homo sapiens
<300> PUBLICATION INFORMATION:
<308> DATABASE ACCESSION NUMBER: NCBI/NP_057513
<309> DATABASE ENTRY DATE: 2009-03-29
<313> RELEVANT RESIDUES IN SEQ ID NO: (1)..(210)

<400> SEQUENCE: 30

```
Met Gln Arg Pro Glu Ala Trp Pro Arg Pro His Pro Gly Glu Gly Ala
1               5                   10                  15

Ala Ala Ala Gln Ala Gly Gly Pro Ala Pro Pro Ala Arg Ala Gly Glu
            20                  25                  30

Pro Ser Gly Leu Arg Leu Gln Glu Pro Ser Leu Tyr Thr Ile Lys Ala
        35                  40                  45

Val Phe Ile Leu Asp Asn Asp Gly Arg Arg Leu Leu Ala Lys Tyr Tyr
    50                  55                  60

Asp Asp Thr Phe Pro Ser Met Lys Glu Gln Met Val Phe Glu Lys Asn
65                  70                  75                  80
```

-continued

```
Val Phe Asn Lys Thr Ser Arg Thr Glu Ser Glu Ile Ala Phe Phe Gly
                85                  90                  95

Gly Met Thr Ile Val Tyr Lys Asn Ser Ile Asp Leu Phe Leu Tyr Val
            100                 105                 110

Val Gly Ser Ser Tyr Glu Asn Glu Leu Met Leu Met Ser Val Leu Thr
        115                 120                 125

Cys Leu Phe Glu Ser Leu Asn His Met Leu Arg Lys Asn Val Glu Lys
    130                 135                 140

Arg Trp Leu Leu Glu Asn Met Asp Gly Ala Phe Leu Val Leu Asp Glu
145                 150                 155                 160

Ile Val Asp Gly Gly Val Ile Leu Glu Ser Asp Pro Gln Gln Val Ile
                165                 170                 175

Gln Lys Val Asn Phe Arg Ala Asp Asp Gly Gly Leu Thr Glu Gln Ser
            180                 185                 190

Val Ala Gln Val Leu Gln Ser Ala Lys Glu Gln Ile Lys Trp Ser Leu
        195                 200                 205

Leu Lys
    210
```

DYNAMIC BIO-NANOPARTICLE PLATFORMS

This is a continuation of pending USPTO Utility application Ser. No. 12/399,906, with the title, "DYNAMIC BIO-NANOPARTICLE ELEMENTS, originally filed on Mar. 6, 2009. The invention relates generally to the field of nanoparticles, and more specifically, in one embodiment, to dynamic bio-nanoparticle elements formed from materials comprised of self-assembling protein molecules, which are capable of executing one or more functions and or effect one or more ends, in vivo and or in vitro. In another invention embodiment, the invention relates to a multifunction nanoscale bio-nanoparticle platform, such as a biomedical platform, bio-molecular platform, electronics platform, information processing platform, and the like, using such dynamic bio-nanoparticle elements.

FIELD OF THE INVENTION

Background of the Invention

Structures at the nanoscale are sometimes referred to as nanoparticles. Some nanoparticles comprise cage elements that form cavities and or comprise vesicle elements; examples of which in the prior art teach elements such as nano-carbon endohedral cages (Fullerenes); capsids, the protein shell of a virus; liposomes; lipids; heat shock proteins; ferritins; vault ribonucleoprotein particles; Clathrin protein cages; and Coatomer I/II protein cages, among other various cage- or vesicle-forming elements. Additionally, prior art teaches that protein cage elements can coat vesicle elements; for example, Clathrin and Coatomer coated vesicles (CCV's). Additionally, prior art teaches that one or more types of cargo elements can be located internally with respect to a cage and vesicle element.

A cavity forming protein cage and a cage coated vesicle implementation is taught in issued U.S. Pat. No. 7,393,924 (Jul. 1, 2008, Vitaliano et al.) The cage and cage coated vesicle elements are formed in vitro from a plurality of isolated Clathrin/Coatomer protein subunits. As taught in U.S. Pat. No. 7,393,924, the enhanced functionalization capabilities of the isolated Clathrin and Coatomer I/II protein molecules enable a number of properties and features that make them superior to other cage and cage coated vesicle elements in the prior art.

But the instant invention teaches nanoscale element fabrication, assembly, operation, behavior and properties that are unique from prior protein art that encompasses various types of cavity-forming cage structures formed in vitro from a plurality of self-assembling subunits. For example, a fully formed Clathrin cage element as taught in U.S. Pat. No. 7,393,924, and generally speaking taught in other Clathrin art, is comprised of a plurality of 3-legged triskelia, each triskelion having 6 protein subunits; 3 Clathrin heavy chain and 3 Clathrin light chain subunits.

In marked contrast, the instant invention teaches that complete cages comprised of a plurality of 3-legged triskelia are not required to comprise one or more types of efficacious elements. Instead, in its most essential embodiment the instant invention teaches one or more nanoscale elements of one or more types formed from isolated, synthetic and or recombinant amino acid residues comprising in whole or in part one or more types of Clathrin and or Coatomer I/II proteins of one or more isoforms, including cloned isoforms. These isoforms with their differing amino acid sequences comprise (in this example, humans) the various types of Clathrin heavy chains, the various types of Clathrin light chains, encompass the distinct heavy chain and light chain segments and domains, and in the case of Coatomer, comprise and encompass its domains and subunits, with different combinations of the latter known to exist within Coatomer complexes. Examples of amino acid sequences comprising Clathrin and Coatomer proteins, and their respective isoforms are listed in SEQ ID NO:1 to SEQ ID NO:30. Accordingly, one or more instant invention embodiments may also comprise minimalist, non-cage elements of one or more types. The minimalist element structure afforded by the instant invention affords a much broader and richer variety of element configurations and embodiments than those taught in prior Clathrin or other protein cage art.

For example, freed of the constraints of only forming cavity-forming protein cages in vitro, one or more non-cage invention elements may also form one or more other types of nanoscale elements and structures, enabling new classes and types of applications. Example non-cage embodiments include, but are not limited to, functionalized nano-tubule structures; protein-based nano-dendrimers suitable for biomedical and bio-molecular applications; and self-assembling, stable, bioactive, protein-based, hydrogel nanoparticles (nanogels). In other embodiments, one or more nanoscale elements and structures may be additionally formed and comprised of one or more non-invention elements of one or more types. Such structural plasticity and flexible element functionality are not taught in prior protein cage art.

Prior art often teaches one or more types of protein cages that carry one or more types of additional elements, e.g., cargo, to enable overall functionality and produce efficacious results. However, unlike prior art, the instant invention teaches, in one embodiment, one or more non-cage or cage elements may carry no additional elements like cargo, yet still can comprise inherently efficacious elements of one or more types, like drug elements, but not limited to. In one embodiment, one or more invention elements operating alone and without any additional elements such as cargo and the like comprise unique new types of inherently efficacious agents and elements that are distinctly different in behavior and functionality from prior art, and their unique features correspondingly enable new types of applications.

In another embodiment, one or more elements and or their additional elements in whole or in part may require only minimal functionalization to be efficacious; e.g., they may not require PEGylation or other types of functionalization to operate effectively.

In another embodiment, one or more elements carry one or more types of cargo and the cargo acts as the efficacious element. In another embodiment, one or more elements together with cargo elements act in efficacious concert.

In another embodiment, one or more elements are penetrating elements that enter one or more cells and gain access to the cytosol and intracellular elements of one or more types, including one or more cell organelles. Such elements may, in one embodiment, require minimal functionalization. In another embodiment, one or more elements may comprise one or more membrane fusion elements. These various features are not taught in prior protein cage art. In one embodiment, using cell crossing techniques yield efficacious cancer treatments, gene therapy, and the like.

Further, in cage, cavity, and vesicle prior art, one or more types of additional elements, e.g., cargo, are often inserted into a complex, fully formed structure, a sometimes difficult and laborious process. But the invention, in one or more embodiments, teaches that using utilizing non-cage elements of one or more types makes the addition of one or more elements less difficult as there is no insertion process into a cage, cavity, or vesicle to contend with. In another embodiment, additional element functionalization is simplified by decorating just the external surface of a cage, a feature not taught in prior Clathrin art.

In another embodiment, one or more assay, diagnostic, therapeutic, and prosthetic applications and the like can be performed ensemble using the same bioengineered element.

These various functionalization capabilities enable a highly flexible nano-platform that features improved stability, rigidity, functionality and loading capacity relative to other nanoparticles, and being comprised of ubiquitous proteins, features low antigenicity in one or more embodiments. In one illustrative embodiment, one or more elements may be harmlessly dissolved, passed, and or excreted from the body.

In one embodiment, the current application teaches one or more elements comprising one or more types of hybrid elements and arrangements, which can produce efficacious results. In one embodiment, one or more invention elements are conjugated to natural biological/molecular elements, like cells, but not limited to, forming one or more types of hybrid elements in vitro and or in vivo. Such hybrid elements may operate alone or with additional elements, e.g., with cargo. In another embodiment, such hybrid elements may fuse in vitro and or in vivo with non-invention elements, such as those comprising natural elements in cells, but not limited to. This type of hybrid/fusion capability and flexibility is not taught in the prior art.

In another embodiment, the current application teaches one or more elements, functioning alone or with one or more additional elements, which comprise efficacious replacements for one or more elements of one or more types, including non-invention elements. In one embodiment, one or more elements may replace one or more types of naturally occurring cell elements, to efficacious effect. This replacement capability is not taught in the prior art.

In one embodiment, the instant invention teaches one or more elements, functioning alone or with one or more additional elements, which comprise one or more cellular repair elements, of one or more types; a capability not taught in the prior art. In another embodiment the elements are cellular regeneration elements.

Prior art also does not teach that cage, vesicle elements, or their various subunit elements efficaciously operate in the extra-cellular spaces, e.g., in the synaptic spaces between neurons. But the instant invention teaches one or more types of elements capable of such extracellular operation, including for the in situ remediation, removal and or sequestration of undesirable organic and or non-organic elements.

The invention further teaches a biological model that is consistent, not from the complete cage element level up, but from the minimalist, non-cage element level up, in vitro and in vivo, making drug discovery safer, more efficacious, more time and cost effective, and overall, a much more rapid process than prior art.

In another embodiment, one or more elements may comprise one or more types of minimalist, non-cage elements than that taught in prior art for doing clinical trials of one or more types of agents, including their targeted agent delivery, including high precision dosing.

In one embodiment, the instant invention teaches one or more elements that in whole or in part execute one or more types of actions for creating, spawning, comprising, modifying, repairing, regenerating, reassembling, and or control and regulation of one or more cells, cellular elements, cell organelles, including like actions and behaviors involving cellular processes such as endocytosis, exocytosis, mitosis, trafficking and signaling, communication between cells, receptor upregulation and downregulation, other behaviors, and the like. Failures and defects in any of these cellular elements and processes can lead to diseases, for example, cancer. This type of efficacious behavior is not taught in prior art, including in protein cage art.

In one invention embodiment, one or more elements, with or without additional elements, and in some embodiments with minimal functionalization, enter the central nervous system, including passing the blood brain barrier (BBB) for efficacious effect. Although different protein cage types, e.g., viruses, have been investigated as MRI nano-probes, some types of these cages in prior art did not cross the BBB, and other types in prior art were shown to be immunogenic after crossing the BBB.

In one embodiment, the invention enables post administration delivery of one or more types of agents into the CNS in 30 minutes or less. In other embodiments, delivery of agents occurs in 30 minutes or more. In another embodiment, agents operate in the inter-neuronal spaces. Prior art does not teach such flexible CNS delivery arrangements.

The instant invention teaches self-directing, self-replicating, self-adapting, self-repairing, self-regulating, and or self-regenerating methods for one or more minimalist, non-cage elements, which can also perform on-the-fly target prioritization. Prior protein cage art does not teach such self-modifying methods at a minimalist, non-cage element level.

Prior art does not teach enabling and or utilizing quantum mechanical effects using just one or more minimalist, non-cage elements. But in one embodiment, the instant invention teaches enabling and utilizing such quantum mechanical effects.

The instant invention also teaches a plurality of elements of one or more types that can, in one illustrative embodiment, function as biomedical platform and the like, and in another example embodiment, function as a biomolecular component platform and the like, or as an information processing platform that can carry out algorithmically defined actions, and other types of platforms.

Thus, there exists a need for an improved bio-nano-structure element that overcomes the limitations in the prior art for various types of in vivo and in vitro applications.

SUMMARY OF THE INVENTION

The invention, in one aspect, remedies the deficiencies of the prior art by teaching modifiable, interactive, dynamic bio-nanoparticle elements, some of which may comprise minimalist, non-cage embodiments, with or without one or more additional elements of one or more types located on and or in one or more elements; whose applications, in one or more embodiments, focus on forming in whole or in part one or more nanoscale elements and structures of one or more types that execute one or more functions and or effect one or more ends in vivo and or in vitro.

In one illustrative embodiment, the invention is an improvement over other in vivo biodegradable polymer nanospheres, liposomes, lipids, capsids agent delivery systems, as well as endohedral Fullerenes and other bio-nanoparticles in the prior art because the invention enables, among other unique features:

Simplified nanoscale fabrication

Simplified cargo and other element type attachment.

Cell and organelle crossing, and or membrane fusion.

Low antigenic, "green" nanotechnology.

Interaction, control, and regulation of cellular processes, like endocytosis, exocytosis, mitosis, trafficking and signaling, communication between cells, receptor upregulation and downregulation, other cellular behaviors, and the like.

Entering the CNS, including passing the blood brain barrier, and in some cases, in less than 30 minutes post administration.

One or more elements that carry no additional elements, like cargo, and operating alone produce an efficacious effect, acting like a drug, for example.

Hybrid invention elements comprised of one or more types of non-invention elements, e.g., natural cell elements.

Self-modifying, orchestrated actions at a minimalist, non-cage level using natural control laws that govern biological elements.

Methods and behaviors defined by algorithms.

In one particular embodiment, one or more of self-assembling Clathrin and or Coatomer elements are functionalized, modified and or bioengineered using commercially available biotechnology tools and other tools and techniques known in the art, which makes the invention more versatile and cost-effective than the existing art.

In another embodiment, one or more elements are also comprised of one or more non-invention elements, e.g., one or more invention elements are conjugated to natural biological/molecular elements, like cells, but not limited to, forming one or more types of hybrid elements in vitro and or in vivo.

In one illustrative embodiment, one or more elements can be of any suitable size. According to an illustrative embodiment, one or more elements are nanoscale elements.

The invention, in one embodiment, teaches one or more elements that dynamically and interactively respond to changing in vivo and or in vitro environments; e.g., change of pH, temperature, biochemical, or biological conditions, and the like.

In one embodiment, one or more elements, in one or more configurations, utilize self-directing, self-adapting, self-assembling, self-repairing, self-regenerating, self-regulating, and or self-replicating methods.

In one embodiment, one or more elements, in one or more configurations, utilize goal directed methods.

In one embodiment, one or more elements utilize, respond to, and or exhibit one or more effects, such as quantum mechanical, mechanical, photonic, acoustic, electrical, biochemical and chemical, and the like.

The invention, in one embodiment, provides one or more elements that maintain structural and or functional integrity long enough to do useful work, in vivo and or in vitro.

According to one feature, one or more elements re-supply, repair, reassemble and or regenerate defective, destroyed and or inoperable elements of one or more types, including non-invention elements, in vivo and or in vitro.

In another embodiment, one or more types of elements, unlike other nanoparticles in the art; such as nano-carbon, virus capsids, as well as nano-coating elements like polysorbate; may exhibit no or limited immunogenic, toxic, and or environmental impact effects, and depending on cargo and other element type also may require little or no functionalization, In another embodiment, elements maintain structural integrity at room temperature in vitro and vivo, which eliminates the need for elaborate structure stabilizing mechanisms, like cooling systems.

Another advantage of the invention is that its protein material does not exhibit extreme hydrophobicity.

According to another feature, one or more elements are protected from the external environment, and the invention is stable with respect to dissociation and any element toxicity is sequestered from the surrounding in vivo and or in vitro environment.

In some embodiments, bonding and or attachment methods of one or more types, e.g., covalent, non-covalent, and any other bond type that can be explained by quantum theory, are used to directly attach one or more elements, internally or externally to one or more other elements in an ordered arrangement.

In one embodiment, one or more elements each may bond with one or more other elements, of one or more types, including invention and non-invention elements.

In one embodiment, one or more elements may additionally have located on and or in them one or more cargo elements of one or more types, formed from one or more types of molecules.

In another embodiment, the invention features precise, highly ordered placement of additional elements, like cargo elements, with minimal inter-element spacings on one or more elements and structures.

In one embodiment, one or more cargo elements comprise natural, isolated, synthetic and or recombinant elements.

In one embodiment, one or more cargo carrying elements include in whole or in part one or more non-invention elements of one or more types.

In one embodiment, one or more cargo elements and or cargo carrying elements comprise hybrid elements of one or more types.

In one embodiment, one or more elements of one or more types do not carry cargo elements.

In one embodiment, nanoscale ensembles comprising one or more types of elements allow for a large variety and number of possible cargo element configurations.

In one embodiment, one or more elements may additionally have located on and or in them one or more elements such as ligand elements, receptor elements, adaptor protein elements, and the like, formed from one or more types of molecules, which may also comprise one or more hybrid elements formed from one or more non-invention elements.

In another embodiment, one or more elements may be comprised of one or more elements derived in part from one or more types of elements, for example, but not limited to, an amino acid sequence derived from a Clathrin or Coatomer protein.

In another illustrative embodiment, one or more elements, in one or more configurations, are coated in whole or in part with chemicals, metals, biomaterials, and or other substances, of one or more types.

In another illustrative embodiment, one or more elements, in one or more configurations, comprise one or more organic, inorganic, and or synthetic material elements, of one or more types, in one or more forms and or phases, in whole or in part In one embodiment, one or more elements are radiation shielded, radio frequency (RF) shielded, thermally shielded, chemically shielded, and the like, in whole or in part, and in one or more configurations.

In various embodiments, one or more elements may be of more than one functionalization type, and or express more than one type of functionality.

In one embodiment, one or more elements in whole or in part may require minimal or no functionalization to be efficacious elements, like a drug and the like, but not limited to.

In another embodiment, one or more elements in whole or in part comprise one or more structures, of one or more types.

In another embodiment, one or more elements in whole or in part comprise a shape programmable and or shaped scaffolding system via which one or more elements of one or more types form one or more structures with one or more types of shapes and or functions.

In one embodiment, one or more elements act as one or more types of efficacious replacements for one or more other elements, including non-invention elements, in vitro and or in vivo, e.g., act as replacements for one or more natural elements commonly found in cells, but not limited to. This type of replacement functionality is not taught in prior art, including protein cage art.

According to one approach, various self-assembling and self-directed methods are employed. Elements and or their platforms can be formed from the bottom-up, one element at a time. Another advantage of bottom-up fabrication is that it reduces the amount of superfluous material that surrounds each cargo element, reducing the element's exposure to contaminant background radiation and thereby improving the functional effectiveness of the element.

In one embodiment, the instant application teaches one or more nanoscale elements of one or more types formed from isolated, synthetic and or recombinant amino acid residues comprising in whole or in part one or more types of Clathrin and or Coatomer I/II proteins of one or more isoforms, including cloned isoforms. The efficacious elements may comprise minimalist, non-cage forming elements in one or more embodiments. In other embodiments, one or more Clathrin or Coatomer cage elements comprise efficacious elements.

In one embodiment, one or more elements may additionally comprise a hybrid molecular element formed from one or more other types of molecules.

The instant invention teaches that in one or more non-cage element embodiments it features unique types of dynamic properties and capabilities not found in fully self-assembled, cavity-forming cage structures as taught in the prior art.

In one embodiment, an element is comprised of one or more 3-legged triskelia, each triskelion having 6 protein subunits; 3 Clathrin heavy and 3 light chain subunits. In another example embodiment, the instant invention teaches one or more configurations as being comprised of only 3 Clathrin heavy subunits or only 3 light chain subunits. In another illustrative embodiment, configurations comprised of less than 3 Clathrin heavy or 3 light chain subunits are enabled. In another embodiment, the invention teaches elements comprising in part one or more types of Clathrin and or Coatomer I/II proteins of one or more isoforms Likewise, the invention teaches one or more highly flexible element embodiments formed from Coatomer I/II proteins. In one embodiment, one or more nanoscale elements of one or more types are formed from isolated, synthetic and or recombinant amino acid residues comprising in whole or in part one or more types of Coatomer I/II proteins of one or more isoforms, including cloned isoforms. Components of both COP1 and Clathrin-adaptor coats share the same structure and the same motif-based cargo recognition and accessory factor recruitment mechanisms, which leads to insights on conserved aspects of coat recruitment, polymerization and membrane deformation. These themes point to the way in which evolutionarily conserved features underpin these diverse cell pathways.

In one example embodiment, one or more elements comprised of Coatomer (COPI and COPII) proteins, which can efficaciously act alone or with additional elements, are used instead of Clathrin proteins, preferably in those applications where Coatomer characteristics would be more desirable than those of Clathrin. Coatomer I/II protein elements may, in one or more embodiments, be comprised of one or more alpha, beta, beta', gamma, delta, epsilon and or zeta subunits. Different combinations of these subunits are known to exist within Coatomer complexes. According to an illustrative embodiment, a Coatomer subunit is a nanoscale element. In one invention embodiment, Clathrin and Coatomer elements and one or more methods may be used together in one or more configurations, taking advantage of their respective capabilities.

Freed from the constraints of only assembling into cavity forming cages in vitro, one or more non-cage elements of one or more types may self-assemble into one or more other types of complex elements and or material forms, enabling new classes of applications. For example, but not limited to, using techniques known in the art, bioengineered strands of Clathrin and or Coatomer proteins form functionalized nano-tubules (Zhang, et al. 2007) for biomedical applications and bio-molecular components. In another bioengineered embodiment, invention elements comprise repeatedly branched, highly symmetrical structures, forming protein-based nano-dendrimers suitable for biomedical and bio-molecular applications. In another embodiment, self-assembling, stable, bioactive, protein-based, hydrogel nanoparticles (i.e., nanogels), some with tunable structural properties, are enabled. Generally, hydrogels are of interest to the biomedical field, e.g., for treating trauma, because the hydrated networks can provide a physiological environment where biological species can survive or grow. In other embodiments, one or more other types of non-cage forming structures, elements, and forms of materials comprised of invention elements are formed using techniques known in the art.

Unlike cage, cavity, and vesicle systems in the prior art where one or more additional elements, e.g., cargo, are inserted into a complex, fully formed structure; a sometimes difficult and laborious process; the invention, in one embodiment, teaches that it can be functionalized with one or more additional elements at a much more fundamental nano-element level, e.g., by using non-cage elements of one or more types formed from amino acid residues of Clathrin or Coatomer proteins. Such functionalized, minimalist elements may further self-assemble in vitro into one or more nanoscale structure elements, including cages. This makes the addition of one or more elements easier and simpler as there is no insertion process into a completely formed cage, cavity, or vesicle. In another embodiment, additional element functionalization is simplified by decorating just the external surface of a cage.

According to one illustrative configuration, one or more types of elements, such as cargo elements, may interfere with the invention's overall operation if carried in the same element as other element types. Instead, the problematic elements are carried in a separate element that exclusively carries non-interfering elements, thereby inhibiting disruptive interference of invention operations. Such non-interfering elements may be functionally and or physically linked with other elements carrying other element types.

In one embodiment, one or more elements efficaciously operate alone and carry no additional elements, e.g., cargo. In one embodiment, such solo element functionality produces a unique new type of efficacious element, and its unique features correspondingly enable new types of applications.

Some embodiments include a molecule having an unpaired electron, a transition metal ion, which can be found in the active centers of many proteins (metalloproteins), or a material having any defect that produces an unpaired electron.

According to one in vivo application for enhanced medical imaging, paramagnetic lanthanide, transition metal ion complexes, and the like are cargo elements that modify the NMR relaxation times of nearby proton nuclei of H2O molecules, leading to brighter images and enhanced contrast between areas comprising the contrast agent and the surrounding tissues.

In another illustrative embodiment, one or more elements accept free radical molecules such as nitroxide molecule spin labels for electron paramagnetic resonance (EPR) based invention applications.

In another illustrative embodiment, one or more elements accept and or comprise one or more types of labels and assay strategies, and instruments for detection of one or more such labeled and or assay elements may include, but are not limited to: fluorescence and confocal microscopy, flow cytometry, laser scanning cytometry, fluorescence microplate analysis and biochips, immunoassay systems, nucleic acid-based diagnostics, and the like. In various embodiments, one or more elements meet and or surpass the requirements for label and assay sensitivity, accuracy and convenience.

In another embodiment, one or more types of elements such as comprising in whole or in part one or more large molecule elements, small molecule elements, cargo elements, agent elements, device elements, drug elements, and the like, enter the CNS, including passing the blood brain barrier, in 30 minutes or less and or in 30 minutes or more, post administration, and, depending on cargo and other element type, may require minimal functionalization for such element passage.

In some configurations, one or more elements comprise a cargo element, while in other configurations they comprise multiple elements, of one or more types. In some configurations, one or more or each of the elements and or cargo elements is a metal, and or may include one or more metals. Alternatively, each of the elements and or cargo elements is or includes non-metal elements. In other embodiments, elements and or cargo elements are exclusively non-metal elements that may include gases, as well as other elements like biological elements, drugs, optics, polymers, etc. In another embodiment, one or more elements and or additional elements comprise one or more types of material forms, including a solid, gas, vapor, crystal, and the like. In another embodiment one or more invention and or non-invention elements, in one or more combinations, comprise one or more types of isolated, synthetic and or recombinant elements.

An invention element, in one functionalized configuration, includes receptor molecules; natural, isolated, synthetic and or recombinant, for capturing and ordering the placement of one or more elements, like cargo elements, on one or more elements.

An invention element, in another functionalized configuration, includes adapter molecules; natural, isolated, synthetic and or recombinant, disposed between the receptor molecules and one or more elements to couple the receptor molecules to another element, like to a cargo element.

An invention element, in one functionalized configuration features ligands, natural, isolated, synthetic and or recombinant, including drugs, of one more types attached to receptors and or adapter protein elements.

In one configuration, one or more elements, of one or more types, are attached to one or more types of amino acids on one or more elements.

In another configuration, biotin-avidin is used as a coupler of one or more elements, of one or more types, to one or more elements of one or more types.

In another configurations, PEGylation, a cross-linker, molecular bridge, molecular tether, and the like are used to attach one or more elements, of one or more types, to one or more elements of one or more types.

In one example, molecules of one or more types are attached to a short molecular tether to one or more elements via site directed substitution mutagenesis, followed by reaction of a unique amino acid group with a specific molecular label.

In another embodiment, free radicals, toxic elements, other types of undesirable elements and the like circulating within an in vivo environment are scavenged via molecular tethers, via other elements of one or more types attached to one or more invention elements, and or via direct binding to one or more elements.

In another embodiment, the invention takes full advantage of protein flexibility and plasticity to create elements of one or more types that are bonded, fastened, fused, and or affixed to one or more other elements, of one or more types.

In one illustrative embodiment, one or more elements and or bonded elements are coated in whole or in part with other elements, such as chemical, biological and or metallic materials, and the like. The coating elements may be or include organic, inorganic, and or synthetic materials, or a combination thereof.

In another invention embodiment, site directed mutagenesis is used to incorporate one or more elements, of one or more types, into one or more other elements, of one or more types.

In one embodiment site-directed mutagenesis using one or more types of primer; including its reverse complement; are used to insert one or more DNA sequences of one or more types into one or more coding regions of one or more elements.

In another embodiment, cloning is done of one or more genes encoding one or more elements. In another embodiment, one or more amino acids and or their encoder gene are controlled, regulated, modified, and the like, by one or more methods known in the art to produce an efficacious effect, in vivo and or in vitro.

In one embodiment, one or more elements of one or more types comprise targeted and or non-targeted drug elements, biological elements, other forms of healthcare elements, including cosmetic elements, in one or more configurations or combinations, for diagnosing, remedying, inhibiting, mitigating, curing, and or preventing one or more types of diseases, infections, physical or mental trauma, other forms of physical and mental afflictions, and the like, of one or more types, including types featuring minimal immunogenic and or toxic effects.

In one embodiment, one or more elements are used as a means for evaluating drug advancement and efficacy.

The invention teaches a biological model and or method that is consistent from a minimalist component level up, e.g., amino acid residues comprising in part one or more Clathrin and or Coatomer I/II proteins of one or more isoforms, making drug discovery safer, more efficacious, more time and cost effective, and overall, a much more rapid process.

In one personalized medicine embodiment, the invention reduces drug side effect profiles and or produces greater agent efficacy, as well as excludes agents that may have no efficacy in a particular individual. The invention, in one embodiment, provides for individual patient factors such as genotype, phenotype, age, gender, ethnicity etc., to be taken into account by one or more elements and factored into dosing and administration consideration.

In one embodiment, one or more elements comprise one or more types of pluripotent stem cells and or comprise one or more stem cell delivery methods.

According to one feature, one or more elements may be or include one or more research, therapeutic, diagnostic, vaccine, assay, and or prosthetic agents, in one or more configurations, and thereby constitute one or more types of biomedical elements. Such biomedical elements may be, for example, nano-structured and/or include chemical, biological and/or metallic materials. The biomedical elements may be or include organic, inorganic, and or synthetic materials, or a combination thereof.

Medical, biomedical, bioengineered, and or biological applications and platforms of the instant invention may include, but are not limited to, imaging; sensor; genetic and protein assay; diagnostic; drugs and drug delivery; prosthetic; inter- and extra-cellular tissue; whole organ; circulatory system; medical device; implantable defibrillator; pacemaker; coronary stents; angioplasty device; and other like applications.

In one embodiment, one or more elements comprise one or more applications that perform analysis, of one or more types, of disorders of complex inheritance.

In one embodiment, one or more elements comprise one or more applications that perform analysis, of one or more types, of pharmacologic therapy.

In one embodiment, one or more elements comprise one or more types of prognosis and therapy selection—"thera-diagnostics".

In one embodiment, one or more elements comprise one or more genomic applications of one or more types.

In one embodiment, one or more elements comprise one or more oncology applications of one or more types.

In one or more embodiments, one or more elements may use routes of administration comprising one or methods of one or more types, such as those defined by CDER Data Element Number C-DRG-00301 in the US FDA Data Standards manual. Routes of in vitro administration of one or more elements may also comprise one or more forms.

In one or more embodiments, one or more pharmaceutical and drug formulations of one or more types are used, in whole or in part, such as tablet, capsule, soft galantine capsule, topical, injections, eye drops, syrups and liquids, soap and cosmetics, birth control device, and the like, but not limited to, as well as one or more types of biologics, chemical compounds, water soluble compositions, and the like, but not limited to. In vitro formulations may also comprise one or more formulations of one or more types in one or more embodiments.

According to one feature, one or more elements respond to one or more external and/or internal stimuli, which can be, for example, mechanical, chemical, biochemical, biological, metabolic, covalent, non-covalent, photonic, sonic, acoustical, thermal, fluidic, electromagnetic, magnetic, radioactive, quantum mechanical, or electrical in nature. Examples of such a stimulus response is altering a cargo element carried by an element; the altering of the element itself; causing changes in cellular process like endocytosis, exocytosis, mitosis, trafficking and signaling, and the like, including other conformational changes.

In another embodiment, photonic energy impacting one or more elements produces electrical current, and or photonic energy, e.g., a laser.

In general, in another embodiment, one or more element and or platform are physically and/or functionally cooperative with other suitable types or forms of elements, agents, organisms, materials, substances, components, devices, and or systems, including non-invention elements, in vitro and/or in vivo.

The invention, in one embodiment, provides for a plurality of elements comprising aggregated, complex self-assembled nanoscale structures that dynamically bind together one or more types of endogenous, exogenous, homogeneous, and or heterogeneous elements into one or more complex elements, which also may have one or more payload types.

The invention, in one embodiment, provides a capability for in vivo and in vitro integration of one or more types of elements into other elements, devices and mechanisms, some of which may also be non-invention elements, that also may be linked together functionally or logically, including with other devices and or operators, locally or at a distance, significantly enhancing the overall capabilities of the invention.

In one embodiment, the invention provides for the ability of one or more elements to track, recognize, attack and or destroy multiple targets on the fly, in vivo and in vitro, using dynamic target prioritization for a single element type and or multiple element types.

In one application, one or more elements, including cargo elements, comprise one or more types of targeted agent delivery systems and or agents in vivo or in vitro, including high precision dosing, using, as appropriate, ligands, targeting moieties, and or other vectors. In one application, one or more targeted elements comprise one or more research, remedial, inhibitory, mitigation, preventive, prosthetic, assay, and or other type of bio-molecular agent or device, in one or more combinations, and may altogether comprise a unified element and or platform.

The invention, in one embodiment, provides for a method for targeted delivery systems that leverage and utilize biological control laws and that may act as self-directed systems.

According to another invention embodiment, one or more targeted elements may use molecular-imprint technology, which is used for the production of molecule-specific cavities that mimic the behavior of receptor binding sites, without the temperature sensitivity of natural systems.

According to another feature, biodegradable films may also be used as a pliable template for one or more targeted elements, which are pressed into a biodegradable film and then removed, leaving a physical mold of the element's shape. The film can then be hardened and used by an element to detect a particular element, which may be, but is not limited to, a particular receptor, protein, or cell, since its complex imprint shape on the film will bind only to that particular biological element.

In one embodiment, the invention provides for a targeting system using biodegradable nanocapsules for delivery of one or more elements in vivo or in vitro.

In another application, a nanoscale platform comprised of a plurality of elements performs molecular-level and or cellular-level target site loitering, monitoring, repair, construction and or dynamic, interactive control and regulation of biological systems, in vitro and in vivo.

In another embodiment, one or more elements, including in whole or in part one or more non-invention elements, operating alone or with one or more additional elements, comprise one or more types of membrane fusion elements. In one embodiment, the resulting biological processes and interactions from such fusion may lead to a series of controlled, regulated, extended, modulated, purposefully, and or self-directed methods and or behaviors of elements.

In one example embodiment, one or more elements in whole or in part execute one or more types of actions involving conformational changes, bonding, attachment, and or the fusion of one or more elements to a cell membrane, one or more of which actions may lead to changes in cellular processes, such as endocytosis, exocytosis mitosis, trafficking and signaling, and the like, and or enable the precise dispatch and sequenced delivery of selected agents from an element to a target cell. Alternatively, a series of interlocking steps between a part of a cell membrane, and all, or a subset of the materials comprising an element may cause the cessation of one or more element's delivery to a target cell, and or enable delivery from other sources.

In another configuration, one or more elements dynamically respond to natural environmental conditions and manifest special functions. The various control laws that regulate biochemical reactions and physiological processes often display features that allow biomolecules or biological structures to perform more tasks than are reasonably expected from a simple mechanical device. In one embodiment, the invention takes deliberate advantage of these biological control laws. Via the use of bio- and genetic engineering methods known in the art, the invention makes use of these control laws to dynamically regulate complex in vivo and in vitro biochemical reactions and physiological processes. An example of biological control laws at work is the automatic self-directed, self-assembly of in vitro and in vivo Clathrin and Coatomer proteins.

In one embodiment, intramolecular dynamics of biomolecules and the concerted and interlocking steps of conformational changes lead to deliberately purposeful actions. For example, one or more elements may fit spatially and each step in a process fits temporally (kinetically) with an element of anticipation of the purposeful outcome.

In another example case, the spatially and temporally defined events between the cell and one or more elements may cause the invention to release diagnostic and monitoring agents to determine the most appropriate course of therapeutic action. The calculated utilization of biological control laws by one or more elements may, for example, provide for a sophisticated drug delivery system that provides optimal dosing by altering its drug delivery behavior, as well as producing minimal side effect profiles.

A further advantage of the invention is that it provides elements that can be bioengineered to prevent in vivo uptake by one or more types of organs, tissue, cells, and bone. In the converse, another advantage is that one or more elements can be bioengineered for highly selective uptake by one or more types of targeted cells, tissue, organs, bone, as well as by other organic and inorganic matter. In another embodiment, one or more elements comprise a non-selective uptake, non-targeted drug delivery system.

In another embodiment, the invention provides for the ability of one or more elements to intelligently monitor, control and regulate, react, and further adjust biological processes after delivery of the payload, enabling high precision dosing.

Another advantage of the invention is that Clathrin can cross cell membranes including the blood brain barrier (Gragera et al 1993) and can move through the synaptic clefts (Granseth et al 2007). In one embodiment, bioengineered Clathrin actively transports substances in and out of cells including neurons and blood brain barrier cells.

In another embodiment, one or more elements, operating alone or with one or more additional elements, comprise one or more types of cell membrane crossing elements and gain access to the cytosol and intracellular elements of one or more types, including one or more cell organelles. Such elements may, in one embodiment, require minimal functionalization to cross the cell membrane and or enter a cell organelle.

In one embodiment, one or more elements, in whole or in part, in one or more combinations, take one or more actions to create, spawn, comprise, modify, regenerate, reassemble, and or control and regulate one or more cells, cellular elements and or cellular processes of one or more types.

In one embodiment, one or more elements, in whole or in part, in one or more combinations, take one or more actions to rectify and or repair failures and defects in cellular processes, such as, endocytosis, exocytosis, mitosis, trafficking and signaling, and the like. Such failures and defects can lead to diseases, for example, cancer.

In one embodiment, one or more elements comprise in situ in vivo elements for remediation, removal and or sequestration of one or more types of contaminants, toxins, undesired organic or inorganic elements, and the like.

In one embodiment, one or more elements comprise in situ environmental elements for remediation, removal and or sequestration of one or more types of in vitro environmental contaminants and or toxins; for example, chlorinated solvents TCE, PCE, PCBs, c-DCE, DNAPL, heavy metals (chromium), biofilm, synthetic chemicals, and the like.

In one embodiment, some or all elements may also operate under the control and influence of other in vitro and or in vivo elements, including non-invention elements, and altogether may comprise a scalable, nanoscale platform.

In general, in another aspect, the invention is directed to a method of forming one or more types of scalable platforms, including the steps of providing one or more embodiments of the elements to deliberately carry out a series of tasks of one or more types, which tasks and or methods may be externally directed or internally self-directed, or a combination thereof. In other embodiments, one or more nanoscale platforms may be additionally comprised of one or more non-invention elements and platforms of one or more types.

One or more elements, in one platform embodiment, may also modify, process, manipulate, encode and decode, input, output, transmit, communicate, store and or read information using techniques and methods known in the art, in vivo and in vitro.

In one embodiment, scalable information processing platforms use some or all elements as bits that are programmable into a plurality of logical states. In another configuration, the invention features a scalable information-processing platform that may include one or more elements.

As a general characteristic, one or more elements may take any suitable form, and multiple embodiments may be used as elements, and or further combined in any suitable manner to create one or more cargo carrying and or non-cargo carrying nanoscale elements ("elements"), and or multifunction nanoscale platforms ("platforms") of one or more types, operating in vitro and or in vivo, such as: multiple polypeptide elements and platforms; biological elements and platforms; large molecule elements and platforms; small molecule elements and platforms; biomedical elements and platforms; medical elements and platforms; diagnosis, cure, mitigation, treatment, prevention of disease or other type of drug elements and platforms; targeted and or non-targeted delivery elements and platforms; cell, cell organelles, or cell material crossing elements and platforms; personal medicine elements and platforms; elements and platforms that, post administration, in whole or in part enter the central nervous system, including passing the blood brain barrier in 30 minutes or less and or in 30 minutes or more; healthcare elements and platforms; reproductive health elements and platforms; substance abuse disorder treatment elements and platform; bioengineered elements and platforms; cosmetic elements and platforms; agricultural elements and platforms; sensor elements and platforms; research and development elements and platforms; scientific elements and platforms; crystal elements and platforms; electronic elements and platforms; photonic energy elements and platforms; information processing or storage elements and platforms; energy storage elements and platforms; in situ elements and platforms for remediation, removal and or sequestration of undesirable elements and platforms of one or more types; quantum mechanical elements and platforms; telecommunication elements and platforms; and the like; one or more of which nanoscale elements and platforms may be additionally comprised of one or more non-invention elements and platforms of one or more types, and with or without one or more types of cargo elements located on and or in one or all or a subset of elements.

In general, in a further aspect, the invention is directed to a method of forming one or more formations of nanoscale elements formed in vitro from one or more elements of one or more types formed from isolated, synthetic and or recombinant amino acid residues comprising in whole or in part one or more types of Clathrin and or Coatomer I/II proteins of one or more isoforms, including cloned isoforms; with or without one or more additional elements of one or more types located on and or in one or more elements; forming in whole or in part one or more types of element carrying and or non-element carrying nanoscale elements and structures; one or more of which elements may also comprise one or more non-invention elements of one or more types, forming hybrid elements; wherein one or more elements, using one or more types of methods, executes one or more functions and or effects one or more ends in vivo and or in vitro.

BRIEF DESCRIPTION OF THE DRAWINGS

The foregoing and other aspects of the invention may be more fully understood from the following description, when read together with the accompanying drawings in which like reference numbers indicate like parts.

DESCRIPTION OF THE ILLUSTRATIVE EMBODIMENTS

The instant invention is comprised of one or more formations of nanoscale elements formed in vitro from one or more elements of one or more types formed from isolated, synthetic and or recombinant amino acid residues comprising in whole or in part one or more types of Clathrin and or Coatomer I/II proteins of one or more isoforms, including cloned isoforms, and which operate in vitro and or in vivo. In one embodiment, one or more elements form one or more configurations of one or more types, described below.

Figure 1:
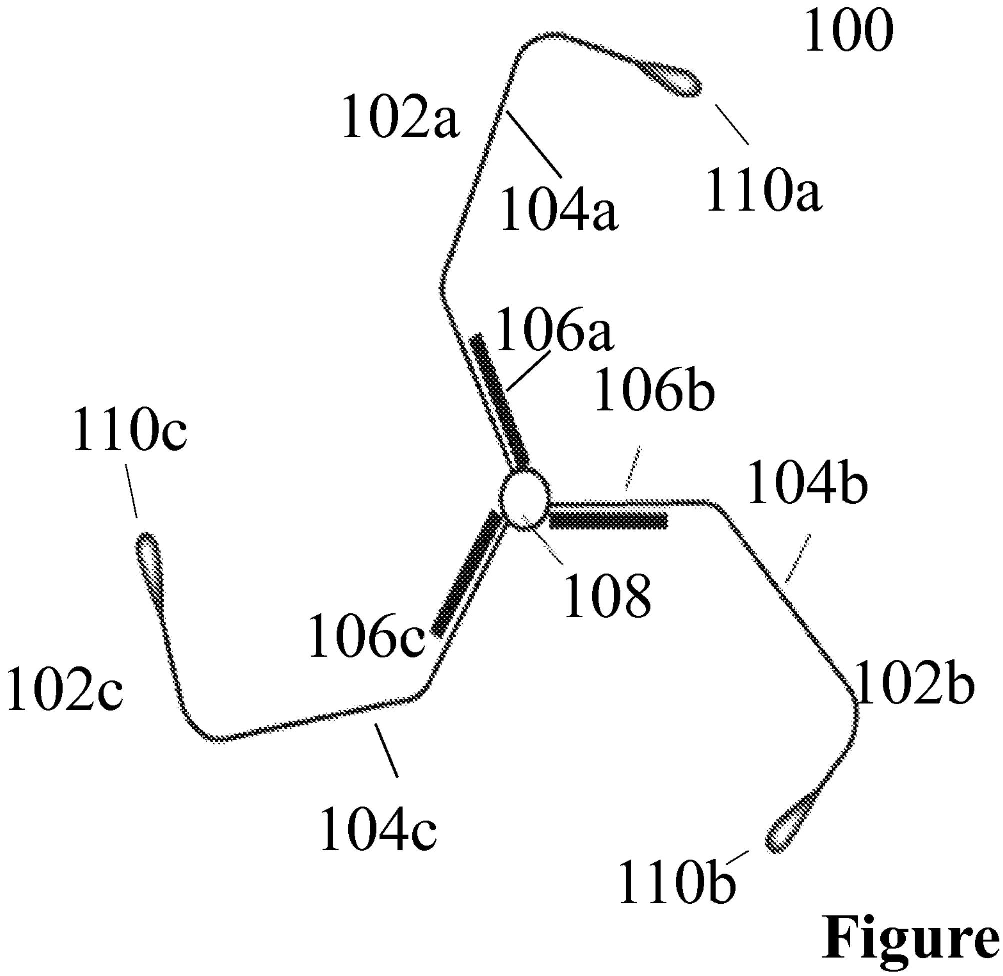
FIG. 1 is a conceptual diagram depicting a Clathrin triskelion comprised of one or more elements of one or more types employed in an illustrative embodiment of the invention.

FIG. 1 is a conceptual diagram illustrating the basic unit of Clathrin, a three-leg pinwheel protein structure, and each complete leg is typically called a 'monomer'. The arrangement of the monomers in the three-dimensional protein is the quaternary structure. Each Clathrin leg monomer is further comprised of two subunits, one 190 kDa subunit ("heavy chain") and one 24-27 kDa subunit ("light chain"). Three, two-subunit Clathrin monomers self-assemble and combine to create triskelion element 100. It is this triskelion morphology that allows Clathrin to form its unique polyhedral network.

In FIG. 1, the assembled triskelion element 100 is comprised of three monomer leg elements 102*a*-102*c*. The three leg elements 102*a*-102*c* extend radially from a hub section 108. The filamentous portion of Clathrin triskelion legs 102*a*-102*c* is formed by a continuous superhelix. A naturally occurring Clathrin leg is about 47.5 nm (475 Å) long. In the instant invention, Clathrin leg length and or molecular weights can be modified and or adjusted by using bioengineering techniques known in the art.

In the case of humans, there are two isoforms each of Clathrin heavy chain (CHC17 and CHC22) and light chain (LCa and LCb) subunits, all encoded by separate genes. CHC17 forms the ubiquitous Clathrin-coated vesicles that mediate membrane traffic. CHC22 is implicated in specialized membrane organization in skeletal muscle. CHC17 is bound and regulated by LCa and LCb, whereas CHC22 does not functionally interact with either light chain.

In one embodiment, a Clathrin triskelion is composed of a trimer of heavy chains 104*a*-104*c* each bound to a single light chain 106*a*-106*c*, respectively. In the case of one isoform embodiment, CHC17 (SEQ ID NO:1), a Clathrin heavy chain element is comprised of a 1675 amino acid residue protein, which is encoded by a gene consisting of 32 exons. In the case of another isoform embodiment, CHC22, a Clathrin heavy chain element is comprised of a 1640 amino acid residue protein (SEQ ID NO:2).

In one or more invention embodiments, efficacious elements formed in part from Clathrin amino acid residues include, but are not limited to, a N-terminal globular domain 110*a*-110*c* (residues 1-494) that interacts with adaptor proteins (e.g., AP-1, AP-2, b-arrestin), a light chain-binding region (residues 1074-1552), and a trimerization domain (residues 1550-1600) near the C-terminus.

One or more of the Clathrin heavy chain amino acid sequences as described in SEQ ID NO:1 and SEQ ID NO:2, but not limited to, and in whole or in part may be modified, altered, adapted or functionalized in one or more ways in one or more embodiments of the invention.

In the illustration, the three Clathrin monomer elements 102*a*-102*c* are comprised of six subunit elements, three of which subunits are the heavy chain subunit elements 104*a*-104*c*. The three heavy chain subunits are comprised of several distinct domains and segments, one or more of which may comprise one or more invention elements in one or more embodiments, and may be functionalized via one or more techniques known in the art.

In general, each heavy chain comprises eight repeated motifs (CHCR 0-7), which make up the proximal, knee, distal and ankle segments of a Clathrin leg. The heavy-chain amino terminus folds into the terminal domain (TD) and is attached to CHCR0 by a helical linker. (Brodsky, 2004). The three Clathrin heavy chains are joined at their C-termini (located within hub element 108), extending into proximal and distal leg domains ending in globular N-terminal domain elements 110*a*-110*c*, and which are responsible for peptide binding. The Clathrin heavy chain terminal domains provide multiple interaction sites for a variety of adaptor proteins (AP) that can bind multiple receptors occupied by ligands. These sites prevent chemical interactions between cargo elements. The heavy chain N-terminal domain elements 110*a*-110*c* are each comprised of a seven-bladed beta-propeller connected to a flexible linker region, respectively. This propeller domain interacts with a host of accessory proteins participating in receptor-mediated endocytosis such as adaptor proteins, non-visual arrestins and the uncoating ATPase, hsc70. The propeller domain is followed by a long filamentous segment, which is interrupted by a bent region between the distal and proximal domains, and ends in the trimerization domain at the C-terminus.

Besides harboring determinants important for driving the association of individual Clathrin molecules during lattice formation, each of the three heavy chain 104*a*-104*c* proximal domains also include binding sites for attaching the three light chain subunit elements 106*a*-106*c*, respectively, forming three complete Clathrin monomers. The three light chain subunits are also comprised of several distinct domains and segments, one or more of which may comprise one or more invention elements in one or more embodiments, and may be functionalized via one or more techniques known in the art.

Among other roles, Clathrin light chains prevent Clathrin heavy chains from interacting with each other. On the other hand, assembly proteins bind to light chains and cause a change in them such that they no longer prevent heavy chains from interacting. Clathrin light chains consist of what has been described as a linear array of domains: regions of protein discernable from the primary sequence or with distinct biochemical properties. These are an N-terminal segment, a region that is 100% conserved between light chains, a portion to which Hsc70 binds, a calcium binding domain, a region which binds the heavy chain, a site for neuronal-specific splice inserts and then finally a calmodulin-binding domain at the C-terminus domain (Royle, 2006). The light chain C-terminal residues are also important for enhancing the in vitro assembly of hub 108 at low pH.

One or more of the Clathrin light chain amino acid sequences as described in SEQ ID NO:12 and SEQ ID NO:13 but not limited to, and in whole or in part may be modified, altered, adapted or functionalized in one or more ways in one or more embodiments of the invention.

In one embodiment, each of the 3 heavy chain subunits 104*a*-104*c* may each have 3 light chains subunits 106*a*-106*c* attached, respectively, forming the typical, three-monomer Clathrin triskelion structure. But in another embodiment, each leg 102*a*-102*c* may include only the 3 Clathrin heavy chain subunits 104*a*-104*c*, respectively, which is distinctly unique from the classic Clathrin monomer configuration. In yet another unique embodiment, only 3, non-attached light chain subunits 106*a*-106*c* are used.

In one distinctive embodiment of the invention, a 3-legged pinwheel configuration 100 is not enabled, and only partial pinwheel structures are used. In one embodiment, a partial pinwheel configuration of one or two legs (one or two Clathrin monomers) is comprised of one or two Clathrin heavy chains and one or two corresponding light chain subunits. In another embodiment, one or two elements comprised of only one or two Clathrin heavy chain subunits are used; e.g., subunits 102*a*, or 102*a*-102*b*. In one embodiment, only one or two unattached light chain subunits are used.

In another distinctive embodiment of the invention, one or more elements of one or more types are formed from isolated, synthetic and or recombinant amino acid residues comprising in part one or more types of Clathrin heavy chain and or light chain proteins of one or more isoforms as described in SEQ ID NO:1, SEQ ID NO:2, SEQ ID NO:12 and SEQ ID NO:13, respectively.

In one embodiment, one or more N-terminal domain elements, e.g., 110*a*, 110*b* and or 110*c* are bioengineered to facilitate, modify, regulate or control peptide binding of one or more types, as well as interaction sites for one or more types of adaptor proteins.

In one embodiment, one or more domain elements of heavy chain subunits and or light chain subunits are bioengineered to facilitate, modify, regulate or control one or more Clathrin protein characteristics and or behaviors in vivo and or in vitro.

Figure 2:
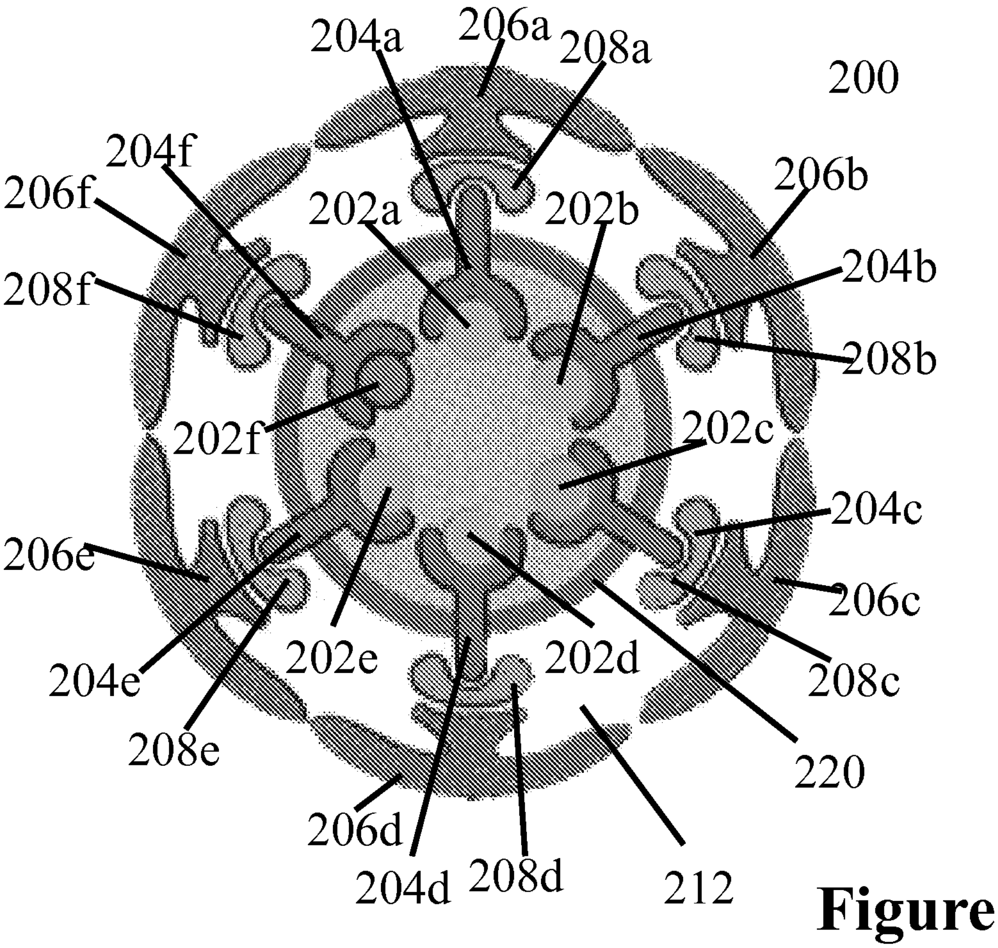
FIG. 2 is a conceptual cross-sectional view of one or more Clathrin protein, receptor, adaptor protein, and cargo elements in an illustrative embodiment.

FIG. 2 is a conceptual cross-sectional view of a biological endohedral consisting of Clathrin protein elements. In this illustrative embodiment, one or more elements 102*a*-102*c*, 106*a*-106*c*, 104*a*-104*c*, 110*a*-110*c*, element 108, and or one or more types of elements formed from isolated, synthetic and or recombinant amino acid residues comprising in whole or in part one or more Clathrin proteins of one or more isoforms, and with or without one or more additional elements of one or more types, may comprise one or more multiple polypeptide elements of one more types. The latter are labeled in FIG. 2 as elements 206*a*, 204*a*, 202*a*, and 208*a*, which are formed in vitro, and also may operate in vitro and or in vivo. One or more of elements 206*a*, 204*a*, 202*a*, and or 208*a* may comprise one or more types of functionalization, include invention and non-invention elements, express one or more types of functionality, and or form one or more types of structures.

In one illustrative embodiment, but not limited to, one or more elements 206*a* may comprise one or more elements 102*a*-102*c*, 106*a*-106*c*, 104*a*-104*c*, 110*a*-110*c*, element 108, and or one or more types of elements formed from isolated, synthetic and or recombinant amino acid residues comprising in whole or in part one or more Clathrin proteins of one or more isoforms, and express one or more types of functionality in one or more embodiments.

In another embodiment, one or more elements 206*a* may be comprised of, and or help comprise one or more types of non-invention elements, such as a natural cell element in one embodiment, comprising one or more types of hybrid elements in one or more embodiments.

In another embodiment, one or more elements 206*a* may be comprised of, and or help comprise one or more types of isolated, synthetic, recombinant and or natural molecules in one or more embodiments.

In one illustrative embodiment, but not limited to, one or more elements 202*a* may comprise cargo elements of one or more types, including natural, isolated, synthetic and or recombinant, including natural and or synthetic ligands and or drugs, and may express more than one type of functionality. In one embodiment, one or more other elements, of one or more types, including invention and non-invention elements each may bond with one or more respective cargo elements 202*a*.

In one embodiment, one or more cargo elements 202*a* are cavity forming and are non-permeable, semi-permeable, and or permeable, and or can change from one permeable state to another. In one embodiment, the cavity forming elements comprise one or more types of elements and or agents, including gas, vapor or fluid, with or without dopants. In one embodiment, one or more cargo cavities elements comprise one or more types of elements and or agents, including one or more types of metals.

In another illustrative embodiment, one or more efficacious cargo elements 202*a* carried on one or more elements may comprise the total functionality. In another embodiment, one or more other elements, of one or more types, including invention and non-invention elements may act in concert with one or more cargo elements 202*a* to achieve ensemble efficacy.

In one embodiment, but not limited to, one or more elements 204*a* may comprise attachment and or receptor elements for one or more elements 202*a* of one or more type, and or express more than one type of functionality. In one embodiment, one or more other elements, of one or more types, including invention and non-invention elements each may bond with one or more respective elements 204*a*. In another embodiment, receptor molecules 204*a* can be bioengineered to recognize and associate with specific molecules, which may also be synthetic and or natural ligands and or drugs. In another embodiment, receptor molecules 204*a* can be natural, isolated, synthetic and or recombinant.

In one embodiment, but not limited to, one or more elements 208*a* of the instant invention may comprise the major types of adaptor elements, like the heterotetrameric adaptor protein (AP) elements, and the monomeric GGA (Golgi-localizing, Gamma-adaptin ear domain homology, ARF-binding proteins) adaptors. In one illustrative embodiment, elements 208*a* comprise one or more small sigma subunits of various adaptins from different AP adaptor elements. The AP complex family has six members in mammals: AP-1A, AP-2, AP-3A and AP-4 are ubiquitously expressed. The other two members, AP-5 and AP-6, are cell-type specific isoforms of AP-1A and AP-3A: the epithelium-specific AP-1B and the neuron-restricted AP-3B. (Ohno, 2006). In another embodiment, AP180, like AP-2 and AP-3, binds to N-terminal domains 110*a*-110*c* of Clathrin. In one embodiment, one or more AP elements may be functionalized at one or more heavy chain terminal domain elements 110*a*-110*c*. In one embodiment, one or more other elements, of one or more types, including invention and non-invention elements each may bond with one or more respective elements 208*a*. In another embodiment, adapter molecules 208*a* are bioengineered to recognize specific receptor molecules and to couple the receptor molecules to Clathrin and or Coatomer protein elements. In another embodiment, adapter molecules 208*a* can be natural, isolated, synthetic and or recombinant.

In one embodiment, one or more elements 206*a*, 204*a*, and or 208*a* operate alone without cargo element 202*a*, and comprise one or more types of inherently efficacious solo acting elements.

In one embodiment, unlike prior Clathrin art, a plurality of elements 206*a*, 204*a*, and or 208*a* operate without cargo elements 202*a*, and comprise an inherently efficacious cage element 212 of one or more types, like a drug element, for example, which is unlike prior Clathrin art.

In one embodiment, also unlike prior Clathrin art, a plurality of elements 206*a*, with or without one or more additional other elements comprise cage element 212, and element 212 has one or more elements, of one or more types and affixed via one or methods, located on the outside part of cage element 212; that is, located outside the cavity formed by cage 212. In another embodiment, further unlike prior Clathrin art, a plurality of elements 206*a*, with or without one or more additional other elements, comprise cage element 212, and element 212 has one or more elements, of one or more types and affixed via one or methods, located on both the outside, and inside parts (i.e., located within the cage cavity), of cage element 212.

According to one invention feature, cargo attachment element 204*a* and or element 208*a* shields cargo element 202*a* in the same element 206*a* from interacting. According to another feature, the shielding properties of element 206*a* shields and inhibits chemical and molecular interactions between it and the external environment. According to a further feature, element 206*a* protectively sequesters cargo elements 202*a* from the external environment.

In another embodiment, one or more non-invention, "natural" Clathrin elements 206*b*-206*f* (the term "natural" hereinafter generally refers to non-isolated, non-recombinant, and non-synthetic protein elements) join with one or more isolated, recombinant, and or synthetic elements; in this example, 206*a*; to form a natural/invention hybrid Clathrin cage element 212. In another embodiment, hybrid cage element 212 may also be comprised of natural cage element 220, which is a vesicle, forming a hybrid Clathrin Coated Vesicle.

Figure 3:
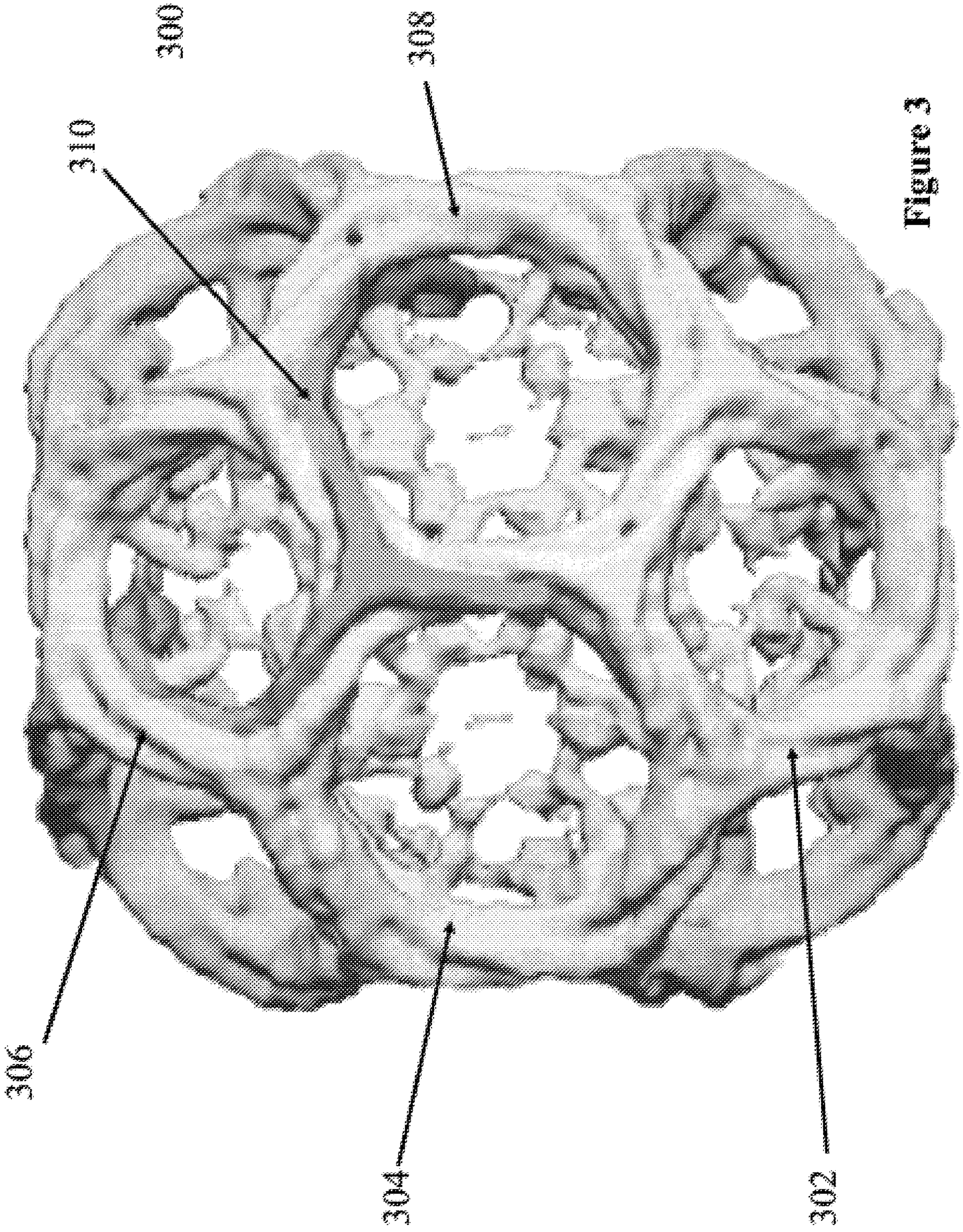
FIG. 3 is a computer generated frontal view of an actual Clathrin cage comprised of a plurality of Clathrin triskelia, and, in an illustrative embodiment, comprising one or more invention elements.

FIG. 3 is a computer generated frontal view of a Clathrin cage 300 comprised of a plurality of natural Clathrin triskelia elements 302-308, respectively. In an illustrative embodiment, element 310 is an invention element, comprised of three heavy chain elements 104*a*-104*c*—which may or may not include three respective light chain elements 106*a*-106*c*—forming a hybrid or fused cage 300 comprised of natural elements and invention elements. In this role, element 310 comprises an efficacious replacement for a natural triskelia element.

Figure 4:
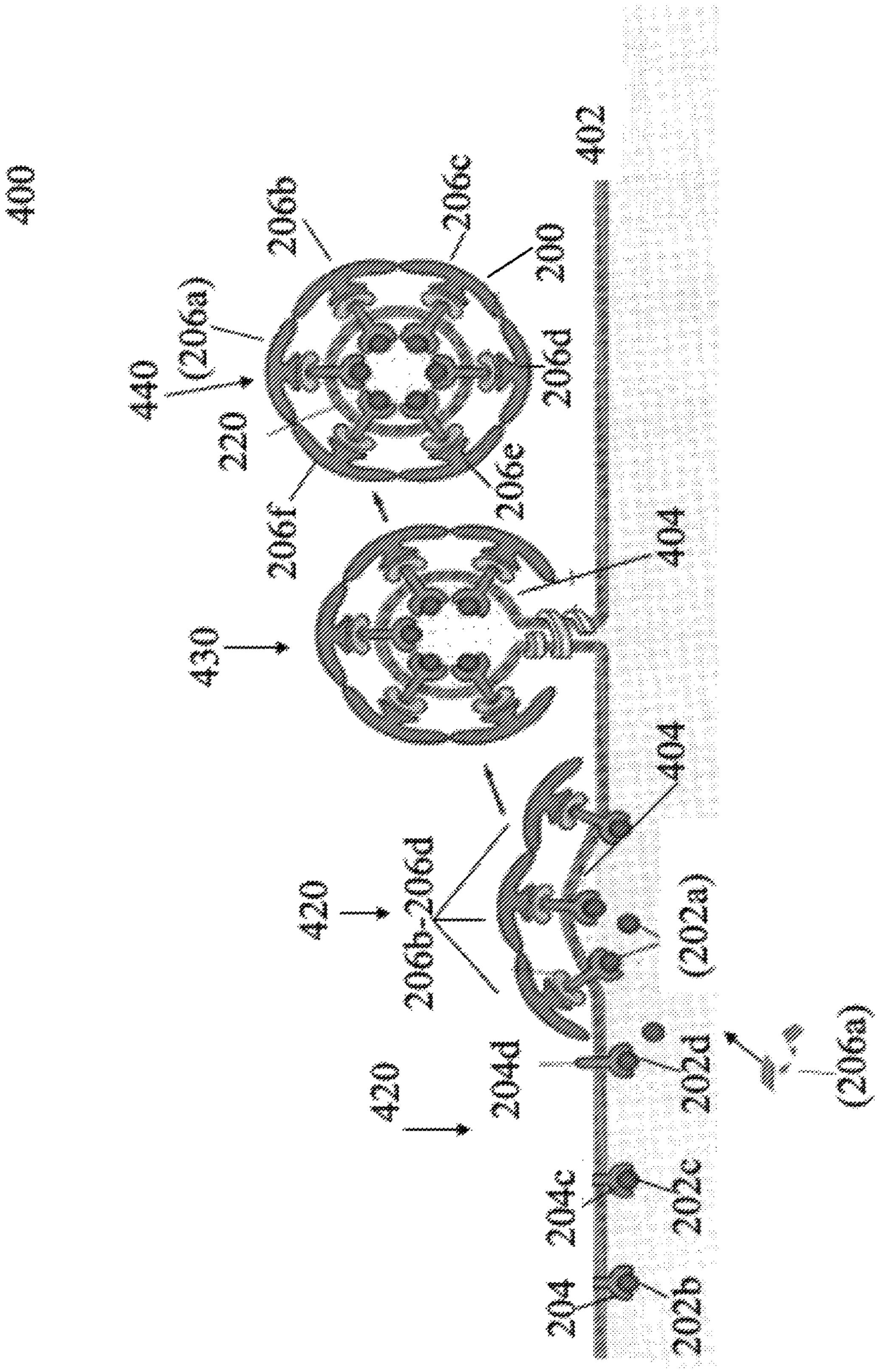
FIG. 4 is a flow diagram depicting conceptually the formation of individual Clathrin elements during endocytosis, which also serves to illustrate how the instant invention operates in one or more embodiments.

FIG. 4 is a flow diagram 400 depicting, conceptually, the formation of a plurality of natural Clathrin elements 206*b*-2026*f*, and, in this example, along with invention element (206*a*) into cage 200, which at step 440, shows Clathrin coated vesicle 220. The process by which natural Clathrin molecules 206*b*-206*d* obtain natural cargo molecules 202*b*, 202*c*, and 202*d* in this example is known as Clathrin mediated endocytosis (CME), a process wherein a cell takes in macromolecules by forming vesicles derived from the plasma membrane. Endocytosis is crucial to cellular function. Via CME, cells internalize cargo attachment elements, transmembrane channels, transporters and extracellular ligands such as hormones, growth factors and nutrients.

In one embodiment, one or more invention elements are biologically engineered to take or induce one or more types of actions, such as to create, spawn, comprise, modify, repair, regenerate, reassemble, and or control and regulate CME, as well as exocytosis, mitosis, trafficking, signaling processes, other behaviors, and the like. Defects and disorders in any of these critical cellular processes can lead to disease, and one or more types of these processes may be modified in one or more embodiments of the instant invention, for example, to achieve therapeutic effect.

In one embodiment, the instant invention takes or induces one or more efficacious actions involving receptor-mediated endocytosis that encompass nutrient uptake (LDL, transferrin, etc.), membrane recycling, membrane protein recycling, antigen uptake, synaptic vesicle recycling, and signaling receptor down-regulation.

In one or more embodiments, one or more invention elements comprise counterparts to natural Clathrin proteins that may inherently behave as a drug; e.g., one or more invention elements are functionalized for in vivo delivery and carry no additional elements, such as cargo. Such solo acting element embodiments would interact in one or more ways with natural cells and their processes, and by so doing diagnose, regulate and or cure one or more diseases and disorders relating to endocytosis.

An increase of a cellular component is called upregulation. Upregulation is an increase in the number of receptors, e.g., see elements 204*b*, 204*c*, and 204*d* in FIG. 4, on the surface of target cells, making the cells more sensitive to a hormone or another agent. For example, there is an increase in uterine oxytocin receptors in the third trimester of pregnancy, promoting the contraction of the smooth muscle of the uterus. In one or more embodiments, one or more invention elements, either by acting alone and or in part with other elements of one or more types, including natural and or non-invention elements, efficaciously modify, control and regulate, interfere with, create, and or spawn elements, and or induce actions or behaviors that increase the upregulation of one or more types of receptors of the surfaces of target cells.

On the other hand there is downregulation, an example of which is the cellular decrease in the number of receptors to a molecule, such as a hormone or neurotransmitter, which reduces the cell's sensitivity to the molecule. In the literature, downregulation is the process by which a cell decreases the quantity of a cellular component, such as RNA or protein, in response to an external variable. In one or more embodiments, one or more invention elements, either by acting alone and or in part with other elements of one or more types, including natural and or non-invention elements, efficaciously modify, control and regulate, interfere with, create, and or spawn elements, and or induce actions or behaviors that increase the downregulation of one or more types of receptors.

Exocytosis is the reverse process of endocytosis, whereby a cell directs secretory vesicles out of the cell membrane. These membrane-bound vesicles contain soluble proteins to be secreted to the extracellular environment as well as membrane proteins and lipids that are sent to become components of the cell membrane. Exocytotic vesicles are usually not Clathrin-coated; most of them have no coat at all. However, two observations suggest that Clathrin effectively 'tracks' vesicle proteins leaving a synapse. In one study (Granseth, et al, 2008) the amount of a Clathrin light chain (LC) tagged with the element mRFP leaving the synapse was proportional to the number of vesicles released by the stimulus, as assessed by the amplitude of a sypHy signal (sypHy is an improved fluorescent reporter of exocytosis). Second, in the same study the movement of LC-mRFP began without a significant delay and peaked with the sypHy signal. The movement of Clathrin out of the synapse together with synaptophysin and synaptobrevin is most easily explained as representing CME (Clathrin mediated endocytosis) of vesicles at sites removed from the active zone. This interpretation is consistent with studies showing that the machinery for CME is not at the active zone, but in the surrounding regions of membrane (Heuser & Reese, 1973; Ringstad et al. 1999; Qualmann et al. 2000; Teng &Wilkinson, 2000). Thus, Clathrin is naturally found in the extracellular space and may play a role in regulating exocytosis and or endocytosis. In one or more illustrative embodiment, one or more elements of one or more types may efficaciously operate in inter- and or extra-cellular spaces of one or more types; for example, perform remediation, sequestration, or removal of one or more types of undesirable elements.

Membrane trafficking only occurs during interphase. As the cell enters mitosis, Clathrin-mediated membrane traffic is rapidly shut down and only resumes in late telophase. Clathrin may therefore have a separate function that is distinct from membrane trafficking, which operates during mitosis. Clathrin is thus a multifunction protein: during interphase its function is in membrane trafficking and during mitosis it has a role in stabilizing spindle fibers (Royle, 2006). In one invention embodiment, mitosis may be efficaciously controlled and regulated, modified, and or induced via one or more methods and instances of the instant invention.

In another embodiment, one or more elements are comprised of, but not limited to, one or more isolated, synthetic, and or recombinant adaptor protein molecules, tubulin protein molecules, dynamin protein molecules, epsin protein molecules, endophilin protein molecules, synaptotagmin protein molecules, and or other types of protein molecules associated with Clathrin and Coatomer proteins and processes, for efficacious effect.

In another embodiment, one or more natural adaptor protein molecules, tubulin protein molecules, dynamin protein molecules, epsin protein molecules, endophilin protein molecules, synaptotagmin protein molecules, and or other types of protein molecules involved with associated with Clathrin and Coatomer proteins and processes form efficacious hybrid elements when also comprised of one or more types of invention elements.

The CME process involves a dynamic interaction between Clathrin and a wide range of other protein molecules, and altering the compositions and behaviors of the various molecular parties involved. For example, the cell uses endocytosis to control and regulate the density of receptors on the cell surface and to acquire nutrients. Endocytosis of ligand-activated cargo attachment elements is essential for the proper attenuation of a variety of signal transduction processes, as well as for co-localization of activated cargo attachment elements with downstream signaling molecules. Endocytosis also counterbalances secretion, preventing continuous expansion of the plasma membrane. Endocytosis thus internalizes macromolecules and fluid, and after sorting, directs the internalized molecules for degradation or recycling.

The endocytosis process begins when proteins bound to cargo attachment elements accumulate in coated pits 404, which are specialized regions of the cell membrane 402 where it is indented and coated on its cytoplasmic side with a bristle-like coat composed of two natural proteins: Clathrin and protein adapters. Most, if not all, intracellular transport vesicles are encased in a proteinaceous coat, one class of which is Clathrin-coated vesicles (CCVs). CCVs also mediate the transport of lysosomal hydrolases from the trans- Golgi network, as well as the efficient internalization of extracellular solutes such as nutrients, hormones, growth factors, and immunoglobulins at the plasma membrane.

Clathrin also transports proteins from the Golgi to other organelles. In neurons, endocytosis is critical to allow rapid synaptic vesicle regeneration. Besides Clathrin, there are other coat-forming proteins, such as COP I and COP II, which mediate intracellular traffic and there are Clathrin-independent endocytic pathways which mediate internalisation of a variety of cargo (Royle, 2006).

In one invention embodiment, the natural endocytosis process is transformed into a versatile therapeutic method to regulate the intensity, localization, half-life and function of signaling elements (signalosomes) that form in cells upon, for example, binding of growth factors, cytokines and morphogens to their cognate receptors. In one example embodiment, the invention rectifies breakdowns in the function of endocytic adaptors that might facilitate impairment of tissue homeostasis and consequent tumor development. In another illustrative embodiment, one or more invention elements, acting alone or not, interact with natural adaptor proteins required for appropriate receptor downregulation and which play distinct roles in oncogenesis. (Crosetto, et al. 2005) In another embodiment, CME elements might also comprise one or more invention cargo elements (202*a* in FIG. 4), which can be drugs, other ligands, and the like.

In one embodiment, referring to FIG. 4, a natural Clathrin coated vesicle 220 is desired to form to endocytose over-expressed natural receptor elements 204*b* and 204*c* that are initially located outside cell membrane 402. The appearance of one or more types of invention elements, such as element (206*a*) in the illustrative example, outside cell membrane 402 and or by crossing 402, dynamically begin to create, induce, spawn, mediate, control and regulate, regenerate, and or interact with one or more natural endocytosis processes and behaviors. With the prompting of one or more types of invention Clathrin elements, one or more biological processes acting on cell membrane 402 induce a Clathrin bud 404 to form at 420.

As shown at 430 and 440, after forming completely around bud 404, natural Clathrin elements 206*b*-206*d* pinch off (scission) from membrane 402 with the desired over expressed receptors 204*b* and 204*c* held inside vesicle 220. After excision, bud 404 has evolved into a plurality of natural Clathrin elements 206*b*-206*f*, some of which are attached to one or more types of over expressed receptor elements 204*b* and 204*c*, as well as attached to other receptor elements; which in this example are the normally expressed natural elements 204*d*.

In one illustrative embodiment, the otherwise all-natural plurality of Clathrin elements in FIG. 4 includes one or more non-cargo carrying; solo acting invention elements (206*a*), forming a "hybrid" CCV 440 with the desired efficacious properties and behavior. This hybrid CCV then follows normal pathways within the cell, causing downregulation of the desired over-expressed receptor elements, which may be associated with one or more types of neurotransmitters, viruses, cholesterol, as well as with other cargo types, restoring a cell to its normal, healthy state.

In another illustrative embodiment, natural Clathrin coated vesicle structure 440 in FIG. 4 is additionally comprised of one or more non-cargo carrying invention receptor element 204*a* and or adaptor element 208*a* (as illustrated in FIG. 2), forming a hybrid or fused Clathrin coated vesicle 440 in FIG. 4, with the desired efficacious properties and behavior. In another embodiment, one or more hybridized and or invention elements may enter the cell nucleus and or other organelles and cell elements.

The fusion and or participatory actions of one or more non-additional element carrying, solo acting invention elements 206*a*, 204*a*, and or 208*a* in FIG. 2 may yield a therapeutic effect, and are an example embodiment of inherently efficacious invention elements in action. In another embodiment, natural or hybrid CCV 440 in FIG. 4 also includes one or more invention cargo molecules (202*a*) that may have been transported into the cell via their attachment to one or more natural and or invention receptor elements.

Referring again to FIG. 4, in another example embodiment, a therapeutic effect is accomplished via one or more invention elements by regulating EGFR (epidermal growth factor receptor), which exists on the cell surface and is activated by binding of its specific ligands including epidermal growth factor and transforming growth factor a (TGFa).

When these natural cargo attachment elements are activated, cells rapidly clear them from the surface and destroy them. Control of EGF receptor signaling is performed by Clathrin-mediated endocytosis. Natural Clathrin coats also exist on endosomes and are involved in endosomal sorting of the EGFR. A defect in this overall process will likely lead to uninhibited growth of cells and tumors. EGFR expression, over-expression, or mutation is associated with cancer progression, advanced disease, drug resistance, aggressive disease, poor prognosis, and reduced survival. EGFR is considered one of the main proteins elevated in breast, lung, and prostrate cancers, among others. Brain cancer is also implicated with over-expressed EGFR. Other work has shown that using monoclonal antibodies for EGFR, or anti-EGFR, has proven an effective strategy for getting nanoparticles to specifically attach themselves to cancer cells. Additional work has shown effectiveness of EGFR as the cancer-targeting pathway. In one embodiment, CME, cell fusion, cell penetrating, and or one or more types of other participatory actions of one or more solo operating, efficacious invention elements 206*a*, 204*a*, and or 208*a* in FIG. 2 may yield a therapeutic effect in controlling, regulating, or mediating EGFR activity. In another example embodiment of modulating EGFR activity, cargo elements (202*a*) in FIG. 4 may comprise one or one or more types of cancer drugs or biologicals delivered directly into cells and organelles that are transported into the cell via their attachment to one or more natural and or invention receptor elements during CME, by cell fusion, by directly penetrating cell membrane 402, and or by one or more types of other participatory actions. In another embodiment, invention cargo elements (202*a*) may comprise one or more diagnostic agents, or combine one or more diagnostic agents and therapeutic agents in the same payload. In one or more embodiments, one or more invention elements of one or more types may thus comprise an efficacious method for the diagnosis, treatment, remedying, curing, and or prevention of one or more types of cancers, including those cancer types that fall outside the scope of EGFR-related activity.

Figure 5:
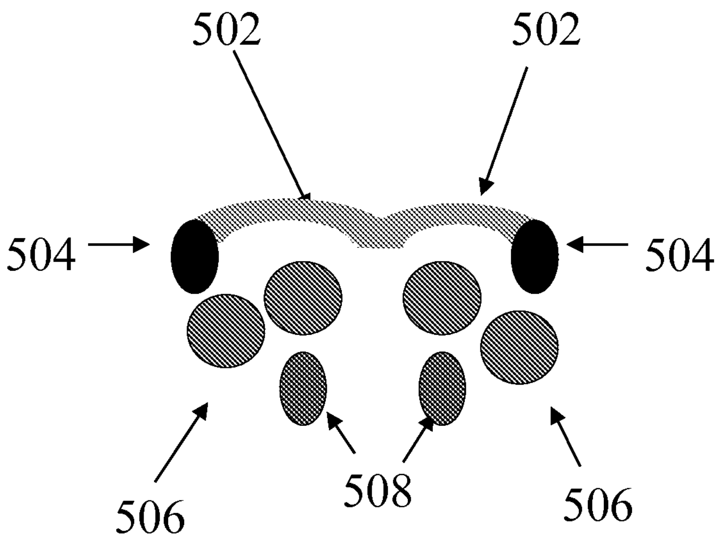
FIG. 5 is a conceptual diagram depicting Coatomer I/II protein comprised of one or more subunit and domain elements of the type employed in an illustrative embodiment of the invention.

FIG. 5 is a conceptual diagram illustrating the basic units of Coatomer I and II proteins. COPII and Clathrin cages are both constructed from ∂-solenoid and β-propeller building blocks (Fotin et al., 2004b; ter Haar et al., 1998; Ybe et al., 1999). In various embodiments of the invention, one or more elements of one or more types are formed from isolated, synthetic and or recombinant amino acid residues comprising in whole or in part one or more types of Coatomer proteins of one or more isoforms, including cloned isoforms. Examples of various Coatomer subunit amino sequences are listed in SEQ ID NO:15, SEQ ID NO:18, SEQ ID NO:21, SEQ ID NO:26, SEQ ID NO:27, SEQ ID NO: 29, and SEQ ID NO:30. In another embodiment, one or more Coatomer subunit amino acid sequences may be modified, altered, adapted or functionalized in one or more ways in one or more embodiments of the invention.

In one embodiment, Coatomer is comprised of seven distinct subunits: alpha, beta, beta', gamma, delta, epsilon and zeta subunits, respectively.

In Clathrin, a triskelion assembly unit lies at each vertex, and the ∂-solenoid legs of neighboring triskelia interdigitate extensively as they extend toward the adjacent vertices; the β-propeller is not part of the architectural core and instead projects in toward the membrane to interact with adaptor molecules (Fotin et al., 2004; Kirchhausen, 2000). In contrast, the COPII assembly unit is a rod that constitutes the edge of a cuboctahedron, and four rods converge to form the vertex with no interdigitation of assembly units. ∂-solenoid domains form the core of the edge, but, unlike Clathrin, the COPII vertices are formed from β-propellers. In summary, the COPII and Clathrin lattices seem not to share common construction principles other than the use of ∂-solenoid and β-propeller folds.

Crystallographic analysis of the Coatomer II assembly unit reveals a 28 nm long rod, element 502, comprising a central solenoid dimer capped by two β propeller domains, elements 504, at each end. GTPase, elements 508, bind to adaptor elements 506, which bind to elements 502. In the illustration, element 502*a* is an invention element that acts as an efficacious replacement element for one or more natural element 502, forming a hybrid Coatomer element. The structural geometry and properties of COPI coats remain to be determined. However, by analogy to the COPII and Clathrin structural units, they probably involve a preassembled cage protein (CP) scaffold that is generated by the β-propeller-containing and ∂-solenoid-containing subunits and an adaptor protein (AP) subcomplex. Together these could form an AP-CP heptaheteromeric functional unit in the cytosol. (Gurka, et al. 2006)

COPI and COPII play a major role in exocytosis, as also can their invention element counterparts. Clathrin can also play a role in exocytosis, but to a lesser extent than Coatomer. The exocytosis process refers to the fusion of intracellular vesicles with the plasma membrane. It occurs via two major processes, a constitutive pathway and a regulated pathway. These are the major ways that the cell secretes materials, wherein a cell secretes macromolecules (large molecules) by fusion of vesicles with the plasma membrane. Coatomer-coated vesicles, which are typically less than fifty nanometers in size, are also involved in vesicular transport between the Golgi apparatus, endoplasmic reticulum and plasma membrane. Coatomer I vesicles shuttle elements from the Golgi to the endoplasmic reticulum (ER). Coatomer II vesicles shuttle elements from the ER to the Golgi. Coat-protein I/II subunits (COPs) require ATP to assemble into a coat and unlike Clathrin coats, the Coatomer coat remains on the vesicle until docking occurs. In some instances, Coatomer proteins are also involved in endocytosis, but are unrelated to Clathrin. Thus, while Clathrin also mediates endocytic protein transport from the ER to the Golgi, Coatomers (COPI, COPII) primarily mediate intra-Golgi transport, as well as the reverse Golgi to ER transport of dilysine-tagged proteins. Coatomers reversibly associate with Golgi (non-Clathrin-coated) vesicles to mediate protein transport and for budding from Golgi membranes. In one or more embodiments, one or more COPI/COPII invention elements and or Clathrin invention elements, either by acting alone and or in part with other elements of one or more types, including natural and or non-invention elements, efficaciously modify, control and regulate, interfere with, create, and or spawn elements and or induce actions or behaviors involving exocytosis.

Cells of the mammalian immune system undergo selective changes in protein glycosylation during differentiation, immune activation, and autoimmune disease. In many, if not most of these types of diseases endocytosis and cellular trafficking and signaling plays a role. Referring again to FIGS. 1, 2, 3, 4, (and 5, in some embodiments), but not limited to, in one embodiment, one or more invention elements of one or more types, in whole or in part selectively interfere with, fuse with, control and regulate, induce, and otherwise modify endocytosis, receptor-specific processing, trafficking and signaling, and other behaviors for efficacious effect in one or more types of autoimmune diseases, including, but not limited to, one or more types of diabetes, CNS autoimmune diseases, and other types of autoimmune diseases that effect the body.

Referring again to FIGS. 1, 2, 3, 4, (and 5 in some embodiments), but not limited to, in one embodiment, one or more invention elements of one or more types selectively interfere with, control and regulate, and or modify secretory products that participate in inflammation and immunoregulation; and also in other embodiments, whereby endocytosis mediated by specific receptors for immunoglobulin or by other opsonins is important in removal of damaged self or foreign particles. In another embodiment, defects in membrane receptor function, whether inherited or acquired, and the pathogenesis of immune diseases may be remedied, inhibited, mitigated, and or prevented.

Referring again to FIGS. 1, 2, 3, 4, and 5, in one embodiment, but not limited to, one or more invention elements of one or more types efficaciously fuse with and or functionally replace one or more natural elements commonly found in endocytosis, exocytosis, mitosis, trafficking and signaling, and the like, either by acting alone and or in part with other elements of one or more types, including natural and or non-invention elements.

Referring again to FIGS. 1, 2, 3, 4, and 5, but not limited to, in another embodiment, one or more invention elements of one or more types efficaciously cross over into a cell, its elements, and or its organelles, such as its nucleus, either by acting alone and or in part with other elements of one or more types, including natural and or non-invention elements.

Referring again to FIGS. 1, 2, 3, 4, and 5, in another embodiment, but not limited to, one or more invention elements efficaciously create, spawn, comprise, modify, repair, regenerate, reassemble, and or control and regulate one or more natural elements commonly found in endocytosis, exocytosis, mitosis, trafficking and signaling, other cellular behaviors, and the like, either by acting alone and or in part with other elements of one or more types, including natural and or non-invention elements.

Referring again to FIGS. 1, 2, 3, 4, and 5, in another embodiment, but not limited to, one or more invention elements efficaciously utilize natural and or genetically engineered elements to encode components of the intracellular sorting machinery that mediate the selective trafficking of lipids and proteins in the secretory and endocytic pathways, to efficacious effect.

Referring again to FIGS. 1, 2, 3, 4, and 5, in another embodiment, but not limited to, one or more invention elements efficaciously utilize genetic agents and elements, including, but not limited to, proteins; peptides; DNA and DNA variants; RNA and RNA variants such as mRNA, iRNA and siRNA; RNA-induced silencing complex (RISC), other genetic-modifying agents and methods, and the like.

In another embodiment, but not limited to, one or more invention elements efficaciously utilize one or more oligonucleotides in antisense therapy. These antisense DNA drugs work by binding to messenger RNAs from disease genes, so that the genetic code in the RNA cannot be read, stopping the production of the disease-causing protein.

In another illustrative embodiment, one or more elements may comprise one or more RNAi (RNA interference) elements and or RNAi variants such as small interfering RNA molecules (siRNA), but not limited to, that may collaborate with proteins in the cell and also may form a nanoscale element called a RISC (RNA-Induced Silencing Complex). RNAi and or RISCs may be used to head off a genetic disease before the first symptom appears, based on an analysis of an individual's predisposition to certain diseases. This methodology is a way of silencing a specific gene, for example, genes that direct cancer cells to proliferate or that create overproduction of proteins that cause rheumatoid arthritis. Basically, RNAi works by scanning RNA templates that may cause a disease and cleaving that RNA template, and enzymes then destroying the template before it can complete its actions on the offending DNA. One of the key barriers to successful RNAi therapy is their finding their way to a specific site in the body and then the RNAi not degrading rapidly before it can do useful work. In one illustrative embodiment, RNAi, siRNA, RISC elements and or other suitable methods may be targeted by an invention element such that one or more such RNA elements seek out and destroy potentially harmful genetic elements and or other genetic processes.

As noted in the literature, Clathrin heavy chain is known to be a cytosolic protein that functions as a vesicle transporter. However, the Clathrin heavy chain exists not only in cytosol but also in cell nuclei. The p53 gene, in which mutations have been found in >50% of human cancers, encodes a protein that plays an important role in preventing tumorigenesis. Clathrin heavy chain expression enhances p53-dependent transactivation, whereas the reduction of Clathrin heavy chain expression by RNA interference (RNAi) attenuates its transcriptional activity. Moreover, Clathrin heavy chain binds to the p53-responsive promoter in vivo and stabilizes p53-p300 interaction to promote p53-mediated transcription. Thus, nuclear Clathrin heavy chain is required for the transactivation of p53 target genes and plays a distinct role from Clathrin-mediated endocytosis (Enari, et al 2006). In one embodiment, p53 and or one or more other types of genes, their diseases and disorders, and or RNAi related activities may be efficaciously controlled and regulated, mitigated, prevented, and or modified via one or more embodiments of the instant invention.

Referring again to FIGS. 1,2,3,4, and 5, in another embodiment, but not limited to, one or more elements, acting alone or not, would achieve therapeutic effect by deliberately controlling and regulating, or modifying faulty exocytosis and or endocytosis processes that produce disorders and diseases. This is a health critical situation, as the role of dopamine receptors and transporters; the excitability of dopaminergic neurons; and the regulation of extracellular dopamine levels in the brain, especially in relation to the diseased state, has proven to be imperative for a further understanding of dopaminergic neurotransmission as a whole. For example, dopaminergic neurotransmission critically depends on exocytotic release and neuronal uptake of dopamine, as well as on diffusion away from the release site. Once target cells are reached, dopamine can bind to and activate dopamine receptors. The subsequent cellular response depends on the type of dopamine receptor that is activated and the signal transduction mechanisms that are coupled to these receptors. Disturbances in one or more of the above-mentioned aspects of dopaminergic transmission could lead to severe neurological and neuropsychiatric disorders such as Parkinson's disease, depression, addiction, schizophrenia, attention deficit hyperactivity disorder, restless legs syndrome, Tourette syndrome, and the like, and in or more invention embodiments, one or more such disorders may be efficaciously treated.

Referring again to FIGS. 1,2,3,4, and 5, in another embodiment, but not limited to, one or more elements, during some operations may interact with, for example, an externally applied magnetic field, like during NMR. However, since invention protein elements are electrically neutral, only minimal (e.g., no) structural distortion of the elements occurs in the presence of the magnetic field. Therefore, using invention elements to capture other types of elements, which may be, for example, one or more NMR contrast agents for developmental imaging and diagnostic studies, and which contrast agents may also be capable of crossing cellular membranes, protects and extends the utility of the invention.

Referring again to FIGS. 1,2,3,4, and 5, in another embodiment, but not limited to, one or more elements may comprise, for example, one or more metal ions including, but not limited to, the gadolinium (III) chelate compounds of DTPA, DO3A, DOTA and other variations of these linear and macrocyclic ligands that act as targeted and or non-targeted contrast agents.

Direct Gd3+–OH2 chemical bonds, which exchange rapidly with other bulk H2O molecules, produce the mechanism whereby unpaired electrons on Gd3+ relax the proton nuclei of many nearby H2O molecules. Accordingly, the behavior of T1 contrast agents, such as those based on gadolinium requires good direct contact with tissue water molecules (spin-lattice relaxation mechanism) to be efficient. Thus, it is often preferable to bind them to the external surface of the carrier. (Hooker, et al. 2007) In one embodiment, one or more elements facilitate better contact to tissue water because one or more contrast agents of one or more types are not located in the interior part of a cage (in its cavity), but rather, located on much more exposed non-cage elements of one or more types. In one embodiment, one or more cage element 212 has one or more contrast agents of one or more types located on the outside part of cage element 212; or on both the inside and outside parts of element 212.

In another illustrative embodiment, one or more imaging or study elements comprise one or more treated manganese minerals, such as oxides, silicates, and carbonates for imaging and study enhancement.

Besides Gd3 complexes, there is another important class of contrast agents for MRI that is based on polysaccharide coated iron oxide particles. Their peculiarity stems from the fact that their blood half-life and distribution to different organs of the reticuloendothelial system (RES) depend upon the particle size (Aime, et al 1998). In one embodiment, one or more elements comprise one or more of a wide range of lanthano-invention labeled derivatives for custom-designed contrast agents.

In another embodiment, one or more elements comprise one or more therapeutic agents in addition to one or more imaging contrast and diagnostic agents.

In another illustrative embodiment, targeted and or non-targeted in vivo delivery of one or more elements are internally and or externally monitored, directed, activated, deactivated and or regulated, locally and or at a remote distance by, for example, but not limited to, NMR, ESR, ultrasound, radio transmissions, and or biochemical reactions.

Additionally, in other embodiments, NMR is combined with other techniques, such as ENDOR, which combines the best aspects of ESR and NMR, to yield high sensitivity and nuclear selectivity, respectively, for in vivo and in vitro studies.

In one embodiment, one or more different sized, paramagnetic coated, quantum dots, and or photonic dots are used as one or more contrast markers in magnetic resonance imaging (Mulder, et al., 2009). In other embodiments, one or more different sized quantum dots, and or photonic dots may be used in positron emission tomography (PET) for in-vivo molecular imaging, or as fluorescent tracers in optical microscopy.

In another configuration, one or more types of elements comprise one or more radiodiagnostic agents for nuclear medicine.

Referring again to FIG. 2, in further illustrative embodiments, free-floating cargo may be carried in cavity forming cargo elements 202*a* that comprise a fluid, gas, or vapor; which free-floating cargo, for example, may be one or more molecular ensembles for enhanced medical imaging, and which cargo may also be carrying one or more therapeutic agents.

Referring again to FIGS. 1, 2, 3, 4, and 5, in another embodiment, but not limited to, one or more invention elements comprise one or more types of elements in whole or in part, such as one or more drug and pharmacological elements; biological elements; biomedical or medical elements; and the like, including healthcare elements; bioengineered elements; cosmetic elements; and the like.

Referring again to FIGS. 1, 2, 3, 4, and 5, but not limited to, in one embodiment, one or more elements of one or more types comprise targeted and or non-targeted drug delivery elements, including their high precision dosing, or other forms of healthcare elements for diagnosing, remedying, inhibiting, mitigating, curing, and or preventing one or more types of diseases, infections, physical or mental trauma, or other forms of physical and mental afflictions.

Referring again to FIGS. 1, 2, 3, 4, and 5, but not limited to, in one embodiment, one or more elements comprise an in vitro and or in vivo model and or system for research study, including a model, method, and or system for the research and development of new drugs, therapies, prosthetics, and drug delivery systems, including an accelerated drug discovery process.

Referring again to FIGS. 1, 2, 3, 4, and 5, in another embodiment, but not limited to, one or more elements, acting alone or not, are utilized for studying, discovering, preventing, curing, mitigating, and or healing one or more types of animal, tree, plant, grain, grass, agricultural, vegetable, and or fungal diseases, disorders, infestations, and or blights.

Referring again to FIGS. 1, 2, 3, 4, and 5, in another embodiment, but not limited to, one or more elements are used for studying, discovering, designing, and or enabling of genetically engineered elements, for example, one or more types of genes, cells, and other biological elements and products in animals, trees, plants, grains, grasses, agriculture, vegetables and fungi.

In another illustrative embodiment, one or more elements comprise one or more methods for nourishing and or promoting healthy growth in one or more types of animals, trees, plants, grains, grasses, agriculture, vegetables and or fungi.

Referring again to FIGS. 2 and 4, in another embodiment, but not limited to, the heat shock cognate protein, hsc70, and its molecular co-chaperone auxilin, help to regulate the natural endocytosis aftermath of natural CCV uncoating and disassembly. Hsc70 also promotes uncoating and disassembly of Coatomer I and II vesicles. In cells over-expressing ATPase-deficient hsc70 mutants, uncoating of CCVs is inhibited in vivo. In one embodiment, bioengineered elements may be used to regulate under or over expression of hsc70 and or auxilin. In one example embodiment, using a monoclonal antibody or other agent type as cargo against hsc70 blocks the hsc70-mediated release of invention and or non-invention Clathrin from coated vesicles. In another example embodiment, or more auxilin elements comprise invention elements.

In one illustrative embodiment, one or more elements are stable with respect to dissociation, including one or more associated non-invention elements.

In another illustrative embodiment, disassembly and dissolution of one or more elements are deliberately inhibited and control and regulated, including one or more associated non-invention elements.

In one illustrative embodiment, one or more elements remain stable for a time certain or estimated time before the onset of dissociation, including one or more associated non-invention elements.

In one illustrative embodiment, dissociation of one or more elements may occur in whole or in part, including one or more associated non-invention elements.

In one illustrative embodiment, one or more cargo elements may comprise one or more uncoating and dissociation agents and or use one or more methods for controlled and regulated release of agents or cargo from one or more elements, including one or more associated non-invention elements.

In another embodiment, disassembly and dissolution of one or more elements, including one or more associated non-invention elements are inhibited, controlled and regulated, and or promoted by using one or more specific agents, stimuli, and or other methods.

In one embodiment, but not limited to, one or more invention elements of one or more types are formed in vitro via the following protocols, which may be modified and or substituted by one or more other types of protocols in one or more invention embodiments: (Adapted from Campbell, C et al., Biochemistry 23, 4420-4426 (1984), Pearse & Robinson, EMBO J. 9:1951-7 (1984), and Zhu, et. al., Methods in Enzymology, 328, 2001, Kedersh N, et al., J. Cell Biology 103, 1986.)

(Adapted from Campbell, C et al., Biochemistry 23, 4420-4426 (1984), Pearse & Robinson, EMBO J. 9:1951-7 (1984), and Zhu, et. al., Methods in Enzymology, 328, 2001, Kedersh N, et al., J. Cell Biology 103, 1986.)

Part I. Method of Differential Centrifugation.

1. Make up 1 L of a buffer (buffer A) that comprises: 50 mM Mes pH 6.5, 100 mM NaCl, 1 mM EGTA, 0.5 mM $MgCl_2$, 0.02% $NaN_3$, 1 mM DTT a day prior to experiment and storage at 4° C.
2. Add 1:100 PMSF proteases inhibitor to buffer A (200 ul/20 ml).

3. Collect and wash 14 rat brains (~2.0 g) and livers (~20.0 g). Wash and place the brains in ice-cold buffer A. Perfuse the livers with ice-cold PBS and collect them in ice-cold buffer A.
4. Mince and homogenize the brains in a Potter-Elvehjem grinder with 2 volume of ice-cold buffer A per total brain wet weight (~90 ml). Do the same with the livers (~400 ml).
5. Centrifuge the homogenate at 23,000 g (11,900 rpm) in a Sorvall GSA or at 13,000 rpm in a Sorvall SS34 rotor for 45 min at 4° C.
6. Collect the supernatant and centrifuge at 43,000 g (18,000 rpm) in a Sorvall SS34 rotor or at 20,000 rpm in a ti 45 Beckman rotor for 1 h at 4° C.
7. Resuspend the pellet in 10 ml of ice-cold buffer A, use a loose-fitting Teflon-glass Dounce homogenizer.
8. Collect homogenate in a 50 ml conical tube. Wash pestle and glass homogenizer with 5 ml of buffer A, and add this to homogenate until total volume is 15 ml. Add 1:100 PMSF
9. Dilute the homogenate 1:1 with 15 ml of 12.5% Ficoll/12.5% sucrose (both in ice-cold buffer A), and mix by inversion to ensure homogeneity.
10. Centrifuge at 43,000 g (18,000 rpm) in a Sorvall SS34 rotor or at 20,000 rpm in a ti 45 Beckman rotor for 30 min at 4° C.
11. Collect the supernatant in a graduate cylinder and dilute it 1:5 in ice-cold buffer A. Add 1:100 PMSF
12. Centrifuge the supernatant at 100,000 g (33,000 rpm) in a Beckman 70.1Ti rotor or at 31,100 rpm in a ti 45 Beckman rotor for 1 h at 4° C.
13. Collect pellet and resuspend in 5-10 ml of ice-cold buffer A by using a loose-fitting Teflon-glass Dounce homogenizer. Add 1:100 PMSF
14. Leave the homogenate on ice for about 30 min, and take an aliquot of 10 ul for EM, and dilute 1:10 for brain, 1:100 for liver.

Part II. Purification of CCVs Using Density Gradients (Zhu's CCVs and Clathrin Coat Preparation). Submit the Crude Clathrin-Coated Vesicles from Fresh Rat Brain to Discontinuous Sucrose Gradient for Remove Contaminating Vaults.

1. CCVs resuspended in (5-10 ml) buffer A
2. Preparer a discontinuous sucrose gradient in SW28 tubes by carefully layering 5 ml of 40%, 5 ml of 30%, 6 ml of 20%, 8.5 ml of 10%, and 8.5 of 5% sucrose solutions in buffer A from bottom to top.
3. CCVs (5-10 ml) is laid on top of the gradient and centrifuged at 100,000 g (25,000 rpm) in a SW28 rotor for 1 hr at 4° C.
4. Collect twenty-six 1.5 ml factions from the top.
5. Small aliquots from every other faction are analyzed for CCVs using 10% SDS-PAGE. [Fractions comprising the CCVs (typically fractions 12-21 as numbered from the top of the gradient) are combined, diluted with 3 volumes of buffer A, and centrifuge at 112,000 g (31,100 rpm) in a ti 45 Beckman rotor for 1 h at 4° C. or at 33,000 rpm in a Beckman 70.1Ti rotor for 1 h at 4° C. Add 1:100 PMSF]
6. Resuspend the pellet in ice-cold buffer A, do a protein assay to yield an approximate concentration. Usually add 1 to 2 ml of buffer A.
7. Aliquot the homogenate in aliquots of 200 ul and store at −80° C. Take an aliquot of 10 ul each for EM and SDS-gel PAGE.

Part III. Isolation of Triskelia and APs from CCVs Using Keen's Method.

1. Dialyze CCVs against 0.01M Tris buffer, Ph 8.5, 3 mM azide for 5 hours.
2. Centrifuge at 240,000 g (51,200 rpm) for 20 min at 4° C. Because you are using low amount of sample; (IF we have less than 2 mL, Do not use the lid or close the centrifuge tubes of the 70.1 Ti rotor.) The soluble coat proteins comprising triskelial and APs are separated from the residual Clathrin-coat vesicle membranes.
3. Collect the soluble fraction and do protein assay.
4. Take an aliquot of 10 ul for EM and 50 ul for SDS-gel PAGE.

Part IV. Separation by FPLC of AP-1 from AP-2 with Hydroxyapatite Column

Solutions:

Stocks:

| | |
|---|---|
| 1M $NaH_2PO_4$; pH 7.1 | (30 g/250 ml) |
| 5M NaCl | |
| 10% $NaN_3$ | |

Low $PO_4$ buffer (500 ml):

| | |
|---|---|
| 10 mM $NaH_2PO_4$; pH 7.1 | (5 ml of stock) |
| 100 mM NaCl | (10 ml of stock) |
| 0.02% $NaN_3$ | (1 ml of stock) |
| 0.1% beta-Mercaptoethanol | (0.5 ml) |
| | (RT) |

High $PO_4$ buffer (200 ml):

| | |
|---|---|
| 500 mM $NaH_2PO_4$; pH 7.1 | (100 ml of stock) |
| 100 mM NaCl | (4 ml of stock) |
| 0.02% $NaN_3$ | (0.4 ml of stock) |
| 0.1% beta-Mercaptoethanol | (0.2 ml) |
| | (RT) |

Both buffers need to be filtered and degassed prior to use.

AP Buffer:

| | |
|---|---|
| 100 mM MES, pH 7.0 | 39 g/2 l |
| 150 mM NaCl | 17.5 g/2 l |
| 1 mM EDTA | 4 ml of 500 mM solution/2 l |
| 0.02% $NaN_3$ | 4 ml of 10% solution/2 l |
| 0.5 mM DTT | -> add just before use |
| | (4° C.) |

Hydroxyapatite Column:

5 ml Econo-Pac CHT-II from BioRad; the column is stored at 4° C. in low $PO_4$ buffer Procedure:

Connect the hydroxyapatite column to the FPLC system via the BioRad adaptors. Put a 0.2μ syringe filter at the inlet of the column.

Use the following FPLC settings:

Sensitivity: 1

Flow: 1 ml/min

Chart Recorder speed: 0.5 cm/min

Make sure the fraction collector is set at "ml" and a volume of "1"

Pump A is used for the low $PO_4$ buffer; Pump B for the high PO4 buffer. Wash the pumps with Valve 1 in position "3".

Once the FPLC system is set up, start washing the column with 20 ml of high PO4 buffer (=20 min). Be sure to switch on UV-Lamp.

This is followed by equilibration of the column with low PO4 buffer; i.e. until the baseline is stable. The backpressure of the system should be approx. 0.1 MPa and must not exceed 0.35 Mpa.

During the equilibration phase (Valve 1 in position "1"="Load"), the 50 ml superloop is loaded with the AP sample (Pump C; 5 ml/min).

With the column equilibrated and the superloop loaded, switch Valve 1 into position "2"="Inject". The APs are injected over the column at a flow rate of 1 ml/min.

After the injection is completed, continue running low PO4 buffer over the column until the baseline is stable. Don't forget to prepare 1.5 ml tubes for the fraction collector.

AP-1 and AP-2 are then eluted from the column using Method 6:

| | | |
|---|---|---|
| 0.0 | CONC % B | 0.0 |
| 0.0 | VALVE.POS | 1.1 |
| 0.0 | CM/ML | 0.50 |
| 0.0 | PORT.SET | 6.1 |
| 40.0 | CONC % B | 0.0 |
| 40.0 | ML/MIN | 1.00 |
| 50.0 | CONC % B | 100 |

The elution profiles for AP-1 and AP-2 tend to vary considerably from one purification to another; AP-1 is eluted first.

AP-1 tends to be eluted from the column in three to four 1 ml fractions, usually starting at around #13. AP-2 is usually eluted in up to 15 fractions, starting at around #25. The fractions comprising the APs need to be verified by SDS-PAGE (two gels of 10% or 12%)

Wash column with low PO4 buffer; store at 4° C.

Pooled AP-1 fractions and pooled AP-2 fractions are dialyzed against 1 liter of AP buffer overnight, and for a few more hours after exchanging the buffer (4° C.). The samples are then stored at 4° C.

Typically, the concentration for Clathrin (peak fractions) is approx. 0.5 mg/ml, for AP-1 and AP-2 between 0.3-0.5 mg/ml.

According to one illustrative embodiment, but is not limited to, recombinant Clathrin formation may be achieved in the following exemplar manner. Stoichiometric quantities of adaptor elements 208*a* comprising AP-1 and AP-2 are required for Clathrin self-assembly at physiological pH. However, in vitro Clathrin self-assembly occurs spontaneously below about pH 6.5. Recombinant terminal and distal domain fragments are produced and combined with recombinant-produced hub fragments in assembly buffer as described below in order to induce formation of one or more Clathrin elements, such as those comprising elements 206*a*, for use in the invention.

In one illustrative technique, bovine Clathrin heavy chain cDNA encoding heavy chain amino acids 1-1074 (SEQ ID NO: 1) is cloned into the pET23d vector (Novagen) between the NcoI (234) and XhoI (158) sites. Expression of the cloned sequence results in a terminal and distal domain fragments having a C-terminal polyhistidine tag. Hub fragments corresponding to amino acids 1074-1675 (SEQ ID NO: 1) are cloned into vector pET15b (Novagen) between the BamHI (319) and XhoI (324) sites. Expression of the hub fragments produces the proximal leg domain and central trimerization domain of the Clathrin hub with an N-terminal polyhistidine tag. Vectors comprising the heavy chain and hub domains are expressed in *E. coli* by induction with 0.8 mM isopropyl-B-D-thiogalactopyranoside for 3 hours at 30 degrees Celsius. Expressed proteins are isolated, recombinant, and or synthetic from bacterial lysate in binding buffer (50 mM Tris-HCl (pH7.9), 0.5M NaCl, 5 mM imidazole) in a nickel affinity resin using the polyhistidine tag. Proteins are eluted with 206a mM EDTA and dialyzed against 50 mM Tris-HCl (pH7.9). Hub fragments are further isolated, recombinant, and or synthetic using size exclusion chromatography on a Superose 6 column (Pharmacia).

In another exemplar technique, Clathrin assembly reactions are performed using expressed heavy chain and hub fragments by overnight dialysis at 4 degrees Celsius in assembly buffer (100 mM 2-(N-morpholino) ethanesulfonic acid, pH 6.7, 0.5 mM MgCl2, 1 mM EGTA, 1 MM Tris(2-carboxyethyl)-phosphine hydrochloride, 3 mM CaCl2. Assembly reactions are centrifuged for 5 minutes at 12,000 rpm. The supernatant is then centrifuged for 45 minutes at 45,000 rpm (100,000×g). The pellets are resuspended in assembly buffer, and protein composition is determined on SDS-PAGE. The efficiency of element 206*a* formation can be determined by electron microscopy by diluting assembly reactions 1:5 in 10 mM Tris pH7.9, and placing aliquots on a glow-discharged carbon-coated grid, using 1% uranyl acetate as the stain.

According to another illustrative embodiment, but is not limited to, recombinant Clathrin formation may be achieved in the following exemplar manner, as described by Rapoport, et al. (MBC 2008): A cDNA encoding rat Clathrin heavy chain (Kirchhausen et al., 1987a) is used as a template to generate full-length (1675 HC), nested C-terminal truncations (1661 HC, 1643 HC, 1637 HC, 1630 HC, and 1596 HC), internal deletions (1675 PIVYGQ HC, 1643 PIVYGQ HC, and 1675 QLMLTA HC), and mutations (1643LML-AAA HC) of the heavy chain; each is then subcloned into the insect cell expression vector pFastBac1 (Invitrogen, Carlsbad, Calif.). A cDNA encoding rat liver Clathrin light chain LCa (Kirchhausen et al., 1987b) is used as the template to subclone the region encoding the full light chain (residues 1-256) into the insect cell expression vector pFastBacHTb. The final construct (rLCa1i) comprises at its N terminus a 6×-His-tag followed by a linker of 20 residues. Baculoviruses suitable for infection and expression are generated with the Bac-to-Bac system (BD Biosciences, San Jose, Calif.). Virus stocks are obtained after four rounds of amplification, and they are kept in the dark at 4° C. The open reading frame of rat brain Clathrin light chain LCa1 is also used as a template to subclone it into the bacterial expression vector pET28b (Novagen, Madison, Wis.) between the NcoI and EcoRI restriction sites so as to generate a native, nontagged light chain. All constructs are verified by DNA sequencing. Clathrin heavy chains together with light chain are expressed in Hi5 insect cells (1 L, 1-1.5 206a cells/ml) grown for 2-3 d in spinner flasks at 27° C. in Excell 420 medium after coinfection with the appropriate viruses. Alternatively, Clathrin heavy chain only is expressed in a similar way. The cells are centrifuged at 1000 rpm for 10 min at room temperature by using an H6000A rotor (Sorvall, Newton, Conn.), and the pellets are resuspended in 20 ml lysis buffer (50 mM Tris, pH 8.0, 300 mM NaCl, 1 mM EDTA, 3 mM mercaptoethanol, and half of a tablet of Complete Protease Inhibitor Cocktail [Roche Applied Science, Indianapolis, Ind.]). The resuspended pellets are sonicated for 1 min on ice (Flat tip at 20% power, Ultrasonic processor XL; Heat Systems, Farmingdale, N.Y.), cell debris is removed by centrifugation at 90,000 rpm for 20 min at 4° C. by using a TLA 100.4 rotor (Beckman Coulter, Fullerton, Calif.), and the supernatant (20 ml) is dialyzed at 4° C. for 12 h against 2×2 1 of cage buffer (20 mM [2-(N-morpholino) ethanesulfonic acid] MES, pH 6.2, 2 mMCaCl2, 0.02% NaN3, and 0.5 m Mdithiothreitol [DTT]). The sample is then centrifuged at 4° C., first at low speed (1000 rpm for 10 min) to remove large aggregates and then at high speed (54,000 rpm for 1 h) by using a Ti rotor (Beckman Coulter). The pellet, primarily comprising Clathrin (presumably assembled as cages) is resuspended in 6 ml of 100 mM MES, pH 6.5, 3 mM EDTA, 0.5 mM MgCl2, 0.02% NaN3, 0.5 mM DTT, and 0.5 mM phenylmethylsulfonyl fluoride) followed by addition of 3 ml of 2.4MTris, pH 7.4, 1 mM DTT, and incubation for 20 min at room temperature, a condition used to dissociate native Clathrin assemblies. The sample is centrifuged at 90,000 rpm for 20 min at 4° C. by using a TLA 100.4 rotor, and most of the Clathrin is recovered in the supernatant. The resulting sample is subjected to gel filtration chromatography (90 cm×0=3 cm column comprising Sephacryl-S 500 [GE Healthcare, Little Chalfont, Buckinghamshire, United Kingdom] in 0.5 M Tris, pH 7.4, 0.04% NaN3, and 0.5 mM DTT) at room temperature and with a flow of 2 ml/min. Fractions of 5.5 ml comprising the Clathrin peak (100 ml) are pooled and then subjected to adsorption chromatography (5 ml, hydroxyapatite, Econo-Pac CHT-II; Bio-Rad, Hercules, Calif.); the column is pre-equilibrated with low phosphate buffer (10 mM NaH2PO4, pH 7.1, 100 mM NaCl, 0.02% NaN3, and 0.5 mM DTT) and eluted with a linear gradient from low to high phosphate concentration (500 mM NaH2PO4, pH 7.1, 100 mM NaCl, 0.02% NaN3, and 0.5 mM DTT) at room temperature with a flow of 1 ml/min. Fractions (1 ml) are collected into microcentrifuge tubes comprising 2 l of 0.5 M EDTA. Typical Clathrin yields are in the range of 3-40 mg per 1 l of cell culture. Western blot analysis is used to confirm the expression of Clathrin heavy and light chains. The rat Clathrin light chain rLCalb is expressed in *Escherichia coli* strain BL21(DE3). The bacteria are grown in Luria-Bertani (LB) medium comprising 30 mg/1 kanamycin at 37° C. with shaking (250 rpm) to an optical density of 0.5. Expression is induced by addition of isopropyl-d-thiogalactoside (IPTG) (final concentration, 0.6 mM). After 3 h, the cell are harvested by centrifugation at 5000 rpm for 10 min at 4° C. by using an H6000A rotor (Sorvall) and resuspended in ice-cold lysis buffer (20 mM Bis-Tris adjusted to pH 6.0 at room temperature, 0.5 mM dithiothreitol, 1 mM EDTA, and Complete Protease Inhibitor Cocktail) by using 20 ml of lysis buffer per 3.5 g of wet cell weight. The suspension is placed into a glass vessel, and the vessel is immersed in boiling water for 4 min and then chilled on ice. The boiled suspension is centrifuged at 54,000 rpm for 30 min at 4° C. by using a 60Ti rotor (Beckman Coulter) to remove the precipitated material. rLCalb is purified from the filtered supernatant (0.2-msyringe filter) by anion exchange chromatography at 4° C. on a HiTrap MonoQ column equilibrated with buffer A (20 mM Bis-Tris, adjusted to pH 6.0 at room temperature, and 0.5 mM dithiothreitol) and eluted using a linear gradient from 0 to 32% buffer B (20mMBis-Tris, adjusted to pH 6.0 at room temperature, 0.5 mM dithiothreitol, and 1 M NaCl). For the in vitro reconstitution of Clathrin, recombinant heavy chain (expressed in insect cells without light chain) is mixed with excess rLCalb (expressed in bacteria) by using a weight ratio of 3:1 (equivalent to a molar ratio HC:LC of 1:2.4) just before cage or coat assembly for 40 min at room temperature.

Part V. Clathrin Coat Formation

Reagents

1. Coat formation buffer

| | |
|---|---|
| 80 mM Mes hydrate pH 6.5 | 31.23 g/2 L |
| 20 mM NaCl | 2.34 g/2 L |
| 2 mM EDTA | 8 mL of 500 mM stock solution/2 L |
| 0.4 mM DTT | 1.6 mL of 500 mM stock solution/2 L |

2. Clathrin

3. AP-2

Procedure (1) Place a solution of clathrin and AP-2 into a dialysis chamber clathrin: AP-2=3:1 to 4:1 (w/w)

(2) Dialyze over night against coat formation buffer; replace buffer and dialyze for an additional 3-4 h.

(3) Transfer to a centrifuge tube, centrifuge to remove larger aggregates rotor: TLA-100.4, 12000 rpm, 4° C., 10 min (4) Transfer supernatant to fresh centrifuge tube, centrifuge to collect coats rotor: TLA-100.4, 65000 rpm, 4° C., 12 min (5) Immediately withdraw supernatant with a 1 mL pipette.

(6) Wash carefully with buffer around the pellet.

(7) Resuspend the pellet by adding buffer, allowing to stand at room temperature for 10-15 min, then slowly wash buffer over the pellet to resuspend using a micro-pipettor (avoid foaming)

volume: 120-150 µL for a pellet of ~3 mm diameter

Part VI. Clathrin Cage Formation

Reagents

1. Cage Formation Buffer:

20 mM Mes, pH 6.2 (3.9 g/1) (7.8 g121)

2 mM CaCl2 (2 ml of 1M/1) (4 ml of 1M/21)

0.02% NaN3 (2 ml of 10%/1) (4 ml of 10%/21)

0.5 mM DTT (1 ml of 500 mM/1) (2 ml of 500 mM/21)

2. Clathrin

Procedure (1) Place a solution of Clathrin (0.5-1 mg/mL) into a dialysis chamber (2) Dialyze over night against cage formation buffer; replace buffer and dialyze for an additional 3-4 h.

(3) Transfer to a centrifuge tube, centrifuge to remove larger aggregates rotor: TLA-100.4, 12000 rpm, 4° C., 10 min (4) Transfer supernatant to fresh centrifuge tube, centrifuge to collect coats rotor: TLA-100.4, 65000 rpm, 4° C., 12 min (5) Immediately withdraw supernatant with a 1 mL pipette.

(6) Wash carefully with buffer around the pellet.

(7) Resuspend the pellet by adding buffer, allowing to stand at room temperature for 10-15 min, then slowly wash buffer over the pellet to resuspend using a micropipettor (avoid foaming)

Production of Recombinant Auxilin

A protein chimera of glutathione transferase (GST) with bovine auxilin (spanning residues 547-910) is generated by fusion in the vector pGEX4T-1 and then used for expression in *E. coli* BL21 (Fotin et al., 2004a). The bacteria are grown in LB medium supplemented with ampicillin to an OD600 0.5-0.6 at 37° C. Protein expression is induced by addition of 1 mM IPTG (final concentration) and the cells grown for another 4 h at 25° C. The cells (from 1 l of culture) are centrifuged at 5000 rpm for 15 min at 4° C., and the pellet is kept frozen overnight. The pellet is resuspended in 25 ml of pGEX lysis buffer (20 mM HEPES, pH 7.6, 100 mM KCl, 0.2 mM EDTA, 20% glycerol, 1 mM DTT, and half a tablet of Complete Protease Inhibitor Cocktail) and sonicated on ice using three consecutive sonication cycles of 60, 30, and 30 s (standard microtip, 20% power). The sample is centrifuged at 45,000 rpm for 1 h at 4° C. by using a 60Ti rotor, and the supernatant mixed with 0.5 ml of a 50% (vol/vol) slurry of glutathione-Sepharose 4 beads (GE Healthcare). After 2 h of end-over-end rotation at 4° C., the beads are poured into a propylene Econo-Column (Bio-Rad), washed with 15 ml of pGEX lysis buffer, and then washed with 15 ml of 25 mM HEPES, pH 7.0, 100 mM NaCl, and 0.1 mM EGTA. Elution of GST-auxilin (in 2 ml) is achieved by supplementing the solution with 50 mM glutathione, adjusted to pH 8. These steps are carried out at 4° C. Release of the GST portion is achieved by incubation of 1 mg of GST-auxilin with 1 U of thrombin at room temperature for 6 h. Proteolysis is ended by addition of 1 mg of Pefabloc SC (Roche Applied Science). The 40-Da auxilin fragment is further purified using a Mono S column (Pharmacia, Peapack, N.J.). The sample is first dialyzed overnight against MES buffer A (50 mM MES, pH 6.7, 1 mM EDTA, and 3 mM-mercaptoethanol), and then it is loaded onto the column (pre-equilibrated with MES buffer A) and eluted with a linear gradient of buffer A and with MES buffer B (50 mM MES, pH 6.7, 500 mM NaCl, 1 mM EDTA, and 3 mM-mercaptoethanol) at a flow of 1 ml/min. The auxilin sample is stored at 80° C. with 20% glycerol (final concentration).

Production of Recombinant Hsc70

N-terminal 6×-His-tagged bovine Hsc70 (full length) cloned into the pET21avector is expressed in *E. coli* BL21. The bacteria are grown at 37° C. in LB supplemented with 0.1 mg/ml ampicillin to an OD600 of 0.5, transferred to 28° C., and induced with 0.1 mM IPTG for 5 h. The cells are centrifuged at 5000 rpm for 15 min at 4° C., and the pellets from 11 culture resuspended in 25 ml 50 mM Tris, pH 8.0, 300 mM NaCl, 1 mM ATP, 2 mM MgCl2, 10 mM-mercaptoethanol, and half a tablet of Complete Protease Inhibitor Cocktail without EDTA. The supernatant obtained after sonication and centrifugation (as with auxilin) is mixed with 1 ml of 50% (vol/vol) slurry of nickelnitrilotriacetic acid-agarose beads (QIAGEN, Valencia, Calif.) for 4 h by endover-end rotation at 4° C. The beads are placed into an Econo Pac column and then washed with 30 ml of 50 mM Tris, pH 8.0, 300 mM NaCl, 10 mM-mercaptoethanol, 10 mM imidazole, 1 mM ATP, and 1 mM MgCl2). Hsc70 is then eluted at 4° C. with 5-6 ml of the same solution supplemented with 200 mMimidazole. Fractions of 1 ml are collected into microcentrifuge tubes comprising 40 1 of 0.1 M EGTA. The samples comprising 20% glycerol (final concentration) are stored at 80° C.

According to another illustrative embodiment, Clathrin and or Coatomer I/II proteins are extracted and prepared from Clathrin and or Coatomer I/II coated vesicles obtained from non-rat, non-bovine organic tissue, including from human tissue, in whole or in part. In another embodiment, Clathrin and or Coatomer I/II coated proteins are extracted and prepared from Clathrin and or Coatomer I/II coated vesicles obtained by donor/recipient tissue matching using established techniques. In another embodiment, Clathrin and or Coatomer I/II proteins are prepared, in whole or in part, by using stem cells, cloning and or other genetic manipulation techniques known in the prior art to produce genetically matched tissue for a donor recipient.

According to one illustrative embodiment, the coat protein I (COPI) assembly process is carried out by preparing Coatomer subunits from cytosolic preparations, including methods, but are not limited to, as essentially described in Spang, et al., Proc. Natl. Acad. Sci. USA. 1998 Sep. 15; 95 (19): 11199-11204. Coatomer, a nanoscale element comprised of seven distinct subunits (alpha, beta, beta', gamma, delta, epsilon and zeta subunits, respectively) and ADP-ribosylation factor (ARF, an N-myristylated small GTP-binding protein) are the only cytoplasmic proteins needed.

In another illustrative embodiment, the coat protein I (COPI) assembly process is carried out by preparing Coatomer subunits from cytosolic preparations, including methods, but are not limited to, as essentially described in Sheff, et al, The Journal Of Biological Chemistry, Vol. 271, No. 12, Issue Of March 22, Pp. 7230-7236, 1996 *"Purification of Rat Liver Coatomer* (*COPI*")—Purification of rat liver Coatomer is accomplished through a substantial modification of the method of Waters and Rothman (13). Unless otherwise noted, all operations are performed at 4° C. Approximately 250 g of fresh liver from 10-15 adult Sprague-Dawley rats (Harlan Sprague-Dawley) are homogenized in 2 volumes of buffer (25 mM Tris, pH 7.5, 320 mM sucrose, 500 mM KCl, 2 mM EDTA, 1 mM dithiothreitol) comprising protease inhibitors (2 mg/ml pepstatin A, antipain, and leupeptin; 1 mM phenylmethylsulfonyl fluoride) using a polytron homogenizer with 1.5-cm cutter assembly at maximum speed for three 1-min bursts on ice with 1-min rests. The lysate is cleared by sequential centrifugation at 9000 3 g for 15 min followed by centrifugation of the supernatant at 100,000 3 g for 1 h. This material (S100) is stored at 270° C. for up to 4 months. For a typical purification, 150 ml of S100 is diluted 6-fold with cytosol buffer (25 mM Tris, pH 7.5, 1 mM dithiothreitol, 1 mM EDTA plus protease inhibitors as above). Protein concentration is 5 mg/ml. Ammonium sulfate is added to 25% of saturation and stirred for 15 min on ice, and then precipitate is removed by centrifugation, and the supernatant is brought to ammonium sulfate at 45% of saturation with stirring on ice. The precipitate is collected by centrifugation and redissolved in 150 ml of cytosol buffer. An additional 120 ml of cytosol buffer is added and then 30 ml of 60% (w/v) polyethylene glycol 3350 in distilled H2O with gentle stirring. The mixture is incubated at 4° C. for 30 min, and the precipitate is collected by centrifugation at 10,000 3 g for 15 min. The precipitate is resuspended in 20 ml of G buffer (10 mM Tris, pH 7.5, 0.2 mM ATP, 0.2 mM CaCl2), the insoluble material is removed by centrifugation, and the supernatant is passed over a 20-ml column comprising 250 mg of DNase-I (Sigma) coupled to agarose (Affi-Gel-10, Bio-Rad, prepared according to the manufacturer's directions) to remove contaminating actin and actin binding proteins. Eluent is desalted into cytosol buffer using 10 DG desalting columns (Bio-Rad) and applied to a 50-ml DEAE cellulose column (DE52, Whatman) equilibrated in cytosol buffer. COPI is eluted with a 100-400 mM KCl gradient over 200 ml, with the elution of COPI followed by spot blot on nitrocellulose using EAGE antibody. In a final step, peak COPI fractions are pooled, diluted 1:1 with cytosol buffer, and applied to a 1-ml Mono-Q column (Pharmacia) equilibrated in cytosol buffer and mounted on a fast protein liquid chromatography apparatus (Pharmacia). The column is swished with 300 mM NaCl and then eluted with a 350-400 mM NaCl gradient over 20 ml. COPI, as assayed by the presence of b-COP on a spot blot using EAGE antibody, eluted as a single peak. The presence and purity of COPI is confirmed by SDS-PAGE. An alternative final step is employed in preparing samples for two-dimensional dimensional gels. Here, DEAE eluent is concentrated in a Centricon-30 microconcentration (Amicon) to 400 ml and applied to a 24-ml Superose-6

(Pharmacia) column equilibrated in cytosol buffer with 50 mM KCl. As with Mono-Q, COPI eluted in a single peak. This final step produces a somewhat lower yield and comprises some contaminants between 30 and 100 KD by SDS-PAGE. For copurification of labeled CHO cytosol and rat liver COPI, all quantities are divided by 3, 1 ml of labeled cytosol is added to 50 ml of rat liver S100, and the Mono-Q column is used as the final step.

The increasing interest in the targeting of foreign moieties at sites in the body where their activity is required is addressed by the invention in one more embodiments. It is important that agents, like drugs, particularly those having undesirable side effects, are delivered to the site where they are supposed to act. Many molecular species require that they be delivered in a site specific manner, often to particular cells, for example, polynucleotides (anti-sense or ribozymes), metabolic co-factors or imaging agents. One such system has been described by Wu et al., J. Biol. Chem., 263, 14621-14624 and WO-A-9206180, in which a nucleic acid useful for gene therapy is conjugated with polylysine linked to galactose which is recognized by the asialoglycoprotein cargo attachment elements on the surface of cells to be targeted. However, there are many occasions, such as in the delivery of a cytotoxic drug, when it would not be satisfactory to use a delivery system in which the targeting and or masking moiety and or vector to be delivered is so exposed. This need is addressed by various delivery system embodiments of the invention that possess the flexibility to target a wide range of biologically active foreign moieties.

In one embodiment, the invention includes one or more elements having one or more suitable sites for subsequent attachment of a targeting and or masking moiety and or vector, and one or more elements having one or more surfaces and or protein coats to which one or more targeting and or masking moieties and or vectors have already been attached.

In one embodiment, one or more masking moieties are attached to the surface of one or more invention elements. These masking moieties prevent the recognition by a specific cell surface and instead allows for intravenous administration applications. For example, the surface masking characteristics may be provided by poly (ethylene glycol) (PEG) by using various PEG-PLA and PLGA mixtures. PEG conjugation masks the protein's surface, reduces its renal filtration, prevents the approach of antibodies or antigen processing cells and reduces its degradation by proteolytic enzymes. In one embodiment, PEGylated elements significantly improve element stability and prevent leakage of agents from elements. Studies have shown that protein-based nanoparticles and liposomes without PEGs have a short circulation time due to rapid uptake by macrophages of the reticulo-endothelial system (RES), primarily in the liver and spleen. Finally, PEG conveys to molecules its physicochemical properties and therefore modifies biodistribution and solubility of peptide and non-peptide nanoparticles. Thus, recent studies have used mostly nanoparticles with PEGs. The PEG coating is highly hydrated and this layer protects against interactions with molecular and biological components in the blood stream, as well as nonspecific binding to tissue. In one embodiment, one or more elements, in one or more configurations, are internally and or externally attached, coated, and treated, in whole or in part by using steric stabilizers including, but not limited to, steric stabilizers selected among dipalmitoyl phosphatidyl ethanolamine-PEG, PEG-stearate, the esters of the fatty acids from the myristic acid to the docosanoic acid with methyl ether PEG, the diacylphosphatidyl ethanolamines esterified with methyl ether PEG and the polylactates and the polyglycolactates esterified with methyl ether PEG. In one embodiment, one or more elements are not required to be PEGylated to efficaciously operate.

In another embodiment, one or more elements, and in one or more configurations are internally and or externally coated or treated in whole or in part with surfactants, including, but not limited to, surfactant agents selected among soy-bean phosphatidylcholine, dioleyl phosphatidylcholine, dipalmitoyl phosphatidylcholine, hydrogenated soy-bean phosphatidylcholine, phosphatidylethanolamine and phosphatidylserine), and or with cosurfactants, including, but not limited to cosurfactant agents selected among ethanol, propanol, isopropanol, butanol, sodium taurocholate, sodium glycocholate, propylene glycol, butyric acid and benzoic acid.

In one or more embodiments, ligands can be of one or more efficacious types, such as drugs, and may be bioengineered, and or comprise isolated, recombinant, synthetic, and or cloned elements.

In one embodiment, one or more types of ligands may be functionalized and or attached in one or more ways to one or more elements.

In one embodiment, ligands are natural ligands of one or more types. In another embodiment, one or more types of natural ligands are modified and or functionalized. In another embodiment, invention element ligands and natural element ligands are combined to comprise one or more types of hybrid ligand elements.

In another embodiment, the course of a natural ligand and or invention ligand element during cellular signaling, trafficking, downregulation, upregulation, endocytosis, exocytosis, and other cellular entry or exit, cellular inter- and or intra-actions, and the like, may be efficaciously controlled, regulated, and or modified by one or more elements to yield one or more diagnosis, cure, mitigation, treatment, prevention of disease, or other types of efficacious effects, and the like.

Examples of some natural ligands, but not limited to, that may be subject to efficacious control, modification, and or regulation in one or more invention embodiments are listed below:

Toxins and lectins, e.g.,
- Diptheria Toxin
- *Pseudomonas* toxin
- Cholera toxin
- Ricin
- Concanavalin A Viruses, e.g.,
- Rous sarcoma virus
- Semliki forest virus
- Vesicular stomatitis virus
- Adenovirus
- Influenza
- West Nile Serum transport proteins and antibodies, e.g.,
- Transferrin
- Low density lipoprotein
- Transcobalamin
- Yolk proteins
- IgE
- Polymeric Ig
- Maternal Ig IgG, via Fc receptors Hormones and Growth Factors, e.g.,
- Insulin
- Epidermal Growth Factor Growth Hormone
Thyroid stimulating hormone
Nerve Growth Factor
Calcitonin
Glucagon
Prolactin
Luteinizing Hormone
Thyroid hormone
Platelet Derived Growth Factor
Interferon
Catecholamines LDL
Neurotransmitters
Substance P
A neurotransmitter known to stimulate pain receptors In one or more embodiments, one or more elements are conjugated (bonded) with one or more other elements (e.g., ligands), agents, materials, and or substances of one or more types, including those developed by 3rd parties, which may be used singly or mixed together in one or more configurations for medical and biological research, diagnosis, therapy, or prosthetic purposes. One or more biomedical elements such as ligands and other types of biomedical functionalization elements may be directly and or indirectly attached, bonded, fastened, cross-linked, and or affixed to and or incorporated into one or more invention elements, as well as one or more non-invention and or natural elements. In one embodiment, attachment is achieved via molecular tethers. In another embodiment, no molecular tether is involved. In one configuration, a free radical molecule may be attached directly to one or more invention elements. In another embodiment, one or more elements may be bonded, fastened, and or affixed to one or more elements by being included in a modified protein sequence of one or more elements or bonded elements; by using a spacer; by covalent bonding; by site directed mutagenesis; by genetically engineered mutation and or modification; by peptides; by proteins; by DNA; by antibodies; by monoclonal antibodies; by recombinant elements; and via other bioengineering techniques and methods known in the art.

According to one embodiment, the protein amino acid sequence of one or more elements are modified to provide a site suitable for attachment thereto of an in vivo or in vitro targeting and or masking moiety. In one illustrative embodiment, one or more target-specific ligands and or targeting moieties are directly attached to one or more elements via one or more amino acid groups, and or attached via one or more short molecular tethers.

In another embodiment, one or more functionalization elements, of one or more types, comprise highly specific targeting agents, such as, but not limited to, antibodies, peptides or small molecules, large molecules, and other functional ligands, such as fluorophores and permeation enhancers, and the so functionalized nanoparticles may target receptors, transporter, enzymes and or intracellular processes in vivo with high affinity and specificity.

In one illustrative embodiment, one or more elements such as diagnostic, therapeutic, prosthetic, and or assay agents, but not limited to, are delivered to a target in vivo or in vitro using a variety of guidance techniques, including for example, optical (photonic), acoustic, electric, biological, chemical, mechanical reactions and forces, but not limited to, and one or more elements may be delivered singly and or in one or more configurations to one or more targets.

In another illustrative embodiment, one or more elements comprise one or more diagnostic agents like imaging contrast or radioactive agents to perform site designation, site specificity, and site retention for targeted in vivo delivery of therapeutics; the latter may also comprise part of the same diagnostic payload.

In one illustrative embodiment, the invention enables targeted agent delivery systems that retain their structural integrity and that may also loiter for a calculated period of time at the targeted area of concern after delivery of agent payload.

In one illustrative embodiment, one or more elements comprise molecules arranged in specific patterns. The pattern of elements precisely mirrors or mimics a spatial or physical pattern a target cell in a human or animal body expects to see and will recognize, and one or more elements are accepted by the target cell, which can be a cancer cell or HIV infected cell, for example.

In one embodiment, gold metal nanoparticle probes with sensor ligands and using electrical charges are bonded to one or more elements, and or attached to ligands, targeting moieties, and or vectors. The gold particles carry short strands of artificial DNA (oligonucleotides) tailored to match known segments of biological DNA that are implicated in, or linked to, disease.

Target-specific ligand binding and any subsequent changes within or to one or more elements may be a result of either covalent or non-covalent interactions—the latter including hydrogen bonding, ionic interactions, Van der Waals interactions, and hydrophobic bonds—depending on the application, system design, receptor design, cargo type and or the interaction/application environment.

In another illustrative embodiment, one or more elements, ligands, targeting moieties, vectors, and the like utilize the method of chirality.

In another illustrative embodiment, reactions and forces arise from one or more ligands and or targeting moieties binding to targets, including covalent and non-covalent interactions, which ligands are tethered and or directly attached to one or more invention elements. Ligand binding to one or more specific targets may produce one or more conformational changes sufficient to deform and or rupture one or one or more elements in whole or in part, thereby causing one or more elements to be released. The targeting moieties can be selected by one of ordinary skill in the art keeping in mind the specific cell surface to be targeted. For example, if one wishes to target the asialoglycoprotein receptor on the hepatocytes in the liver, an appropriate targeting moiety would be clustered trigalactosamine. Once a specific targeting moiety has been selected for a particular cell to target, the different targeting moieties can be attached either by covalent linkage directly onto the surface of one or more invention elements, or by indirect linkage via, for example, a biotin-avidin bridge. In another embodiment, depolymerization (e.g., by cytosolic Hsc 70) of the Clathrin and or Coatomer element exposes one or more transmembrane proteins (V-SNARE) that direct one or more elements to their destinations by binding to a specific T-SNARE protein on the target organelle. The fusion protein SNAP25 causes the one or more elements to fuse with the target membrane In one embodiment, avidin is attached covalently to the surface of one or more elements and a biotinylated ligand attaches non-covalently to the avidin. In another embodiment, biotin is covalently attached to the surface of one or more invention elements, and then avidin is used as a bridge between the biotinylated polymer and the biotinylated ligand. Targeting agents may also include one or more biocompounds, or portions thereof, that interact specifically with individual cells, small groups of cells, or large categories of cells. Examples of useful targeting agents include, but are not limited to, low-density lipoproteins (LDS's), transferrin, asiaglycoproteins, gp120 envelope protein of the human immunodeficiency virus (HIV), and diphtheria toxin, antibodies, and carbohydrates. A variety of agents that direct compositions to particular cells are known in the prior art (see, for example, Cotten et al., Methods Enzym, 1993, 217, 618).

In another illustrative embodiment, one or more classical structural activity relationships (SARs) based drug discovery approaches are combined with one or more other techniques to form a specific case of targeted drug delivery, for example, but not limited to, one or more structural metabolism relationships (SMRs) that in combination with SARs are sometimes termed as retrometabolic drug design approaches. These active drugs are designed to undergo singular metabolic deactivation after they achieve their therapeutic roles, and may produce specific action at the site of application without affecting the rest of the body.

In another illustrative embodiment, one or more elements comprise one or more agent functionalities and or methods that produce targeting by changing molecular properties of an overall target molecule, as a result of enzymatic conversion, but also, for example, may involve one or more pharmacophores. These elements, sometimes referred to as the targetor (Tor) moiety, are converted by site-specific enzymes to active functions. In addition to the Tor moiety, one or more other functions may be introduced into elements for in vivo use, which can be named as "protector functions" that serve as lipophilicity modifiers or protectors of certain functional groups in therapeutic agent molecules.

In other illustrative embodiments, one or more other types of targeting delivery systems and methods n be used, for example, but not limited to, in whole or in part in one or more configurations: surfactants (surface-active substances) and or cosurfactants; enzymatic physical-chemical-based targeting; site-specific enzyme-activated targeting; vectors, such as ligand-based, non-viral-based, and Protein/DNA polyplex vector targeting; receptor-based chemical targeting; organic and or inorganic synthetic elements; transmembrane proteins (V-SNARE); peptides, including peptides that cross cell membranes and home specifically to certain diseases; nanostructured dendrimers and hyperbranched polymers; molecular Trojan horses; adenovirus, herpes simplex virus, adeno-associated virus or other virus vectors for targeted delivery that do not cause toxicity; antibodies, including monoclonal antibodies; nanoparticles, including polymer nanoparticles like polymer, polybutylcyanoacrylate, and ethyl alcohol nanoparticles; immunotoxins; hormonal therapy; tissue-specific gene expression; gene therapy; pegylated immunoliposomes; anti-sense therapy; biological elements and or agents, including biological elements and agents conjugated with other agents, such as transferrin, but not limited to such; chemical elements and agents; devices, systems, and or mechanisms; liposomes, including liposomes conjugated with transferrin, but not limited to such; conformationally-constrained peptide drugs targeted at the blood-brain barrier; endogenous blood brain barrier and or blood tumor capillary transporters; inhibiting and or modulating blood brain barrier active efflux transporters; air and or other gas bubbles; blood brain barrier breaking and or disrupting elements and agents; blood brain barrier tight junction separating and or endocytoses elements and agents; vector-mediated delivery of opioid peptides to the brain; brain drug delivery of peptides and protein drugs via vector-mediated transport at the blood brain barrier, neurotrophic, neuroprotective, and various peptides and drugs, and the like.

In another illustrative embodiment, one or more elements cross various in vivo biological barriers, such as the transmucosal passage, and may also cross the blood-brain barrier (BBB) and the blood-cerebrospinal fluid (CSF) barrier for targeted and or non-targeted in vivo delivery of CNS agents and elements. In one embodiment, one or more BBB-passing elements comprise small and or large molecule drugs.

Natural Clathrin, and in particular its ability to 'track' vesicle proteins leaving a synapse into the extracellular space (Granseth, et al 2007) indicates that the protein is not immediately scavenged by phages and other "housecleaning" elements in the brain, and further, may move freely about CNS spaces. In one embodiment, one or more elements efficaciously move through the CNS spaces and comprise in situ elements for remediation, removal, and or sequestration of one or more types of contaminants, toxic elements, undesirable organic or inorganic elements, and the like.

In another embodiment, extensive modification and functionalization of agents and elements may not be required for CNS entrance and or BBB passage. Only minimal functionalization may be required, depending on cargo and element type.

In another embodiment, one or more CNS-entering and or BBB-passing elements of one or more types may behave as a drug by themselves—i.e., they efficaciously operate alone without carrying additional elements, e.g., cargo elements. In another embodiment, one or more elements of one or more types carry one or more additional elements of one more types past the BBB.

In another illustrative embodiment, one or more elements enter the CNS and or cross the blood brain barrier for targeted delivery of agents and elements, including, but not limited to, small and or large molecules, non-lipid-soluble micromolecules, macromolecules, light sources, hydrophilic and or hydrophobic agents, such as therapeutic, diagnostic, and prosthetic agents, and other structured cargo to specific cells and areas within the brain, and such agents and or cargo may comprise one or more sensor agents, assay agents, diagnostic agents, prosthetic agents, and also may comprise agents like central nervous system drugs, antibiotics, and antineoplastic agents of one or more types, but are not limited to such.

In another embodiment, one or more elements are capable of circumventing the fluid-brain barriers by intracellular routes related to three separate and distinct endocytic processes. The three endocytic processes from the least to the most specific are fluid- or bulk-phase endocytosis, adsorptive endocytosis, and receptor-mediated endocytosis.

There are several transport mechanisms and techniques known in the art to be involved in the uptake of nanoparticles by the brain across the BBB (Lockman et al. 2002, Begley, 2004, de Boer et al. 2007), one or more of which may be utilized in one or more invention embodiments. These mechanisms and techniques include: simple diffusion of lipophilic molecules, the BBB-specific influx transporters, including organic anion and cation transporters and transcytosis or endocytosis. In one embodiment, one or more elements are internalized at the BBB by one or two different endocytosis mechanisms: receptor-mediated endocytosis (RME) and adsorptive-mediated endocytosis (AME). AME is triggered by an electrostatic interaction between the positively charged moiety of the peptide and the negatively charged region of the plasma membrane. In contrast, RME is specific to certain peptides such as insulin and transferrin.

In one embodiment, delivery through the blood-brain barrier of one or more types of small or large molecule cargo elements, and or molecules with polar functional groups is accomplished via chimeric peptides. The latter are formed when a transportable vector, such as cationized albumin, lectins, or a receptor-specific monoclonal antibody, is conjugated to a therapeutic compound that is normally not transported through the BBB. In one embodiment, conjugation of drugs to transport vectors is facilitated by, but not limited to, the use of avidin-biotin technology. In another embodiment, chimeric peptides are not required to pass through the blood-brain barrier, depending on cargo and element types.

In another illustrative embodiment, one or more elements may be coated with one or more surfactants and or cosurfactants, including, but not limited to, polysorbate 20, 40, 60 and 80, and or with one or more other materials and substances to cross various biological barriers, such as the transmucosal passage, and also to overcome the blood-brain barrier (BBB), the transmucosal passage, and the blood-cerebrospinal fluid barrier (CSG) for targeted delivery of agents and elements nanoparticles. In another embodiment, surfactants and or cosurfactants are not required to achieve such BBB-passing functionality, depending on cargo and element type. E.g., in the prior art, it has been shown that using such surfactants and co-surfactants can cause an immunogenic response.

In another illustrative embodiment, one or more elements may be cationized to facilitate blood brain barrier passage. In another embodiment, cationization is not required to achieve such functionality, depending on cargo and element type.

In another illustrative embodiment, one or more elements cross the blood brain barrier due to disruption of the barrier by acoustic techniques, such as by using ultrasound.

In another embodiment, zonula occludens toxin and its eukaryotic analogue, zonulin, (zot) are protein ligands attached to one or more invention elements. Zonulin, the natural ligand of the Zot target receptor, interacts with these cargo attachment elements at the blood brain barrier, unlocking the tight junctions (TJ) in the brain that regulate the blood-brain barrier at that receptor. TJ-unlocking allows passage of one or more elements through the BBB, and thereby enables delivery of small and large molecules, non-lipid-soluble micromolecules, macromolecules, light sources, and other structured cargo elements to the brain. In another embodiment, Zonulin is not required to pass through the blood-brain barrier, depending on cargo and element types.

Extracellular pathways circumventing the fluid-brain barriers in humans are comparable in the CNS of rodents and a subhuman primate. The most highly documented extracellular route is through the circumventricular organs (e.g., median eminence, organum vasculosum of the lamina terminalis, subfornical organ, and area postrema), all of which comprise fenestrated capillaries and, therefore, lie outside the BBB. In one embodiment, blood-borne macromolecules; specifically fluid-phase molecules released by the invention; escaping fenestrated vessels supplying the circumventricular organs move extracellularly into adjacent brain areas located behind the BBB.

The potential intracellular and extracellular pathways that blood-borne substances carried within one or more elements may follow in various embodiments for circumventing the fluid-brain barriers and entry to the CNS are therefore numerous, and various invention embodiments are used as appropriate. One invention embodiment, for example, uses the nasal cavity as a route for delivery of one or more types of drugs and other agents, especially for systemically acting drugs that are difficult to deliver via routes other than injection. Embodiments for the use of the nasal cavity for drug delivery also extend to circumventing the blood brain barrier. Drugs have been shown to reach the CNS from the nasal cavity by a direct transport across the olfactory region situated at the loft of the nasal cavity. It is the only site in the human body where the nervous system is in direct contact with the surrounding environment. In one embodiment, the nasal route would be important for rapid uptake of one or more types of drugs used in crisis treatments and management, such as for acute pain, epilepsy, psychic agitation, and for one or more other types of centrally acting drugs where the pathway from nose to brain provides a faster and more specific therapeutic effect. Furthermore, in another embodiment, the trigeminal nerve and, in animals, the vomeronasal organ also connects the nasal cavity with the brain tissue. One or more methods of nasal delivery to the CNS, which may also be used by the instant invention, but not limited to, are described in Dhuria, et al, 2008; Ma et al, 2007; and Thorne et al. 1995.

The nasal cavity has a relatively large absorptive surface area and the high vascularity of the nasal mucosa ensures that absorbed compounds are rapidly removed (Mainardes, et al 2006). In one embodiment, two routes, singly or in combination, are used via which one or more types of molecules are transported from the olfactory epithelium into the CNS and/or CSF. The first is the epithelial pathway, where one or more types of compounds pass paracellularly across the olfactory epithelium into the perineural spaces, crossing the cribriform plate and entering the subarachnoid space filled with CSF. From here the molecules can diffuse into the brain tissue or will be cleared by the CSF flow into the lymphatic vessels and subsequently into the systemic circulation. The second embodiment utilizes the olfactory nerve pathway, where compounds may be internalized into the olfactory neurones and pass inside the neuron through the cribriform plate into the olfactory bulb. In another embodiment, it is possible that further transport into the brain can occur by bridging the synapses between the neurons. After reaching the brain tissue, the drugs are cleared either via the CSF flow or via efflux pumps such as p-glycoprotein at the BBB into the systemic circulation. Despite the potential of the nasal route, there are some factors that limit the intranasal absorption of drugs. These barriers include the physical removal from the site of deposition in the nasal cavity by the mucociliary clearance mechanisms, enzymatic degradation in the mucus layer and nasal epithelium and the low permeability of the nasal epithelium removed (Mainardes, et al 2006). Colloidal carriers systems, such as nanoparticles and liposomes have demonstrated great efficacy in increasing drug bioavailability via the nasal route (Illum, 2002) In one invention embodiment, one or more elements comprise a colloidal carrier for enhanced nasal delivery of one or more elements, of one or more types.

Further, in one embodiment, it is possible to greatly improve the nasal absorption of one or more types of drugs and other elements by administering them in combination with an absorption enhancer that promotes the transport of the drug across the nasal membrane. Another invention embodiment comprises a nasal drug-delivery system that combines an absorption enhancing activity with a bioadhesive effect, which increases the residence time of the formulation in the nasal cavity. In one embodiment, this method can be even more effective for improving the nasal absorption of polar drugs. In one or more embodiments, a wide range of absorption enhancer systems can be utilized. In another embodiment, depending on cargo and element types, minimal functionalization may be required to take advantage of nasal absorption for efficacious passage to brain cells.

In another illustrative embodiment, one or more elements and in one or more configurations comprise in vivo and or in vitro sensor systems, assay systems, therapeutic drugs and other suitable methods to do genetic-based (trait-based) and or phenotype (state-based) drug dosing. In one embodiment, drugs are delivered at optimally effective and safe doses per each individual.

The invention, in one embodiment, provides for individual patient factors such as genotype, phenotype, age, gender, ethnicity etc., to be taken into account by one or more elements and factored into dosing and administration consideration. It has been demonstrated that inter-individual response variability can be 40-fold or more with practically all classes of psychotropic drugs. This makes it difficult to formulate rational guidelines for dosing and interpretation of biological parameters (such as plasma or serum drug concentrations) that might be associated with a therapeutic response. Although much remains unknown, a number of factors have been characterized as important determinants of patient-to-patient variability. These encompass genetics, disease state, nutritional status, concurrent use of drugs, and other pharmacoactive substances, including demographic factors such as age, gender, and ethnicity. Therefore, there is a requirement for in vivo systems that analyze many of these factors and dynamically adjust dosing accordingly.

In one embodiment, one or more elements comprise one or more personalized medicine elements, and which elements' efficacy may be increased, because responses arising from one or more individual variability factors; such as, but not limited to, genotype, phenotype, disease state, metabolic state, nutritional status, coninstant use of drugs, and other pharmacoactive substances, and also demographic factors such as age, and ethnicity; are factored into the elements, pre-delivery and or post delivery. Side effect profiles may also be reduced via such personalized medicine embodiments.

In one embodiment, one or more elements comprise one or more patented drugs; drugs that are about to go off patent; have already gone off patent (generics); and or their active metabolites, and which drugs' efficacy may be beneficially altered and or enhanced by use of the invention. These beneficial changes in the status of an existing drug may be achieved by the invention in one or more embodiments, for example, but not limited to: the ability to target specific areas in the body; to pass the blood brain barrier; to cross over into cells and their organelles; to fuse with cell membranes; to gain access to the cytosol; to offer the benefits of low antigenicity or minimal immunogenic effects; to modify, regulate, and or control cellular processes; to more efficiently and efficaciously carry drugs; and or to dynamically and or statically adjust the drug's responses and dosages arising from inter-individual variability due to one or more factors, such as, but not limited to, genotype, phenotype, disease state, metabolic state, nutritional status, coninstant use of drugs, and other pharmacoactive substances, and also demographic factors such as age, gender, and ethnicity of the patient. New patent filings for about to go off patent drugs and drugs already off patent may be enabled by one or more invention embodiments, such as affording increased drug efficacy, and or by enabling a better safety profile for the drug in question.

In various embodiments, the instant invention can carry one or more types of biomedical or healthcare elements, for example and without limitation: one or more therapeutic elements; pharmaceutical elements; diagnostic elements; assay elements; cosmetic elements; agents for treating one or more types of autoimmune diseases; agents for treating one or more types of infectious diseases; biological elements; radioactive agents or nuclear medicine agents; contrast agents; nano-scale biosensors; restorative agents; regenerative agents; cell, tissue, organ or circulatory repair elements; drug discovery agents; drug designer agents; drug research and development agents; drug fabrication agents; drug control and regulation agents; drug modifier agents; targeted drug delivery agents; clinical drug trial agents; antibiotics; antibacterials; vaccines; antiviral and anti-parasitic drugs; cytostatics; vitamins; proteins and peptides, including enzymes; hormones or other biological elements; prosthetic elements; intelligent nano-prostheses that supplement or enhance cell, tissue, or organ functioning; surgical elements; magnetic iron oxide nanoparticles; nano-scale biosensors; assays; diagnostic systems or nano-devices for in vivo delivery of targeted therapy to combat diseases, such as cancer and HIV, and the like, including other types and forms of drug elements for the diagnosis, cure, mitigation, treatment, prevention of disease. Some or all such elements may operate under the control and influence of various other elements and or methods and comprise another type of invention platform.

In another illustrative embodiment, one or more elements in whole or in part, cure, mitigate, or treat one or more types of bodily injuries and insults, including traumatic injury, blood clots, and the like, but not limited to.

In one embodiment, nano-engineered scaffolds comprised of a plurality of elements are able to support and promote cellular differentiation and growth in injured or degenerated regions.

In one illustrative embodiment, one or more elements comprise one or more types of small and or large molecules and may utilize one or more methods to enter the CNS and or cross the blood brain barrier, in whole or in part, for delivery of one or more assay, diagnostic, therapeutic agents, and drugs, of one or more types, to cells and or targeted areas within the brain, like, for example: contrast agents; central nervous system drugs; antibiotics; antineoplastic agents, which may be used for treating malignant brain tumors (primary and or metastasized, of one or more types) or benign neoplasms; Parkinson's agents; Multiple Sclerosis agents; epilepsy agents; meningitis agents; Alzheimer's disease agents; HIV infection agents; memory agents; stroke agents; coma agents; and the like; or comprise one or more psychotropic agents or therapies of one or more types to study, diagnose, cure, mitigate, or treat of one or more types of mental health and illness, including, but not limited to, stress; anxiety; depression; mania; bipolar disorder; attention deficit (hyperactivity) disorder; panic attacks; phobias; addictions; anger; rage; suicidal thoughts and tendencies; substance abuse disorder; post traumatic stress disorder; psychoses; mental retardation; autism; delirium symptoms; schizophrenia; neuroses; and or enhancing memory; cognition; cognitive functioning; the effects of cognitive therapy, and the like; including other types and forms of drug elements for the diagnosis, cure, mitigation, treatment, or prevention of one or more types of CNS diseases. In another illustrative embodiment, one or more elements enter the CNS, including crossing the blood brain barrier, in whole or in part, to diagnose, cure, mitigate, or treat one or more types of CNS injuries and insults, including traumatic brain injury, blood clots, and the like, but not limited to.

In one embodiment, one or more elements promote neuroprotection by limiting the damaging effects of free radicals generated after head injury, a major factor contributing to neuropsychiatric degenerative disorders (e.g., Alzheimer's).

In one embodiment, nano-engineered scaffolds comprised of a plurality of elements are able to support and promote neuronal differentiation and growth in injured or degenerated brain regions.

In another illustrative embodiment, one or more elements comprise a light source, for use, for example, but not limited to, in a photodynamic therapy (PDT) system for age related macular degeneracy (AMD).

Compounds such as drugs, amino acids, carbohydrates, proteins, nucleotide bases, hormones, pesticides and co-enzymes have been successfully used in the prior art for the preparation of selective recognition matrices. A wide variety of print molecules have been used in various imprinting protocols known in the art. Of all the imprinting strategies known in the art, it has become evident that the use of non-covalent interactions between the print molecule and the functional monomers is the more versatile. The apparent weakness of these interaction types, when considered individually, may be overcome by allowing a multitude of interaction points simultaneously. Together with the fast association and dissociation kinetics of these bond types, so that in a short time many possible combinations can be checked before the correct partners associate, this protocol has proven advantageous. Furthermore, the use of non-covalent interactions in the imprinting step closely resembles the recognition pattern observed in nature. Example invention molecular imprint embodiments in the art include, but are not limited to:

Fragmented polymer monoliths
Composite polymer beads
Polymer beads from suspension, emulsion or dispersion polymerization
In-situ polymerization
Polymer particles bound in thin layers
Polymer membranes
Surface-imprinted polymer phases In one illustrative embodiment, the invention uses molecular-imprint technology, wherein biodegradable films are used as a pliable template for elements, which elements are pressed into a film and then removed, leaving a physical mold of the element's shape. In one embodiment, this can facilitate catalysis of certain reactions and may also be used for shape selective separations. In other embodiments, imprinted polymers may facilitate the fabrication of elements to achieve selective diffusion; as chromatographic supports for the separation of enantiomers and oligonucleotides by invention elements; to provide the recognition element for an invention chemical sensor; and for the synthesis of polymeric materials that mimic biological cargo attachment elements and are targeted by invention elements, and or play a role in the design of new drugs. In one embodiment, this invention process provides for imprinted biodegradable capsule production with target or site-specific feature sizes at the molecular level. Other invention embodiments may utilize imprinted membranes and thin films that also function as an artificial cell wall for the selective transport of targeted drugs, peptides and biologically important molecules.

Surface imprinting involves the following steps: The print molecule, usually a large one, is first allowed to form adducts with functional monomers in solution and the formed elements are subsequently allowed to bind to an activated surface such as silica wafers or glass surfaces. Thus, with this technique, a designed imprinted (imaged) surface is obtained. This approach should potentially be valuable for creating specific cell binding surfaces. When preparing molecularly imprinted polymer monoliths against large imprint species, there is a risk of permanent entrapment of the template in the polymer after polymerization. When using thin polymeric layers or imprinted surfaces this drawback may be overcome.

In one embodiment, imprinted nanocapsules using techniques known in the art and as discussed above, one or more elements utilize and or constitute a nanocapsule with manifold, multi-tiered capabilities for in vivo administration and targeted delivery. The imprinted nanocapsule is delivered in vivo to detect and target a particular in vitro imprinted biological element, which may be, but is not limited to, a particular type of receptor, protein, or cell, since its imprint shape on the nanocapsule will only bind in vivo to that particular biological element target. The molecular-level imprint process thereby provides for targeting one or more elements using biodegradable nanocapsules for in vivo agent delivery. In addition, vectors and targeting moieties, and blood brain barrier, transmucosal, and CSF barrier breaching elements, and other elements and substances may also be attached to the surface of the molecular imprint nanocapsule or otherwise be conjugated to it.

In another illustrative embodiment, one or more elements may be used in conjunction with molecularly imprinted polymers known in the art as recognition elements in biosensor-like devices. In one embodiment, imprinted polymer embodiments may be highly resistant sensing element alternatives.

In another illustrative embodiment, one or more elements are encapsulated in whole or in part in one or more biodegradable controlled-release polymers, which polymers may also be conjugated with other elements and agents. The polymer capsule, and or one or more elements may also be coated with one or more surfactants and or cosurfactants and or with other materials and substances. One or more targeting and or masking moieties and or other targeting vectors may also be attached on the polymer surface, and or on one or more elements.

In one embodiment, one or more elements are put into one or more biodegradable controlled-release polymeric capsules, and these elements transform "dumb" polymeric delivery capsules into "smart" systems.

In the instance of polymeric nanocapsules, which may be molecular imprinted or not, illustrative controlled-release polymeric nanocapsule embodiments of the invention may include one or more of the following delivery systems, but not limited to, and in one or more configurations:

1. Diffusion-controlled systems
2. Water penetration-controlled delivery devices
3. Chemically controlled systems
4. Drugs covalently attached to polymer backbone systems, which delivery systems can be further subdivided into soluble systems and insoluble systems. Insoluble systems are used as a subcutaneous or intramuscular implant for the controlled release of the chemically tethered therapeutic agent. Soluble systems are used in targeting applications.
5. Drug release determined predominantly by erosion systems, whereby certain polymers can undergo a hydrolysis reaction at decreasing rates from the surface of a device inward, and under special circumstances the reaction can be largely confined to the outer layers of a solid device. Two such polymers are poly (ortho esters) and polyanhydrides, because the rates of hydrolysis of these polymers can be varied within very wide limits, considerable control over the rate of drug release can be achieved.

6. Poly (ortho esters) systems, which are highly hydrophobic polymers that comprise acid-sensitive linkages in the polymer backbone.
7. Polyanhydrides materials as bioerodible matrices for the controlled release of therapeutic agents. Aliphatic polyanhydrides hydrolyze very rapidly while aromatic polyanhydrides hydrolyze very slowly, and excellent control and regulate over the hydrolysis rate can be achieved by using copolymers of aliphatic and aromatic polyanhydrides. In this way, erosion rates over many days have been demonstrated, and erosions rates measured in years have been projected.

The form in which the foreign moiety, vector and or cargo are held within one or more elements will depend on the release properties and methods required. For release at the targeted site, it will be important to ensure that the right conditions prevail, for example, to permit cell localization and internalization via receptor mediated endocytosis.

In one illustrative embodiment, the invention enables one or more types of delivery systems that engage in an iterative, interactive, and dynamic dialog with one or more targets; follow a sequence of actions governed by biological control laws and methods; and or use behaviors and methods as defined by graphs and or an algebra, for example, a Lie algebra. In one illustrative example, one or more elements follow an algorithm expressed by the invention, such as in this illustrative embodiment:

1) One or more elements, that may be with or without cargo elements, docks and or loiters on or near one or more cell membranes,
2) One or more elements enter one or more target cells, while one or more other elements continue to loiter nearby or stay docked at the cell membrane.
3) The docked and or loitering element elements wait for a time period,
4) The targeted cell produces one or more reactions, for example, manufactures and or secretes an agent in response to the element's docking and or delivering its cargo,
5) The docked element and or loitering elements analyze the new cell behavior and or its secretions,
6) The docked element or loitering elements undergo a conformational change in response to the cell's new behavior,
7) The docked element and or loitering elements self-adapt, producing yet another conformational change in the cell, and or releases another round of one or more agents that are taken up by the targeted cell, and,
8) The foregoing process is repeated as required to achieve an efficacious effect.

In another embodiment, one or more light sources comprised of one or more elements operate in an intelligently staged sequence or orchestrated series of actions, which may be multiplexed or done in parallel by using one or more light and thermal energy emitting sources and methods. By using one or more light and or thermal energy emitting sources, optical and or thermal energies from one or more light sources operate on one or more photosensitive and or thermal sensitive elements comprising one or more elements that also comprise one or more entrapped agents. This method results in a staged series of overall actions that follow an intelligently ordered sequence of events. In an example embodiment, first a diagnostic agent from one or more elements is released by an optical and or thermal trigger, and the agent's positive finding of a disease, like cancer or HIV then causes one or more therapeutic agents to be released from the same and or other one or more other elements by one or more optical and or thermal triggers. Agent dosages are released in calculated amounts, and the dosages may be non-targeted or targeted.

In another illustrative embodiment, cavity-forming cargo elements have one or more compartments that in whole or in part are separated by one or more barriers, for example, but not limited to, one or more phospholipid membrane barriers and or one or more barriers comprised of molecular-imprinted films. The barriers may exhibit structural transitions due to internal or external stimuli. In one embodiment, agents or cargo entrapped within one or more elements remain sequestered within their respective compartments until a change in barrier permeability state is triggered by contact, for example, by a ligand, with one or more specific targets or sites. The subsequent biochemical and or biological reactions cause the barriers to alter states into an opened state and release entrapped cargo and agents from one or more invention elements. In one example embodiment, binary mixtures of therapeutic and or diagnostic agents are mixed together as needed to dynamically and more efficaciously deal with a disease or disorder.

The invention, in one or more embodiments, comprises in whole or in part one or more elements, components, devices, systems, and the like, of one or more types, formed by using one or more engineering disciplines and related engineering technology disciplines of one or more types. Listed below are some such example invention embodiments, but are not limited to.

In one embodiment, the invention remedies the deficiencies of prior art by providing one or more elements of one or more types, a plurality of which may also comprise one or more nanoscale platforms of one or more types. A platform according to the invention may be used, for example, in biomedical, electronics, telecommunications, and information processing applications.

Figure 6:
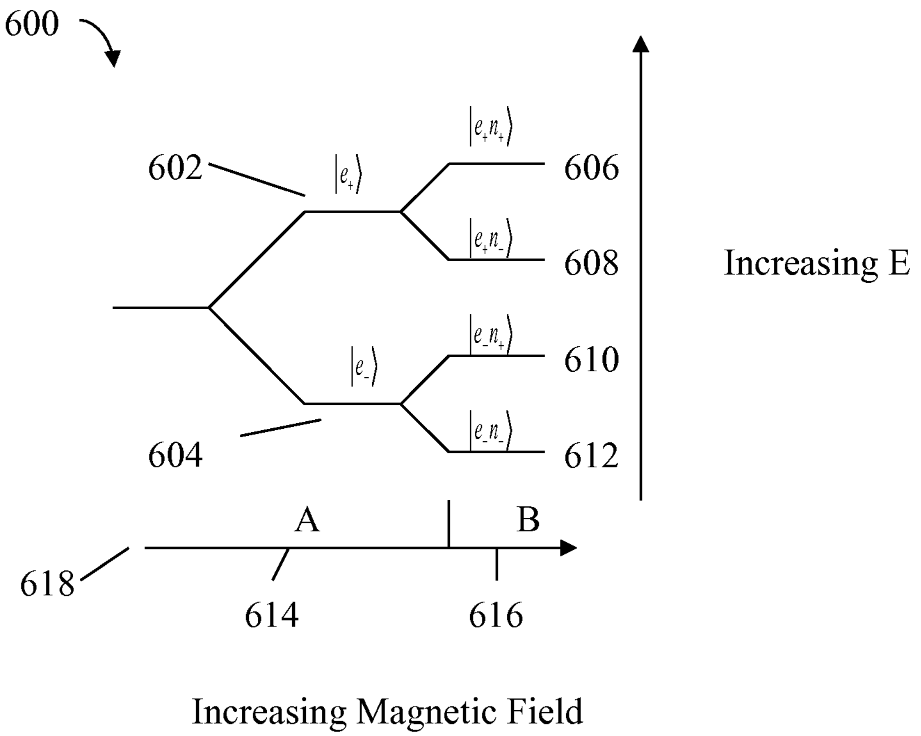
FIG. 6 is an exemplary energy level diagram 600 illustrating the energy levels associated with a hyperfine interaction between electron and nuclear spin in the presence of magnetic fields.

FIG. 6 is an exemplary energy level diagram 600 illustrating the energy levels associated with a hyperfine interaction between electron and nuclear spin in the presence of magnetic fields of the type used to do ESR spin label studies, which may be done in vivo and in vitro in one invention embodiment. The hyperfine interaction is a strictly quantum mechanical phenomenon. In an atom, the electron possesses an intrinsic quantum mechanical quantity known as spin. The nucleus of an atom also possesses spin. Intrinsic spin tends to generate a spin magnetic moment that is capable of interacting with other magnetic moments and fields. Generally, the spin magnetic moment of the nucleus does not interact with the spin magnetic moment of the electron. However, in the presence of a strong magnetic field, the spin magnetic moments of the electron and nucleus become coupled and interact.

In one illustrative embodiment, the electron is excited using pulses of electromagnetic radiation while maintaining its spin configuration. The source of the electromagnetic radiation may be, for example, an ordinary lamp, an LED, a time-varying magnetic field generator, a laser, or an electromagnetic field generator. A hyperfine interaction gives rise to electron nuclear double resonance (ENDOR) techniques. According to one illustrative embodiment of the invention, room temperature EPR and ENDOR techniques known in the art are used for performing in vivo spin probe studies.

In another embodiment, one or more elements comprise one or more diagnostic agents, and during the same NMR/MRI, or EPR, or ESR, or ESEEM, or ENDOR, or PET, or SPECT, or OCT operation, one or more elements use quantum information processing techniques known in the art can modify, process, manipulate, encode and decode, input, output, transmit, communicate, store and read information using one or more modulated signals, methodologies, or carrier signals of one or more types.

In one embodiment, one or more invention elements in one or more configurations, are bonded, tethered, or otherwise incorporated into one or more invention and or non-invention elements, comprising functionalized nanoscale elements, components, devices, systems, and or platforms such as, but not limited to, nano-lasers, quantum dots; photonic dots; nanoscale DNA chips; protein assay chips; assay elements; environmental, protein, phenotype, DNA, and or metabolic assay and analysis elements.

In another embodiment, one or more elements may comprise a bio-lasing structure, in vivo or in vitro.

In one embodiment, one or more elements in one or more configurations comprise nano-sensor elements; including, but not limited to, radioactivity sensors; chemical sensors; biological sensors; electromagnetic sensors; acoustic sensors; visible, infrared, and or ultraviolet wavelength sensors; tactile sensors; pressure sensors; volumetric sensors; flow sensors; and temperature sensors; and one or more of which sensors may constitute a bio-molecular device.

In one embodiment, one or more elements and or platforms utilize and or employ one or more types of transmitter and or receiver elements as sensors and or for transmission of information of one or more types in vivo and in vitro.

In another embodiment, one or more elements and in one or more configurations comprise one or more nanoscale elements, components, devices, systems, and or platforms that input, read out, process, analyze, output and report on information gathered by one or more types of diagnostic, test, label, tag, reporter, sensor, and or assay elements.

In one embodiment, quantum dots and or photonic dots are released in vivo or in vitro from one or more elements, and the quantum dots and or photonic dots are coated in whole or in part in one or more surfactants, cosurfactants, and other materials or sequestering substances.

In one embodiment, quantum dots are tagged to one or more elements. The specific wavelength glow of the quantum dots enables the identification of specific pathologies, disorders, metabolic states, proteins or DNA making it possible to diagnose various diseases.

In one embodiment, one or more nanoscale quantum dot assays using tiny permutations of color tag a million or more different proteins or genetic sequences in a process called multiplexing. In one embodiment, one or more quantum dots of various sizes are excited at the same wavelength but have different emission wavelengths, and act as probes in experiments where multiple fluorescent measurements need to be made simultaneously, such as flow cytometry or confocal microscopy.

In another illustrative embodiment, one or more elements are sufficient to implement in vivo or in vitro genetic and protein nanoscale optical biological assay systems and methods. In one illustrative configuration, one or more elements comprise one or more nano-scale DNA chips known in the art, and or one or more nano-scale DNA chips known in the art to detect DNA samples formed from bonding with the target DNA on a chip, and or reference DNA nano-chips.

In another illustrative configuration, one or more elements comprise one or more protein array techniques known in the art. The array surfaces are designed to bind to one or more hydrophobic, hydrophilic (cation or anion) or specific ligands, and also include a protein array reader known in the art.

In another illustrative embodiment, one or more elements are used in a multiplexed analysis system or method that provides a nanoscale replacement for DNA-chip technology and can be used for the analysis of genetic variance, proteomics, and gene expression.

In another embodiment, one or more elements produce specific light emissions and or thermal energies caused by their coming into contact with a particular metabolic state, medical disorder, disease pathology, genotype, phenotype and or other specific stimuli. One or more entrapped agents carried by one or more elements are thereby selectively triggered and released. In doing so, they form a targeted agent delivery system without exposing the entire body—or an indiscriminate area—to a similar dose of light, thermal energy, and or agents. The agents may be delivered in vivo by means known in the art.

In one illustrative embodiment, photonic energies from one or more elements thermally operate on one or more other elements that may have one or more entrapped materials, such as, but not limited to, therapeutic, diagnostic, and or therapeutic agents within an aqueous interior, and or that may have one or more entrapped nanoparticles such as liposomes, micelles, proteins, other biological and or bioengineered elements, including organic, inorganic, and synthetic materials, and or that may have one or more hydrophobic materials bound to a lipid bilayer membrane. The well-known permeability increase at the phase transition temperature provides a means to trigger release of an entrapped agent, like, for example release of a therapeutic agent in locally heated tissues. In one embodiment, efficient in vivo or in vitro release of entrapped agents at non-targeted and or targeted sites are triggered by light emitted by one or more light sources when the one or more elements comprise a photoisomerisable species.

In another embodiment, the method of one or more LuxR proteins and lux bioluminescence genes and or other luminescent causing genes known in the art are utilized and are bioengineered and incorporated into one or more elements, ligands, targeting moieties, and or vectors, which may also be conjugated with one or more other elements, materials, and substances. In one embodiment, luminescent causing genes provide optical pumping sufficient to excite one or more quantum dots and or photonic dots.

In an illustrative embodiment, in vivo release from one or more cargo elements comprised of one or more entrapped liposomal and or non-liposomal-entrapped agents are optically triggered by photons emitted by light sources of one or more types. In one illustrative embodiment, one or more light sources produce specific light wavelength emissions caused by their coming into contact with, for example, a specific disease at in vivo target site and causes diagnostic, therapeutic, and or prosthetic agents comprised in a photosensitive invention delivery system to be triggered and released from one or more invention elements, thereby forming a highly targeted drug delivery system. For example, in one embodiment, one or more cargo elements comprise an amphipathic lipid, such as a phospholipid, having two chains derived from fatty acid that allow the lipid to pack into a bilayer structure. One or more photosensitizers may be incorporated into the entrapped materials' cavity and or membranes.

In one illustrative embodiment, a phospholipid (1,2-(4'-n-butylphenyl)azo-4"(-phenylbutyroyl))-glycero-3-phosphocholine ('Bis-Azo PC'), is substituted with azobenzene moieties in both acyl chains that can be photoisomerised by a fast nanolaser pulse. One or more other photoisomeris able species can be used in other embodiments. Agent release from one or more cargo elements occurs on the milliseconds timescale and photosensitised cargo elements thereby serve as light sensitive elements to allow for the triggered release of agents from one or more invention elements. In one embodiment, cholesterol additives may be used. The addition of cholesterol may have a marked effect on kinetics of agent release from cargo elements, and in some circumstances can result in substantial enhancement of light sensitivity in one or more photosensitised elements comprising one or more invention elements, In another embodiment, thermal and photosensitive activation systems acting together comprise one or more elements.

The invention, in one embodiment, comprises an in vitro and or in vivo nanoscale, biomolecular electronics element and or nano-electronics element, i.e., bio-molecular devices, which may be employed in a scalable, intelligent, biomolecular electronics device platform and or a nano-electronics device platform. The platform may also be comprised of one or more non-invention elements and devices, such as crystals, conductors, insulators, semiconductors, MEMS, and circuits, but not limited to such. And further, the platform may also be coated in one or more surfactants and or cosurfactants and or metals, elements, materials and substances.

In one embodiment, one or more elements and or platforms are used for biomolecular electronic and or nanoelectronic devices. Biological molecules, particularly proteins and lipids are used to perform the basic properties necessary for the functioning of biomolecular electronic devices. These biological materials conduct and transfer molecules from one location to another, are capable of major color changes on application of an electric field or light and can produce cascades that can be used for amplification of an optical or an electronic signal. All these properties can be applied to electronic switches, gates, storage devices, biosensors, biological transistors, to name just a few. In general, the electrical properties of bilayer lipid membranes are easily measurable for signal generation and transduction. In one embodiment, hybrid elements comprising cells with intact plasma membranes can be considered to act as tiny capacitors under the influence of an electric field. Whereas sufficiently high field strength may increase the membrane potential past a critical point leading to the breakdown of the membrane, experimental care must be taken. (Dielectric breakdown of biological membrane occurs at about 1 volt across the membrane.) On the other hand, the use of electrostatic potentials around the lipid molecules is very attractive, because they are controllable.

In one embodiment, one or more elements comprise nanoscale elements, components, devices, systems and or platforms, in one or more configurations, which form connectors for carrying information from a storage, processing or communications element or device to another, of one or more types.

In one embodiment, one or more elements comprise one or more information processing elements, components, devices, systems and or platforms such as, for example, but not limited to, encoders and decoders, memory, logic gates, registers, circuits, wiring and connectors, input and output elements, analog to digital and digital to analog converters and system architectures known in the art.

In one embodiment, one or more invention elements comprise nanoscale elements, components, devices, systems and or platforms that modify, process, manipulate, encode and decode, input, output, transmit, communicate, store and read various forms and types of information using a variety of suitable techniques known in the art, in vivo and in vitro.

A scalable information-processing invention platform may also include an encoder, e.g., a predetermined or specific DNA sequence that deliberately encodes at least a subset of the elements to take the form of specified sequence, as well as a decoder for reading information from at least a subset of the protein-based information processing elements. Examples of such a bio-system decoder are, but not limited to, a dye-based protein assay, a quantum dot-based assay, or other protein assay methods known in the art. Another example of encoders/decoders is the use of NMR and ESR and other methods known in the art that can effect and discern protein behaviors and their physical characteristics. Another example of encoders/decoders is the use of photons of different wavelengths and photo detectors.

In one embodiment, one or more elements comprise in vitro and or in vivo nanoscale information processing elements, components, devices, systems and or platform, which may follow and execute algorithms of one or more types expressed by or use biological control and regulate laws, processes, and or methods, and or geometrically derived algorithms such as graphs and Lie algebras, including Clifford algebras, but not limited to.

In another embodiment, one or more elements comprise a cognitive information processing element, device, and or platform of one or more types that follow and execute algorithms expressed by or use biological control and regulate laws and or processes, and or geometrically derived algorithms such as graphs and Lie algebras, including Clifford algebras, but not limited to.

In another embodiment, one or more elements comprise a hybrid digital and analog information processing element, device, and or platform of one or more types, wherein enlisting the rich repertoire of biochemical reactions and adopting a nested hierarchical organization makes intermixing of digital an analog processing possible in bio-computing applications.

In one embodiment, one or more elements comprise one or more nanoscale information processing elements, components, devices, systems and or platform that utilize photons emitted by invention light sources of one or more types as the basis of computation and or transmission and communication.

According to one illustrative embodiment, one or more elements comprise one or more nano-computer elements, components, devices, systems and or platforms of one or more types that are programmable, and or autonomous acting, and or do cognitive processing, which bio-nano-computers may also utilize self-replicating, self-adapting, self-repairing, self-regulating, and or self-regenerating methods, and which are used for applications at the cellular, molecular, and nanoscale level that may include, but are not limited to, biomedical imaging, sensors, diagnostic systems, assay systems, therapeutic systems, drug delivery systems, prosthetic systems, cybernetic systems, cellular-level nanofabrication systems, and inter- and intra-cellular imaging, repair, and engineering systems, the monitoring, sensing, imaging, diagnosing, repairing, constructing, fabricating, and or control and regulating of organic and or inorganic elements, and which bio-nano-computer elements and or platforms also may utilize and leverage biological control and regulate laws and or methods, and or geometrically derived algorithms such as graphs and Lie algebras, including Clifford algebras, but not limited to, in the performance of their tasks.

In one illustrative embodiment, one or more element chains are created via a molecular bridge group. To align the elements with respect to one another and also with respect to an external magnetic or electrical field. In one embodiment, one or more elements and or platforms and in one or more configurations are embedded in another material, like liquid crystal.

In one embodiment, one or more elements and or platforms and in one or more configurations are coated completely and or partially in a metal.

In another embodiment, one or more elements and or platforms and in one or more configurations are coated completely and or partially in reflective and or non-reflective coatings.

In one embodiment, one or more elements and or platforms and in one or more configurations are used to coat completely and or partially metals, crystals, insulators, conductors, semiconductor components, wires, and devices.

In another illustrative embodiment, one or more elements and or platforms and in one or more configurations facilitate the externally and or mechanistically directed alignment of, for example, but not limited to, biological elements, various other non-invention nanoparticles, carbon nanotubes, crystals, conductors, semiconductors, insulators, and or other devices, materials and substances, which aligned assemblies may further be coated in one or more surfactants and or metals, elements, materials and substances.

In one embodiment, one or more elements in one or more configurations include other types of nanoparticle elements such as, but not limited to, polymer-based, polybutylcyanoacrylate-based, and cetyl alcohol-based nanoparticles, empty cage Fullerenes, endohedral Fullerenes, carbon nanotubes, cells, liposomes, capsids, dendrimers, micelles, and the like.

In another illustrative embodiment, one or more elements and or platforms of one or more types in whole or in part enable a shape programmable and or scaffolding system to which one or elements of one or more types, including natural and or non-invention elements are affixed and or further form more one or more structures of one more types In one embodiment, one or more elements and or platforms in one or more configurations form and or include optical elements such as, but not limited to, optics; optoelectronic elements; photoelectric elements; photodetectors; and photosensitive elements, which optical elements may also be coated or treated in whole or in part with materials that affect their optical properties.

In one embodiment, one or more elements and or platforms and in one or more configurations form and or include imaging elements and sensors, such as, but not limited to, CCDs and CMOS optical elements.

In one embodiment, one or more elements and or platforms, in one or more configurations include and or comprise photonic to electrical energy conversion elements.

In one embodiment, one or more elements and or platforms form one or more electronic circuits, which circuit may also be comprised of one or more other elements such as empty Fullerenes, endohedral Fullerenes, nanotubes, crystals, insulators, conductors, semiconductors, and or other materials, substances and devices, which circuits also may be coated in one or more surfactants and or cosurfactants and or other materials and substances.

In one embodiment, one or more elements and or platforms are switched on or off and or change states by applying an electric field, and may also comprise one or more transistors or devices in another embodiment.

In another embodiment, one or more elements and or platforms and in one or more configurations; self-assemble, and or are shape-programmed, and or use biological control and regulate laws, processes and methods, and or use geometrically derived algorithms such as graphs and Lie algebras, including Clifford algebras, but not limited to, and or are mechanically assembled via lithography, and or utilize other externally directed techniques and methods known the art, and or some combination thereof; form natural positions that are associated with electronic circuits and or information processing devices, such as atomic and molecular scale device design, their interconnection, nanofabrication and circuit architectures.

According to one illustrative embodiment, one or more elements and or platforms comprise one or more crystal structures and elements, of one or more types.

According to one illustrative embodiment, one or more elements and or platforms comprise one or more desiccated elements, of one or more types.

According to one illustrative embodiment, one or more invention comprise one or more hydrated and or rehydrated elements and or platforms, of one or more types.

According to one illustrative embodiment, one or more elements and or platforms comprise one or more rehydration elements and or platforms, of one or more types.

According to one illustrative embodiment, one or more elements and or platforms are embedded and or incorporated into one or more materials, substances, devices, agents, devices, systems, organisms, and or mechanisms of one or more types.

In another illustrative embodiment, one or more elements and or platforms comprise one or more magnetic nanoparticles of one or more types.

In one embodiment, one or more elements and or platforms are nanoscale recording memory media or components, which may incorporate metals, ferromagnetic materials, and or ferroelectric materials and elements, and or may form into magnetic rings, and or may form vertically polarized magnetic domains and or form magnetic domains on isolated islands of one or more types.

In one embodiment, one or more elements and or platforms are nanoscale photovoltaic cells or components of one or more types.

In one embodiment, one or more elements are nanoscale batteries or components of one or more type for storing electronic charge.

In one embodiment, one or more elements and or platforms comprise a nanoscale environmental hazard-screening device, and or comprise an in situ remediation, removal and or sequestration component or system of one or more types.

In one embodiment, one or more elements and or platforms comprise an opto-electronic device, system or component of one or more types.

In one illustrative embodiment, embodiment, one or more elements comprise one or more nanoscale passive and or active linear or nonlinear optic components, and or particle detectors, and or other elements sufficient to implement in vivo or in vitro optical system arrays and methods.

In another embodiment, one or more elements comprise in vivo or in vitro detection, diagnostic and tracking agents for chemical, biological, and or nuclear elements and activities, but not limited to such.

In one embodiment, one or more elements and or platforms comprise a spin-based electronics element or system of one or more types.

In one embodiment, one or more elements and or platforms exploit the Coulomb blockade-like properties of self-assembled proteins, wherein a single particle at a time may move through a transmembrane protein-based channel.

In one embodiment, one or more elements and or platforms utilize and or exploit the Casimir effect, which is a small attractive force that acts between two closely parallel, uncharged conducting elements. It is due to quantum vacuum fluctuations of the electromagnetic field.

In some illustrative embodiments, one or more elements and or platforms and in one or more configurations are physically linked via molecular addends of one or more types, but are not limited to such addend types.

In other illustrative configurations, one or more elements and or platforms are functionally linked via photonic, chemical, electromagnetic, electrical and/or quantum (non-classical) interactions of one or more types, including the Internet, to work and cooperate locally and/or remotely.

One or more elements and or platforms of one or more types may be encapsulated, packaged, stored, incorporated, and or utilize one or more methods known in the art, including for example, but not limited to: catheters; injections, including intramuscular injections; syringes; droppers and bulbs; pills; intravenous means; oral means; anal means; capsules; nanocapsules; nanoparticles; nano-devices; prescriptions; hospital and medical supplies; dental supplies; non-prescriptions; medications; over the counter products and remedies; alternative medicine supplies, systems, products and devices; hair care products; splints, casts, walkers, crutches, canes, wheelchairs, and other ambulatory aids; natural foods; vitamin and mineral supplements; first aid products; emergency health care procedures, systems, devices, and products, including combat medicine; health care products; grafts; skin patches; bandages; adhesives; wraps; masks; markers; powders; granules; geriatric care products; pediatric care products; diagnostic devices, systems, and products; medical imaging devices, systems, and products; telemedicine devices, systems, and products; in vivo monitoring systems, products, systems, and devices; in vitro monitoring systems, products, systems, and devices; laundry products; chemical, nuclear and biological sensors; sensors; bio-sensors; environmental sensors; combat systems, clothing, uniforms, and protective gear; food preparation products; food testing and safety devices, systems, and products; food storage wraps, systems, devices, and products; water treatment devices, systems and products; waste storage, management, and treatment systems and products; sewerage systems and products; plumbing systems and products; bed and bath products; animal care and veterinary products; animal feed; animal slaughter systems and products; cooking products; cookware; forensic devices, systems and products; home and office cleaning products; home products; office products; personal products; industrial products; home and office care products; paper products; personal hygiene products; sexual hygiene and safety products; sexual reproduction devices, systems, and products; sexual arousal products and devices; dental and dental care products; oral hygiene products, devices, and systems; robotic products, systems and devices; cybernetic devices; jewelry; novelties; solvents; agro-products; plants; animals; vehicles; biologicals; chemicals; cells; tissue; organs; proteins; liposomes; phages; micelles; peptides; antibodies; monoclonal antibodies; DNA; RNA; IRNA; siRNA; RISC; cloning; human contact; micro-electromechanical systems (MEMS) and other types of nano-systems; food utensils; tools; appliances; consumer electronics; paints and finishes; heating, ventilation and air conditioning systems; construction, building, home and office materials; water; milk; food and other edible or chewable substances and items; prostheses; food and drink additives and supplements; drinks; beverages; soaps; creams; ointments; salves; topical agents; cosmetics; beautifying agents; liquids; fluids; oils; gels; adhesives; aerosols; vapors; airborne methods; pumps; fragrances and perfumes; textiles; sporting and athletic goods and devices; physical work out and training systems, devices, and products; sports medicine systems, devices, and products; recreational products and gear; shoes, clothing, and apparel; eyewear; sprays; dyes; biological elements; organ transplants; implants; stents; prosthetic devices; artificial skin, blood, limbs, joints, bones, cells, eyes, organs, and other artificial body parts and biological elements; subcutaneous means; incisions; surgical means; and in-patient and out-patient medical procedures.

The above-described embodiments have been set forth to describe more completely and concretely the present invention, and are not to be construed as limiting the invention. It is further intended that all matter and the description and drawings be interpreted as illustrative and not in a limiting sense. That is, while various embodiments of the invention have been described in detail, other alterations, which will be apparent to those skilled in the prior art, are intended to be embraced within the spirit and scope of the invention.

In view of the foregoing, what is claimed is:

1. A nanoparticle comprising a clathrin triskelion linked to (a) a cargo selected from the group consisting of a therapeutic or diagnostic agent or a targeting moiety, and (b) a masking moiety, wherein the clathrin triskelion comprises three human clathrin heavy chains of SEQ ID NO:1, and wherein the masking moiety is polyethylene glycol, surfactant, or cosurfactant.

2. The nanoparticle of claim 1, wherein the therapeutic or diagnostic agent is a growth factor, imaging contrast agent, imaging tracer agent, radiodiagnostic agent, nucleic acid, oligonucleotide, peptide, carbohydrate, phospholipid, antineoplastic agent, metal, chemical, vaccine, vitamin, hormone, antibiotic, or antibody.

3. A nanoparticle comprising a clathrin triskelion covalently linked to a cargo selected from the group consisting of a therapeutic or diagnostic agent, a targeting moiety, and a masking moiety, wherein the clathrin triskelion comprises three human clathrin heavy chains of SEQ ID NO:1, and wherein the targeting moiety is an antibody, peptide, fluorophore, permeation enhancer, amino sugar, lipoprotein, toxin, transferrin, or glycoprotein.

4. The nanoparticle of claim 3, wherein the fluorophore is excitable by an infrared, visible, or ultraviolet light.

5. The nanoparticle of claim 2, wherein the imaging contrast agent comprises a gadolinium-based contrast agent, magnetic iron oxide, or manganese-based contrast agent.

6. The nanoparticle of claim 5, wherein the gadolinium-based contrast agent comprises a chelating agent selected from the group consisting of: Diethylene triamine pentaacetic acid (DTPA), 1,4,7,10-Tetraazacyclododecane-1,4,7-triacetic acid trisodium salt (DO3A), and 1,4,7,10-Tetraazacyclododecane-1,4,7,10-tetraacetic acid (DOTA).

7. The nanoparticle of claim 2, wherein the growth factor comprises epidermal growth factor, transforming growth factor a (TGFa), nerve growth factor, neurotrophic factor, or platelet derived growth factor.

8. The nanoparticle of claim 2, wherein the nucleic acid is an mRNA, RNAi, siRNA, RNA-induced silencing complex (RISC), or DNA.

9. The nanoparticle of claim 2, wherein the hormone comprises insulin, thyroid stimulating hormone, thyroid hormone, growth hormone, calcitonin, glucagon, prolactin, or Luteinizing Hormone.

10. The nanoparticle of claim 2, wherein the antibody is a monoclonal antibody.

11. The nanoparticle of claim 1, wherein at least one of the human clathrin heavy chains of SEQ ID NO: 1 is linked to the cargo.

12. The nanoparticle of claim 11, wherein the human clathrin heavy chain of SEQ ID NO: 1 is linked to the cargo via biotin-avidin interaction, PEGylation, cross-linking, molecular tether, non-covalent or covalent bonding.

13. A nanoparticle comprising a clathrin triskelion linked to a cargo selected from the group consisting of a therapeutic or diagnostic agent, a targeting moiety, and a masking moiety, wherein the clathrin triskelion comprises three human clathrin heavy chains of SEQ ID NO:1, and wherein at least one of the human clathrin heavy chains of SEQ ID NO: 1 forms a fusion protein with the cargo.

14. The nanoparticle of claim 13, wherein the therapeutic or diagnostic agent is a growth factor, peptide, hormone, antibody, lipoprotein, or glycoprotein.

15. The nanoparticle of claim 14, wherein the growth factor comprises epidermal growth factor, transforming growth factor a (TGFa), nerve growth factor, neurotrophic factor, or platelet derived growth factor.

16. The nanoparticle of claim 14, wherein the hormone comprises insulin, thyroid stimulating hormone, thyroid hormone, growth hormone, calcitonin, glucagon, prolactin, or Luteinizing Hormone.

17. The nanoparticle of claim 14, wherein the antibody is a monoclonal antibody.

18. The nanoparticle of claim 1, wherein the nanoparticle is not linked to a targeting moiety.

19. The nanoparticle of claim 1, wherein one or more of the human clathrin heavy chain is further linked to one human clathrin light chain.

* * * * *

UNITED STATES PATENT AND TRADEMARK OFFICE

CERTIFICATE OF CORRECTION

PATENT NO. : 11,096,901 B2
APPLICATION NO. : 13/847058
DATED : August 24, 2021
INVENTOR(S) : Franco Vitaliano and Gordana Vitaliano It is certified that error appears in the above-identified patent and that said Letters Patent is hereby corrected as shown below:

In the Claims

Column 215, Line 62, Claim 7, delete "factor a (TGFa)," and insert -- factor α (TGFα), --

Column 216, Line 52, Claim 15, delete "factor a (TGFa)," and insert -- factor α (TGFα), --

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*